US012569673B2

(12) United States Patent
Danitz et al.

(10) Patent No.: US 12,569,673 B2
(45) **Date of Patent: *Mar. 10, 2026**

(54) METHODS OF TREATMENT WITH A ROBOTIC SURGICAL SYSTEM

(71) Applicant: Pulse Biosciences, Inc., Hayward, CA (US)

(72) Inventors: David J. Danitz, San Jose, CA (US); Cameron D. Hinman, Thurmond, NC (US); Kenneth R. Krieg, Fremont, CA (US); Kevin L. Moss, Lathrop, CA (US); Christopher J. Foster, San Francisco, CA (US); Darrin R. Uecker, San Mateo, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 406 days.

This patent is subject to a terminal disclaimer.

(21) Appl. No.: 18/186,621

(22) Filed: Mar. 20, 2023

(65) Prior Publication Data

US 2023/0248415 A1     Aug. 10, 2023

Related U.S. Application Data

(63) Continuation of application No. 17/077,744, filed on Oct. 22, 2020, now Pat. No. 11,638,815, which is a
(Continued)

(51) Int. Cl.
*A61N 1/05* (2006.01)
*A61B 17/00* (2006.01)
(Continued)

(52) U.S. Cl.
CPC ............ *A61N 1/0502* (2013.01); *A61B 18/14* (2013.01); *A61B 34/32* (2016.02); *A61B 34/37* (2016.02);
(Continued)

(58) Field of Classification Search
CPC ......... A61B 34/25; A61B 34/30; A61B 34/32; A61B 34/35; A61B 34/37; A61B 34/71;
(Continued)

(56) References Cited

U.S. PATENT DOCUMENTS 4,043,342  A    8/1977  Morrison
5,074,802  A   12/1991  Gratziani et al.
(Continued)

FOREIGN PATENT DOCUMENTS

CA       2838411  A1    1/2005
WO    WO99/06101  A1    2/1999
(Continued)

OTHER PUBLICATIONS

Anand et al., "Nano-Pulse Electro-Signaling treatment of murine tumors significantly reduces the percentage of regulatory T cells in the treated tumor," Journal for Immunotherapy of Cancer: 31 st Annual Meeting and Associated Programs of the Society for Immunotherapy of Cancer (SITC 2016), Part Two, National Harbor, MD, USA; p. 214; Nov. 16, 2018.
(Continued)

*Primary Examiner* — Brian T Gedeon
(74) *Attorney, Agent, or Firm* — Shay Glenn LLP

(57) ABSTRACT

Described herein are methods and systems for using the treatment tip apparatuses and high-voltage connectors with robotic surgical systems. For example, retractable treatment tip apparatuses (e.g., devices, systems, etc.) including one, or more preferably a plurality, of electrodes that are protected by a housing (which may be retractable) until pressed against the tissue for deployment of the electrodes and delivery of a therapeutic treatment, are disclosed. In particular, these apparatuses may include a plurality of treatment needle electrodes and may be configured for the delivery of nanosecond pulsed electric fields. Also described
(Continued)

herein are high-voltage connectors configured to provide high-voltage energy, such as nsPEF pulses, from a generator to the retractable treatment tip apparatuses.

22 Claims, 69 Drawing Sheets

Related U.S. Application Data continuation of application No. 15/920,389, filed on Mar. 13, 2018, now Pat. No. 10,857,347, which is a continuation-in-part of application No. PCT/US2017/052340, filed on Sep. 19, 2017.

(60) Provisional application No. 62/618,022, filed on Jan. 16, 2018.

(51) Int. Cl.

| | |
|---|---|
| *A61B 18/00* | (2006.01) |
| *A61B 18/14* | (2006.01) |
| *A61B 34/32* | (2016.01) |
| *A61B 34/37* | (2016.01) |
| *A61B 90/00* | (2016.01) |
| *A61N 1/40* | (2006.01) |

(52) U.S. Cl.
CPC ...... *A61N 1/40* (2013.01); *A61B 2018/00702* (2013.01); *A61B 2018/1425* (2013.01); *A61B 2018/1432* (2013.01); *A61B 18/1445* (2013.01)

(58) Field of Classification Search
CPC .......... A61B 34/76; A61B 2017/00482; A61B 2017/00477; A61B 2017/00973; A61B 18/14; A61B 18/1206
See application file for complete search history.

(56) References Cited

U.S. PATENT DOCUMENTS

| | | | |
|---|---|---|---|
| 5,568,035 | A | 10/1996 | Kato et al. |
| 5,635,776 | A | 6/1997 | Imi |
| 5,688,253 | A | 11/1997 | Paradis |
| 5,702,359 | A | 12/1997 | Hofmann et al. |
| 5,718,246 | A | 2/1998 | Vona |
| 5,735,827 | A | 4/1998 | Adwers et al. |
| 5,769,827 | A | 6/1998 | Demichele et al. |
| 5,774,348 | A | 6/1998 | Druce et al. |
| 5,792,122 | A | 8/1998 | Brimhall et al. |
| 5,798,579 | A | 8/1998 | McPhee |
| 5,902,272 | A | 5/1999 | Eggers et al. |
| 5,907,484 | A | 5/1999 | Kowshik et al. |
| 6,008,690 | A | 12/1999 | Takeshima et al. |
| 6,009,347 | A | 12/1999 | Hofmann |
| 6,010,487 | A | 1/2000 | Demichele et al. |
| 6,017,354 | A | 1/2000 | Culp et al. |
| 6,026,003 | A | 2/2000 | Moore et al. |
| 6,048,789 | A | 4/2000 | Vines et al. |
| 6,137,276 | A | 10/2000 | Rudolph |
| 6,181,964 | B1 | 1/2001 | Hofmann et al. |
| 6,190,381 | B1 | 2/2001 | Olsen et al. |
| 6,221,056 | B1 | 4/2001 | Silverman |
| 6,246,200 | B1 | 6/2001 | Blumenkranz et al. |
| 6,326,177 | B1 | 12/2001 | Schoenbach et al. |
| 6,331,181 | B1 | 12/2001 | Tierney et al. |
| 6,508,786 | B2 | 1/2003 | Huitema et al. |
| 6,633,093 | B1 | 10/2003 | Rim et al. |
| 6,654,636 | B1 | 11/2003 | Dev et al. |
| 6,697,670 | B2 | 2/2004 | Chomenky et al. |
| 6,743,211 | B1 | 6/2004 | Prausnitz et al. |
| 6,770,081 | B1 | 8/2004 | Cooper et al. |
| 6,831,377 | B2 | 12/2004 | Yampolsky et al. |
| 7,395,112 | B2 | 7/2008 | Keisari et al. |
| 7,496,401 | B2 | 2/2009 | Bernabei |
| 7,666,191 | B2 | 2/2010 | Orban et al. |
| 7,699,855 | B2 | 4/2010 | Anderson et al. |
| 7,767,433 | B2 | 8/2010 | Kuthi et al. |
| 7,855,904 | B2 | 12/2010 | Kirbie et al. |
| RE42,277 | E | 4/2011 | Jaafar et al. |
| 7,937,143 | B2 | 5/2011 | Demarais et al. |
| 7,938,824 | B2 | 5/2011 | Chomenky et al. |
| 8,000,813 | B2 | 8/2011 | Schoenbach et al. |
| 8,216,224 | B2 | 7/2012 | Morris et al. |
| 8,429,582 | B1 | 4/2013 | Lai et al. |
| 8,512,334 | B2 | 8/2013 | Nuccitelli et al. |
| 8,688,227 | B2 | 4/2014 | Nuccitelli et al. |
| 8,814,833 | B2 | 8/2014 | Farrell et al. |
| 8,822,222 | B2 | 9/2014 | Beebe et al. |
| 8,852,208 | B2 | 10/2014 | Gomez et al. |
| 8,979,912 | B2 | 3/2015 | Na et al. |
| 9,101,337 | B2 | 8/2015 | Hoegerle et al. |
| 9,101,764 | B2 | 8/2015 | Nuccitelli et al. |
| 9,414,881 | B2 | 8/2016 | Callas et al. |
| 9,629,991 | B1 | 4/2017 | O'Brien et al. |
| 9,724,155 | B2 | 8/2017 | Nuccitelli et al. |
| 9,895,520 | B2 | 2/2018 | Burton et al. |
| 9,931,161 | B2 | 4/2018 | Willis |
| 9,953,815 | B2 | 4/2018 | Griebeler |
| 9,956,391 | B2 | 5/2018 | Weissberg et al. |
| 9,960,763 | B2 | 5/2018 | Miller et al. |
| 9,999,467 | B2 | 6/2018 | Moss et al. |
| 10,022,695 | B2 | 7/2018 | Zhang et al. |
| 10,154,869 | B2 | 12/2018 | Onik et al. |
| 10,154,876 | B2 | 12/2018 | Callas et al. |
| 10,252,050 | B2 | 4/2019 | Kreis et al. |
| 10,857,347 | B2 | 12/2020 | Danitz et al. |
| 11,167,125 | B2 | 11/2021 | Moss et al. |
| 11,571,569 | B2 | 2/2023 | Danitz et al. |
| 11,638,815 | B2 | 5/2023 | Danitz et al. |
| 2001/0025177 | A1 | 9/2001 | Woloszko et al. |
| 2002/0120260 | A1 | 8/2002 | Morris et al. |
| 2002/0193833 | A1 | 12/2002 | Dimmer et al. |
| 2003/0204161 | A1 | 10/2003 | Ferek Petric |
| 2003/0229316 | A1 | 12/2003 | Hwang et al. |
| 2003/0233087 | A1 | 12/2003 | Chen et al. |
| 2004/0080964 | A1 | 4/2004 | Buchmann |
| 2004/0181237 | A1 | 9/2004 | Forde et al. |
| 2004/0186466 | A1 | 9/2004 | Chomenky et al. |
| 2004/0240241 | A1 | 12/2004 | Chueh et al. |
| 2004/0267254 | A1 | 12/2004 | Manzo et al. |
| 2005/0119627 | A1 | 6/2005 | Crawford |
| 2005/0119649 | A1 | 6/2005 | Swanson |
| 2005/0171534 | A1 | 8/2005 | Habib |
| 2006/0015147 | A1 | 1/2006 | Persson et al. |
| 2006/0062074 | A1 | 3/2006 | Gundersen et al. |
| 2006/0079886 | A1 | 4/2006 | Orszulak et al. |
| 2006/0090723 | A1 | 5/2006 | Stuart |
| 2006/0139977 | A1 | 6/2006 | Oicles et al. |
| 2007/0129626 | A1 | 6/2007 | Mahesh et al. |
| 2008/0015516 | A1 | 1/2008 | Lavi |
| 2008/0031337 | A1 | 2/2008 | Hasegawa et al. |
| 2008/0077189 | A1 | 3/2008 | Ostroff |
| 2008/0231337 | A1 | 9/2008 | Krishnaswamy et al. |
| 2009/0012513 | A1 | 1/2009 | Utley et al. |
| 2009/0198231 | A1 | 8/2009 | Esser et al. |
| 2009/0247944 | A1 | 10/2009 | Kirschenman et al. |
| 2009/0299362 | A1 | 12/2009 | Long et al. |
| 2010/0038971 | A1 | 2/2010 | Sanders et al. |
| 2010/0042095 | A1 | 2/2010 | Bigley et al. |
| 2010/0049194 | A1 | 2/2010 | Hart et al. |
| 2010/0063496 | A1 | 3/2010 | Trovato et al. |
| 2010/0240995 | A1 | 9/2010 | Nucciteli et al. |
| 2010/0331758 | A1 | 12/2010 | Davalos et al. |
| 2011/0015630 | A1 | 1/2011 | Azure |
| 2011/0092973 | A1 | 4/2011 | Nuccitelli et al. |
| 2011/0112527 | A1 | 5/2011 | Hamilton et al. |
| 2011/0118729 | A1 | 5/2011 | Heeren et al. |
| 2011/0144641 | A1 | 6/2011 | Dimalanta et al. |
| 2011/0160514 | A1 | 6/2011 | Long et al. |
| 2011/0264179 | A1 | 10/2011 | Eckerdal |
| 2011/0270249 | A1 | 11/2011 | Utley et al. |
| 2011/0319833 | A1 | 12/2011 | Chun et al. |
| 2012/0109263 | A1 | 5/2012 | Kolb et al. |

(56)　　　　References Cited

U.S. PATENT DOCUMENTS

| | | |
|---|---|---|
| 2012/0130269 A1 | 5/2012 | Rea |
| 2012/0136282 A1 | 5/2012 | Rosenberg et al. |
| 2012/0158078 A1 | 6/2012 | Moulder et al. |
| 2012/0277624 A1 | 11/2012 | Cucin |
| 2012/0277763 A1 | 11/2012 | Greenblatt et al. |
| 2012/0310230 A1 | 12/2012 | Willis |
| 2013/0018441 A1 | 1/2013 | Childs |
| 2013/0060246 A1 | 3/2013 | Knopp et al. |
| 2013/0190836 A1 | 7/2013 | McCreery |
| 2013/0289358 A1 | 10/2013 | Melsky et al. |
| 2013/0302409 A1 | 11/2013 | Fuchs et al. |
| 2013/0345697 A1 | 12/2013 | Garcia et al. |
| 2014/0005658 A1 | 1/2014 | Rosenbegr |
| 2014/0046322 A1 | 2/2014 | Callas et al. |
| 2014/0081256 A1 | 3/2014 | Carmel et al. |
| 2014/0155963 A1 | 6/2014 | Ko |
| 2014/0194789 A1 | 7/2014 | Ko |
| 2014/0200403 A1 | 7/2014 | West et al. |
| 2014/0228835 A1 | 8/2014 | Mielekamp et al. |
| 2014/0277219 A1 | 9/2014 | Nanda |
| 2014/0336638 A1 | 11/2014 | Deem et al. |
| 2014/0364797 A1 | 12/2014 | Schoenbach et al. |
| 2015/0032100 A1 | 1/2015 | Coulson et al. |
| 2015/0065946 A1 | 3/2015 | Gehl et al. |
| 2015/0201991 A1 | 7/2015 | Zemlin |
| 2015/0230855 A1 | 8/2015 | Chomenky et al. |
| 2015/0230858 A1 | 8/2015 | Long et al. |
| 2015/0272657 A1 | 10/2015 | Yates et al. |
| 2015/0318846 A1 | 11/2015 | Prager et al. |
| 2016/0192999 A1 | 7/2016 | Stulen et al. |
| 2016/0271380 A1 | 9/2016 | Poon et al. |
| 2016/0296269 A1 | 10/2016 | Rubinsky et al. |
| 2016/0317216 A1 | 11/2016 | Hermes et al. |
| 2016/0338761 A1 | 11/2016 | Chomenky et al. |
| 2016/0361109 A1 | 12/2016 | Weaver et al. |
| 2016/0367310 A1 | 12/2016 | Onik et al. |
| 2017/0127987 A1 | 5/2017 | Hezi-Yamit et al. |
| 2017/0209695 A1 | 7/2017 | Solomon |
| 2017/0216353 A1 | 8/2017 | Nuccitelli et al. |
| 2017/0245928 A1 | 8/2017 | Xiao et al. |
| 2017/0246455 A1 | 8/2017 | Athos et al. |
| 2017/0281274 A1 | 10/2017 | Santana |
| 2017/0319851 A1 | 11/2017 | Athos et al. |
| 2017/0348525 A1 | 12/2017 | Sano et al. |
| 2018/0078755 A1 | 3/2018 | Kreis et al. |
| 2018/0110557 A1 | 4/2018 | Muratori et al. |
| 2018/0154141 A1 | 6/2018 | Ahn |
| 2018/0154142 A1 | 6/2018 | Guo et al. |
| 2018/0177543 A1 | 6/2018 | You et al. |
| 2018/0243558 A1 | 8/2018 | Athos et al. |
| 2019/0009084 A1 | 1/2019 | Stadelmann et al. |
| 2019/0046791 A1 | 2/2019 | Ebbers et al. |
| 2019/0109591 A1 | 4/2019 | Miller et al. |
| 2019/0269904 A1 | 9/2019 | Kreis et al. |
| 2021/0370049 A1 | 12/2021 | Moss et al. |
| 2025/0010063 A1 | 1/2025 | Moss et al. |

FOREIGN PATENT DOCUMENTS

| | | |
|---|---|---|
| WO | WO03/076006 A2 | 9/2003 |
| WO | WO2011/146498 A2 | 11/2011 |
| WO | WO2011/163264 A2 | 12/2011 |
| WO | WO2013/143603 A1 | 10/2013 |
| WO | WO2014/060854 A1 | 4/2014 |
| WO | WO2016/089781 A1 | 6/2016 |
| WO | WO2017/200954 A1 | 11/2017 |
| WO | WO2017/201394 A1 | 11/2017 |
| WO | WO2017/223120 A1 | 12/2017 |
| WO | WO2018/075946 A1 | 4/2018 |
| WO | WO2018/089506 A1 | 5/2018 |
| WO | WO2018/106672 A1 | 6/2018 |

OTHER PUBLICATIONS

Anand et al.; Adaptive immune response to nano-pulse stimulation (NPS); Nov. 11, 2016, Poster presentation at the 31st Annual Meeting and Associated Programs of the Society for Immunotherapy of Cancer; 1 page; retreived rom the internet (http://pulsebiosciences. com/assets/Pulse%20AIR%20poster.pdf); on Mar. 13, 2018.

Baker et al.; Stacking power Mosfets for use in high speed instrumentation; Review of scientific instruments; 63(12; pp. 5799-5801; Dec. 1992.

Beebe; Hepatocellular carcinoma ablation and possible immunity in the age of nanosecond pulsed electric fields; Journal of Hepatocellular carcinoma; No. 2; pp. 49-55; May 2015.

Bhosale et al.; Design and Simulation of 50 kV, 50 A Solid State Marx Generator; International Conference on Magnetics, Machines & Drives (AICERA—2014 iGMMD), IEEE; pp. 1-5; Jul. 24, 2014.

Carey et al.; Marx Generator Design and Performance; IEEE; InPower Modulator Symposium, 2002 High-Voltage Workshop; Conference Record of the Twenty-Fifth International; Applied Physical Electronics, Austin TX; 4 pages; Jun. 2002.

Casey et al.; Solid-State Marx Bank Modulator for the Next Generation Linear Collider; Conference Record of the 26th; IEEE; International Power Modulator Symposium and 2004 High Voltage Workshop (PMC), San Francisco, California; pp. 257-260; May 23-26, 2004.

Cook et.al.; Design and Testing of a Fast, 50 kV Solid-State Kicker Pulser; IEEE; Inconference record of the International Power Modulator Symposium 2002; pp. 106-109; Lawrence Livermore National lab; 6 pages; Jun. 24, 2002.

European Supplemental Search Report mailed Oct. 25, 2021 for European Patent Application No. 19741761.1; 11 pages.

Extended European Search Report mailed Feb. 11, 2022 for European Patent Application 19741574.8; 8 pages.

Final Office action mailed Jul. 5, 2019 for U.S. Appl. No. 15/269,273; 12 pages.

Garon et al.; In Vitro and In Vivo Evaluation and a Case Report of Intense Nanosecond Pulsed Electric Field as a Local Therapy for Human Malignancies; International Journal of Cancer; 121(3): pp. 675-682; Aug. 2007.

Gaudreau et al; Solid-State Pulsed Power Systems for the Next Linear Collider; IEEE; InPulsed Power Plasma Science, 2001, PPPS-2001. Digest of Technical Papers; vol. 1; pp. 298-301; Jun. 17, 2001.

Gundersen et al.; Nanosecond pulse generator using a fast recovery diode; IEEE; InProceedings of the 26th Inernational Pulsed Modulator Conference; 603-606; (year of pub. sufficiently earlier than effective US filing date and any foreign priority date) 2004.

International Search Report and Written Opinion mailed Apr. 21, 2016 for PCT/US2015/63025; 9 pages.

International Search Report and Written Opinion mailed Apr. 21, 2017 for PCT/US2017/015884; 12 pages.

International Search Report and Written Opinion mailed Apr. 29, 2019 for PCT/US2019/013484; 21 pages.

International Search Report and Written Opinion mailed Dec. 11, 2018 for PCT/US2018/045433; 16 pages.

International Search Report and Written Opinion mailed Feb. 27, 2018 for PCT/US2017/060654; 18 pages.

International Search Report and Written Opinion mailed Jan. 8, 2018 for PCT/US2017/05340; 10 pages.

International Search Report and Written Opinion mailed Jul. 21, 2017 for PCT/US2017/032744; 11 pages.

International Search Report and Written Opinion mailed May 1, 2019 for PCT/US2019/013545; 10 pages.

International Search Report and Written Opinion mailed May 25, 2017 for PCT/US2017/015881; 13 pages.

International Search Report mailed Feb. 27, 2018 for PCT/US2017/057698; 5 pages.

International Search Report mailed Mar. 22, 2018 for PCT/US2017/064685; 6 pages.

International Search Report mailed May 22, 2018 for PCT/US2018/019213; 4 pages.

Invitation To Pay Additional Fees And, Where Applicable, Protest Fee mailed Mar. 15, 2017 for PCT/US2017/015881; 2 pages.

(56)                    References Cited

OTHER PUBLICATIONS

Jiang et al.; Marx Generator Using Power Mosfets; IEEE; InPulsed Power Conference, PPC/09; pp. 408-410; Jun. 28, 2009.

Kirbie et al.; An All Solid State Pulse Power Source for High PRF induction Accesierators; InPower Modulator Symposium, 1988; Conference Rceord of the 1988 Twenty-Third International, Rancho Mirage, Ca.;; pp. 6-11; 6 pages; Jun. 22-25, 1998.

Krasnykh et al.; A Solid State Marx Type Modulator for Driving a TWT; Conference Record of the 24th International Power Modulator Sypolsium 2000; pp. 209-211; Jun. 26, 2000.

Mcdaniel et al., Nanosecond pulsed electric field treatment of tumor cell lines triggers immunogenic cell death (ICD); Nov. 11, 2016, Poster presentation at the 31st Annual Meeting and Associated Programs of the Society for Immunotherapy of Cancer (SITC 2016), National Harbor, MD, USA; 1 page; retrieved from the Internet (http://pulsebiosciences.com/assets/Pulse%20ICD%20poster.pdf) on Mar. 13, 2018.

Mcdaniel et al.; P329 Nanosecond pulsed electric field treatment of tumor cell lines triggers immunogenic cell death (ICD); Journal for Immuno Therapy of Cancer: 31st Annual Meeting and Associated Programs of the Society for Immunotherapy of Cancer (SITC 2016): part two: National Harbor, MD, USA, p. 175; Nov. 16, 2016.

Non Final Office Action mailed Dec. 26, 2018 for U.S. Appl. No. 15/269,273, 8 pages.

Okamura et al.; Development of the High Repetitive impulse Voltage Generator Using Semiconductor Switches; IEEE; InPulsed Power Conference; Digest of Technical Papers, 12 th IEEE International; vol. 2; pp. 807-810; Jun. 27, 1999.

Preliminary Report on Patentability mailed Mar. 19, 2019 for PCT/US2017/052340; 6 pages.

Redondo et al.; Solid-State Marx Generator Design with an Energy Recovery ReseS Circuit for Output Transformer Association; InPower Electronics Spelalists Conference, 2007, PESC, IEEE 2007; pp. 2987-2992; (5 pages); Jun. 17, 2007.

Richter-Sand et al.; Marx-Stacked IGBT Modulators for High Voltage. High Power Applications; IEEE; InPower Modulator Symposium, 2002 and 2002 High-Voltage Workshop., Conference Record of the Twenty-Fifth International 2002; pp. 390-393; Jun. 30, 2002.

Sack et al.; Design Considerations for a Fast Stacked-MOSFET Switch; IEEE Transactions on Plasma Science; 41(10); pp. 2630-2636; Oct. 2013.

Tang et al.; Diode Opening Switch Based Nanosecond High Voltage Pulse Generators for Biological and Medical Applications; IEEE Transactions on Dielectrics and Electrical Insulation; 14(4); pp. 878-883; Aug. 2007.

Wang et al.; Solid-State High Voltage Nanosecond Pulse Generator; IEEE InPulsed Power Conference;pp. 1199-1202; 4 pages; Jun. 13, 2005.

Yao et al.; FPGA-Controlled All-Solid-State Nanosecond Pulse Generator for Biological Applications; IEEE Transactions on Plasma Science; 40(10; pp. 2366-2372; Oct. 2012.

Yatim et al.; RIPK1 and NF-xB signaling in dying cells determines cross-priming of CD8+T cells; Science; 350(6258); pp. 328-334; Oct. 16, 2015.

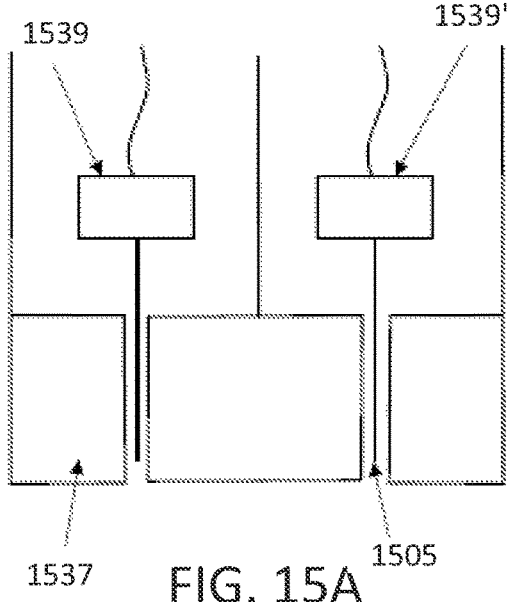
1539
1537    FIG. 15A    1505
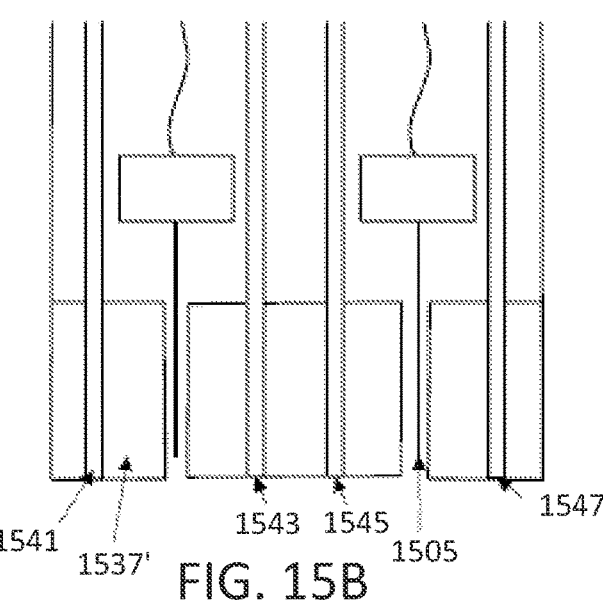
1539'
1541   1537'   FIG. 15B   1543   1545   1505   1547
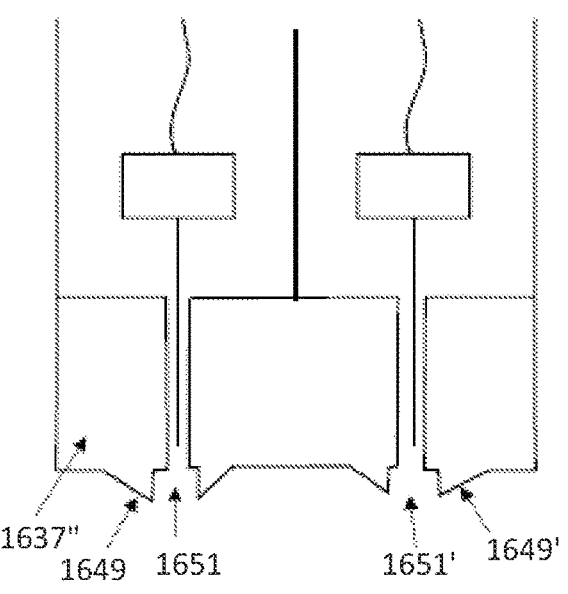
1637"   1649   1651   1651'   1649'
FIG. 16A
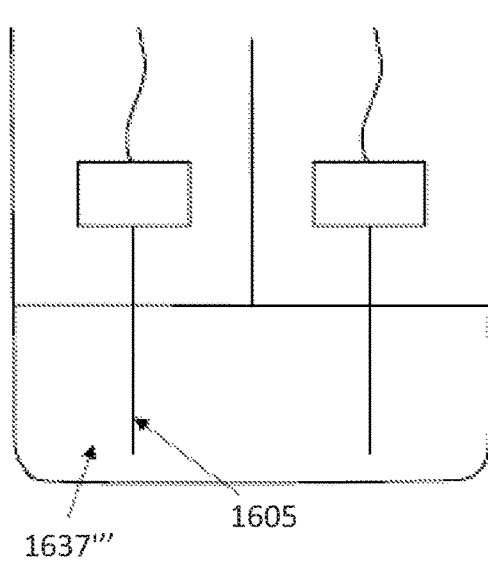
1637'''    1605
FIG. 16B

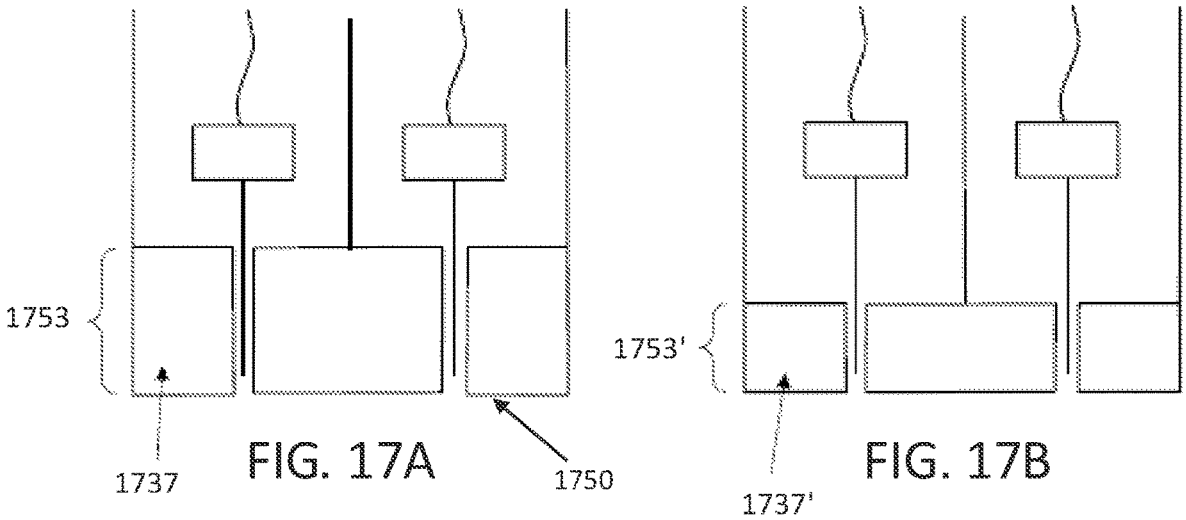
1753
1737     FIG. 17A     1750
1753'
1737'     FIG. 17B
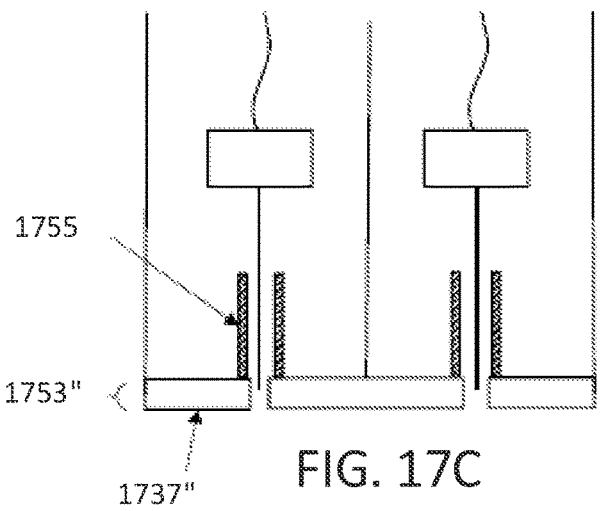
1755
1753"
1737"     FIG. 17C

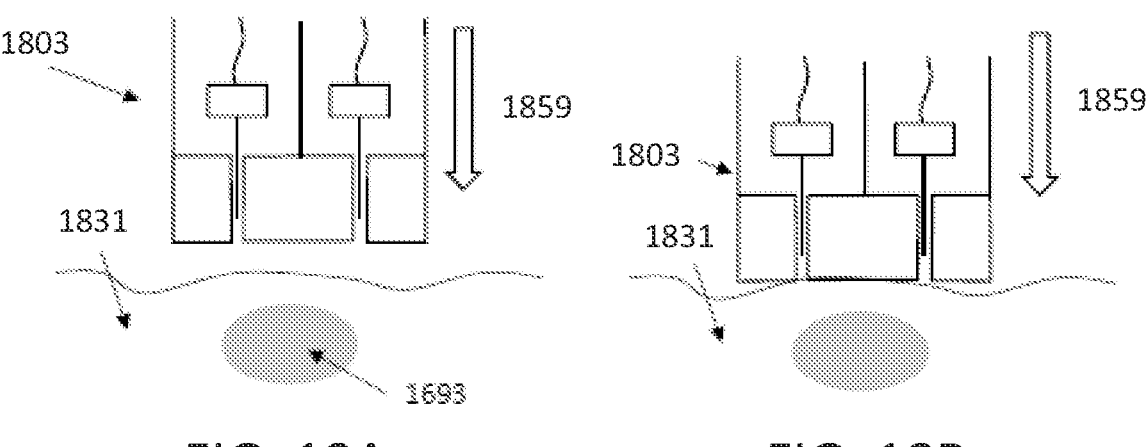
FIG. 18A                              FIG. 18B
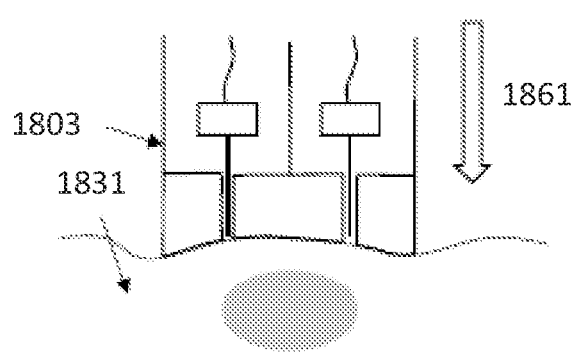 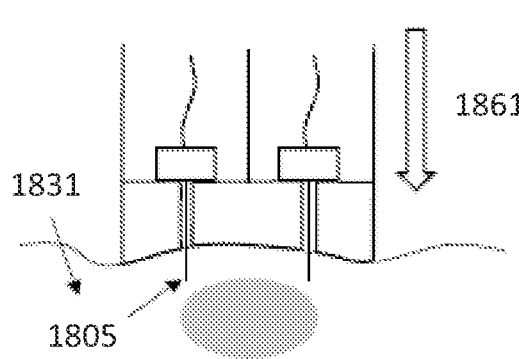
FIG. 18C                              FIG. 18D
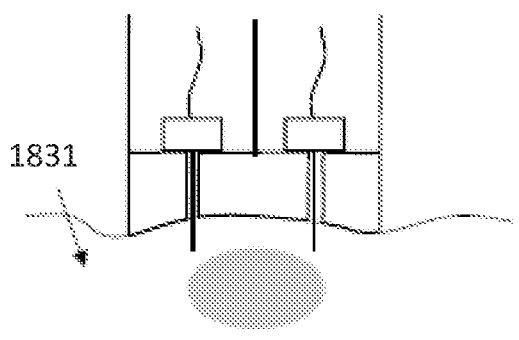 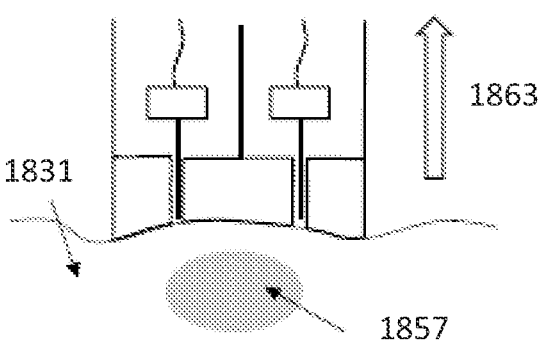
FIG. 18E                              FIG. 18F

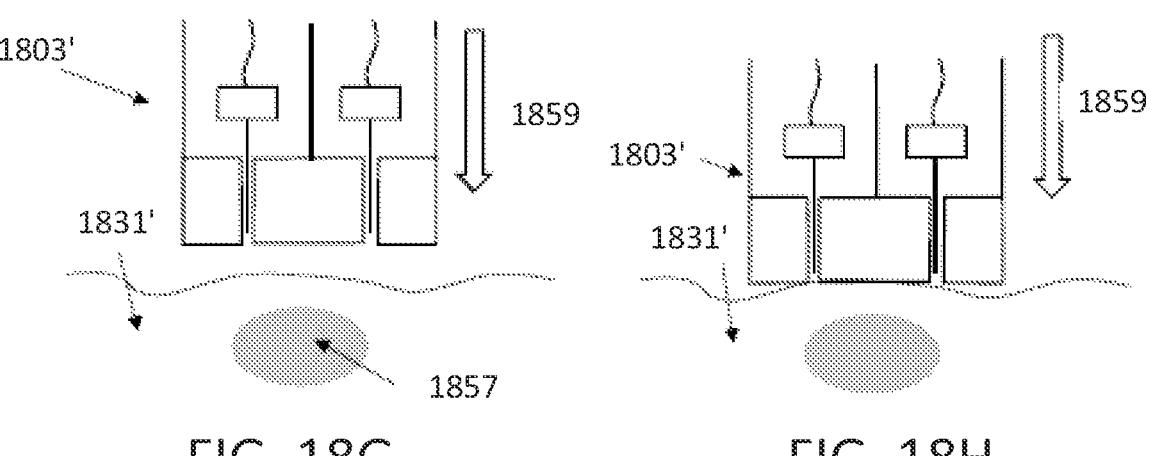
FIG. 18G                    FIG. 18H
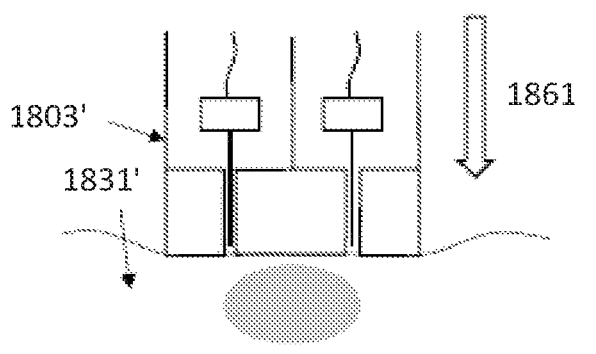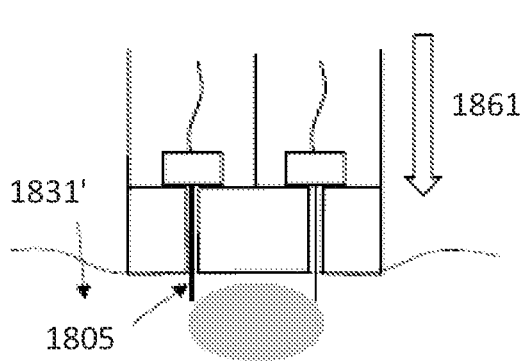
FIG. 18I                    FIG. 18J
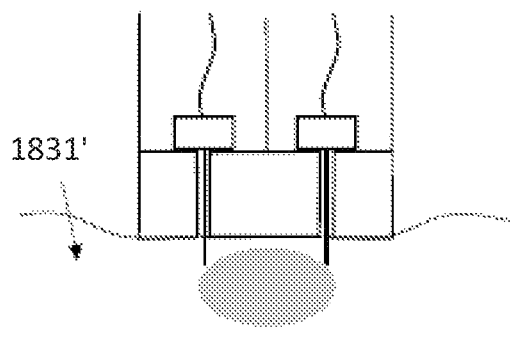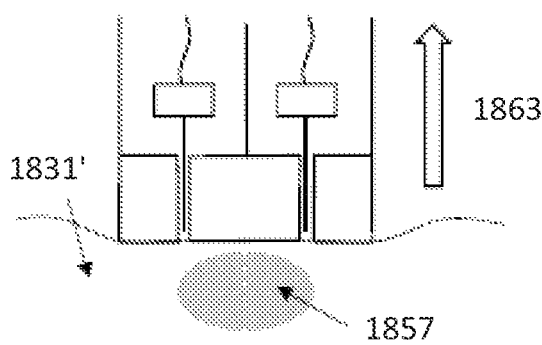
FIG. 18K                    FIG. 18L

DETAIL H

SECTION L-L

SECTION L-L

SECTION Q-Q

SECTION A-A

DETAIL B

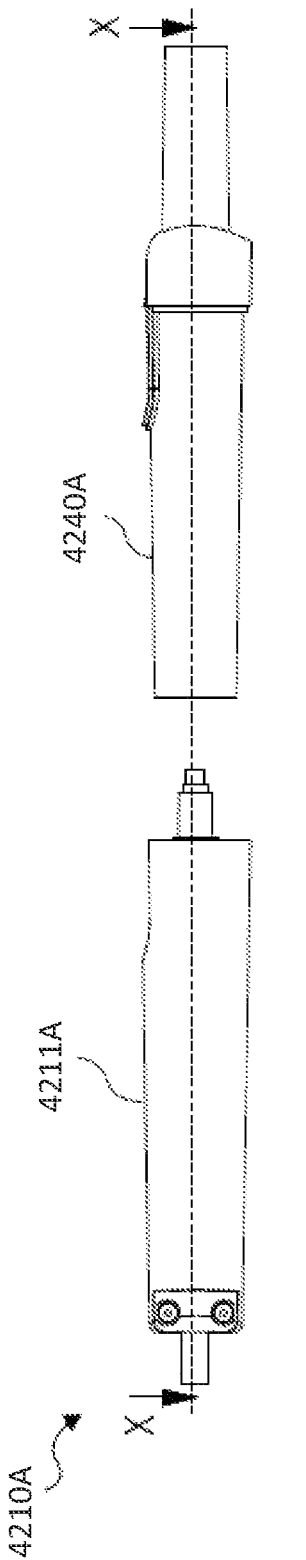
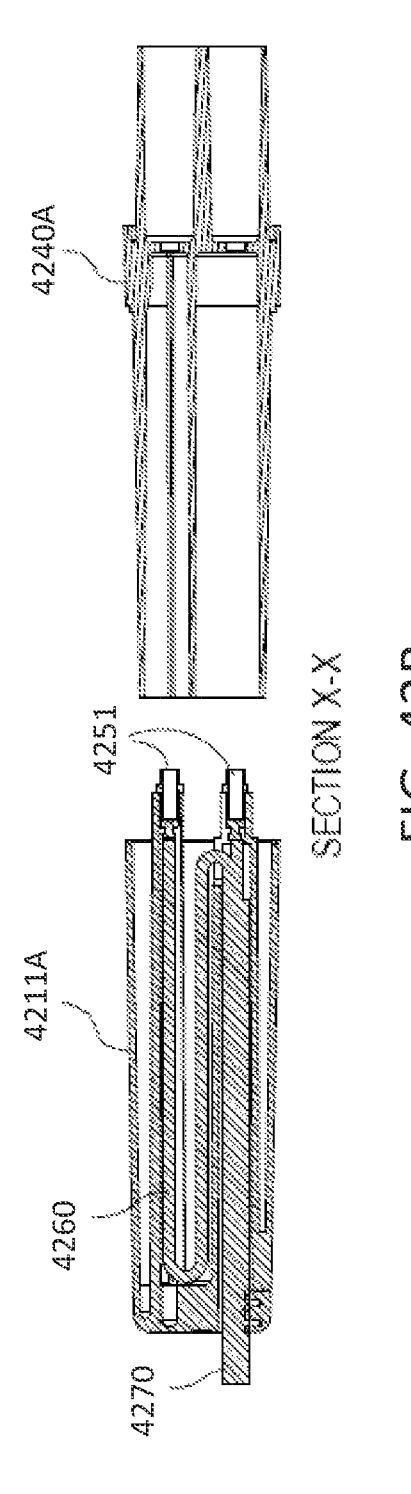
SECTION X-X
FIG. 42B

FIG. 47A
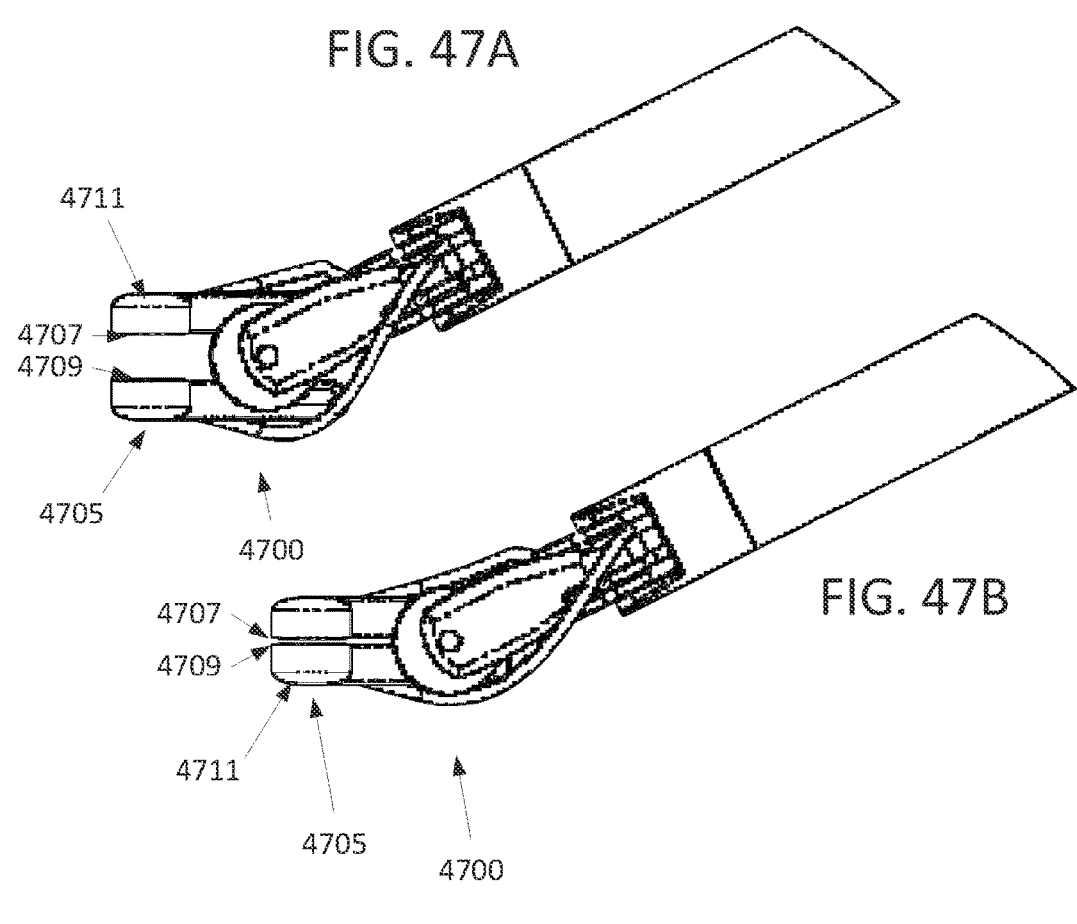
FIG. 47B
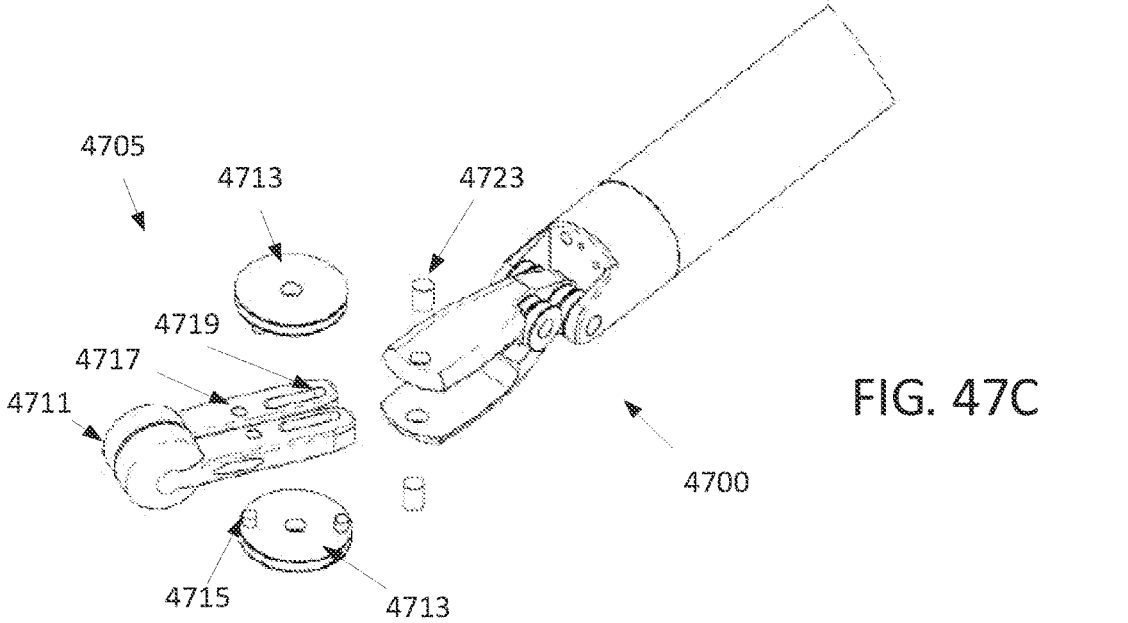
FIG. 47C

FIG. 48A
4800
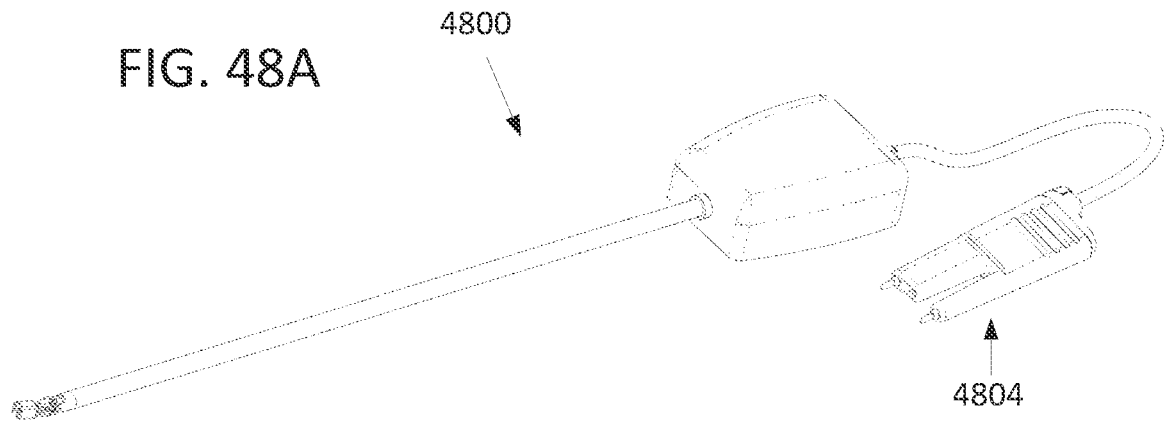
4804
4800
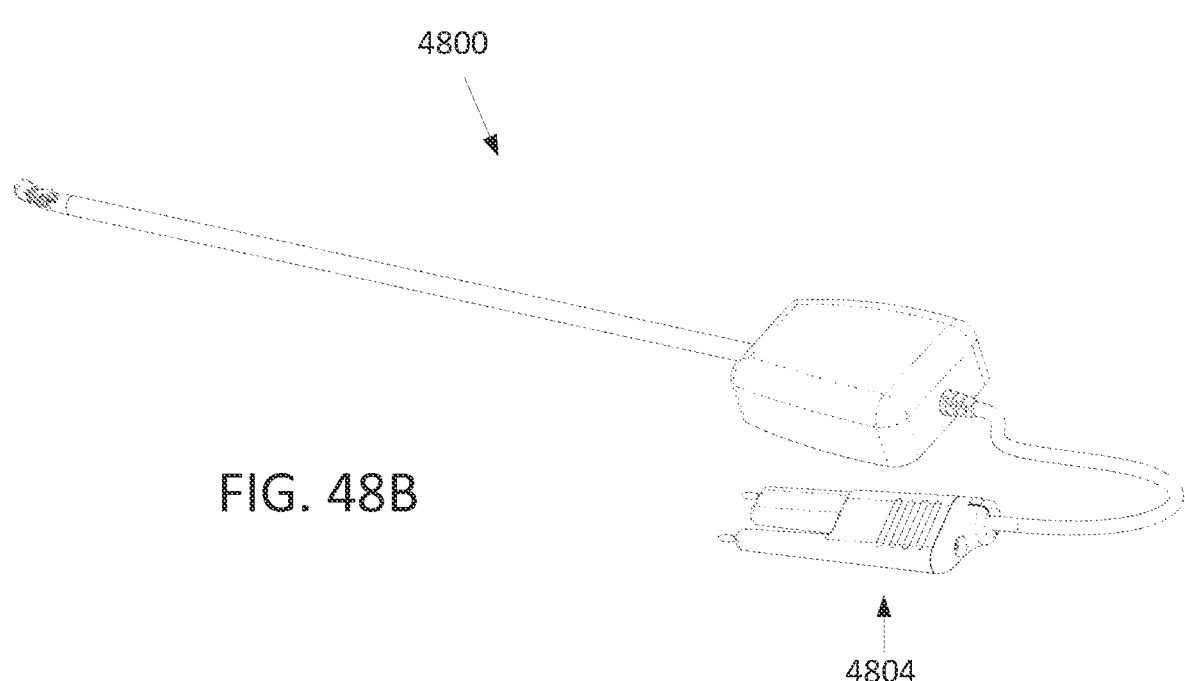
FIG. 48B
4804

FIG. 53

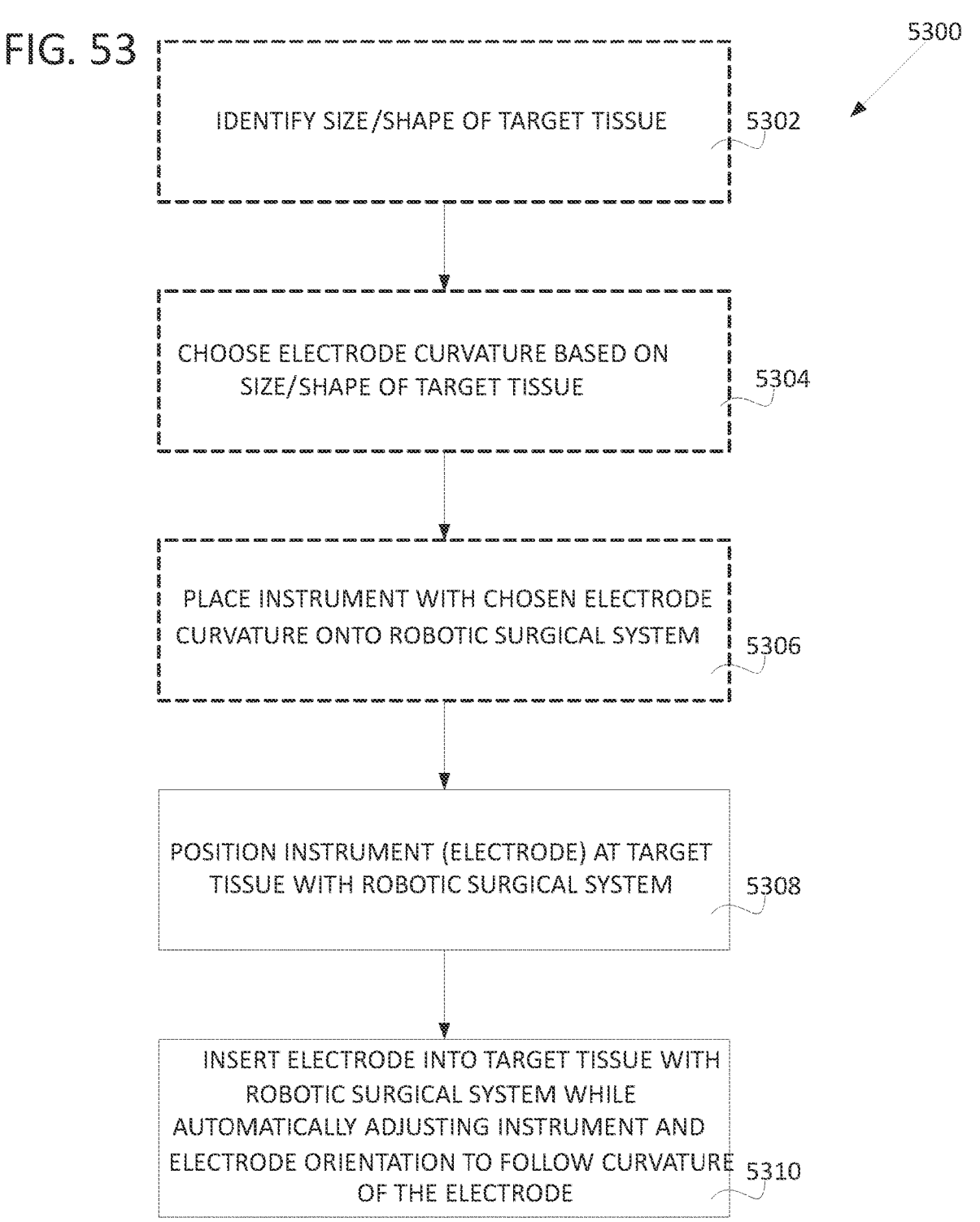

5300

IDENTIFY SIZE/SHAPE OF TARGET TISSUE    5302

CHOOSE ELECTRODE CURVATURE BASED ON
SIZE/SHAPE OF TARGET TISSUE    5304

PLACE INSTRUMENT WITH CHOSEN ELECTRODE
CURVATURE ONTO ROBOTIC SURGICAL SYSTEM    5306

POSITION INSTRUMENT (ELECTRODE) AT TARGET
TISSUE WITH ROBOTIC SURGICAL SYSTEM    5308

INSERT ELECTRODE INTO TARGET TISSUE WITH
ROBOTIC SURGICAL SYSTEM WHILE
AUTOMATICALLY ADJUSTING INSTRUMENT AND
ELECTRODE ORIENTATION TO FOLLOW CURVATURE
OF THE ELECTRODE    5310

Figure 54:
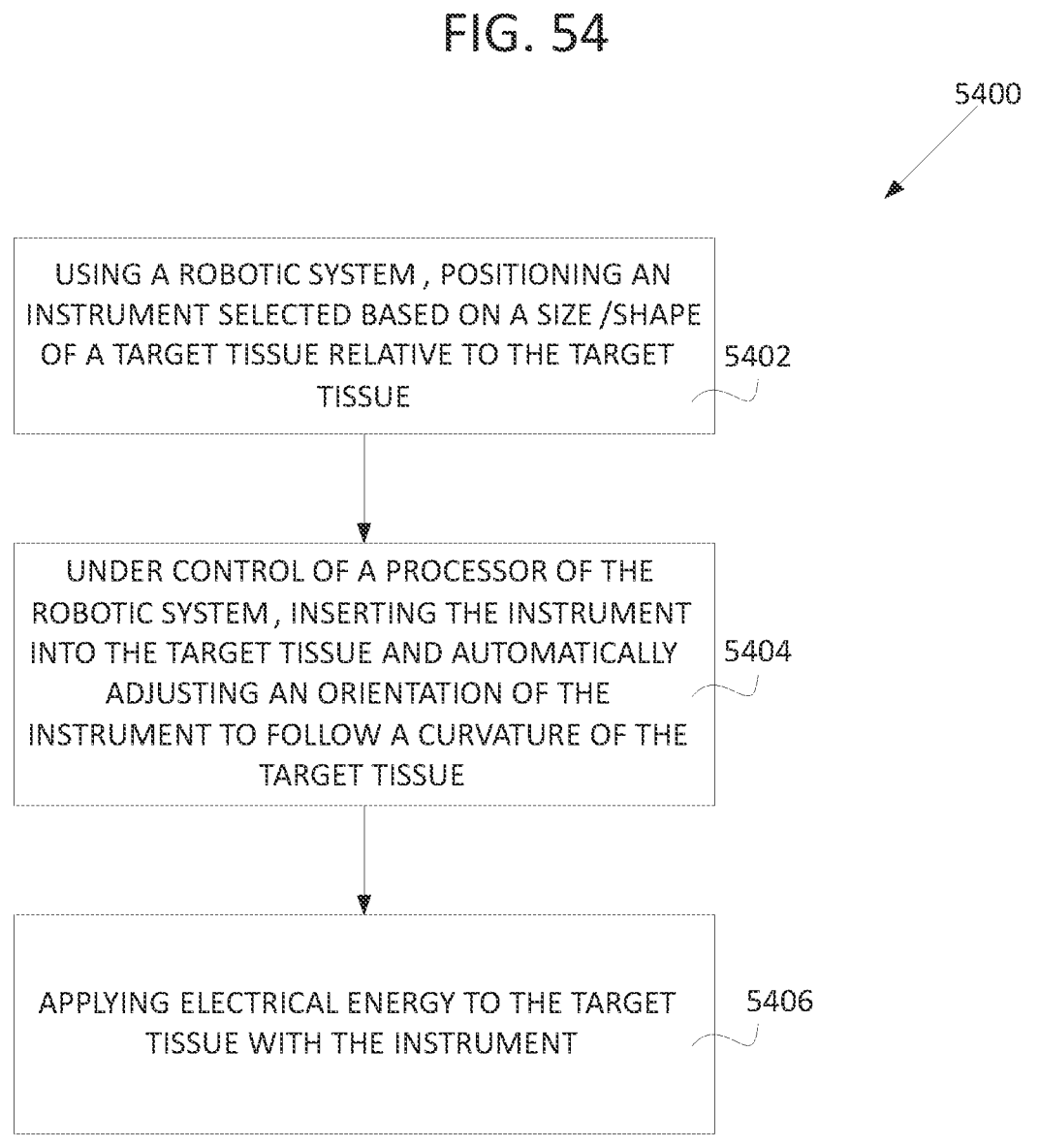

USING A ROBOTIC SYSTEM , POSITIONING AN
INSTRUMENT SELECTED BASED ON A SIZE /SHAPE
OF A TARGET TISSUE RELATIVE TO THE TARGET        5402
TISSUE

UNDER CONTROL OF A PROCESSOR OF THE
ROBOTIC SYSTEM , INSERTING THE INSTRUMENT
INTO THE TARGET TISSUE AND AUTOMATICALLY        5404
ADJUSTING AN ORIENTATION OF THE
INSTRUMENT TO FOLLOW A CURVATURE OF THE
TARGET TISSUE

APPLYING ELECTRICAL ENERGY TO THE TARGET        5406
TISSUE WITH THE INSTRUMENT

FIG. 56

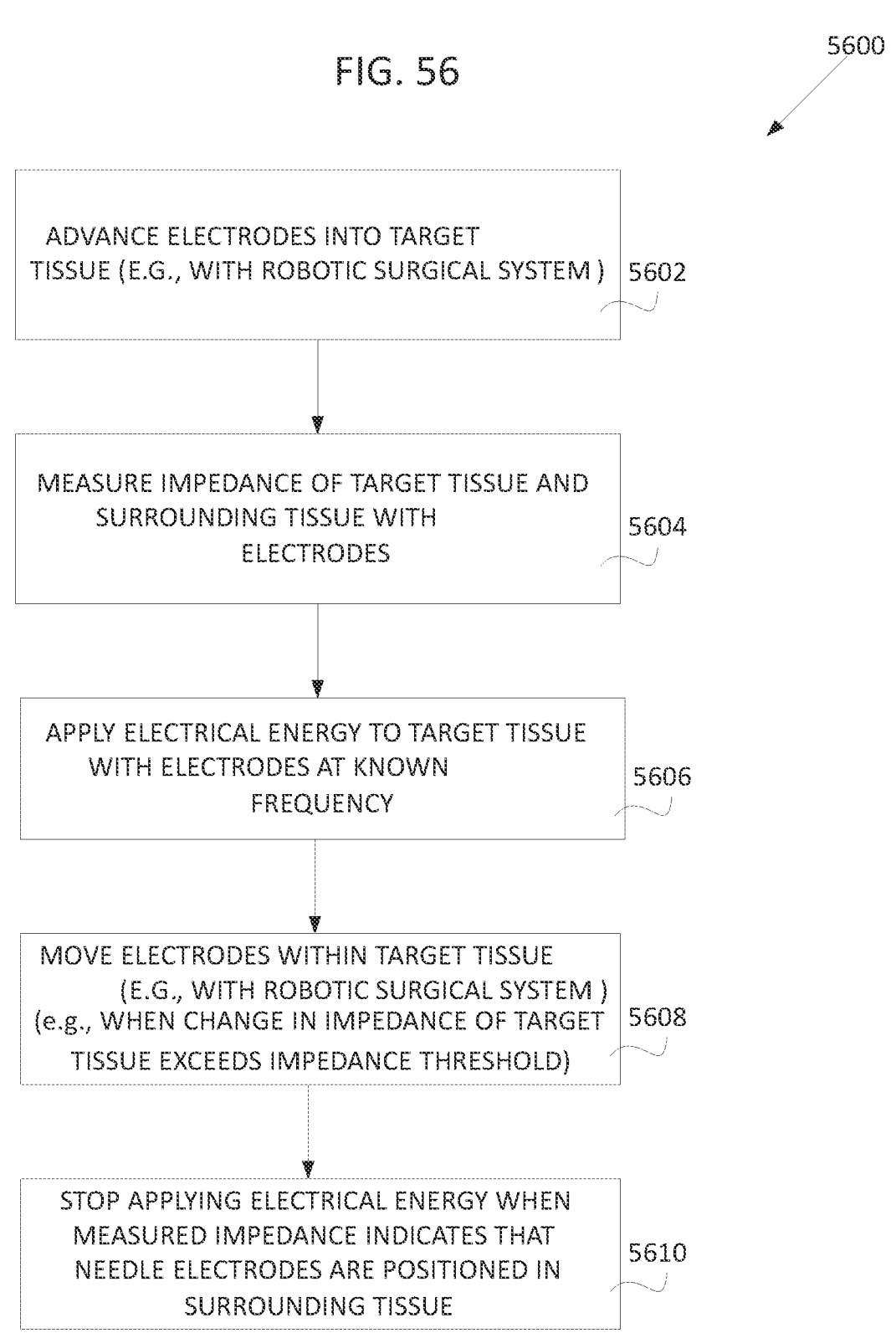

5600

ADVANCE ELECTRODES INTO TARGET
TISSUE (E.G., WITH ROBOTIC SURGICAL SYSTEM )  5602

MEASURE IMPEDANCE OF TARGET TISSUE AND
SURROUNDING TISSUE WITH
ELECTRODES  5604

APPLY ELECTRICAL ENERGY TO TARGET TISSUE
WITH ELECTRODES AT KNOWN
FREQUENCY  5606

MOVE ELECTRODES WITHIN TARGET TISSUE
(E.G., WITH ROBOTIC SURGICAL SYSTEM )
(e.g., WHEN CHANGE IN IMPEDANCE OF TARGET  5608
TISSUE EXCEEDS IMPEDANCE THRESHOLD)

STOP APPLYING ELECTRICAL ENERGY WHEN
MEASURED IMPEDANCE INDICATES THAT
NEEDLE ELECTRODES ARE POSITIONED IN  5610
SURROUNDING TISSUE

METHODS OF TREATMENT WITH A ROBOTIC SURGICAL SYSTEM

CROSS REFERENCE TO RELATED APPLICATIONS

This patent application is a continuation of U.S. patent application Ser. No. 17/077,744, filed Oct. 22, 2020, titled "TREATMENT INSTRUMENT AND HIGH-VOLTAGE CONNECTORS FOR ROBOTIC SURGICAL SYSTEM," now U.S. Patent Application Publication No. 2021/0085958, which is a continuation of U.S. patent application Ser. No. 15/920,389 filed Mar. 13, 2018, titled "TREATMENT INSTRUMENT AND HIGH-VOLTAGE CONNECTORS FOR ROBOTIC SURGICAL SYSTEM," now U.S. Pat. No. 10,857,347, which is a continuation-in-part of International Patent Application No. PCT/US2017/052340, filed Sep. 19, 2017, titled "HIGH VOLTAGE CONNECTORS AND ELECTRODES FOR PULSE GENERATORS." U.S. patent application Ser. No. 15/920,389 also claims priority to U.S. Provisional Patent Application No. 62/618,022, filed Jan. 16, 2018, titled "TREATMENT TIP WITH PROTECTED NEEDLES," each of the above-mentioned applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are robotic surgical systems that may be used to perform surgical operations to treat patients. Specifically, the robotic surgical systems described herein can include instruments that apply high-voltage, ultra-short electrical pulses to treat patients. Described herein are the robotic surgical systems, instruments, and high-voltage electrical connectors between the instruments and robotic surgical systems, and methods of use.

BACKGROUND

Ultra-short, high-field strength electric pulses have been described for electroperturbation of biological cells. For example, electric pulses may be used in treatment of human cells and tissue including tumor cells, such as basal cell carcinoma, squamous cell carcinoma, and melanoma. The voltage induced across a cell membrane may depend on the pulse length and pulse amplitude. Pulses longer than about 1 microsecond may charge the outer cell membrane and lead to opening of pores, either temporarily or permanently. Permanent openings may result in instant or near instant cell death. Pulses shorter than about 1 microsecond may affect the cell interior without adversely or permanently affecting the outer cell membrane, and result in a delayed cell death with intact cell membranes. Such shorter pulses with a field strength varying in the range of 10 kV/cm to 100 kV/cm may trigger apoptosis (i.e. programmed cell death) in some or all of the cells exposed to the described field strength and pulse duration. These higher electric field strengths and shorter electric pulses may be useful in manipulating intracellular structures, such as nuclei and mitochondria.

Nanosecond high voltage pulse generators have been proposed for biological and medical applications. For example, see: Gundersen et al. "Nanosecond Pulse Generator Using a Fast Recovery Diode", IEEE 26th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Schoenbach et al. "Method and Apparatus for Intracellular Electro-Manipulation", U.S. Pat. No. 6,326,177; Gundersen et al., "Method for Intracellular Modifications Within Living Cells Using Pulsed Electric Fields", U.S. Patent Publication No. 2006/0062074; Kuthi et al., "High Voltage Nanosecond Pulse Generator Using Fast Recovery Diodes for Cell Electro-Manipulation", U.S. Pat. No. 7,767,433; Krishnaswamy et al., "Compact Subnanosecond High Voltage Pulse Generation System for Cell Electro-Manipulation", U.S. Patent Publication No. 2008/0231337; and Sanders et al. "Nanosecond Pulse Generator", U.S. Patent Publication No. 2010/0038971. The entire content of these publications is incorporated herein by reference.

Because of the extremely high therapeutic voltages, as well as the very fast pulse times, applicators for delivery of such nanopulse stimulation devices must be configured so as to avoid arcing between the applicators. In some cases, the applicator may be configured to penetrate into the tissue for application and may include multiple needle-type electrodes. Such applicators may be particularly difficult to use with high-voltage systems while avoiding dangerous arcing.

In recent years, robotic surgery, or robotic-assisted surgery, using a robotic system to perform or aid in surgical procedures has become more and more common. The robotic systems can perform surgical procedures automatically, or in the case of robotic-assisted surgery, can perform surgical procedures in a master-slave relationship in which a surgeon directs the movement of the robotic system with a telemanipulator or computer. Robotic surgery can provide improved precision, miniaturization, and healing time over traditional surgical methods, can be used in a broad range of surgical procedures, including general surgery, gynecology, cardiology and electrophysiology, and neurosurgery, just to name a few. With a growing popularity of such procedures there is a need for the improved instruments and devices for use with high-voltage systems that could be also implemented in the robotic medical applications.

The methods and apparatuses described and illustrated herein may address the issues discussed above.

SUMMARY OF THE DISCLOSURE

Described herein are apparatuses (including retractable treatment tip applicator) and methods for the treatment of tissue that may more effectively apply therapeutic stimulation, including but not limited to ultra-short, high field strength electric pulse stimulation, while avoiding the risk of arcing or otherwise harming the tissue. These applicators may be particularly well suited, for example, for treatments of various diseases, skin disorders, and abnormal tissue growth. These applications may be also particularly well suited for use with various fully and partially automated systems, such as robotic systems.

In particular, the apparatuses described herein may be configured as single-use treatment tips that can be used with a variety of different re-usable generator systems, as will be described in greater detail herein.

Furthermore, the apparatuses described herein may be integrated into instruments that are configured to be mounted onto a robotic arm of a robotic system, such as robotic medical treatment system or robotic surgical system. While for convenience of description the present disclosure may refer to the robotic surgical system, however, it should be understood that such robotic surgical system is intended to cover any robotic medical treatment system (including cosmetic, surgical, diagnostic, etc.). The instruments can be guided and controlled by the robotic surgical system during a surgical procedure.

The methods and apparatuses described herein include treatment tips having a retractable distal tip region that may protect and insulate a plurality of treatment needle electrodes through which high-voltage rapidly pulsed energy may be delivered into the tissue. These apparatuses (devices and systems, including disposable treatment tips) may address various issues with existing treatment tips. In particular, these apparatuses may be configured safely and reliably to deliver nanopulse stimulation. Nanopulse stimulation may be referred to as nanosecond pulsed electric field (nsPEF) stimulation, or Nano-Pulsed Stimulation (NPS), and may include an electric field with a sub-microsecond pulse width of between 0.1 nanoseconds (ns) and 1000 nanoseconds, or shorter, such as 1 picosecond. It is sometimes referred to as sub-microsecond pulsed electric field. NPS often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz. NPS have been found to trigger apoptosis, for example, in the diseased tissue or abnormal growth, such as cancerous or benign tumors. Selective treatment of such tumors with NPS can induce apoptosis within the tumor cells without substantially affecting normal cells in the surrounding tissue due to its non-thermal nature. An example of nsPEF applied to biological cells is shown and described in U.S. Pat. No. 6,326,177 (to Schoenbach et al.), which is incorporated herein by reference in its entirety for all purposes. There exists a need for electrodes to deliver NPS pulses generated by a pulse generator to subjects with minimal distortion and with maximum utility and safety. A subject may be a patient (human or non-human, including animals). A user may operate the apparatuses described herein on a subject. The user may be a physician (doctor, surgeon, etc.), medical technician, nurse, or care provider.

A distal end of the needle housing may include an electrical insulator. This electrical insulator may be integral to the needle housing distal end (e.g., distal-facing end or tissue-facing end), or it may be a cover or sleeve. For example, the needle housing may be formed at least in part of the insulating material, or the insulating material may be added to other material forming the needle housing.

In general, the electrical insulator may comprise a soft, insulating material having a durometer of 60 or less on the Shore A hardness scale.

The treatment tip housing may be formed of a rigid, polymeric or other material and may be configured as a unitary (e.g., single piece) body, or it may be formed of multiple parts, e.g., segments, etc.) coupled together. The treatment tip housing may extend proximally, and may include a proximal connection region for connecting (and particularly, releasably connecting) to a reusable applicator shaft ("reusable shaft"). The connection may be a mechanical connection for coupling the treatment tip (which may be single-use or limited-use, e.g., disposable), such as a latch, snap, or the like. The treatment tip may be hollow.

The retractable treatment tip may include a retractable needle housing that extends from within a distal end of the treatment tip housing. The retractable needle housing may be configured to slide at least partially (or completely) into the treatment tip housing and may extend partially out of the apparatus. In general, the retractable needle housing may move relative to the other portions of the treatment tip, and in particular, the retractable needle housing may move relative to the treatment tip housing and treatment needle electrodes (treatment needle electrodes). The treatment needle electrodes may be fixed relative to the treatment tip housing or may be configured to be locked or fixed relative to the treatment tip housing in variations in which the treatment needle electrodes' penetration depth is fixed or adjustable, as will be described in greater detail herein. The retractable treatment tip may partially or more preferably completely enclose the treatment needle electrodes when the apparatus in not deployed. A distal electrically insulating cover may be present on the distal end of the retractable needle housing. The retractable needle housing may be configured to enclose and insulate the treatment needle electrodes.

The distal (e.g., subject-facing) end of the retractable needle housing may generally be electrically insulating, as mentioned. This electrically insulating distal end may be configured to be soft, and in some cases may be deformable. For example, the electrically insulating end may be a material having a durometer of 60 or less on the Shore A hardness scale (e.g., a durometer of 55 or less, a durometer of 50 or less, a durometer of 45 or less, a durometer of 40 or less, a durometer of 35 or less, or in some variations a durometer of at least or greater than about 5, 10, 15, 20, 25, 30, 35 and less than about 40, 45, 50, 55, 60, etc.). The distal electrically insulating end may also be referred to and may function as a distal contact pad for making contact between the end of the distal electrically insulating cover and the subject's tissue. As mentioned, the distal electrically insulating end is typically insulated, and may include or be entirely made of an electrically insulating material having the desired hardness, such as one or more of: silicone, santoprene, or other TPE (Thermoplastic Elastomer) materials. In some variations the distal end of the needle housing includes an electrically insulating cover.

The distal electrically insulating end is typically connected to the distal-facing (e.g., subject tissue-facing) end of the retractable needle housing and may therefore extend or retract with the retractable needle housing.

The distal electrically insulating end may be of any thickness. For example, the distal electrically insulating end may be between about 0.25 mm and 5 mm, (e.g., between about 0.25 mm and 3 cm, between about 0.025 mm and 25 mm, between about 0.25 mm and 2 cm, between about 0.025 mm and 15 mm, between about 0.25 mm and 10 mm, between about 0.25 mm and 5 mm, etc.). The thickness may be uniform or non-uniform. The distal face of the distal electrically insulating end may be flat or substantially flat. For example, the distal electrically insulating end may be shaped to include one or more protrusions (rings, or gasket-regions) around any openings for the treatment needle electrodes through the distal electrically insulating cover. The distal electrically insulating end may form an electrical seal against the tissue to insulate between the treatment needle electrodes, and in particular between treatment needle electrodes of different electrical polarities. For example, in some variations treatment needle electrodes of different electrical polarity pass through different openings in the distal electrically insulating end (and treatment needle electrodes of the same electrical polarity may pass through the same openings through the distal electrically insulating end). For example, ground treatment needle electrodes may pass through different openings in the distal electrically insulating end than non-ground (e.g., "hot" or high/low) electrodes.

As mentioned, the treatment tip housing may include a proximal coupling region configured to couple to an applicator. The proximal coupling region of the treatment tip housing may couple the treatment tip to a hand-held applicator (a reusable treatment applicator), as mentioned. In addition, the proximal coupling region may make an electrical connection between the high-voltage, high-pulse rate generator and the needles in the applicator tip (the plurality of treatment needs). For example, the proximal coupling region may include a plurality of electrical connectors that are in electrical communication with the plurality of treatment needle electrodes.

The treatment needle electrodes generally extend proud of the needle housing and/or the distal electrically insulating end in the deployed configuration. In some variations the treatment needle electrodes (which may also be referred to herein as electrode needles or needle electrodes) may extend through the distal electrically insulating end. For example, the plurality of treatment needle electrodes may be configured to extend through an opening (or multiple openings) in the distal electrically insulating end when the needle housing is retracted. Alternatively, all or some of the treatment needle electrodes may be extended through the distal electrically insulating end by penetrating (making a hole in) the distal electrically insulating end; these punctures or holes may reseal when the retractable needle housing is retracted. In general, the plurality of treatment needle electrodes may be held within the treatment tip housing in an un-deployed state when the bias holds the needle housing distally extended from the treatment tip. Thus, the distal tips (which may be sharp, e.g., tissue-penetrating, beveled, or rounded) of the treatment needle electrodes may be housed entirely within the treatment tip housing when the apparatus is not deployed, and force is not being applied to drive the retractable needle housing proximally or at least insufficient force to overcome the bias force).

In any of the apparatuses described herein, the treatment needle electrodes may be adjustable. For example, the distal-to-proximal length of the plurality of treatment needle electrodes is adjustable. The treatment tip and/or shaft to which it connects may include a control (lever, dial, button, etc.) that advances or retracts the treatment needle electrodes so that they may extend more or less from the retractable needle housing and/or distal electrically insulating end when the retractable needle housing is fully deployed. For example, the apparatus may include a screw mechanism to advance or withdraw the treatment needle electrodes within the tip housing and/or needle housing.

In general, the apparatus may include a stop (e.g., a mechanical stop) within the tip housing that limits the proximal distance that the needle housing may be driven (retracted) when applying the force exceeding the bias force. The mechanical stop may include a rim, ridge, or boss, and may be within the housing. The stop may be adjustable (e.g., using a control on the treatment tip housing and/or shaft). The stop may be adjustable to change the proximal distance that the needle housing may be driven when applying the force exceeding the bias force.

In general, any number of treatment needle electrodes may be used (e.g., typically 2 or more, 3 or more needles, 4 or more needles, 5 or more needles, 6 or more needles, 7 or more needles, etc.). The treatment needle electrodes may be arranged in any configuration, including in a ring, row or two or more rows (parallel rows, crossing rows, etc.). The treatment needle electrodes may be any length, including adjustable lengths, as described above. For example, the treatment needle electrodes may be between about 2 mm and 10 cm long (e.g., between about 2 mm and 9 cm, between about 2 mm and 8 cm, between about 2 mm and 7 cm, between about 2 mm and 6 cm, between about 2 mm and 5 cm, between about 2 mm and 4 cm, between about 1 cm and 10 cm, between 1 cm and about 9 cm, between about 1 cm and 8 cm, between about 1 cm and 7 cm, between about 1 cm and 6 cm, etc.).

Any of these apparatuses may include one or more vacuum ports on the distal end (e.g., through the distal electrically insulating cover). The vacuum ports may apply suction to hold the distal electrically insulating end against the tissue when applying the treatment. The vacuum ports may couple to one or more vacuum lines within the treatment tip housing and/or needle housing and may couple to a vacuum line (e.g., through the reusable shaft). In any of the apparatuses described herein, the shaft may be referred to as a headpiece.

A retractable treatment tip device for delivery of electrical therapy may include: a treatment tip housing having a proximal coupling region comprising a plurality of electrical connectors; a needle housing extending from a distal end of the treatment tip housing, wherein the needle housing is configured to retract proximally into the treatment tip housing; a plurality of treatment needle electrodes within the needle housing in electrical communication with the plurality of electrical connectors; and a bias within the treatment tip housing driving the needle housing distally with a bias force so that the plurality of treatment needs are fully enclosed within the needle housing; a distal electrically insulating end on the distal end of the needle housing, wherein the distal electrically insulating end comprises a soft material, further wherein the plurality of treatment needle electrodes are exposed through the distal electrically insulating end when the needle housing is driven against a subject's tissue with a force exceeding the bias force so that the needle housing is driven proximally relative to the plurality of treatment needle electrodes.

Also described herein are methods for treating a subject using any of the apparatuses described herein. For example, a method of applying electrical therapy to a subject may comprise: positioning a retractable treatment tip against a subject's tissue, wherein the retractable treatment tip comprises a needle housing extending from a distal end of a treatment tip housing, the needle housing having an electrically insulting distal end, a plurality of treatment needle electrodes within the needle housing, and a bias, further wherein the retractable treatment tip is in an un-deployed configuration in which a distal tip of each of the plurality of treatment needle electrodes is within the needle housing; deploying the retractable treatment tip by moving the plurality of treatment tip electrodes and needle housing relative to each other so that the plurality of treatment tip electrodes extend distally from the needle housing and into the subject's tissue such that the electrically insulating distal end is applied against the tissue to electrically isolate the plurality of treatment needle electrodes from each other; and applying energy to the tissue from the plurality of treatment needle electrodes.

Deploying may comprise releasing a release lock to allow the bias to drive the plurality of treatment needle electrodes distally. Alternatively or additionally, in some variations, deploying may comprise pushing the retractable treatment tip against the subject's tissue with a force that is greater than a bias force of the bias to drive the needle housing proximally relative to the plurality of treatment needle electrodes.

For example, described herein are methods of applying high-voltage nanosecond pulse electrical therapy. Any of these methods may include: positioning a retractable treatment tip against a subject's tissue, wherein the retractable treatment tip comprises a needle housing extending from a distal end of a treatment tip housing, a bias driving the needle housing distally with a bias force, a plurality of treatment needle electrodes within the needle housing, and a distal insulating end covering the needles within the needle housing; pushing the retractable treatment tip against the subject's tissue with a force that is greater than the bias force to drive the needle housing proximally relative to the plurality of needles while penetrating the tissue with the plurality of needles and driving the electrically insulating end against the tissue to electrically isolate the plurality of needles from each other; and applying high-voltage nanosecond electrical pulses to the tissue from the plurality of needles.

In general, any of the apparatuses described herein may be used without the need for an additional insulating gel (e.g., non-conductive gel) between the subject's tissue and the apparatus, including the retractable treatment tip. For example, any of these methods may include applying energy (e.g., high-voltage nanosecond electrical pulses) without any insulating gel between the skin and the retractable treatment tip.

Any of these methods may include coupling the treatment tip (referred to herein as a "retractable treatment tip" as the needle housing region may retract away from the treatment needle electrodes) to a reusable shaft by connecting at least two electrical connectors on a proximal end of the retractable treatment tip to electrical contacts on the reusable shaft. The treatment tips described herein may be configured so that the electrical connections connect as the mechanical connection(s) are engaged. A lock or fastener may be included on either or both the treatment tip and/or reusable shaft to hold the treatment tip engaged with the reusable shaft. Any of these methods may include locking or removably securing the treatment tip to the shaft.

In general, the application high-voltage nanosecond electrical pulses may include applying a train of sub-microsecond electrical pulses having a pulse width of between 0.1 nanoseconds (ns) and 1000 nanoseconds. Applying high-voltage nanosecond electrical pulses may include applying a train of sub-microsecond electrical pulses having peak voltages or between 10 kilovolts per centimeter (kV/cm) and 500 kV/cm. Applying high-voltage nanosecond electrical pulses may include applying a train of sub-microsecond electrical pulses at a frequency or between 0.1 per second (Hz) to 10,000 Hz.

Any of the methods described herein may be methods of treating skin. For example, positioning the retractable treatment tip against the subject's tissue may include positioning the retractable treatment tip against the subject's skin. Any of these methods may comprise applying high-voltage nanosecond electrical pulses to the subject's tissue to treat one or more of: organ tissue cancer, skin cancer, cherry angioma, warts, keloids/scars, molluscum angioma, necrobiosis lipoidica (NBL), melisma, lipoma epidermal/sebaceous cyst, basal cell carcinoma, aging skin, benign tumors, precancerous tumors. Alternatively, or additionally, these methods may be methods of any other body tissue, including non-skin tissue (respiratory tissue, lung tissue, breast tissue, liver tissue, etc.).

As mentioned the length of the electrodes may be selectable. Thus, any of these methods may include selecting the length of the plurality of treatment needle electrodes prior to pushing the retractable tip against the subject's tissue. In some variations the length of the insulation on the electrodes may also be selectable/adjustable.

In general, to use the applicator, it may be pushed against the tissue with sufficient force to retract the needle housing and to drive the needles into the tissue. The needles may be driven into the tissue to a predetermined depth, which may be set by the stop (e.g., preventing the needle housing from retracting any further, and therefore stopping the needles from pushing into the tissue any further. For example, pushing the retractable treatment tip against the subject's tissue with the force that is greater than the bias force to drive the needle housing proximally relative to the plurality of needles may comprise compressing a spring bias within the treatment tip housing to retract the needle housing proximally into the treatment tip housing so that the plurality of treatment needle electrodes extend distally from the needle housing. Thus, pushing the retractable treatment tip against the subject's tissue may comprise penetrating the electrically insulating end by the plurality of treatment needle electrodes.

The retractable treatment tip devices, particularly those having a retractable needle housing as described herein, may reduce or eliminate arcing between the needle electrodes even when these needles are not adequately coated with a non-conductive (e.g., insulating) material, such as a non-conductive gel. Allowing the needles to remain retracted into the treatment tip housing (and the retractable needle housing) when not in use or inserted into tissue may prevent arcing between the electrodes.

The apparatuses described herein may also include a soft rubber or silicone tip (e.g., an insulating cover), as described above. This insulating end may reduce arcing. For example, a soft rubber or silicone at the tip may function like a Vaseline or other non-conductive gel to reduce arcing, thereby, improving the case of use.

The retractable treatment tip devices may also improve the safety for the user during use or handling. With the needles housed within the needle housing when not in use, accidental scratching or punctures may be avoided. The retractable treatment tip devices may also reduce the likelihood of the treatment tip getting damaged during shipping or handling.

The applicator devices described herein may be used with one or more of the apparatuses (e.g., pulse generators) disclosed in any of the co-owned U.S. patent publication numbers: US2017/0245928, US2017/0246455, and U.S. patent application Ser. Nos. 15/444,738 and 15/347,728, all incorporated by reference herein in their entirety.

According to further aspect of the disclosure, a method of treating a target tissue with a robotic surgical system is disclosed. The method may comprise: advancing an instrument operatively connected to a movable arm of a robotic system to a target tissue, the instrument comprising at least one electrode; inserting the at least one electrode into the target tissue; applying pulsed electrical therapy to the target tissue with the at least one electrode; and advancing the at least one electrode further into the target tissue under control of the robotic system while applying pulsed electrical therapy to the target tissue with the at least one electrode. In some implementations the at least one electrode is advanced further into the target tissue under the robotic system only between pulses of the pulsed electrical therapy (for example, only between some of the pulses). In other implementations the at least one electrode may be advanced further into the target tissue only during pulses of the pulsed electrical therapy (including, for example, only during some of the pulses). The treatment of the target tissue may comprise nano-pulsed stimulation. In some embodiments, the robotic system may be a master/slave system where a user directs operation of the robotic system. In some embodiments, the robotic system may automatically perform the advancing, inserting, applying, and advancing steps under imaging guidance.

According to another aspect, a system for treating a target tissue is provided. The system comprising at least one movable arm; an instrument mounted to the at least one movable arm, the instrument comprising at least one electrode; and one or more processors configured to perform the steps of the above method.

According to one aspect, a robotic system can control delivery of energy to a target tissue based on tissue impedance measurements. A method can include advancing needle electrodes into a target tissue, for example, with a robotic surgical system; measuring an impedance of the target tissue and/or surrounding tissue, for example, with the needle electrodes; applying electrical energy to the target tissue; moving or directing movement of the needle within the target tissue (e.g., with the robotic surgical system) when a change in the impedance of the target tissue exceeds an impedance threshold. In some embodiments, the method may comprise instead of the moving step or in addition to the moving step, stopping applying electrical energy when the measured impedance indicates that the needle electrodes are positioned in surrounding tissue and not the target tissue. The moving or directing movement may be in various directions, for example, up and down, to the left, to the right, and any other appropriate direction.

Further, some inventive aspects according to the present disclosure include high-voltage electrodes and high-voltage connectors.

Some inventive aspects include a high voltage connector positioned or located on a robotic arm of a robotic surgical system. The high voltage connector can provide high voltage to electrodes on an instrument of the robotic surgical system.

In one aspect, a robotic surgical system is provided, comprising a robotic arm, a high-voltage connector disposed on the robotic arm, the high-voltage connector comprising an outlet having electrical terminals, a surgical instrument comprising a connector configured to mate with the outlet, the connector having electrical terminals, and at least two insulative portions, wherein the at least two insulative portions are on the outlet or the connector, and the other of the outlet or the connector includes holes into which the at least two insulative portions mate, wherein one or both of the at least two insulative portions is sized and configured to provide a minimum clearance distance between the electrical terminals of the outlet or between the electrical terminals of the connector, the minimum clearance distance including distance across surfaces of an insulative portion or a hole.

The surgical instrument can include a number of optional features. In one aspect, the surgical instrument further comprises a shaft and a treatment tip disposed on a distal end of the shaft. The surgical instrument can include a conductor disposed in the shaft and configured to electrically couple the connector of the surgical instrument to the treatment tip. The conductor can be, for example, a pair of high-voltage conductors or a high-voltage coaxial cable. In some examples, the conductor is surrounded by a ground or shield wire.

As will be described in greater detail below, the system can be configured to deliver nano-pulsed stimulation to a target tissue.

In one aspect, the treatment tip comprises a grasping electrode tip, the grasping electrode tip comprising a first electrode and a second electrode, wherein the first and second electrodes are configured to maintain a parallel orientation as the grasping electrode is opened and closed.

In another aspect, the treatment tip comprises at least one electrode. The electrode(s) can be, for example, needle electrodes, plate electrodes, or curved electrodes.

The system can further include a robotic controller configured to control movement of the robotic arm and/or the surgical instrument. In one aspect, the robotic controller is configured to advance at least one curved electrode into a target tissue and to automatically adjust an orientation and position of the surgical instrument and the curved electrode to follow a curvature of the curved electrode as it is advanced into the target tissue.

The electrode comprises at least two conductive terminals and a safety structure configured to provide one or more of the following minimum clearance distances: i) a minimum clearance distance between the at least two conductive terminals, ii) a minimum clearance distance between each of the at least two conductive terminals and conductive structures on the robotic surgical system, or iii) both minimum clearance distances.

In some embodiments, the electrode includes a tip comprising an insulative tip housing, a plurality of therapeutic terminals supported by the tip insulative housing, and connection terminals connected with the therapeutic terminals. The apparatus also includes a shaft comprising an insulative shaft housing, electrical connectors adapted to mate with the connection terminals of the tip, the electrical connectors connected to an input cable, and a sleeved receptacle. The apparatus includes an insulative boss or other portion having a wiring channel within, the insulative portion mating with the sleeved receptacle. One of the sleeved receptacle and insulative portion is within the tip, and the other of the sleeved receptacle and insulative portion is within the shaft, the tip and shaft mating together. One or both of the insulative portion and the sleeved receptacle is sized and configured to provide a minimum clearance distance between the connection terminals, the minimum clearance distance including distance across internal surfaces of the sleeved receptacle, insulative boss, or wiring channel.

A robotic surgical system for a high voltage electric stimulation treatment is also provided, the system comprising at least one robotic arm, at least two high-voltage output terminals disposed on the at least one robotic arm, an instrument coupled to the at least one robotic arm, the instrument comprising a tip having an insulative housing, the insulative housing having a sleeved receptacle and at least two tip wiring channels sealed from one another within the insulative housing, at least two insulative portions that project from a bottom of the sleeved receptacle toward an opening of the sleeved receptacle, an inside of each insulative portion forming a portion of one of the tip wiring channels, at least two high-voltage input terminals, each terminal located atop one of the respective insulative portions, the at least two high voltage input terminals being configured to mate with the at least two high-voltage output terminals of the robotic arm, and a set of therapeutic needle electrodes extending from the insulative housing, wherein one or both of the insulative portion and the sleeved receptacle is sized and configured to provide a minimum clearance distance between the high voltage input terminals, the minimum clearance distance including distance across surfaces of the insulative portions or tip wiring channels.

One inventive aspect includes a high voltage therapeutic electrode apparatus, the apparatus including a tip comprising an insulative tip housing, a plurality of therapeutic terminals supported by the tip insulative housing, and connection terminals connected with the therapeutic terminals. The apparatus includes a shaft comprising an insulative shaft housing, electrical connectors adapted to mate with the connection terminals of the tip, the electrical connectors connected to an input cable. The apparatus includes a sleeved receptacle and an insulative boss or other portion having a wiring channel within, the insulative portion mating with the sleeved receptacle. One of the sleeved receptacle and insulative portion is within the tip, and the other of the sleeved receptacle and insulative portion is within the shaft, the tip and shaft mating together. One or both of the insulative portion and the sleeved receptacle is sized and configured to a minimum clearance distance between one of the connection terminals and conductive structures on the robotic surgical system, the minimum clearance distance including distance across internal surfaces of the sleeved receptacle, insulative portion, or wiring channel.

An insulative safety structure can be configured to provide the minimum clearance distance between the therapeutic terminals and a shaft. The insulative safety structure can include a boss, skirt, skirt hole, shield, finger stop, or other safety structure.

One inventive aspect includes a high voltage connector apparatus including an outlet having electrical terminals and a connector configured to mate with the outlet, the connector having electrical terminals. The apparatus includes at least two insulative bosses or other portions, wherein the at least two insulative portions is on the outlet or the connector, and the other of the outlet of the connector includes holes into which the at least two insulative portions mate. One or both of the insulative portion and the sleeved receptacle is sized and configured to provide a minimum clearance distance between the electrical terminals of the outlet or between the electrical terminals of the connector, the minimum clearance distance including distance across surfaces of an insulative boss or a hole.

The apparatus can further include a skirt and a skirt hole configured to mate with the skirt, wherein the skirt is on the outlet or the connector, and the skirt hole is on the other of the outlet or connector, the skirt providing the minimum clearance distance between the electrical terminals of the outlet or between the electrical terminals of the connector.

One inventive aspect includes a swappable or fixed, non-swappable tip apparatus for a high voltage nanosecond pulsed electric field (nsPEF) therapeutic electrode. The apparatus includes an insulative housing for a tip, the insulative housing having a sleeved receptacle, at least two tip wiring channels sealed from one another within the housing, at least two insulative bosses or other portions that project from a bottom of the sleeved receptacle toward an opening of the sleeved receptacle, an inside of each insulative portion forming a portion of one of the tip wiring channels, a pair of high voltage input terminals, each terminal located atop one of the respective insulative portions, a set of therapeutic needle electrodes extending from the insulative housing, and internal electrical wires, each internal electrical wire segregated in one of the tip wiring channels and connecting at least one of the therapeutic needle electrodes to one of the input terminals.

One inventive aspect includes a tip apparatus for a high voltage nanosecond pulsed electric field (nsPEF) therapeutic electrode. The apparatus includes an insulative housing for a tip, the insulative housing having a sleeved receptacle, at least two tip wiring channels sealed from one another within the housing, at least two insulative bosses or other portions that project from a bottom of the sleeved receptacle toward an opening of the sleeved receptacle, an inside of each insulative portion forming a portion of one of the tip wiring channels, a pair of high voltage input terminals, each terminal located atop one of the respective insulative portions, and a set of therapeutic needle electrodes extending from the insulative housing. One or both of the insulative portion and the sleeved receptacle is sized and configured to provide a minimum clearance distance between the high voltage terminals, the minimum clearance distance including distance across surfaces of the insulative portions or tip wiring channels.

One inventive aspect is an electrode electrically connectable to a pulse generator. The electrode is configured to deliver a pulse generated by the pulse generator to a patient, and includes a plurality of therapeutic terminals configured to deliver the pulse to the patient, first and second electrical pulse inlet holes, and a first pulse input terminal, where the first pulse input terminal is in the first electrical pulse inlet hole and is spaced apart from an entrance to the first electrical pulse inlet hole by a distance greater than about 2.5 cm, and the first pulse input terminal is electrically connected with one or more of the therapeutic terminals. The electrode also includes a second pulse input terminal, where the second pulse input terminal is in the second electrical pulse inlet hole and is spaced apart from an entrance to the second electrical pulse inlet hole by a distance greater than about 2.5 cm, and where the second pulse input terminal is electrically connected with one or more of the therapeutic terminals.

The electrode can further include a cable, the cable being electrically connected with the first connection terminal by a first wire extending from the cable, the cable being electrically connected with the second connection terminal by a second wire extending from the cable, wherein the cable is connectable to a pulse generator. The first wire may not be insulated, and a first portion of the second wire may be routed from the cable away from the second connection terminal, and a second portion of the second wire may be routed from the first portion toward the second connection terminal. The shaft can include first and second bosses, wherein the first wire extends from the cable to the first connection terminal through the first boss, wherein the second wire extends from the cable to the second connection terminal through the second boss, wherein the first boss includes a first slot extending along a side of the first boss, and wherein the second boss includes a second slot extending along a side of the second boss.

According to a further inventive concept a system and method is provided for using an instrument with one or more curved electrodes. A method of treating a target tissue with a robotic surgical system is provided, comprising using a robotic system to position an instrument with at least one curved needle electrode relative to a target tissue, the instrument selected based on one or more of a size, shape or curvature of the target tissue, under control of a processor of the robotic system insert the instrument into the target tissue while automatically adjusting an orientation of the instrument to follow a curvature of the target tissue, apply electrical energy to the target tissue with the instrument.

In one aspect, the method can further comprise identifying the size, shape or curvature of the target tissue, wherein the identifying step comprises using a user interface of the robotic system to indicate the curvature of the one or more curved needle electrodes. The identifying step can be performed, for example, by the robotic system with a use of an imaging system or otherwise.

A robotic surgical system is also provided, comprising at least one robotic arm, an instrument mounted to the robotic arm, the instrument comprising at least one curved needle electrode, at least one processor configured for positioning the instrument relative to a target tissue, the instrument is selected based on one or more of a size, shape or curvature of the target tissue, inserting the instrument into the target tissue while adjusting an orientation of the instrument to follow a curvature of the target tissue and/or the selected curved electrode, and applying electrical energy to the target tissue with the instrument. The processor may be further configured for selecting or allowing selection of the instrument based on one or more of a size, shape or curvature of the target tissue.

According to yet another aspect, described herein is a robotic system for delivery of electrical therapy, the system comprising a robotic arm, a high-voltage connector disposed on the robotic arm; a treatment tip housing configured to be coupled to the high-voltage connector of the robotic arm, a needle housing extending from a distal end of the treatment tip housing, a plurality of treatment needle electrodes within the needle housing, wherein the device has an un-deployed configuration in which the distal ends of the treatment needle electrodes are within the needle housing and a deployed configuration in which the plurality of treatment needle electrodes extend through the needle housing, further wherein the needle housing and treatment needle electrodes are configured to move relative to each other to convert between the un-deployed and the deployed configurations, and a bias within the treatment tip housing exerting a bias force to oppose conversion from the un-deployed to the deployed configuration or from the deployed to un-deployed configuration.

In some embodiments, the system can further comprise a conductor configured to electrically connect the plurality of treatment needle electrodes to the high-voltage connector. The conductor can be, for example, a pair of high-voltage conductors or a high-voltage coaxial cable. In some examples, the conductor is surrounded by a ground or shield wire.

In some implementations the system can also include a high-voltage source electrically coupled to the high voltage connector, wherein the plurality of treatment needle electrodes are configured to deliver nano-pulsed stimulation to a target tissue.

As described above, the system can include a minimum clearance distance. In some examples, the minimum clearance distance equals or exceeds 0.85 centimeters. In one example, the minimum clearance distance is determined based at least in part on an expected voltage applied to the electrical terminals.

The plurality of treatment needle electrodes can have various shapes and sizes. In one aspect, the plurality of treatment needle electrodes comprises at least one curved electrode. In another aspect, the plurality of treatment needle electrodes is configured to retract and extend into the needle housing. The retract/extend of the needle electrodes can be controlled by a robotic controller of the system.

The robotic system can further include a robotic controller configured to control movement of the robotic arm and/or the surgical instrument to advance the at least one curved electrode into a target tissue, wherein the robotic controller is configured to automatically adjust an orientation and position of the at least one curved electrode to follow a curvature of the at least one curved electrode as it is advanced into the target tissue.

In one aspect, the system further includes a proximal coupling region on the treatment tip housing, wherein the proximal coupling region of the treatment tip housing comprises a plurality of electrical connectors that are in electrical communication with the plurality of treatment needle electrodes and the high-voltage connector disposed on the robotic arm. Other and further features and advantages of the present disclosure will become apparent from the following detailed description when read in view of the accompanying figures.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

FIGS. 8A-8E illustrate an example of a retractable treatment tip device. FIG. 8A shows a side perspective view. FIG. 8B is a perspective view of the distal end face, showing the electrodes exposed. FIG. 8C is a proximal end view of the apparatus of FIG. 8A. FIG. 8D shows a partially exploded view of the apparatus of FIG. 8A. FIG. 8E is a fully exploded view of the apparatus of FIG. 8A.

FIGS. 15A-15B schematically illustrate variations of the distal ends of retractable treatment tip devices including different insulating cover regions.

FIGS. 16A-16B schematically illustrate further examples of variations of the distal ends of retractable treatment tip devices including different insulating cover regions.

FIGS. 17A-17C schematically illustrate variations of the distal ends of retractable treatment tip devices including different thicknesses of soft insulating cover regions. FIG. 17C also includes a guide channel region for guiding the treatment needle electrodes into the tissue.

FIGS. 18A-18F illustrate an example of a method of using a retractable treatment tip device to treat tissue (e.g., skin tissue).

FIGS. 18G-18L show another example of a method of using a retractable treatment tip device to treat tissue (e.g., skin tissue) in which the distal end of the retractable needle housing is less soft than in FIGS. 18A-18F.

FIG. 42B illustrates an embodiment of a shaft.

FIGS. 47A-47C illustrate a retractable treatment tip of an instrument for use with a robotic surgical system.

FIGS. 48A-48B illustrate one embodiment of an instrument for use with a robotic surgical system.

FIG. 53 illustrates an example of a method of using an instrument with a robotic system.

FIG. 54 illustrates another example of a method of using an instrument with a robotic system.

FIG. 56 illustrates a flowchart for performing a surgical procedure with a robotic surgical system.

DETAILED DESCRIPTION

Figure 1:
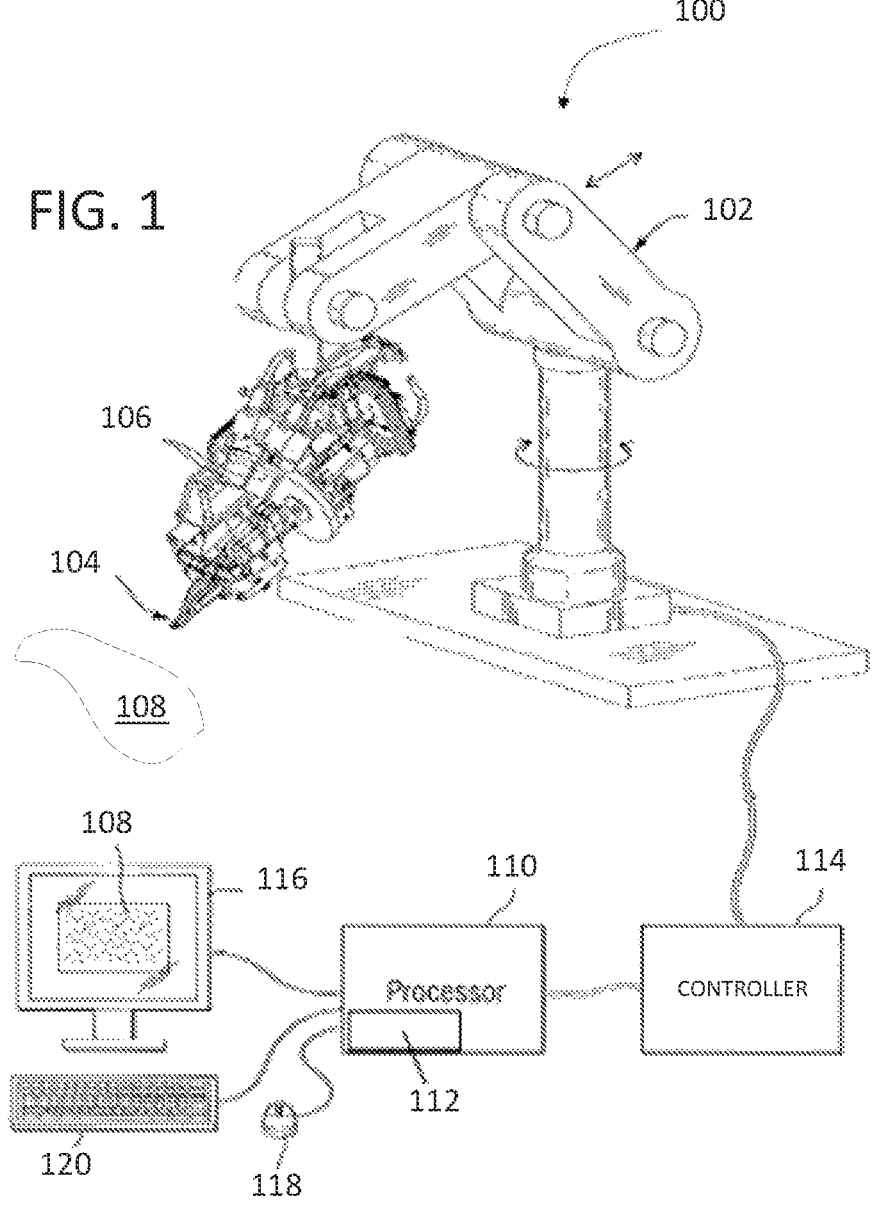
FIG. 1 illustrates one embodiment of a robotic system for use with instruments, devices and methods of the present disclosure.

The methods and apparatuses described herein generally relate to electrical treatment applications. Described herein are systems and methods for providing electrical treatment to a patient. According to one aspect, a robotic system includes a robotic arm and an instrument with a treatment tip are provided. The robotic system can be configured to provide treatment to the patient with the treatment tip. The robotic system can be controlled automatically under imaging guidance, or in other aspects, can be controlled with a master/slave relationship by a user or surgeon controlling the movement of the robotic arms.

According to one aspect, needle electrode applicators having a plurality of needle electrodes, in which the needles are protected by an insulated housing in an un-deployed configuration, and may be extended relative to the needle housing in a deployed configuration, and their use in partially or fully automated systems is disclosed. As will be described in greater detail, the needle housing may operate as an insulating member that prevents electrical arcing between the needle electrodes, even without the need for additional insulating materials, such as an insulating gel, that may otherwise be required.

Typically, the apparatuses described herein include a plurality of needle electrodes that may be exposed by applying force to retract a needle housing relative to the needle electrodes (e.g., by driving the needle housing against the tissue to be treated). The needles may be fixed relative to a treatment tip housing, so that driving the device against the tissue drives the needle electrodes into the tissue and pushes the needle housing back to fully expose the needle electrodes. Alternatively or additionally, it should be understood that the needle electrodes may be retractable and extendable relative to the housing. For example, the needle electrodes may be coupled to a bias member that can be actuated by a control on the apparatus to extend the needles out of the needle housing or retract the needles into the housing. In some variations the needle housing may be fixed relative to the treatment tip housing, and the needle electrodes may be movable. In some variations, the needle electrodes may be configured as part of an auto-injecting assembly in which the needle electrodes are biased (e.g., by a mechanical, electrical, pneumatic or other bias) against a release control (such as a button); when the release control is pressed, the needle electrodes may be ejected into the tissue to be treated. The needle electrodes may be limited by a hard stop and remain within the housing of the disposable tip.

In any of the apparatuses described herein, the distal-facing end of the treatment tip may be electrically insulating. Specifically, the distal (tissue-contacting) face of the needle housing includes an electrically insulating distal end region. Furthermore, the relative movement between the plurality of needle electrodes and the needle housing may allow the needle electrodes to be held in a protected configuration in which the distal ends of the needle electrodes are fully housed within the insulating needle housing; the apparatus may then controllably convert to a deployed configuration in which the needle electrodes are extended out of the needle housing. In the deployed configuration, the needles may be fully extended to a stop position between the needle housing and the needle electrodes; insulation on the distal facing end of the needle housing may surround the needle electrodes (e.g., between needs of different electrical states), thus when pressing the apparatus into the tissue the distal facing end of the needle housing may be pushed against the tissue when the needle electrodes are fully engaged with the tissue, insulating them and preventing arcing.

For example, described herein are retractable treatment tip apparatuses (e.g., devices, systems, etc.) including one, or more, preferably a plurality, of electrodes that are protected by and may be enclosed inside a housing until delivery of a therapeutic treatment. In particular, these apparatuses may include a plurality of treatment needle electrodes ("needle electrodes") and be configured for the delivery of nanosecond pulsed electric fields (nsPEF, or sometimes referred to as sub-microsecond pulsed electric fields), which may include an electric field with a sub-microsecond pulse width of between 0.1 nanoseconds (ns) and 1000 nanoseconds, or shorter, for example, 1 picosecond. NPS often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz. However, although the apparatuses described herein are adapted for, and particularly well suited for the delivery of therapeutic nsPEF, they may also be used as electrodes to deliver other therapeutic treatments, including treatments with continous (non-pulsed) energy, and treatments using slower than nanosecond pulses (e.g., microsecond, millisecond, or longer duration pulses).

The apparatuses described herein may be used to deliver one or more nsPEF treatments to treat various disorders and disease, including but not limited to cancer. It has been shown that nsPEF may be used to treat cancerous tumor cells; selectively and specifically driving them to undergo apoptosis, a programmed cell death, causing tumors to shrink to nonexistence after treatment. It has also been shown that the subject's immune system may be stimulated to attack all similar tumor cells, including those of tumors that are not within the nsPEF-treated tumor. In general, a disease may include any abnormal condition in or on a subject that is associated with abnormal, uncontrolled growths of tissue, including those that are cancerous, pre-cancerous, and benign, or other diseases as known in the art. Apoptosis of a tumor or cell includes an orderly, programmed cell death, or as otherwise known in the art.

As used herein, a "tumor" includes any neoplasm or abnormal, unwanted growth of tissue on or within a subject. A tumor can include a collection of one or more cells exhibiting abnormal growth. There are many types of tumors. A malignant tumor is cancerous, a pre-malignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

In general, any of the apparatuses described herein may be connected to and used with a pulse generator. The retractable treatment tips described herein may be disposable and may be configured for a single or limited use (e.g., single use, single session use, etc.). The retractable treatment tips may be configured to connect or couple (electrically and/or mechanically) to a reusable applicator device, such as a shaft connected to a control system including a pulse generator. The control system may control delivery of electrical pulses through the retractable treatment tip. These apparatuses may be particularly well adapted for delivery of high-energy (high voltage) pulse lengths, for example, of between 10 and 900 nanoseconds, including pulse lengths of between 50 and 300 nanoseconds, or about 100 nanoseconds.

For example, a nanosecond pulse generator system may include any of the retractable treatment tips described herein ("electrodes"), a user control input (e.g., footswitch) and user interface (display, monitor, speaker, etc.). The user control input and interface may be connected to the control circuitry within a housing that holds the electronic components. The retractable treatment tips may be connected to the controller and the electronic components therein through a high voltage connector. Examples of such high voltage connectors are described in the co-pending and co-owned International patent application PCT/US2017/052340, which is herein incorporated by reference in its entirety. The user may input or select treatment parameters, such as a number of pulses, amplitude, pulse duration, and frequency information, via one or more input devices, such as a numeric keypad, touch screen, mice, track pad, stylus, pen, speaker, etc.

In general, a retractable treatment tip for high-voltage electric therapy, such as nanosecond pulse electrical therapy may include a treatment tip housing, a needle housing, a bias driving the needle housing or/and the needles with a bias force, and a plurality of treatment needle electrodes within the needle housing. The retractable distal tip may also comprise a distal electrically insulating cover on the distal end of the needle housing, wherein the plurality of treatment needle electrodes may be exposed through the distal electrically insulating cover. In some embodiments, the needle housing may be driven against a subject's tissue with a force exceeding the bias force to expose the needles. Alternatively or additionally, the needle electrodes may be coupled to a constrained needle bias that may drive the needle electrodes from out of the needle housing when released from the constrained configuration. The needle bias constraint may be released by a button or other control (e.g. on the apparatus) activated by the user, and may drive the needles distally with the needle bias force, which may penetrate the tissue if the needle housing is pressed against the tissue.

In general, apparatuses described herein include high voltage electrodes and a high voltage connectors. The electrodes can include first and second terminals, configured to contact a patient, and a cable, configured to be connected to a pulse generator via the high voltage connector.

Although the various examples and embodiments described herein will use nsPEF as an example, it should be apparent that the general understanding of the various concepts discussed can be applied more broadly to other energies and appropriate applications. It should be understood that although the methods described herein are especially suited for use with a robotic surgical system, they can be applied to other automated and/or computer-implemented applications. For example, devices, systems and methods described herein may be utilized in various ablation procedures (e.g., radiation-based), dermatological procedures (e.g., treating various dermatological conditions, such as skin cancers), general surgery procedures (e.g., pancreatectomy), cardiology (e.g., valve repair), gynecology (e.g., hysterectomy), neurosurgery (e.g., tumor resection) etc. It should be noted that the examples given herein are for the purposes of illustration and example only, the description as set forth is not intended to be exhaustive or limiting.

FIG. 1 is a schematic perspective view of an example of a robotic system 100 for surgical applications. The robotic system 100 includes a robotic arm 102 to which is coupled an instrument 104. Various motors and other movement devices may be incorporated to enable fine movements of an operating tip of the instrument 104 in multiple directions. The robotic system 100 further includes at least one (and preferably two for stereo vision, or more) image acquisition device 106 which may be mounted in a fixed position or coupled (directly or some intervening elements) to the robotic arm 102 or other controllable motion device. The operating tip of the instrument 104 is shown positioned over a tissue 108.

The processor 110 of FIG. 1 comprises an image processor 112 for processing images obtained from the image acquisition device 106. The image processor 112 may be a separate device or it may be incorporated as a part of the processor 110. The processor 110 may also instruct the various movement devices of the robotic arm 102, including the instrument 104, and act, for example, through a controller 114 as schematically shown in FIG. 1. The controller 114 may be operatively coupled to the robotic arm and configured to control the motion of the robotic arm, including the motion based on the images or data acquired by the image acquisition device. Alternatively, controller 114 may be incorporated as a part of the processor 110, so that all processing and controls of all movements of all the tools, the robotic arm and any other moveable parts of the assembly, including those based on the images or data acquired by the image acquisition device, are concentrated in one place. The robotic system 100 may further comprise a monitor 116, mouse 118 and keyboard 120. An image of the tissue 108 can be seen on the imaging display or monitor 116. In addition, the robotic system 100 may comprise other tools, devices and components useful in surgical applications. The system further comprises an interface (not shown) adapted to receive an image data, various parts of the system allow an operator to monitor conditions and provide instructions, as needed. The processor 110 may interact with the imaging device 106 via the interface. The interface may include hardware ports, cables, leads, and other data transmission means, or it may comprise a computer program.

Some non-limiting examples of an image acquisition device 106 shown in FIG. 1 include one or more cameras, such as any commercially available cameras. The image acquisition or imaging device may be held, for example, by a robotic arm, or by any other mechanism or means. Various image acquisition devices or a combination of several devices could be used with any of the embodiments of the systems and methods described herein. The image acquisition device 106 may comprise a device that takes still images, it can also comprise a device capable of real time imaging (e.g., webcam capable of continuously streaming real time information), and/or it could also have a video recording capability (such as a camcorder). While stereo or multi-view imaging devices are very useful in the present disclosure, it is not necessary to employ such geometries or configurations, and the present disclosure is not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the method of the present disclosure. The image acquisition device may be coupled to a processing system 110, shown incorporated with the image processor 112 in FIG. 1, to control the imaging operation and process image data. In some implementation, no imaging device is used.

Typically, the processor 110 operates as a data processing device, for example, it may be incorporated into a computer. The processor 110 may include a central processing unit or parallel processor, and input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor 110 may execute a program that may be configured to include predetermined operations. The processor may access the memory in which may be stored at least one sequence of code instructions comprising the program for performing predetermined operations. The memory and the program may be located within the computer or may be located external thereto. By way of example, and not limitation, a suitable image processor 130 may be a digital processing system which includes one or more processors or other type of device. For example, a processor and/or an image processor may be a controller or any type of personal computer ("PC"). Alternatively, the processor may comprise an Application Specific Integrated Circuit (ASIC) or Field Programmable Gate Array (FPGA). It will be understood by those of ordinary skill in the art that the processor and/or the image processor for use with the present disclosure is programmed and configured to perform various known image processing techniques, for example, segmentation, edge detection, object recognition and selection. These techniques are generally known and do not need to be separately described here. The methods described herein may be implemented on various general or specific purpose computing systems. In certain embodiments, the methods of the present application may be implemented on a specifically configured personal computer or workstation. In other embodiments, the methods may be implemented on a general-purpose workstation, including one connected to a network. Alternatively or additionally, the methods of the disclosure may be, at least partially, implemented on a card for a network device or a general-purpose computing device. The processor/image processor may also include memory, storage devices, and other components generally known in the art and, therefore, they do not need to be described in detail here. The image processor could be used in conjunction with various manual, partially automated and fully automated (including robotic) systems and devices.

The imaging display device 116 may comprise a high resolution computer monitor which may optionally be a touch screen. The imaging display may allow images, such as video or still images, to be readable. Alternatively, the imaging display device 116 can be other touch sensitive devices, including tablet, pocket PC, and other plasma screens. The touch screen may be used to modify the parameters of the hair transplantation procedure, directly through the image display device.

Methods, apparatus and systems of the present disclosure may be carried out by providing a modification interface, or user modification interface, including touch screen, clickable icons, selection buttons in a menu, dialog box, or a roll-down window of an interface that may be provided to feed into the computer. According to another embodiment, the imaging display device 116 may display the selection window and a stylus or keyboard for entering a selection, for example, directly on the display itself. According to one embodiment, commands may be input via the modification interface through a programmable stylus, keyboard, mouse, speech processing system, laser pointer, touch screen, tablet computer, personal digital assistant (PDA), a remote input device (such as a pendant), or other input mechanism. The remote input device may include clickable icons, selection buttons, dialog boxes, or roll-down windows which are the same as or similar to those found on the user modification interface, providing a convenient way for the user to control common user interface functions from their position at the patient's side. Alternatively, the remote input device may only accommodate, for example, a subset of such modification controls, making for a more compact pendant. In yet another embodiment, the remote input device may be configured to accommodate additional modification controls. Moreover, either the remote input device or any other input mechanism may have icons which allow the user to control the robotic arm, allowing the user to move the robotic arm away from the patient, or incorporate a STOP button, enabling the user to terminate operation of the robotic arm or the instrument in the event of an emergency. Alternatively, the modification interface may comprise a dedicated piece of hardware. In some embodiments the selections or adjustment made through the modification interface may be executed by code instructions that may be executed on the computer processor.

Embodiments of the methods of the present disclosure may be implemented using computer software, firmware or hardware. Various programming languages and operating systems may be used to implement the present disclosure. The program that runs the method and system may include a separate program code including a set of instructions for performing a desired operation or may include a plurality of modules that perform such sub-operations of an operation or may be part of a single module of a larger program providing the operation. The modular construction facilitates adding, deleting, updating and/or amending the modules therein and/or features within the modules.

In some embodiments, a user may select a particular method or embodiment of this application, and the processor will run a program or algorithm associated with the selected method. In certain embodiments, various types of position sensors may be used. For example, in certain embodiment, a non-optical encoder may be used where a voltage level or polarity may be adjusted as a function of encoder signal feedback to achieve a desired angle, speed, or force.

The processor for use in the present disclosure may comprise any suitable device programmed and configured to perform various methods described in detail in the present application. In some embodiments modification may be accomplished through the modification interface. For example, the processor for use in the present disclosure may be a processor comprising a set of instructions for executing operations. The system for use according to the disclosures described herein may comprise in addition to a processor an image acquisition device.

Certain embodiments relate to a machine-readable medium (e.g., computer readable media) or computer program products that include program instructions and/or data (including data structures) for performing various computer-implemented operations. A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. It may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

Figure 2:
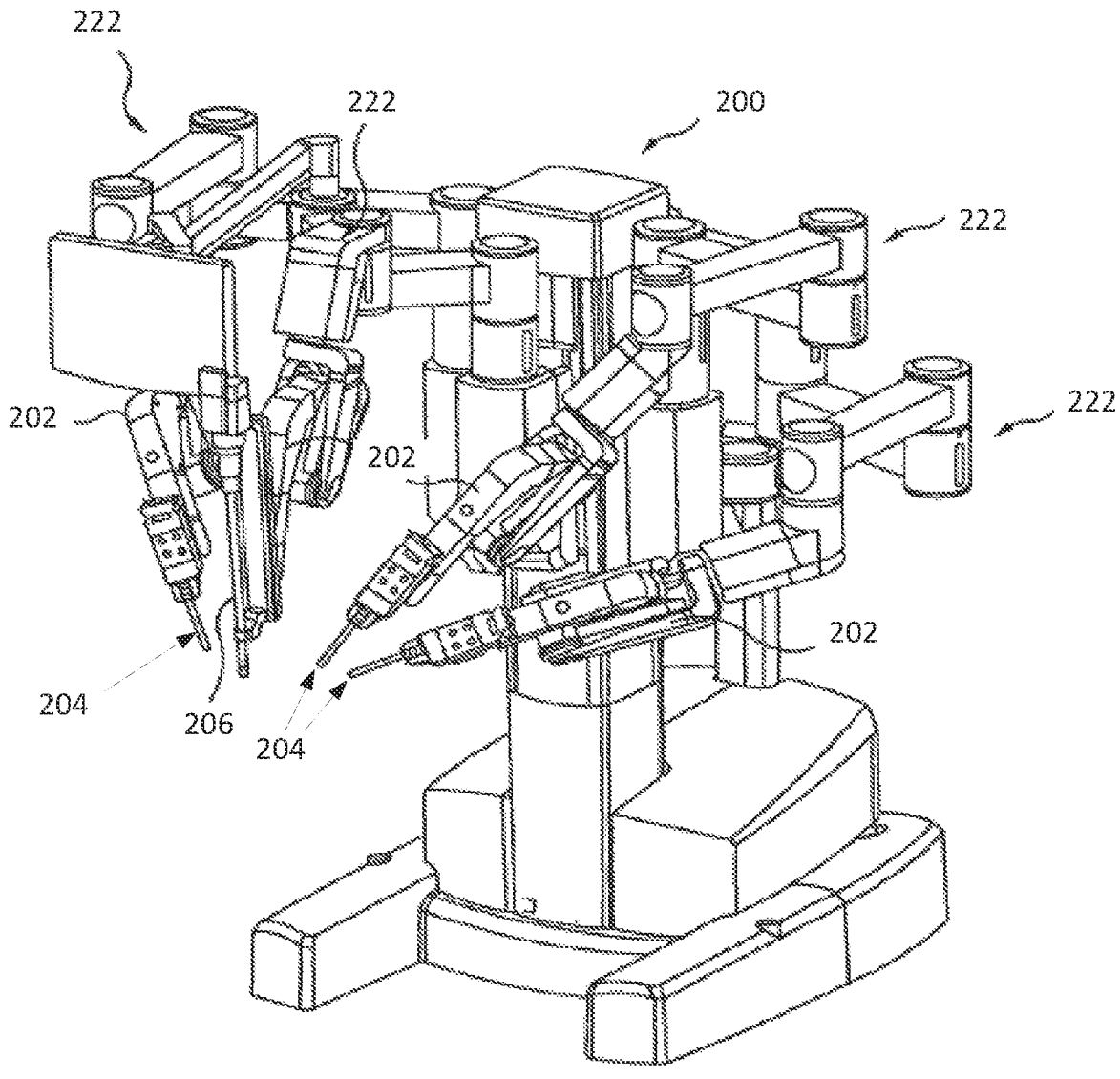
FIGS. 2-4 show another embodiment and features of a robotic surgical system.

FIG. 2 illustrates components of a robotic system 200 for performing minimally invasive robotic surgery. The robotic system 200 of FIG. 2 is designed and sold by Intuitive Surgical, Inc. as the da Vinci® Surgical System, and is described in more detail in U.S. Pat. Nos. 8,429,582 and 6,246,200, the full disclosures of which are incorporated herein by reference. A system operator (generally a surgeon) performs a minimally invasive surgical procedure on a patient lying on an operating table. The system operator sees images presented by a display and manipulates one or more input devices or masters at a surgeon's console. In response to the surgeon's input commands, a computer processor of the console directs movement of surgical instruments 204, effecting servomechanical movement of the instruments via the robotic system including linkages 222 and manipulator arms 202 each having a telescopic insertion axis. In one embodiment, the processor correlates the movement of the instruments 204 so that the motions of the instruments follow the movements of the input devices in the hands of the system operator.

In the example of FIG. 2, robotic system 200 includes at least four robotic manipulator assemblies comprising linkages 222 and manipulator arms 202. However, it should be understood that in other embodiments any number of robotic manipulator assemblies can be implemented in the system. In the illustrated example, the robotic system includes three robotic manipulator assemblies coupled to a surgical instrument 204 for robotic manipulation of tissues, and a fourth robotic manipulator assembly (mounted at the center of the cart in this example) coupled to an imaging device 206 (such as an endoscope/camera probe) configured to capture an image (preferably stereoscopic) of the surgical site. The robotic manipulator assemblies can include a telescopic insertion axis that allows for movement of the mounted surgical instrument 204.

Figure 3:
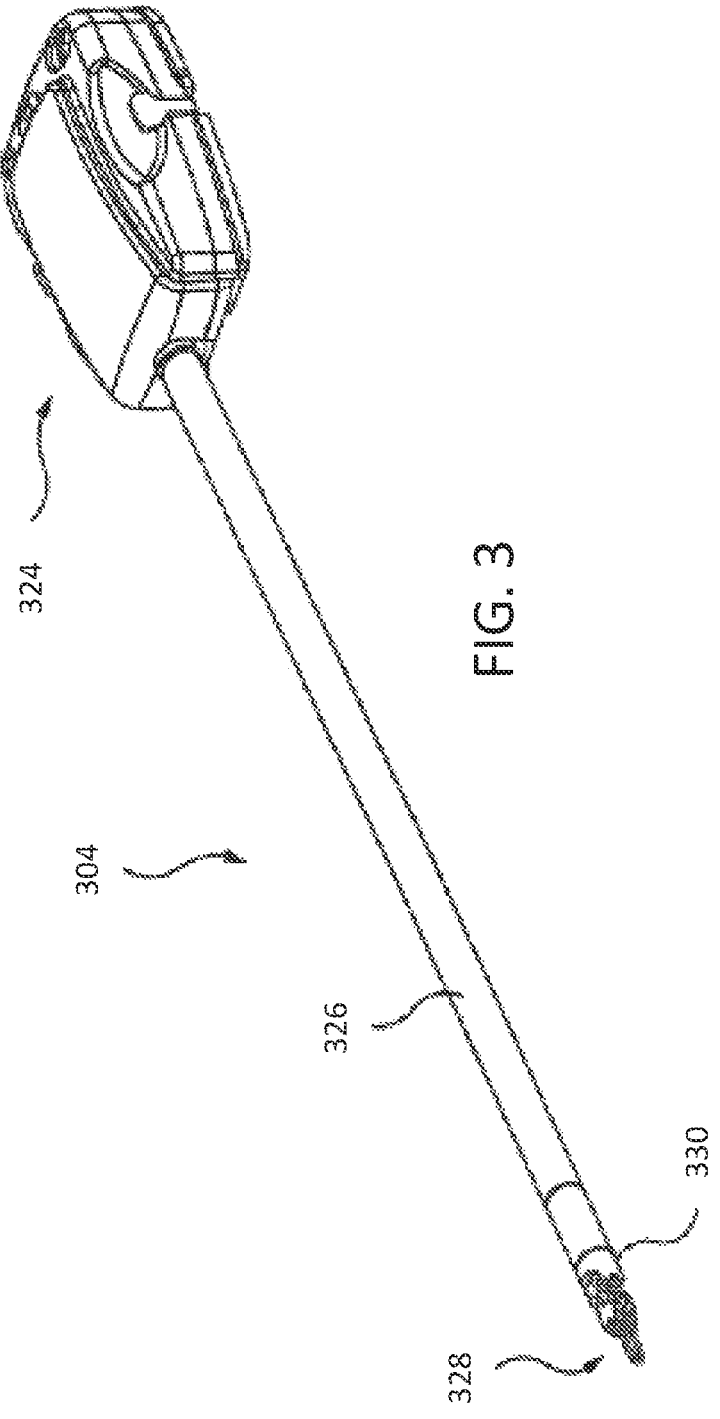

FIG. 3 illustrates a perspective view of an articulated surgical instrument 304 or tool. Instrument 304 has a proximal housing 324 which interfaces with a tool holder or instrument interface of the robotic manipulator assembly described above, generally providing a quick release mounting engagement through a sterile adapter or interface, an example of which is disclosed in U.S. Pat. Nos. 7,666,191 and 7,699,855, which are incorporated by reference herein for all purposes. Instrument 304 includes an elongated shaft 326 supporting an end effector 328 relative to proximal housing 324. The proximal housing 324 accepts and transmits drive signals and drive motion between the robotic manipulator assembly and the end effector. An articulated wrist 330 may provide two degrees of freedom of motion between end effector and shaft, and the shaft may be rotatable relative to proximal housing about the axis of the shaft so as to provide the end effector with three orientational degrees of freedom within the patient's body.

Figure 4:
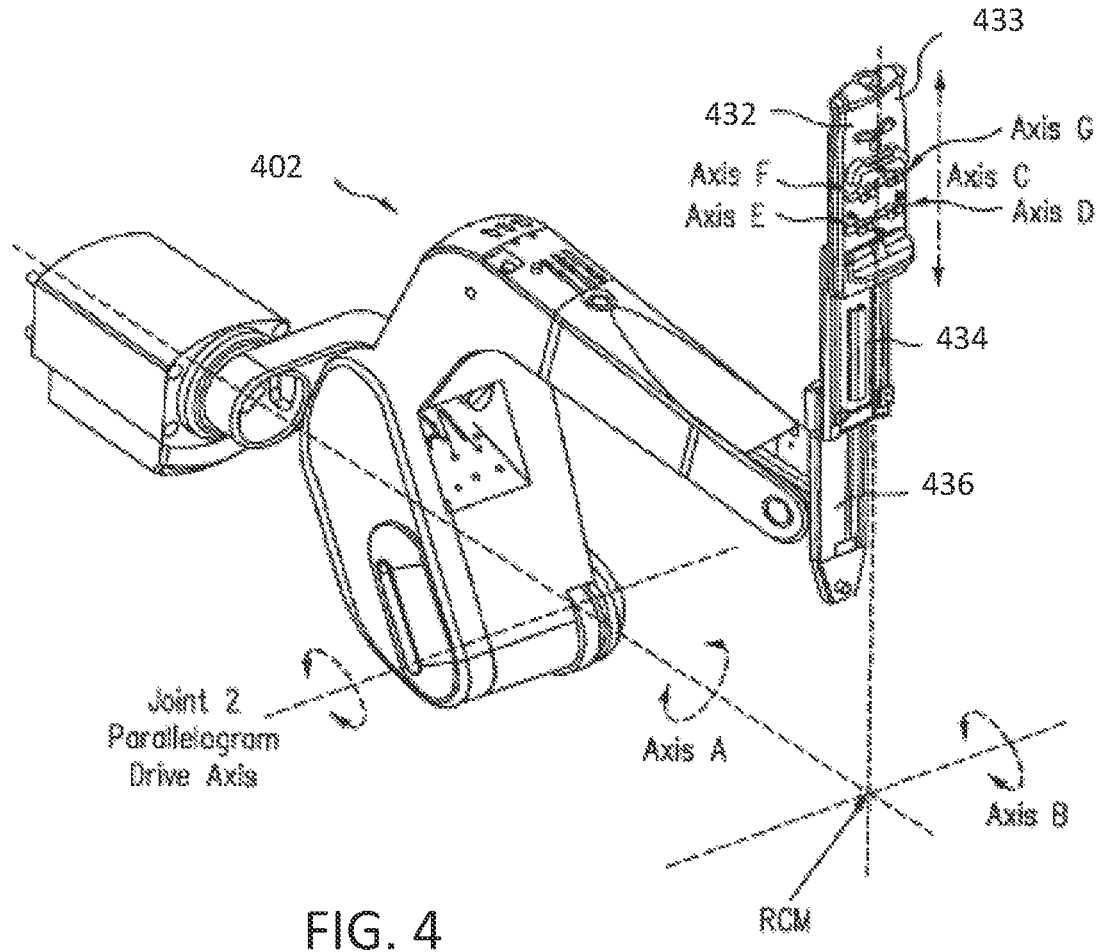

Referring now to FIG. 4, manipulator arms 402 including a telescopic insertion axis is shown in more detail. The insertion axis as illustrated includes a three-stage telescopic linear axis including three links, in one example, movably coupled to one another via bearings, rails, pulleys, and cables, with the links narrowing in width or form factor moving from the proximal link toward the distal link.

First link 432 includes an instrument interface 433 for operably coupling to an instrument (e.g., housing 324 of FIG. 3), and controls the depth of the instrument inside a patient.

Second link 434 is movably coupled between third link 436 and first link 432 to allow the links 432, 434, and 436 to move relative to one another along a lengthwise axis (e.g., axis C) in a telescoping fashion. In one embodiment, link 436 has a narrower form factor than link 434, and link 434 has a narrower form factor than link 432, thus providing for greater visibility near the surgical field.

Motion along axes C through G in manipulator arm 402, are provided by cables extending at least between the proximal and distal links in accordance with the present invention. The robotic arm can then control a tool or instrument operably coupled to the arm. The cables are a component of a transmission system also including drive pulleys, capstans, idler pulleys, and/or output pulleys, which are driven by electric motors. A pulley bank may be located on an underside of link 432 for passing cables and electrical wires between the insertion axis and the manipulator arm.

The drive assembly may further include a plurality of drive motors coupled to the arm for rotation therewith. Yaw and pitch motors control the motion of the arm about the A axis and the B axis, respectively, and drive motors control the motion of the wrist unit and insertion position. In one embodiment, four drive motors are mounted proximally in the arm to control four degrees of freedom of the tool mounted distally on the arm (the D, E, F, and G axes). Also, a proximally mounted motor controls the insertion position of the tool distally on the arm (along the C axis). The drive motors will preferably be coupled to encoders and potentiometers (not shown) to enable the servomechanism. Embodiments of the drive assembly, arm, and other applicable parts are described for example in U.S. Pat. Nos. 6,331,181, 6,491,701, and 6,770,081, the full disclosures of which are incorporated herein by reference for all purposes. The manipulator arm and the drive assembly may also be used with a broad range of positioning devices.

Figure 5:
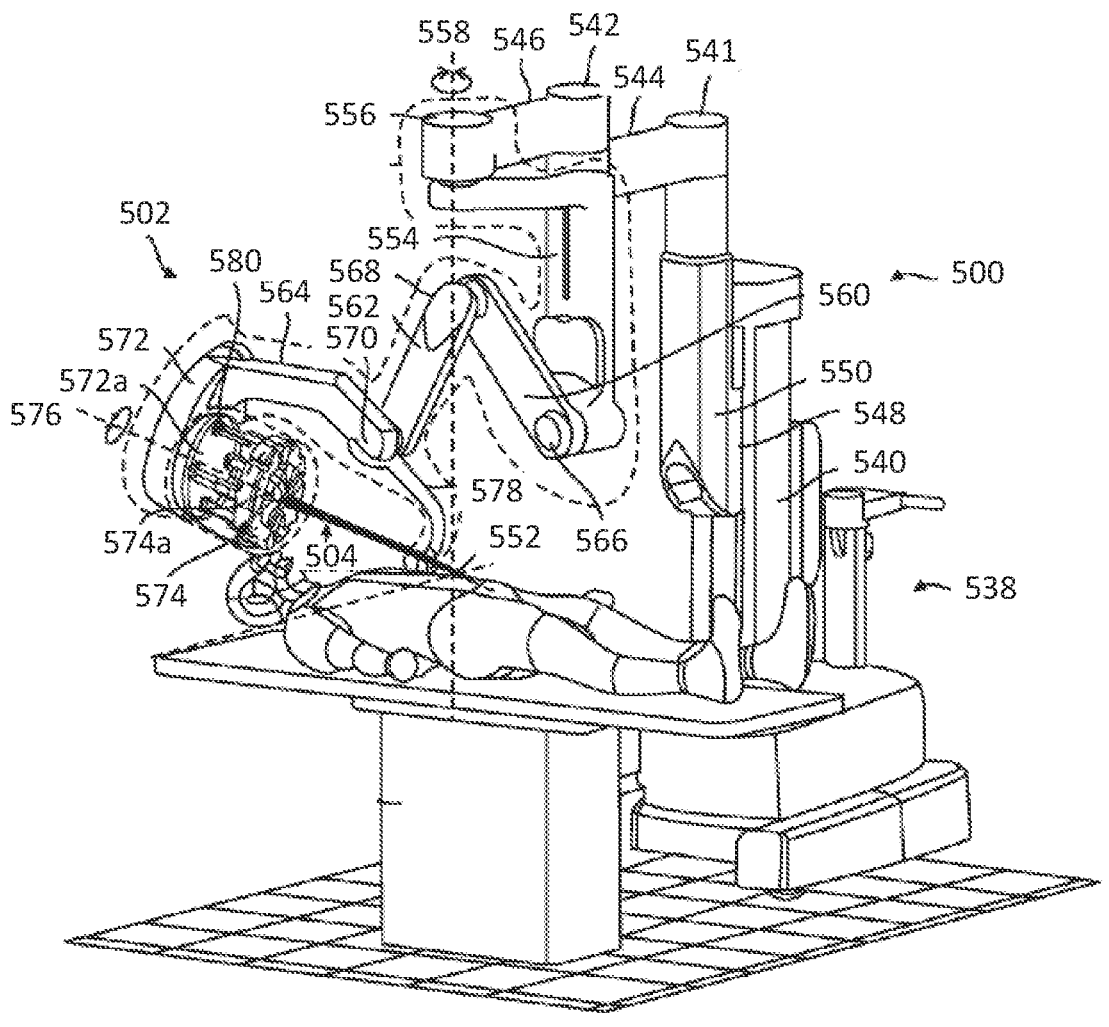
FIG. 5-7 illustrate yet another embodiment of a robotic surgical system.

FIG. 5 illustrates an alternative robotic system 500 in a teleoperated surgical (telesurgical) system. Further details of the system 500 can be found in U.S. Pat. No. 8,852,208, the full disclosures of which are incorporated herein by reference. A surgeon's console and a video system are not shown but are applicable as described above and known telerobotic surgical system architectures. In this embodiment, system 500 includes a floor-mounted base 538. The base may be movable or fixed (e.g., to the floor, ceiling, wall, or other sufficiently rigid structure). Base 538 supports support column 540, and a manipulator arm assembly 502 is coupled to support column 540. The arm assembly includes two passive rotational setup joints 541 and 542, which when their brakes are released allow manual positioning of the coupled setup links 544 and 546. In the depicted embodiment, setup links 544 and 546 move in a horizontal plane (parallel to the floor). The manipulator arm assembly is coupled to support column 540 at a passive sliding setup joint 548 between the column 540 and a vertical setup link 550. Joint 548 allows the manipulator arm to be vertically (perpendicular to the floor) adjusted. Accordingly, the passive setup joints and links may be used to properly position a remote center of motion 552 with reference to the patient. Once the remote center of motion 552 is properly positioned, brakes at each of the joints 548, 541, and 542 are set to prevent the setup portion of the arm from moving.

In addition, the arm assembly includes active joints and links for manipulator arm configuration and movement, instrument manipulation, and instrument insertion. The proximal end of a first manipulator link 554 is coupled to the distal end of setup link 546 via an actively controlled rotational manipulator assembly yaw joint 556. As shown, the rotational manipulator assembly yaw axis 558 of yaw joint 556 is aligned with remote center of motion 552, as illustrated by the vertical dashed line from yaw joint 556 to remote center of motion 552.

The distal end of first manipulator link 554 is coupled to the proximal end of a second manipulator link 560, the distal end of second manipulator link 560 is coupled to the proximal end of a third manipulator link 562, and the distal end of third manipulator link 562 is coupled to the proximal end of a fourth manipulator link 564, by actively controlled rotational joints 566, 568, and 570, respectively. As described above, links 560, 562, and 564 function as a coupled motion mechanism, so that fourth manipulator link 564 automatically moves in concert with second manipulator link 560 when link 560 is actuated. Thus, first manipulator link 554 may be considered an active proximal link, and second through fourth links 560, 562, and 564 may be considered collectively an active distal link. In one embodiment, first link 554 may include a compression spring counterbalance mechanism, as further described below, to counterbalance forces from movement of the distal link about joint 566.

A manipulator assembly platform 572 is coupled to a distal end of fourth link 564. Platform 572 includes a base plate 572*a* upon which instrument manipulator assembly 574 is mounted. As shown in FIG. 5, platform 572 includes a "halo" ring inside which a disk-shaped base plate 572*a* rotates. Configurations other than the halo and disk may be used in other embodiments. Base plate 572*a*'s center of rotation is coincident with a manipulator assembly roll axis 576, as shown by the dashed line that extends through the center of manipulator platform 572 and remote center of motion 552. Instruments 504 are mounted to the instrument manipulators of manipulator assembly 574 on a distal face of the instrument manipulators in one embodiment.

As shown in FIG. 5, instrument manipulator assembly 574 includes four instrument manipulators 574*a*. Each instrument manipulator supports and actuates its associated instrument. In the depicted embodiment, one instrument manipulator 574 a is configured to actuate a camera instrument, and three instrument manipulators 574 a are configured to actuate various other interchangeable surgical instruments that perform surgical and/or diagnostic work at the surgical site. More or fewer instrument manipulators may be used. In some operational configurations, one or more manipulators may not have an associated surgical instrument during some or all of a surgical procedure.

As mentioned above, a surgical instrument 504 is mounted to and actuated by a respective instrument manipulator 574*a*. In accordance with an aspect of the disclosure, each instrument is mounted to its associated manipulator at only the instrument's proximal end. It can be seen in FIG. 5 that this proximal end mounting feature keeps the instrument manipulator assembly 574 and support platform 572 as far from the patient as possible, which for the given instrument geometries allows the actively controlled portion of the manipulator arm to move freely within a maximum range of motion with reference to the patient while not colliding with the patient. The instruments 504 are mounted so that their shafts are clustered around manipulator assembly roll axis 576. Each shaft extends distally from the instrument's force transmission mechanism, and all shafts extend through a single cannula placed at the port into the patient. The cannula is removably held in a fixed position with reference to base plate 572 a by a cannula mount 578, which is coupled to fourth manipulator link 564. A single guide tube is inserted into and freely rotates within the cannula, and each instrument shaft extends through an associated channel in the guide tube. The longitudinal axes of the cannula and guide tube are generally coincident with the roll axis 576. Therefore, the guide tube rotates within the cannula as base plate 572*a* rotates. In some embodiments, a cannula mount may be operably coupled to first manipulator link 554.

Each instrument manipulator 574*a* is movably coupled to an active telescoping insertion mechanism 580 operably coupled to the base plate 572*a* and may be used to insert and withdraw the surgical instrument(s). FIG. 5 illustrates instrument manipulators 574*a* extended a distance toward a distal end of telescoping insertion mechanism 580. Active joints 556, 566, 568, 570 and manipulator platform 572 move in conjunction and/or independently so that a surgical instrument (or assembly) moves around the remote center of motion 552 at an entry port, such as a patient's umbilicus, after the remote center of motion has been established by the passive setup arms and joints.

As shown in FIG. 5, cannula mount 578 is coupled to fourth link 564 near the fourth manipulator link's proximal end. In other aspects, cannula mount 250 may be coupled to another section of the proximal link. As described above, cannula mount 250 is hinged, so that it can swing into a stowed position adjacent fourth link 564 and into an extended position (as shown) to support the cannula. During operation, cannula mount 250 is held in a fixed position relative to fourth link 564 according to one aspect.

Furthermore, links 560, 562, and 564 in conjunction with active joints 566, 568, and 570 may be used to easily manipulate the pitch angle of entry of an instrument through the single entry port while creating space around the single entry port. For example, links 560, 562, and 564 may be positioned to have a form factor "arcing away" from the patient. Such arcing away allows rotation of the manipulator arm about the yaw axis 223 that does not cause a collision of the manipulator arm with the patient. Such arcing away also allows patient side personnel to easily access the manipulator for exchanging instruments and to easily access the entry port for inserting and operating manual instruments (e.g., manual laparoscopic instruments or retraction devices). In yet another example, fourth link 564 has a form factor that arcs away from the remote center of motion and therefore the patient, allowing for greater patient safety. In other terms, the work envelope of the cluster of instrument manipulators 574*a* may approximate a cone, with the tip of the cone at the remote center of motion 552 and the circular end of the cone at the proximal end of the instrument manipulators 574*a*. Such a work envelope results in less interference between the patient and the surgical robotic system, greater range of motion for the system allowing for improved access to the surgical site, and improved access to the patient by surgical staff.

Accordingly, the configuration and geometry of the robotic system 500 in conjunction with its large range of motion allow for multi-quadrant surgery through a single port. Through a single incision, the manipulator may direct the instrument in one direction and easily change direction; e.g., working toward the head or pelvis of a patient and then changing direction toward the pelvis or head of the patient, by moving the manipulator arm about the constantly vertical yaw axis.

This illustrative manipulator arm assembly is used, for example, for instrument assemblies that are operated to move with reference to the remote center of motion. Certain setup and active joints and links in the manipulator arm may be omitted, or joints and links may be added for increased degrees of freedom. It should be understood that the manipulator arm may include various combinations of links, passive, and active joints (redundant DOFs may be provided) to achieve a necessary range of poses for surgery. Furthermore, various surgical instruments alone or instrument assemblies including guide tubes, multiple instruments, and/or multiple guide tubes, and instruments coupled to instrument manipulators (actuator assemblies) via various configurations (e.g., on a proximal face or a distal face of the actuator assembly or transmission mechanism), are applicable in the present disclosure.

Figure 6:
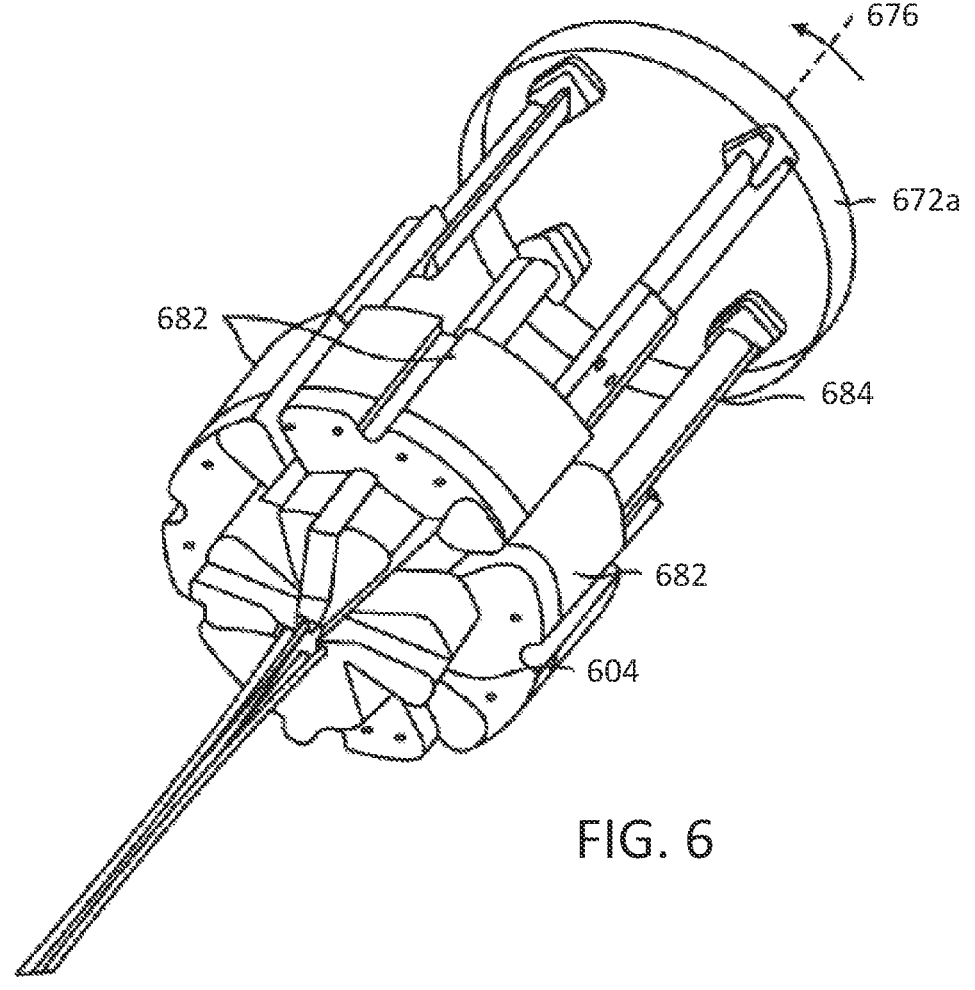

FIG. 6 is a perspective view of an embodiment of a rotatable base plate 672*a* of a manipulator assembly platform, a cluster of four instrument manipulators 682 mounted on the base plate 672*a* to form an instrument manipulator assembly, and four instruments 604 (the proximal portions are illustrated) each mounted to the distal face of an associated instrument manipulator 682. Base plate 672*a* is rotatable about a manipulator assembly roll axis 676, as described above. In one embodiment, roll axis 676 runs through the longitudinal center of a cannula and entry guide assembly, through which the instruments 604 enter a patient's body. Roll axis 676 is also substantially perpendicular to a substantially single plane of the distal face of each instrument manipulator 682, and consequently to a substantially single plane of the proximal face of an instrument mounted to the distal face of an instrument manipulator. Each instrument manipulator 682 includes an insertion mechanism 684 that is coupled to the base plate 672*a*.

It can be seen that an advantage of the telescoping feature of the insertion mechanism 684 is that it provides a larger range of motion when the instrument manipulator moves from its full proximal to its full distal position, with a smaller protruding insertion mechanism when the manipulator is at its full proximal position, than if only a single stationary insertion stage piece is used. The shortened protrusion prevents the insertion mechanism from interfering with the patient during surgery and with operating room personnel, e.g., during instrument changing, when the instrument manipulator is at its proximal position.

As further illustrated in FIG. 6, the telescopic insertion mechanisms 684 are symmetrically mounted to the rotatable base plate 672*a* in one embodiment, and therefore the instrument manipulators 682 and mounted instruments 604 are clustered symmetrically about the roll axis 676. In one embodiment, instrument manipulators 682 and their associated instruments 604 are arranged around the roll axis in a generally pie-wedge layout, with the instrument shafts positioned close to the manipulator assembly roll axis 341. Thus, as the base plate rotates about the roll axis 676, the cluster of instrument manipulators 682 and mounted instruments 604 also rotates about the roll axis.

Figure 7:
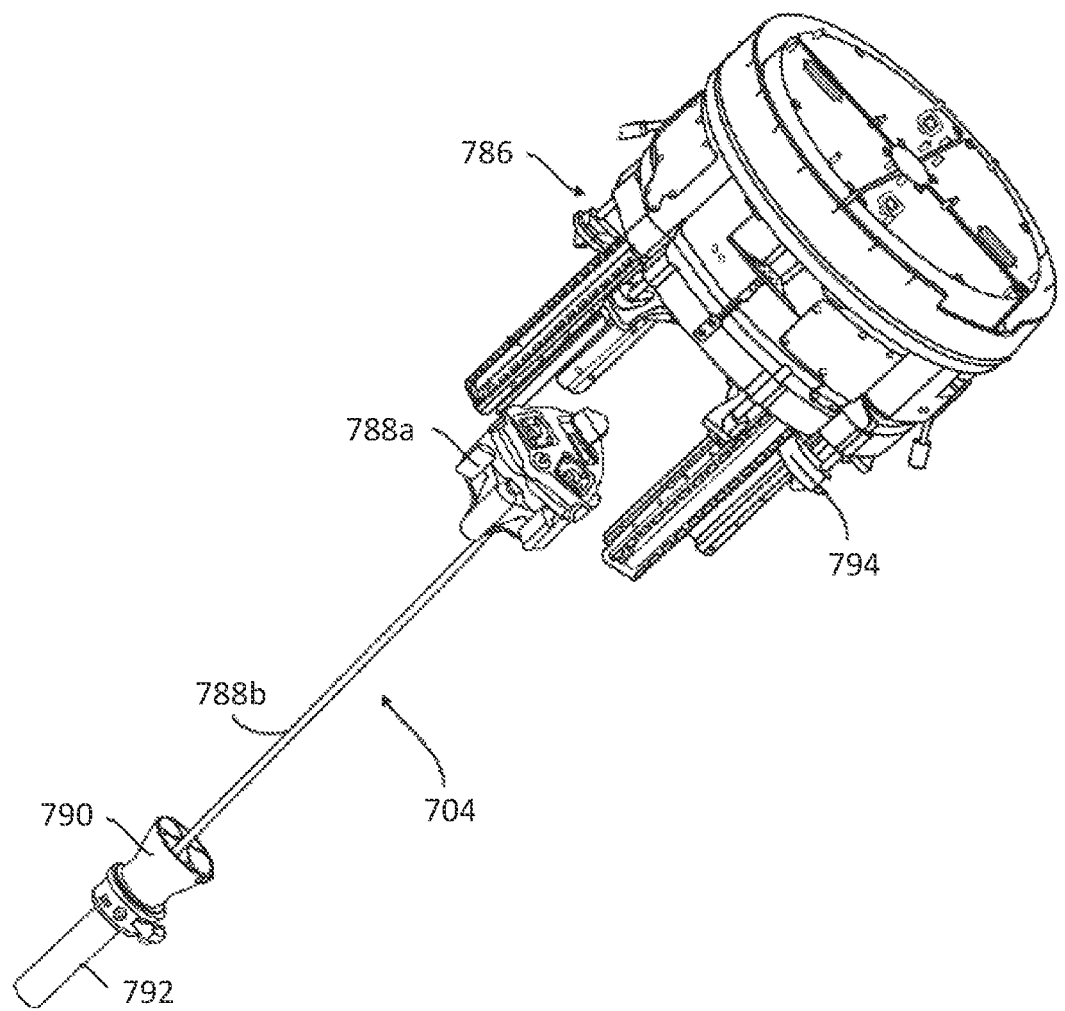

Referring now to FIG. 7, the coupling of a surgical instrument 704 to the sterile adapter 786 is illustrated and described. As shown in FIG. 7, the instrument 704 includes a force transmission mechanism 788*a* and a shaft 788*b*. A tip of shaft 788*b* is placed within an entry guide 790, which is freely rotatable within a cannula 792. FIG. 7 shows tabs on the force transmission mechanism 788*a* of instrument 704 engaged with and aligned by a pair of supports 794.

The surgical instruments described herein can additionally include features useful during robotic surgery or robotic assisted surgery. Various minimally-invasive or NOTES procedures typically require one or more robotic instruments to be inserted into a single or minimally sized hole or lumen in the patient to access the surgical site. The embodiments described below provide surgical instruments with retractable treatment tips to protect both the patient and instrument tip prior to accessing the surgical site.

Figures 8A, 8B, 8C, 8D:
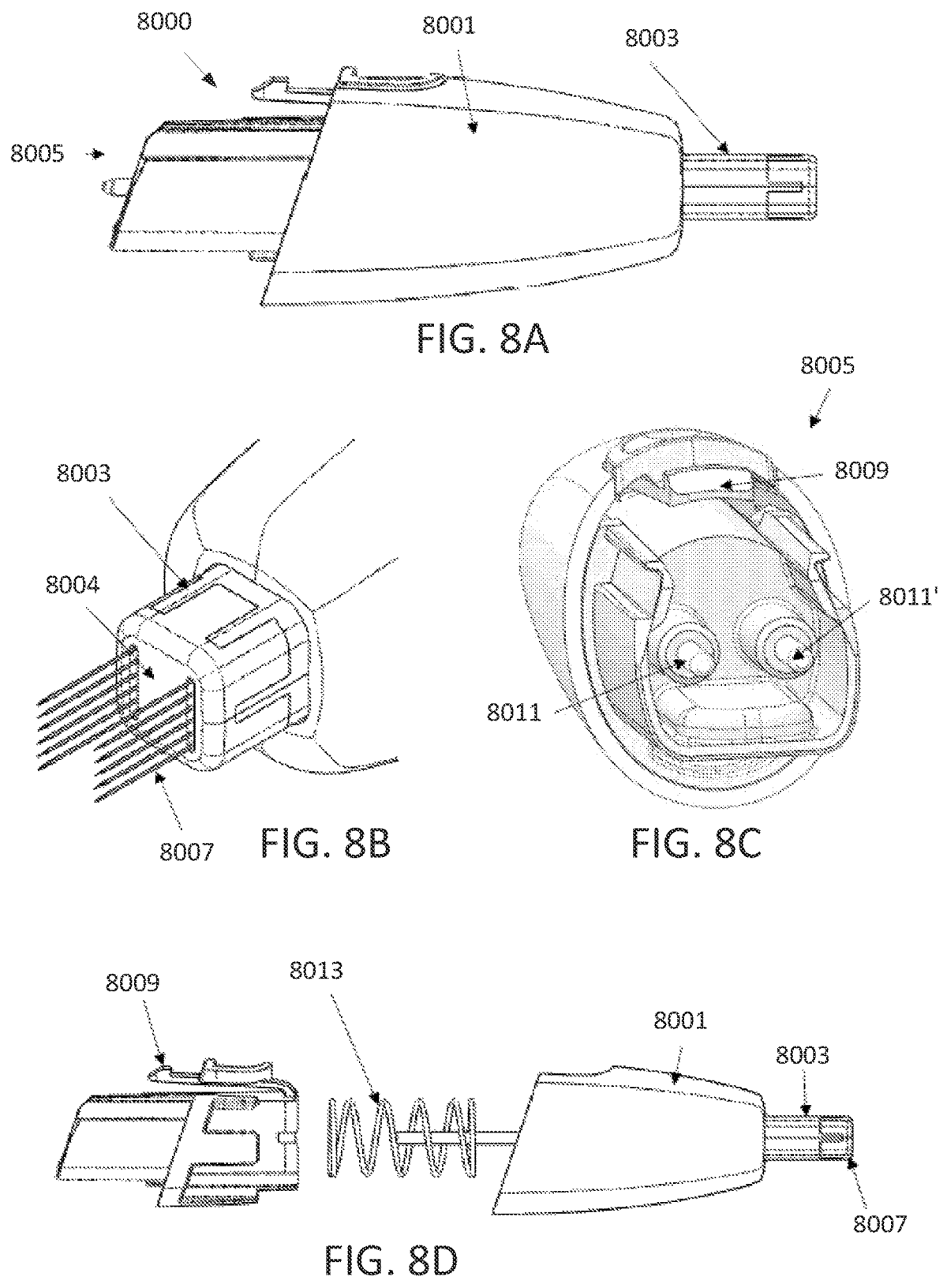
Figure 8E:
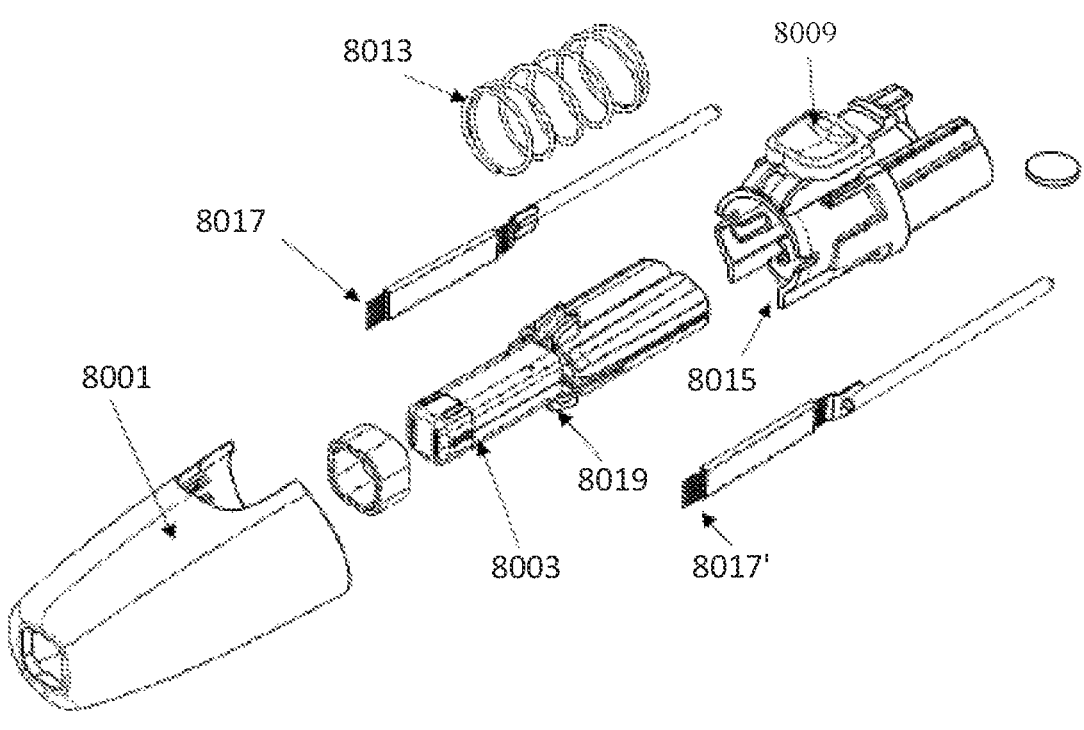

FIGS. 8A-8E illustrate one example of a retractable treatment tip 8000. The retractable treatment tip can be integrated into a surgical instrument and is configured to be coupled or mounted to a robotic system, as described above. In general, any of the retractable treatment tip and needle electrode embodiments described herein can be integrated into a surgical instrument and be coupled to or mounted to a robotic system. In FIG. 8A, the treatment tip is generally elongate (extending proximally to distally) and includes a treatment tip housing 8001, having a slightly elongated, tapered shape. A needle housing 8003 extends from the distal end of the treatment tip housing. A mechanical connector 8009 (as seen in FIG. 8C) on the proximal end 8005 may couple with a shaft, as will be described in detail below, and may also include one or more electrical connectors for coupling with the needle electrodes housed within the needle housing, which may extend from the needle housing as shown in FIG. 8B. FIG. 8B shows a close-up of the needle housing 8003, which is shown having a rectangular cross-section (any shape cross-section may be used). The distal-facing (e.g., tissue facing) end of the needle housing may be covered by an insulating cover 8004. A plurality of treatment needle electrodes 8007 are shown projecting from the at least partially retracted needles housing. In FIG. 8B, the needles are needle electrodes that may have a sharp and beveled distal end, but are cylindrical needles. Any shape needle electrode may be used. The needle electrodes may be insulated or un-insulated; in some variations the treatment needle electrodes are insulated along a portion of their length, but the distal end (e.g., the distal 0.5 mm, 1 mm, 1.2 mm, 1.5 mm, 1.7 mm, 2 mm, etc.) are un-insulated. FIG. 8C shows the proximal end 8005 of the retractable treatment tip. In this example, the retractable treatment tip includes a mechanical connector 8009 (shown by example as a snap or latch) that couples the retractable treatment tip to a shaft. The retractable treatment tip also includes two electrical connectors 8011, 8011'. This proximal end of the retractable treatment tip may couple with the shaft to make both mechanical and electrical connection.

Within the retractable treatment tip housing 8001, in some embodiments the plurality of needles may form part of a needle assembly that is coupled to the treatment tip housing so that the needles are locked in position relative to the treatment tip housing, but not the needle housing 8003. A bias 8013 (shown in the partially exploded view of FIG. 8D by example as a spring) may be used to apply a bias force against the needle housing, to push the needle housing distally. The needle housing 8003 may engage with the treatment tip housing 8001 so that it can otherwise slide proximally and distally. For example, the needle housing and treatment tip housing may slide relative to each other via a channel formed in the treatment tip housing in which a projecting region in the needle housing slides. Alternatively or additionally, the channel may be in the needle housing and the projection may extend from the treatment tip housing. In general, the bias may hold the needle housing distally extended until it reaches a stop position; in some variations a mechanical stop may be included to prevent further distal advancement. The needle housing may be driven proximally by applying force (typically normal to the distal-facing end of the needle housing) to the needle housing. For example, by pushing the distal facing end of the needle housing against the tissue when holding the treatment tip housing (e.g., coupled to a shaft).

FIG. 8E is an exploded view of the retractable treatment tip example shown in FIGS. 8A-8D. The distal portion of the treatment tip housing 8001 connects with a proximal portion 8015 of the treatment tip housing to enclose the bias 8013 and at least a portion of the needle housing, as well as the plurality of needles (e.g., a first set of electrically connected needle electrodes 8017, and a second set of electrically connected needle electrodes 8017') and electrical connectors (not shown). In this example, the mechanical connector 8009 may be used to couple the retractable treatment tip to a shaft (e.g., a reusable shaft). In the example of FIG. 8E, the needle housing includes projections 8019 that slid within the outer treatment tip housing 8001, e.g., in channels within the treatment tip housing. The two halves of the outer treatment tip housing may be connected permanently or removably.

The retractable treatment tips described herein may come in a variety of different sizes and configurations that may be used in multiple indications. For example, the size (e.g., diameter) of the treatment area on the distal face of the apparatus may be varied (e.g., between about 1 mm to 20 mm), and may be any appropriate shape (e.g., rectangular, rounded, triangular, oval, etc.). The treatment needle electrodes (e.g., needle electrodes) may be any appropriate length, and may be a fixed length or the length may be adjustable. For example, the length may be between about 0.2 mm to 60 mm. The diameter of the needles may be any appropriate diameter, e.g., a maximum cross-sectional diameter of between about 0.02 to 1 mm. The treatment electrodes may be insulated. The distal-facing (e.g., flat or beveled) face is typically not insulated, but in some variations a distal-facing length of the treatment needle electrodes extending from the distal end of the treatment needle proximally may be uninsulated as well. For example, the distal end of the needle may be uninsulated to leave an exposed length of between about 0 mm to 20 mm. The length of the insulation may be variable and/or adjustable. For example, the length of the insulation of the needle electrodes may be controllably adjusted to between about 0 mm and about 20 mm.

Figure 9A:
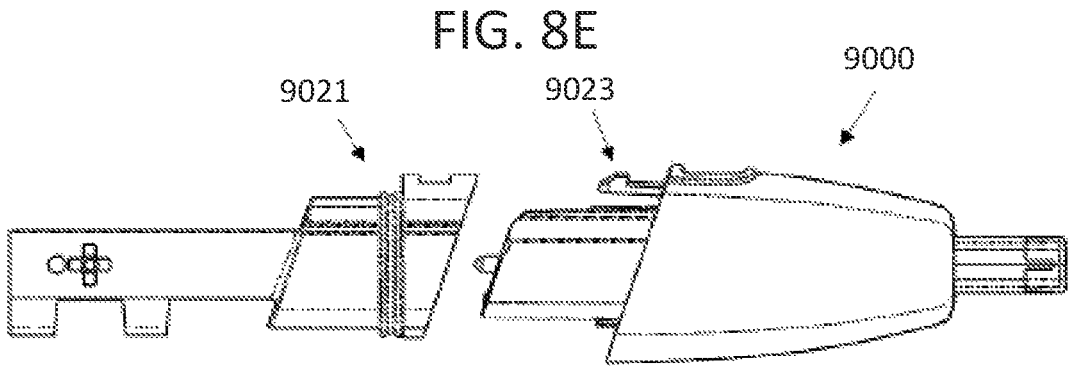
FIG. 9A is a view of the retractable treatment tip device (similar to the one shown in FIG. 8A) before coupling with a portion of a shaft including a mechanical and/or electrical connection.
Figure 9B:
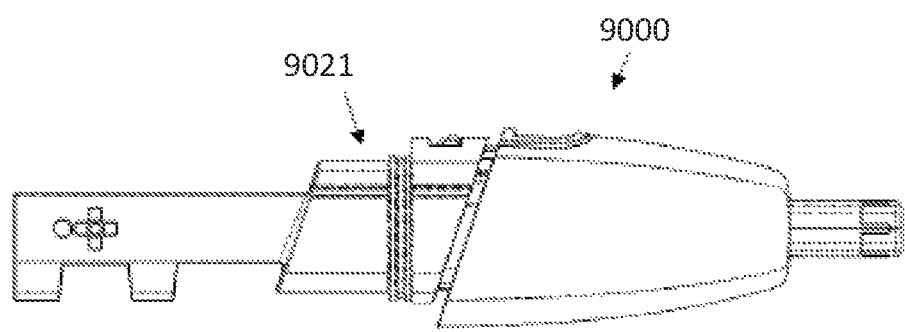
FIG. 9B shows the retractable treatment tip device engaged with the portion of the shaft.

As mentioned, the retractable treatment tip (e.g., a disposable treatment tip) is generally configured to couple with a reusable holder. FIGS. 9A-9B illustrate mechanical and electrical coupling between a retractable treatment tip 9000 and a portion of a reusable shaft 9021. A connector 9023 (shown by example as a clip in FIGS. 9A-9B) may mechanically and releasably secure the retractable treatment tip and the shaft together.

Figure 10A:
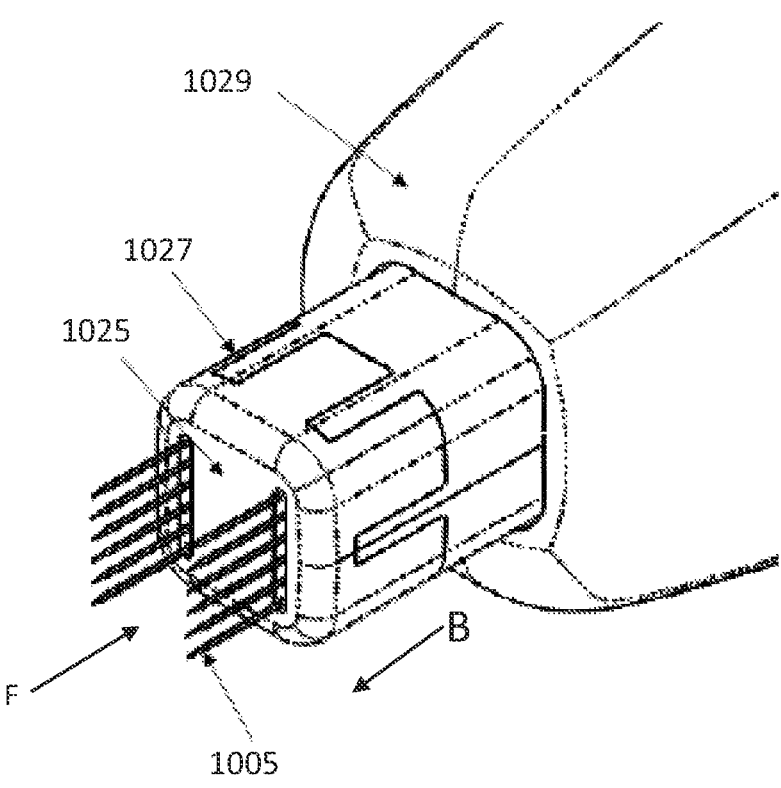
FIG. 10A is an enlarged perspective view of an example of a distal end of a retractable treatment tip device, showing the plurality of exposed needle electrodes.
Figure 10B:
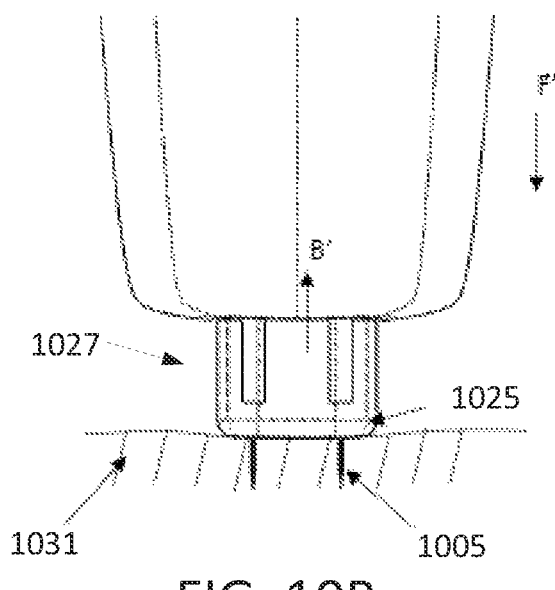
FIG. 10B shows an example of a side view of a retractable treatment tip device applied to tissue with a force against the tissue sufficient to retract the needle housing as the treatment needle electrodes are driven into the tissue.

FIG. 10A shows another view of an example of the distal end of a retractable treatment tip, including an insulating cover 1025 that covers the distal-facing end of the needle housing 1027 with a layer of soft, insulating material. The needle housing may be biased distally out of the treatment tip housing 1029 by a biasing force B, but pushing against the biasing force B (e.g., by driving the retractable treatment tip against the tissue to be treated while keeping in place the shaft to which the retractable treatment tip is coupled) may push the needle housing proximally allowing the treatment needle electrodes to be driven distally into the tissue. This is illustrated in FIG. 10B. In this example, the apparatus is held proximally by a shaft or by the treatment tip housing portion and force F is applied to drive the needle housing 1027 against the tissue 1031. This allows the needles 1005 to be driven into the tissue 1031 while pushing the soft insulating cover 1025 portion of the apparatus against the tissue between the needle electrodes, insulating them relative to each other. The force opposing the biasing force, B', between the tissue and the insulating cover may be greater than the biasing force, B, driving retraction of the needle housing.

Figures 11A, 11B, 12A, 12B:
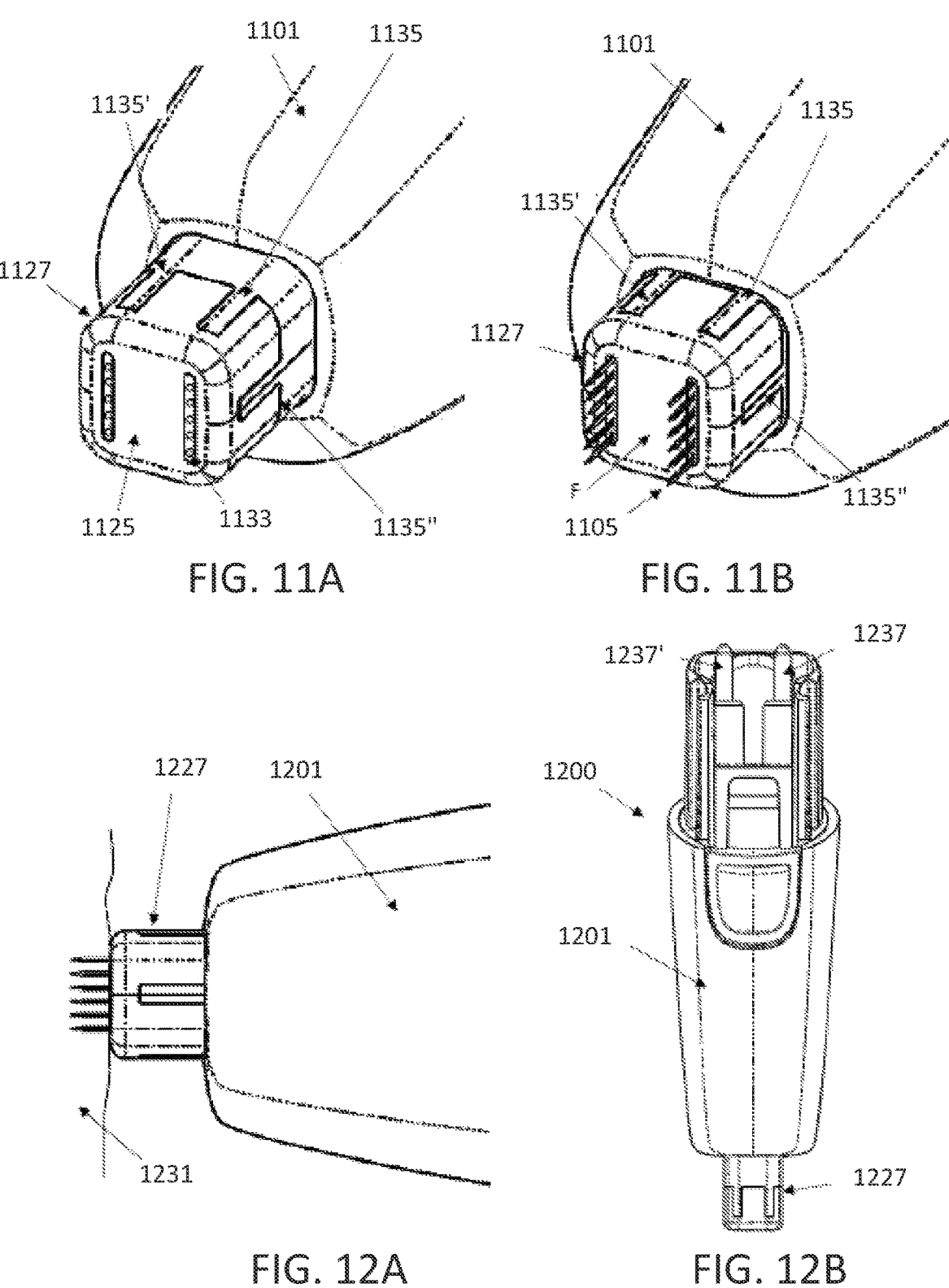
FIG. 11A shows an example of enlarged perspective view of a distal end face of a retractable treatment tip device in which the treatment needle electrodes are fully enclosed in the needle housing.
FIG. 11B shows the retractable treatment tip device of FIG. 11A with a force sufficient to overcome the bias holding the needle housing portion of the retractable treatment tip device distally, exposing the treatment needle electrodes.
FIG. 12A shows a side view of an example of a retractable treatment tip device driven against the tissue so that the sharp treatment needle electrodes are inserted into the tissue while the needle housing is biased against the tissue (e.g., skin).
FIG. 12B is a side view of an example of a retractable treatment tip device in an un-deployed configuration.

FIGS. 11A and 11B illustrate another example of a retractable treatment tip. The retractable treatment tip can be integrated into a surgical instrument and is configured to be coupled or mounted to a robotic system, as described above. In FIG. 11A the distal end of the apparatus is shown with the needle housing 1127 fully extended distally. An internal spring (not shown) may bias the needle housing distally. The needle housing may include a distal insulating cover 1125 that, in this example, has a plurality of openings or holes 1133 through which treatment needle electrodes 1105 may extend when the housing is pushed (by a force, F, greater than the biasing force) into the distal end of the treatment tip housing 1101. In this example the side of the housing may include one or more fiducial markers 1135 that mark the relative position of the needle housing relative to the treatment tip housing 1101 and/or the relative position and orientation of the treatment needle electrodes on the tip. For example, in FIGS. 11A and 11B, the two fiducial lines 1135, 1135' on the tops of the needle housing 1127 are aligned with the rows of needle electrodes once they exit the needle housing. In this way, the user (or an imaging device together with the image processor of the robotic system) may know where the rows of needle electrodes are. The fiducial line 1135" may be on the adjacent side is in the middle of the two rows of needles, as shown. The top of these lines may indicate the fully retracted position of the needle housing and/or the fully extended position of the needle electrodes when deployed. Some or all of these fiducial markers (e.g., lines) on the needle housing, or other markers on the needle housing, may show how far the needle housing is retracted, and/or how far the needles have been inserted into the tissue. For example, lines transverse to the elongate length (e.g., of fiducial lines 1135, 1135', 1135") may include indicators for the needle depth.

FIGS. 12A-12B illustrate another example in which the treatment tip is pushed against a tissue 1231 with sufficient force to drive the treatment needle electrodes into the tissue as the needle housing 1227 is pushed proximally and the soft, insulating distal face of the needle housing is driven against the face of the tissue being treated so that it retracts into the treatment tip housing 1201, as shown. In FIG. 12B, the apparatus 1200 is shown in the un-deployed configuration. Two electrical connectors 1237, 1237" are also shown on the proximal end of the apparatus, shown in this example as male connectors that connect to the treatment needle electrodes.

Figure 13A:
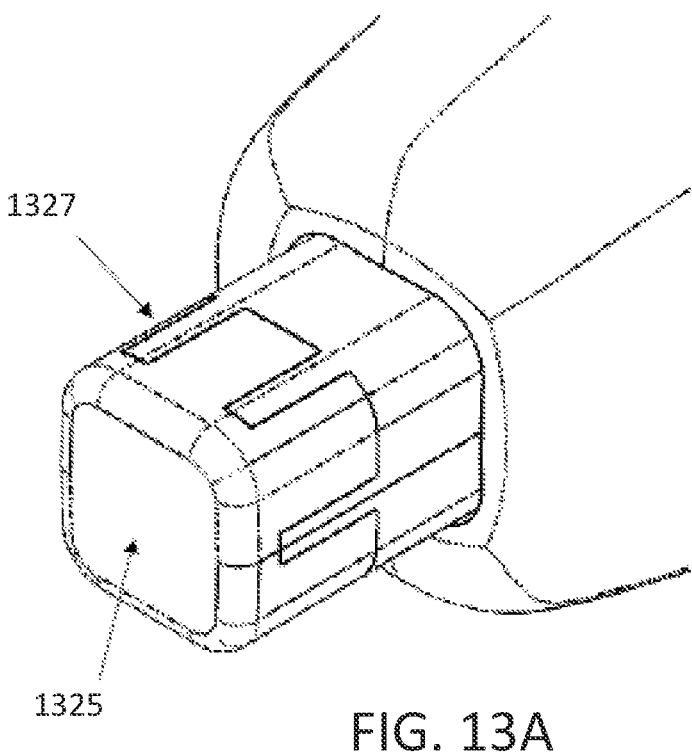
FIG. 13A illustrates an example of a distal end of a retractable treatment tip device including an insulating cover through which electrodes (e.g., needle electrodes) may be driven, as shown in FIG. 13B.
Figure 13B:
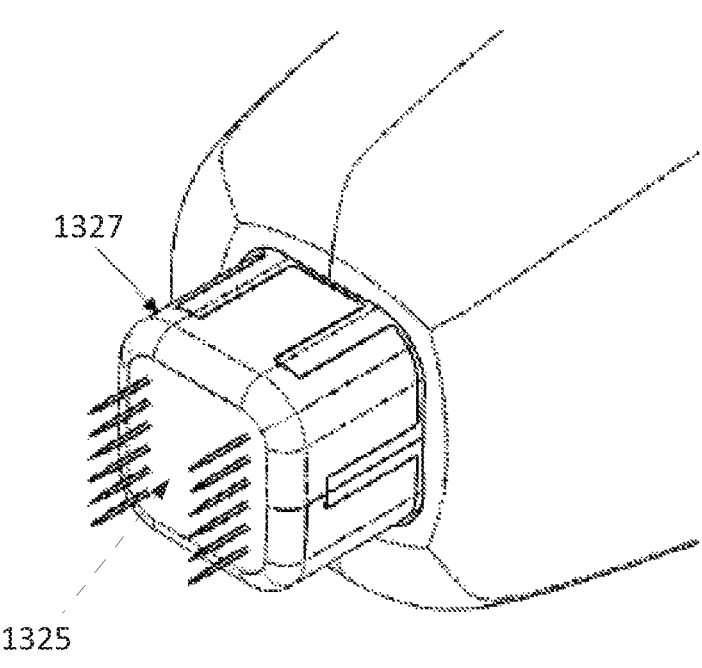

In the example shown in FIGS. 11A and 11B, above, the distal end of the needle housing is covered by an insulating cover that includes holes or opening through which the needles may extend when the needle housing is pushed proximally. In some variations the insulating cover does not include holes or openings and instead the treatment needle electrodes penetrate into and through the soft insulating cover itself. For example, the soft insulting cover may be silicone, santoprene, or other TPE (Thermoplastic Elastomer) materials. This is illustrated in FIGS. 13A-13B. In FIG. 13A the soft insulating cover 1325 is smooth, and does not yet have any openings through it. Retracting the needle housing 1327 by pushing against it with sufficient force to overcome any bias from, e.g., a spring within the housing, as well as the force required to penetrate the thickness of the insulating cover allows the treatment needle electrodes 605 to extend out of the insulating cover, as shown in FIG. 13B.

Figures 14A, 14B:
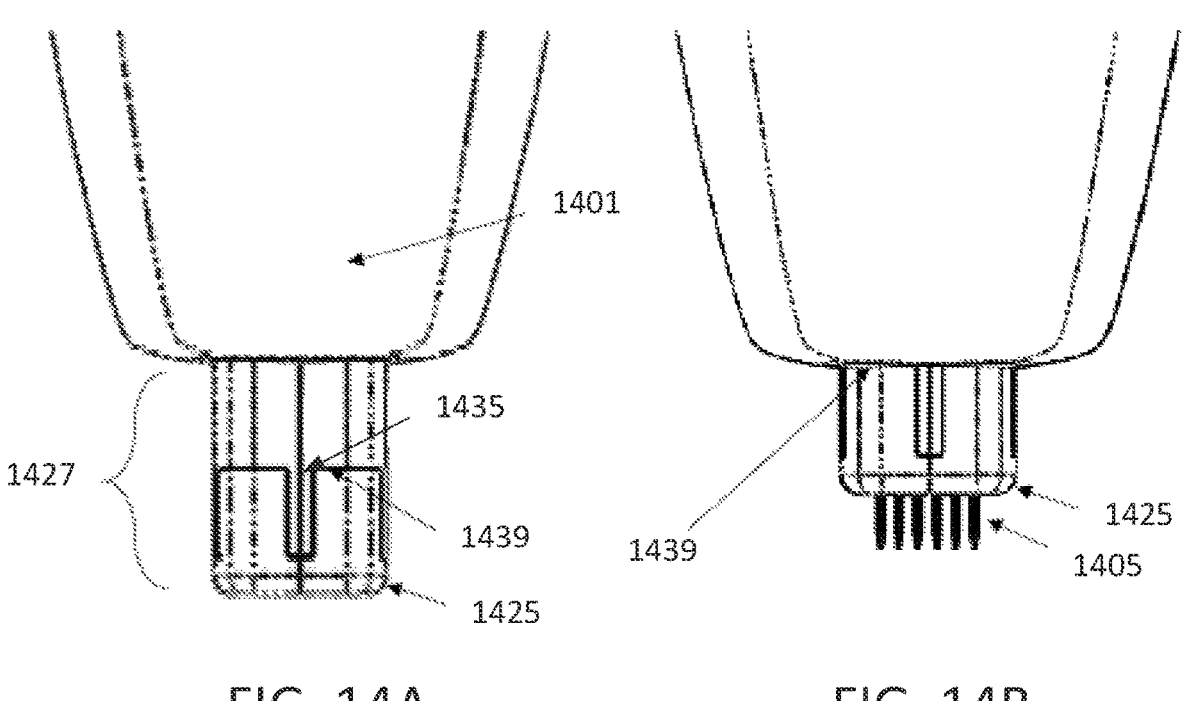
FIG. 14A is an example of a distal end of a retractable treatment tip device in an undeployed configuration.
FIG. 14B shows the distal end of the device in a deployed configuration, in which the needle housing and insulating cover are retracted to expose the needle electrodes.

FIGS. 14A and 14B illustrate another example of a distal end of a retractable treatment tip device in which the apparatus includes a plurality of treatment needle electrodes 1405 extending through a thickness of soft insulting cover 1425 forming the distal end of the needle housing 1427 that extends distally from the distal end of the treatment tip housing 1401. The retractable treatment tip can be integrated into a surgical instrument and is configured to be coupled or mounted to a robotic system, as described above. In FIG. 14A, the border 1439 of the insulating cover 1425 which may extend partially up the lateral side of one or more of the sides of the needle housing may be used to confirm deployment (e.g., retraction of the needle housing and insertion of the needle electrodes into the tissue). As shown in FIG. 14B, when applied against the tissue (not shown), the border 1439 may align with the distal end of the treatment tip housing 1401 when the needles 1405 are fully deployed. Alternatively or additionally, when the two parts of insulating cover 1425 that wrap around the fiducial line 1435 can be longer and when those two wrap-around features are in-line with the treatment tip housing 1401, the needles are fully deployed. Thus, in any of the variations described herein, a fiducial marking (e.g., line) may indicate that the needles are fully deployed. This may be particularly beneficial, as the needle electrodes may be fully deployed into the tissue and not visible to the user. A visual indicator that the needle electrodes are fully deployed may be used to determine when treatment should be triggered.

In use, the distal end of the soft distal end of the needle housing may be configured as an insulator. This insulator maybe an insulator cover, as described above, or it may be the material from which the entire needle housing, or at least a distal end portion of the needle housing, is formed. FIGS. 15A-15B and 16A-16B illustrate alternative variations of needle insulators, including distal insulators and covers. In FIG. 15A the distal face of the needle housing is an insulator 1537 that is formed of a soft material that can be driven against the tissue. The insulator may include openings for one or more of the treatment needle electrodes 1505, shown connected to a needle assembly 1539, 1539'. The soft insulator 1537 may be pushed against the tissue and may conform to the tissue surface, even if the tissue surface is slightly irregular.

In some variations the distal face of the needle housing may include one or more vacuum ports through which suction may be drawn to help secure the needle housing against the tissue to prevent shorting (arcing) between the treatment needle electrodes. In FIG. 15B, the insulator 1537' includes passages forming the suction ports 1541, 1543 1545, 1547. The ports may extend via tubing (e.g., flexible tubing) up to a suction source in the shaft or controller. In other embodiments, the suction ports that secure the needle housing against the tissue to prevent arcing may be used on their own without the insulator. In those embodiments, the suction ports may be formed through the needle housing to the distal end of the needle housing.

In FIG. 16A, the retractable needle housing includes a soft, insulating distal face (shown as a cover 1637'') that includes a sealing region 1649, 1649' around the distal-facing treatment needle openings 1651, 1651'. In some variations these sealing regions are projections and may be ring-shaped or continuous around the openings to permit them to seal and electrically insulate the treatment needle electrodes.

As discussed above, in some variations the insulating cover may not include defined openings, but may be configured to be penetrated by the treatment needle electrodes when the needle housing is retracted or the needles are extended. Another example of this configuration is shown in FIG. 16B, showing an insulating cover 1637'''' that is solid, but may be formed of a material that can be penetrated by the treatment needle electrodes 1605.

In general, the insulator (e.g., insulating cover or insulating distal end) of the retractable needle housing maybe any appropriate thickness. In some variations, particularly those in which the insulating distal end/cover are relatively thin, a needle guide may be included to guide the needles as they extend through and out of the needle housing, preventing bending. For example, FIGS. 17A-17C illustrate retractable needle housings having soft, insulating covers of varying thicknesses 1753. The variation of the insulating cover 1737 shown in FIG. 17A is similar to that shown in FIG. 15A. For comparison, FIG. 17B shows an example of an apparatus having a slightly thinner 1753' soft, insulating cover 1737. Finally, in FIG. 17C, the soft insulating cover 1737'' is thinner 1753'' than that shown in FIG. 15B. In FIG. 17C the needle housing also includes a needle guide 1755 (or a plurality of needle guides). The needle guides may be proximal to the soft, insulating cover, and may be made of a more rigid material. In variations in which a separate insulating cover is used at the distal face of the needle housing, the insulating cover may be any appropriate thickness. For example, the insulating cover may have a thickness (in the distal-facing direction) of between about 0.25 mm and 5 mm.

In use, any of the apparatuses shown herein may be configured to apply energy (e.g., nsPEF) to a tissue. For example, any of these apparatuses may be used to treat a tissue such as skin, liver, lung, breast, etc., or treat a disorder or disease such as cancer. For example, any of these apparatuses may be configured to apply energy to treat a disease, for example, a disease related to dermatology and/or oncology, such as skin cancer, cherry angioma, warts, keloids/scars, aging skin, molluscum angioma, necrobiosis lipoidica (NBL), melisma, lipoma epidermal/sebaceous cyst, basal cell carcinoma.

The use of an applicator tip having a retractable needle housing as described herein may be particularly beneficial. For example, the apparatus may be configured to conform to an irregularly-shaped or textured surface while preventing arcing, which may otherwise be undesirable and painful to the subject. For example, FIGS. 18A-18F illustrate the use of a retractable (biased) needle housing extending from the distal end of the apparatus. In FIG. 18A, the distal end of the applicator tip 1803 is brought in proximity to the tissue 1831, in which a target region 1857 to be treated is present. Thus, the entire applicator tip may be driven with force 1859 against the tissue, as shown in FIG. 18B, first to contact the tissue, then to continue to apply force 1861, which may allow the soft (e.g., semi-compliant) distal-facing insulator of the applicator tip 1803 to conform to the surface of the tissue 1831 to be treated. Distally-directed force 1861 may be applied, as shown in FIGS. 18C-18D, to drive the needles 1805 into the tissue while pushing and retracting the needle housing proximally, allowing the needles to penetrate the tissue and the insulator to insulate between them. Once the needles have been positioned (in this example in FIG. 18E to a maximum depth allowed by the retracted needle housing), power, including in particular nsPEF therapy, may be applied. Thereafter, the applicator tip may be withdrawn, as shown in FIG. 18F by arrow 1863; any therapeutic effect on the target region 1857 may result either immediately or within a reasonably short time period.

In FIGS. 18A-18F, the distal-facing, soft insulating end (e.g., cover) on the needle housing is sufficiently soft that it deforms to fit the tissue, as shown in FIGS. 18B-18C. For example, the durometer of the soft, insulating cover may be less than about of 60 or less on the Shore A hardness scale (e.g., about 55 or less, about 50 or less, about 45 or less, about 40 or less, etc.). Alternatively, in some variations the hardness of the insulating cover may be greater than the hardness of the tissue, so that the tissue may deform (or both the tissue and the soft insulating cover may deform). FIGS. 18G-18L illustrate an example in which the tissue and the soft insulating cover both deform. In FIG. 18G, the distal end of the applicator tip 1803' is brought in proximity to the tissue 1831', in which a target region 1857 to be treated is present. Thus, the entire applicator tip may be driven with force 1859 against the tissue, as shown in FIGS. 18H-18I, first to contact the tissue, then to continue to apply force 1861, so that the distal-facing insulator of the applicator tip 1803 pushes against the surface of the tissue to be treated; in this example, the tissue deforms slightly to match the applicator. The distal-facing insulating end of the needle housing may not be soft (e.g., semi-compliant) or it may be compliant. Thus, the needle housings described herein may include a soft distal cover, or may just be an insulating material (that is not compliant). Distally-directed force 1861, as shown in FIG. 18J, drives the needles 1805 into the tissue while pushing and retracting the needle housing proximally, allowing the needles to penetrate the tissue and the insulator to press against the tissue and insulate between the needles. Once the needles have been positioned (in this example in FIG. 18K to a maximum depth allowed, for example, by the retracted needle housing), as shown in FIG. 18K, power, including in particular nsPEF therapy, may be applied. Thereafter, the applicator tip may be withdrawn, as shown in FIG. 18L by arrow 1863; any therapeutic effect on the target region 1857 may result either immediately or within a reasonably short time period.

Figure 19:
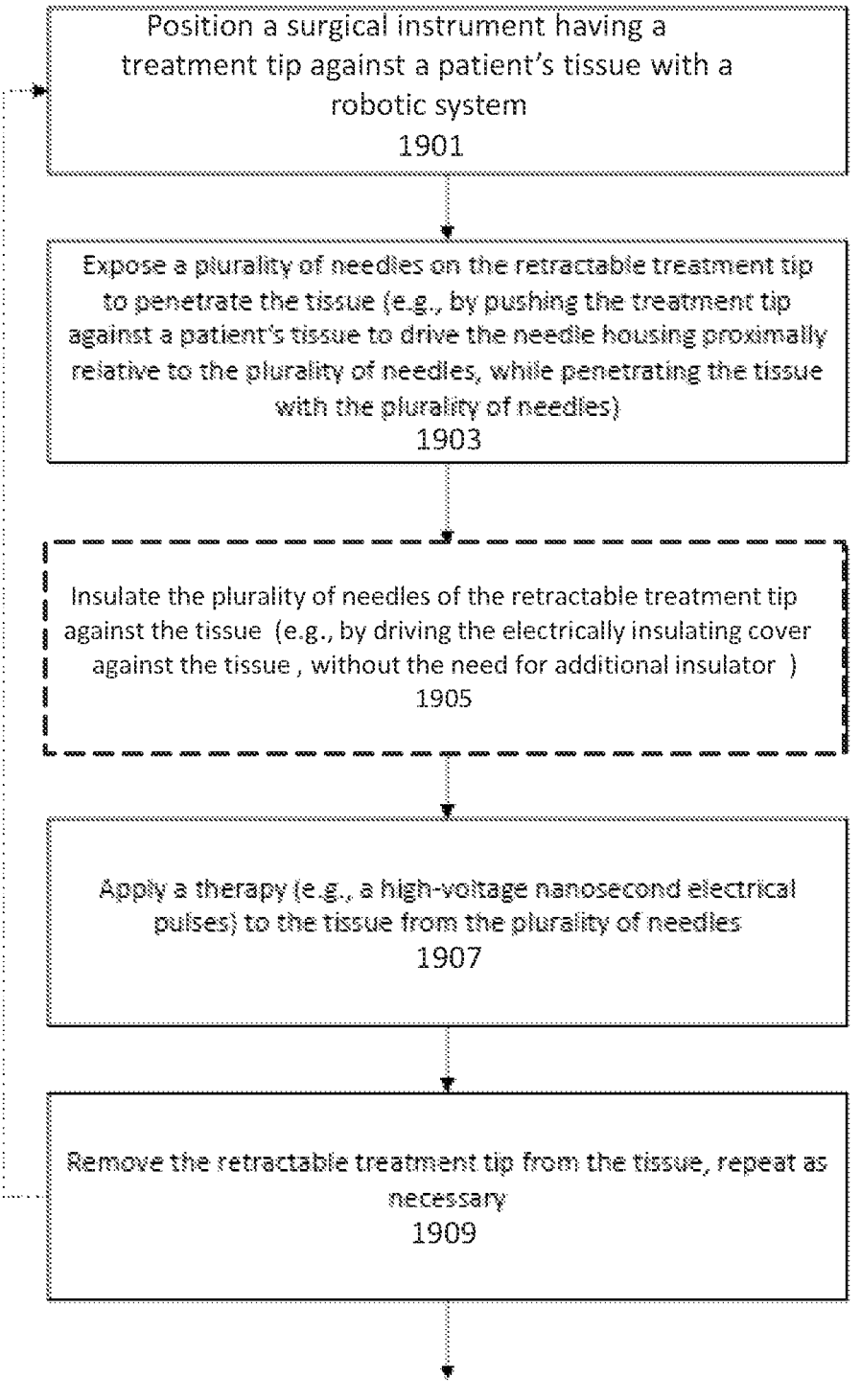
FIG. 19 is a schematic diagram illustrating an example of a method of applying high-voltage pulse electrical therapy as described herein.

FIG. 19 illustrates a flowchart of an example of a general method of treatment. In FIG. 19, the method is, for example, a method of applying high-voltage nanosecond pulse electrical therapy to treat a subject. The method may include, as a preliminary step 1901, initially positioning a surgical instrument having retractable treatment tip against a subject's tissue with a robotic system. The surgical system can comprise, for example, any of the robotic systems described above, including robotic systems having a master/slave relationship and also including fully automated robotic systems, for example, where a processor directs operation of the robotic system, but user may provide input or override automated operation as needed. In step 1903, a plurality of needles of a retractable treatment tip is exposed such that the plurality of needles may penetrate the tissue. In some embodiments, for example, the treatment tip may be pushed against the subject's tissue with a force that is greater than the bias force to drive the needle housing proximally relative to the plurality of needles while penetrating the tissue with the plurality of needles and driving the electrically insulating cover against the tissue to electrically isolate the plurality of needles from each other. Alternatively or additionaly, the necedle electrodes may be deployed by releasing a bias (or by appying a force) to drive the needle electrodes distally relative to the needle housing, exposing them and simultanously, when the distal face of the needle hosuing is held agianst the tissue, into the tissue.

In general, the retractable treatment tip may be any of the applicator tips (treatment tips) described herein, particularly those including a needle or plate electrode extending from a distal end of a treatment tip housing. The retractable treatment tip may be integrated into a surgical instrument and be configured to be coupled or mounted to the robotic system. The retractable treatment tip may also comprise a bias, for example, a bias driving the needle housing distally with a bias force, and a plurality of treatment needle electrodes within the needle housing. The retractable treatment tip may also comprise an insulator, for example, a distal insulating cover covering the needles within the needle housing. In step 1905 (which may occur, for example, simultaneously with the step 1903), the plurality of needles are insulated against the tissue. In some embodiments, the needles may be insulated with the use of an insulator (e.g., insulating cover, or insulating material), or with the use of one or more vacuum ports, or both.

Once the treatment needle electrodes are inserted into the tissue (e.g., skin) to the desired depth, including fully deployed as limited by the needle housing full retraction position, in step 1907 a therapy, such as electrical energy therapy, may be applied to the tissue. For example, high-voltage nanosecond electrical pulses may be applied to the tissue from the plurality of needles. As mentioned above, the step of applying energy may be done without the need for any additional insulator or insulating material (e.g., gel) between the applicator tip and the tissue. Upon completion of the application of energy, in step 1909 the tip may be removed from the tissue (e.g., by withdrawing the applicator tip). If there are additional regions to be treated, the applicator tip may be removed to the new location, typically on the same person, or they may be completely removed.

Figure 20:
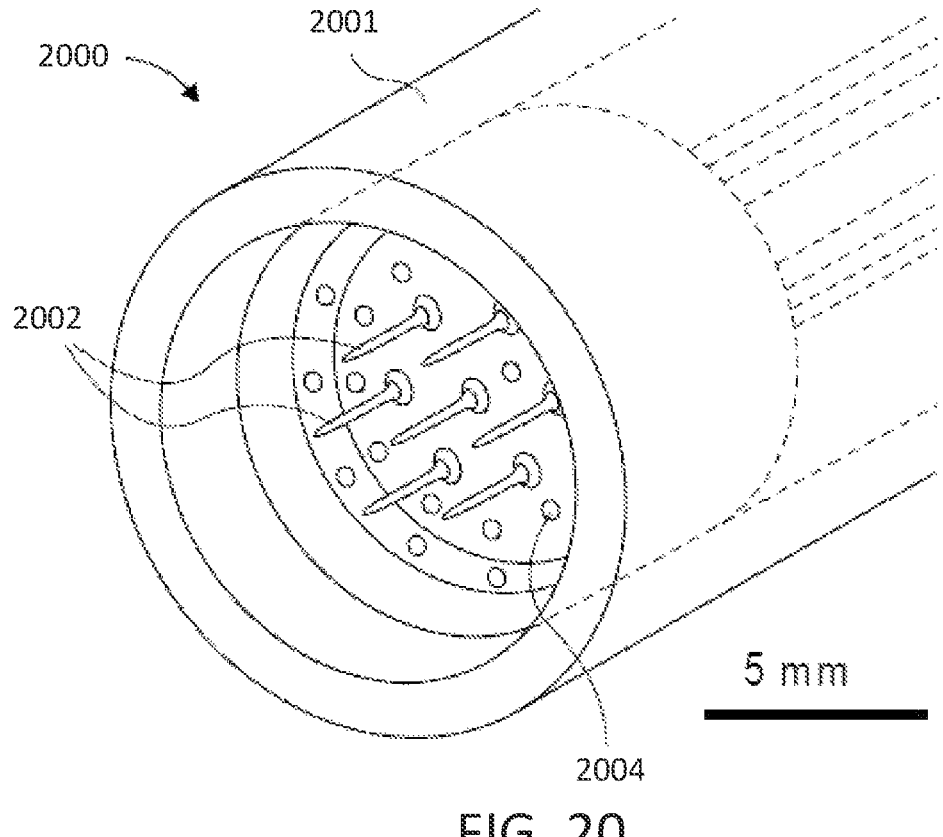
FIG. 20 illustrates a perspective view of a seven-needle electrode in accordance with an embodiment.

FIG. 20 illustrates a perspective view of a seven-needle suction electrode 2000 in accordance with an embodiment. The suction electrode can be integrated into a surgical instrument and is configured to be coupled or mounted to a robotic system, as described above. In electrode 2000, sheath 2001 surrounds seven sharp terminals 2002 with a broad opening at a distal end. When the open end is placed against a tumor, air is evacuated from the resulting chamber through vacuum holes 2004 to draw the entire tumor or a portion thereof into the chamber. The tumor is drawn so that one or more of the terminals 2002 preferably penetrates the tumor. Sharp ends of the terminals 2002 are configured to pierce the tumor. The center terminal 2002 may be at one polarity, and the outer six terminals 2002 may be at the opposite polarity. For example, nanopulsed electric fields can then be precisely applied to the tumor using a nsPEF system.

The terminals 2002 can be opposed, one of each positive and negative pair of terminals 2002 on one side of a tumor and the other electrode of the pair on an opposing side of the tumor. Opposing sides of a tumor can include areas outside or within a tumor, such as if a needle terminal 2002 pierces a portion of the tumor.

Figure 21:
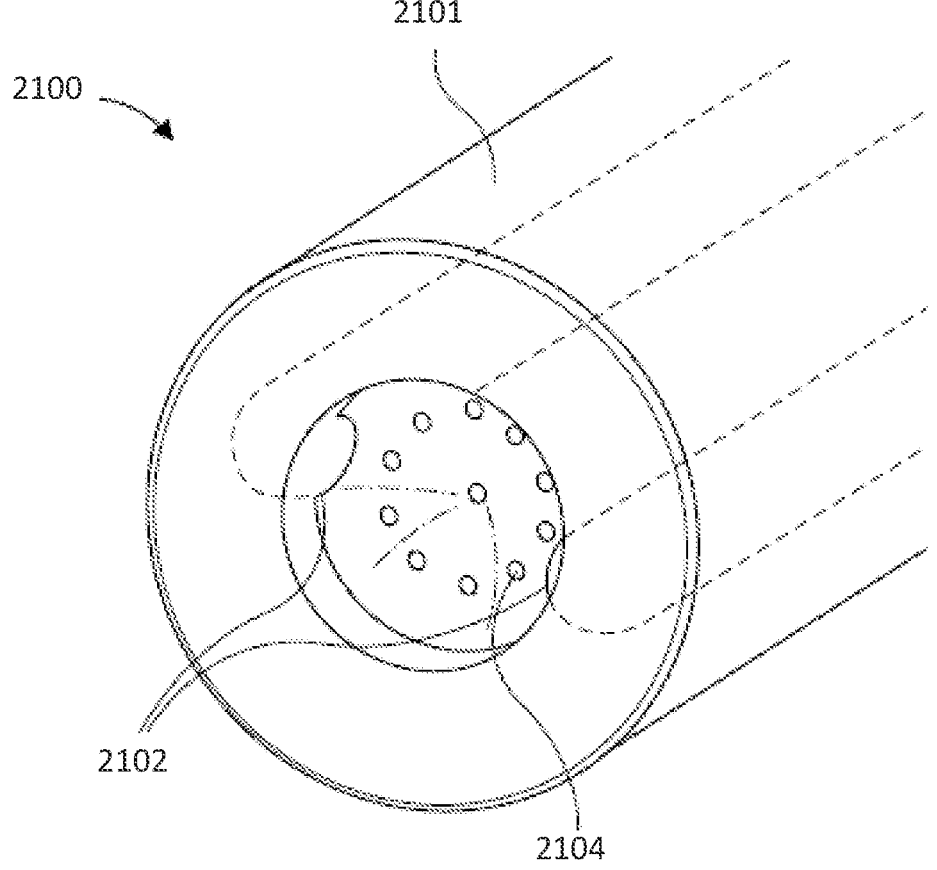
FIG. 21 illustrates a perspective view of a two-pole electrode in accordance with an embodiment.

FIG. 21 illustrates a two-pole suction electrode 2100 in accordance with an embodiment. The suction electrode can be integrated into a surgical instrument and is configured to be coupled or mounted to a robotic system, as described above. In electrode device 2100, sheath 2101 surrounds two broad terminals 2102 on opposite sides of a chamber. When air is evacuated through vacuum holes 2104 and a tumor is pulled within the chamber, the opposing terminals 2102 apply nsPEF pulses to the tumor.

The nature of the electrode used mainly depends upon the shape of the tumor. Its physical size and stiffness can also be taken into account in selection of a particular electrode type.

U.S. Pat. No. 8,688,227 B2 (to Nuccitelli et al.) discloses other suction electrode-based medical instruments and systems for therapeutic electrotherapy, and it is hereby incorporated by reference.

If there are multiple tumors in a subject, a surgeon can select a single tumor to treat based on the tumor's compatibility with electrodes. For example, a tumor that is adjacent to a stomach wall may be more easily accessible than one adjacent a spine or the brain. Because a nsPEF pulse is preferably applied so that the electric field transits through as much tumor mass as possible while minimizing the mass of non-tumor cells that are affected, a clear path to two opposed 'poles' of a tumor may also be a selection criterion.

For tumors on or just underneath the skin of subject, needle terminals can be used percutaneously. For locations deeper within a subject, a retractable terminal can fit onto a robotic surgical system or into a gastroscope, bronchoscope, colonoscope, or other endoscope or laparoscope. For example, a robotic system equipped with the retractable needle terminals can access tissues within the body via a single port or minimally invasive robotic assisted surgery.

Figure 22:
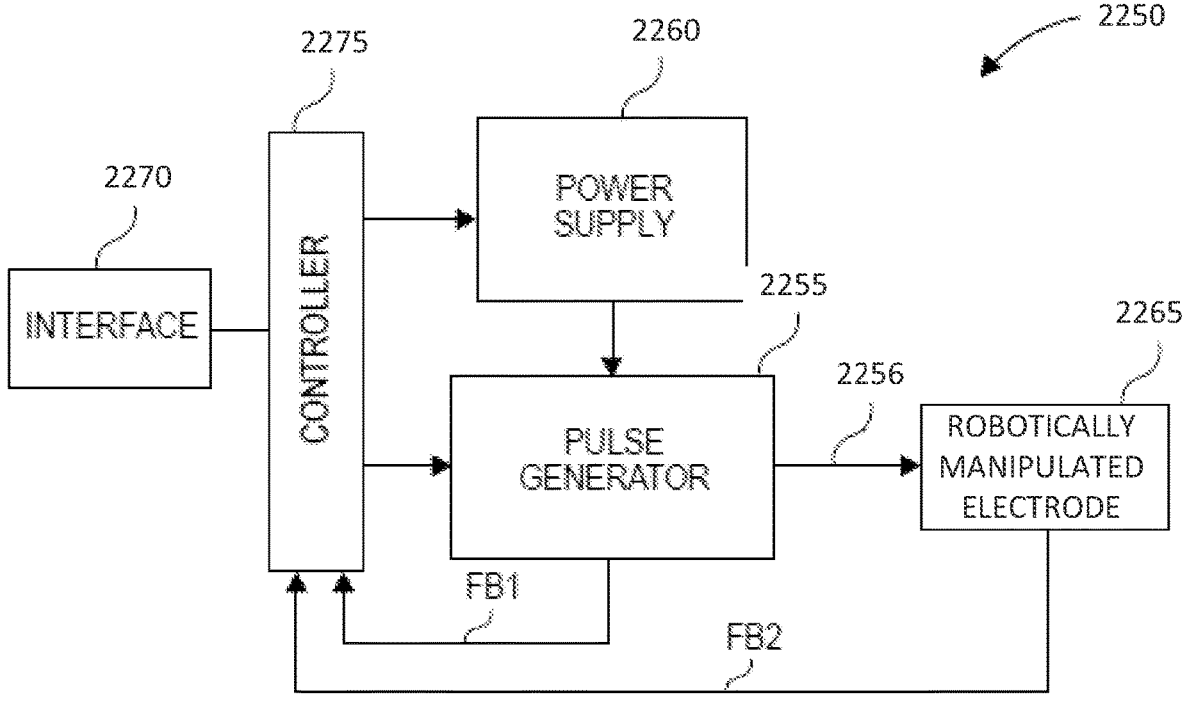
FIG. 22 is a block diagram of an example of nsPEF treatment system.

FIG. 22 is a block diagram of a nsPEF treatment system 2200. NsPEF treatment system 2200 includes pulse generator 2255, power supply 2260, robotically manipulated electrode 2265, interface 2270, and controller 2275.

Pulse generator 2255 may be similar or identical to any of the pulse generator circuits discussed herein. For example, pulse generator 2255 may be configured to generate pulses having a voltage magnitude corresponding with power voltages received from power supply 2260 and having pulse widths and other characteristics corresponding with control signals received from controller 2275. In alternative embodiments, other pulse generator circuits may be used.

Robotically manipulated electrode 2265 may be similar or identical to any of the electrodes discussed herein. The robotically manipulated electrode 2265 can be integrated into a surgical instrument that is mounted or coupled to a robotic system, as described above. Electrode 2265 is configured to receive nsPEF pulses generated by pulse generator 2255 from conductor 2256 and is configured to deliver nsPEF pulses to a patient undergoing therapeutic nsPEF treatment. In alternative embodiments, other therapeutic electrodes may be used.

Power supply 2260 is configured to provide power voltages to pulse generator 2255. In some embodiments, power supply 2260 generates and provides power voltages which have a voltage level corresponding with a control signal from controller 2275.

Interface 2270 is configured to receive input from a user identifying various parameters and characteristics of the nsPEF pulses to be applied to the patient. For example, interface 2270 may be configured to receive input identifying or specifying values for one or more characteristics of one or more nsPEF pulses to be applied to the patient. For example, the characteristics may include one or more of an amplitude, a polarity, a width, a rise time, and a fall time of one or more nsPEF pulses to be applied to the patient. Additionally or alternatively, the characteristics may include one or more of a frequency and a pulse quantity of a sequence of nsPEF pulses to be applied to the patient. Furthermore, the characteristics may additionally or alternatively include a result of the nsPEF pulses to be applied to the patient, such as a maximum temperature for the treated tissue of the patient. Other characteristics may additionally or alternatively be identified or specified by the received input.

In addition, interface 2270 is configured to communicate the characteristics identified or specified by the received input to controller 2275.

Controller 2275 is configured to generate and provide one or more control signals to pulse generator 2255 and to power supply 2260 based at least partly on the communicated characteristics received from interface 2270. Additionally, pulse generator 2255, power supply 2260, and robotically manipulated electrode 2265 are collectively configured to, in response to the control signals from controller 2275, generate nsPEF pulses having characteristics corresponding with the control signals. Examples of the controllers that can be used with various examples of the present discloser are described in the co-owned patent publication 2017/0245928, which is incorporated herein by reference.

In this embodiment, one or both of pulse generator 2255 and robotically manipulated electrode 2265 are configured to generate feedback signals FB1 and FB2 corresponding with or representing measured parametric characteristics of the nsPEF pulses applied to the patient. In some embodiments, the parametric characteristics of the nsPEF pulses represented by the feedback signals FB1 and FB2 include one or more of an amplitude, a polarity, a width, a rise time, and a fall time of the nsPEF pulses. Additionally or alternatively, the parametric characteristics may include a frequency of a sequence of nsPEF pulses. Furthermore, the parametric characteristics may additionally or alternatively include a temperature and/or impedance of the treated tissue of the patient. The feedback signals FB1 and FB2 may correspond or represent other measured parametric characteristics of one or more of the nsPEF pulses applied to the patient, the patient, the environment, and the nsPEF treatment system 2250.

In some embodiments, controller 2275, power supply 2260, pulse generator 2255, and robotically manipulated electrode 2265 collectively form a feedback loop which causes one or more parametric characteristics of the nsPEF pulses applied to the patient to have measured values substantially equal (e.g. within 10% or 1%) to the values of corresponding characteristics identified in the input received by interface 2270.

For example, interface 2270 may receive input specifying a value of 15 kV for an amplitude of the nsPEF pulses applied to the patient. In addition, the controller 2275 may be configured to, in response to a feedback signal FB2 from electrode 2265 or a feedback signal FB1 from pulse generator 2255 indicating that the measured amplitude of the nsPEF pulses applied to the patient is less than (or greater than) 15 kV, change a control signal provided to power supply 2260. In response to the changed control signal, power supply 2260 may be configured to increase (or decrease) the voltage of power signals provided to pulse generator 2255 such that the amplitude of the nsPEF pulses generated and applied to the patient increases (or decreases) to or toward 15 kV. In another example, the controller of the robotic system can move the robotically manipulated electrode based on feedback from the electrode, such as temperature data from the electrode or information related to impedance.

Similarly, interface 2270 may receive input specifying a value of 150 ns for a pulse width of the nsPEF pulses applied to the patient. The controller 2275 may be configured to, in response to a feedback signal FB2 from robotically manipulated electrode 2265 or a feedback signal FB1 from pulse generator 2255 indicating that the measured pulse width of the nsPEF pulses applied to the patient is greater than (or less than) 150 ns, change a control signal provided to pulse generator 2255. In response to the changed control signal, pulse generator 2255 may be configured to generate and apply to the patient nsPEF pulses having decreased (or increased) pulse width. As a result, the feedback signal FB1 or FB2 causes the controller 2275 to generate control signals which cause the pulse generator 2255 to generate and apply nsPEF pulses having pulse widths decreased (or increased) to or toward 150 ns.

In some embodiments, the feedback loop is controlled using a Proportional-Integral-Derivative (PID) method. For example, controller 2275 may be configured to continuously or substantially continuously calculate an error value as the difference between a desired value perceived at interface 2270 and a corresponding measured parameter. In addition, controller 2275 may be configured to continuously or substantially continuously calculate the control signals as a sum of one or more of: a first constant times the error signal, a second constant times an integral of the error signal, and a third constant times a derivative of the error signal.

In some embodiments, the feedback loop is controlled using a lookup table to determine a next value based on a measured value. In some embodiments, the feedback loop is controlled by reducing or increasing a value by a fixed amount or step size based on a determination of whether a measured value is greater than or less than a threshold.

Figure 23:
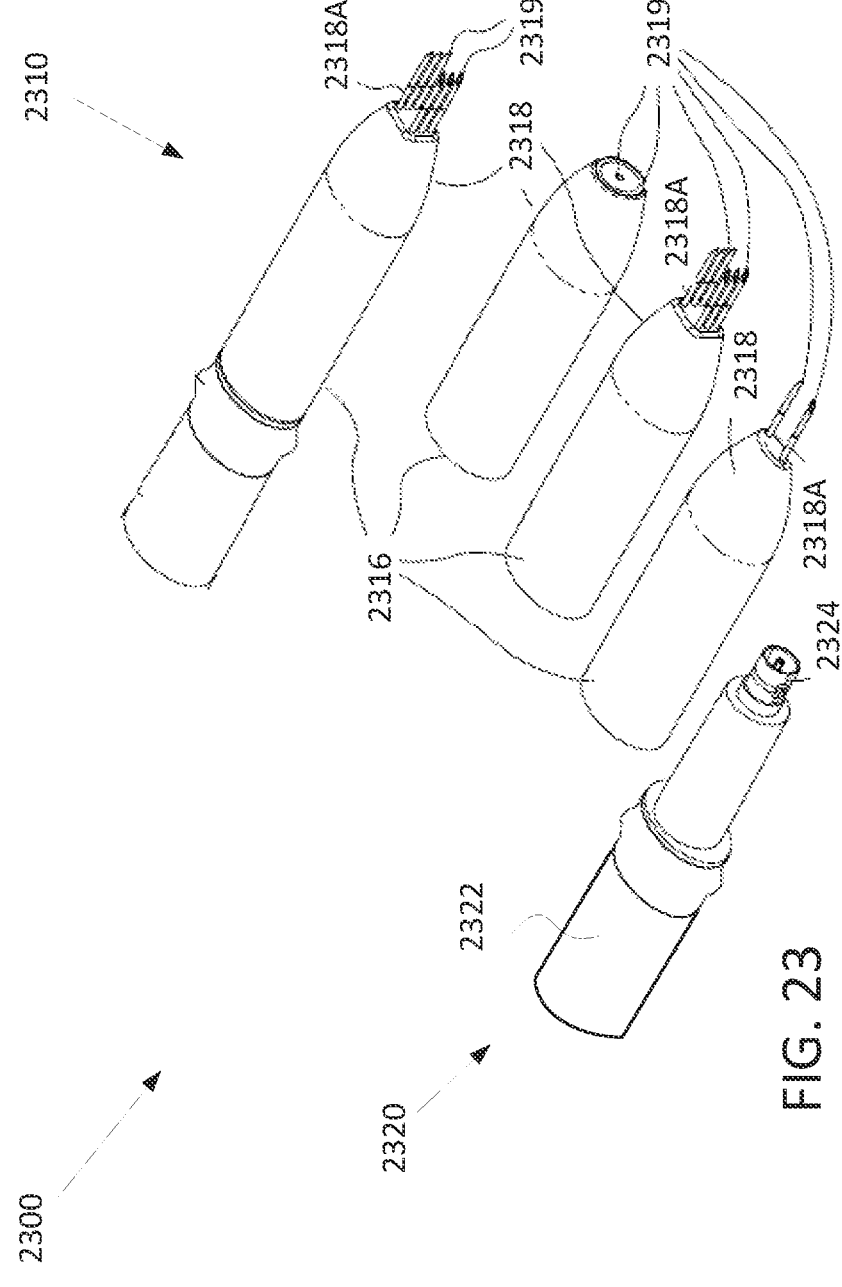
FIG. 23 is an illustration of an electrode which may be used in the electric stimulation treatment systems discussed herein.

FIG. 23 is an illustration of an electrode 2300 which may be used in the robotic surgical systems discussed herein. The electrode 2300 can be mounted on or integrated into a surgical instrument that is coupled or mounted to a robotic surgical system. For example, electrode 2300 may be used to treat a patient with nsPEF pulses. Electrode 2300 includes therapeutic electrode terminals 2319, which are electrically connected to a pulse generator (not shown) through tip 2316 and shaft 2322.

Electrode 2300 is illustrated in complete form as 2310, with the tip 2316 installed over connector 2320. Electrode 2300 includes shaft 2314 and removable, and in some embodiments, disposable, tip 2316. Several embodiments of tips 2316 are illustrated. Other embodiments are contemplated. Tips 2316 include an electrically insulative portion 2318 and an electrically conductive terminals 2319 configured to contact the patient, for example by piercing tissue, and deliver nsPEF pulses to the patient at the points of contact.

In some embodiments, insulative portion 2318 includes extensions 2318A, which each surround a portion of one of the electrically conductive terminals 2319. In some embodiments, the lengths of the extensions 2318A are adjustable with respect to the surface of insulative portion 2318 from which they extend, such that the exposed portion of the electrically conductive terminals 2319 is adjustable. In some embodiments, the lengths of the electrically conductive terminals 2319 are additionally or alternatively adjustable with respect to the surface.

In some embodiments, the exposed electrically conductive terminals 2319, which contact the patient, are adjustable. For example, a distance the conductive terminals 2319 extend from the insulative portions 2318 may be adjustable. In some embodiments, the distance conductive terminals 2319 extend from the insulative portion 2318 is controlled by moving conductive terminals 2319 with respect to insulative portion 2318, which is fixed with respect to shaft 2222. In some embodiments, the distance conductive terminals 2319 extend from the insulative portion 2318 is robotically controlled by moving insulative portion 2318 with respect to conductive terminals 2319, which are fixed with respect to shaft 2222. Additionally or alternatively, a distance between adjacent conductive terminals 2319 may be adjustable.

Connector 2320 includes a shaft 2322 and a high-voltage conductive portion 2324 to provide a high-voltage to the electrically conductive terminals 2319 of electrode 2310.

Figure 24:
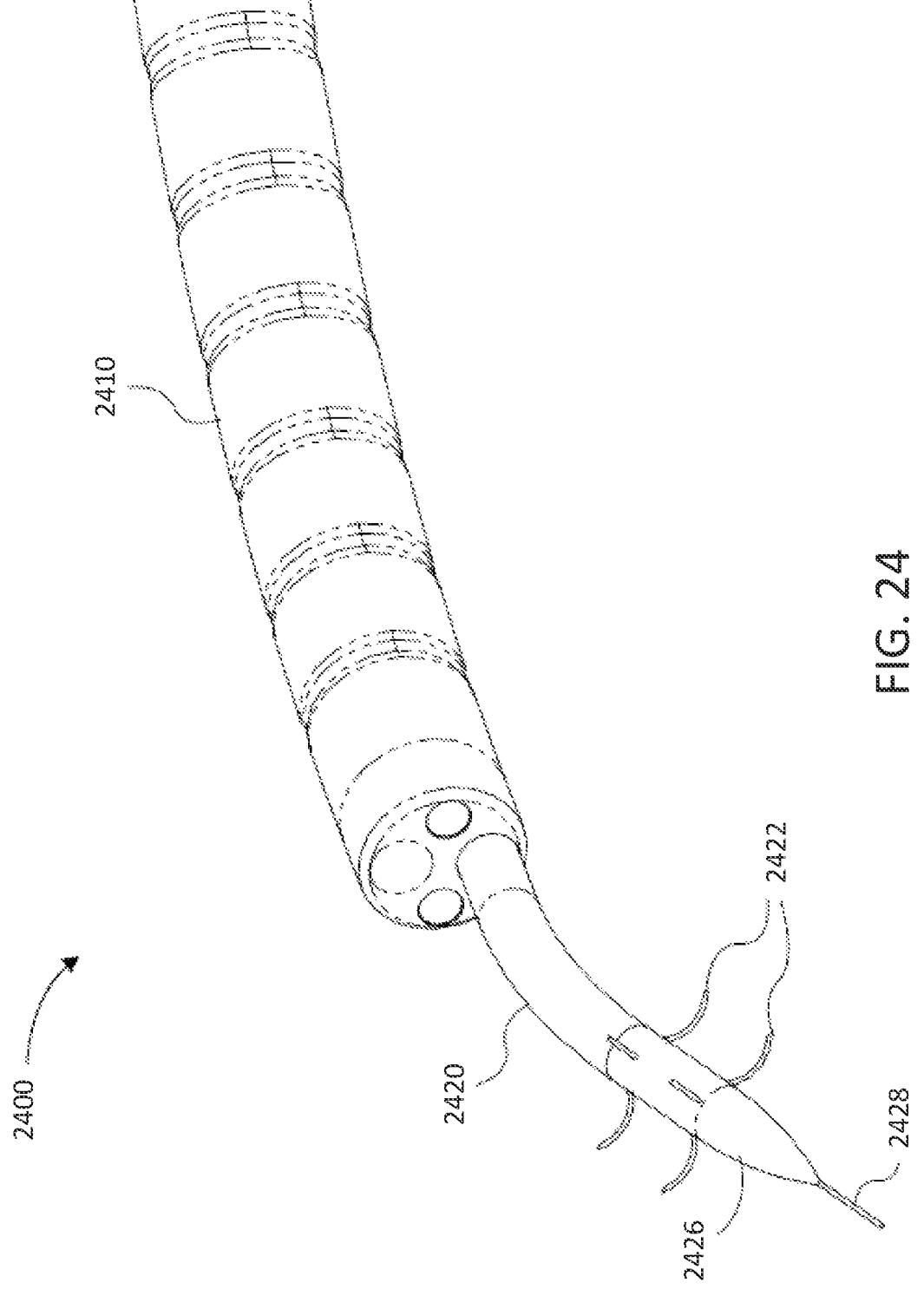
FIG. 24 is an illustration of an instrument which may be used, for example, in the nsPEF treatment systems discussed herein.

FIG. 24 is an illustration of instrument 2400 which may be used in the treatment systems, such as nsPEF treatment systems, or robotic surgical systems discussed herein. In one embodiment, the instrument 2400 is particularly suited for a robotic surgical system that performs NOTES or minimally invasive surgical procedures, as described above. For example, instrument 2400 may be used, for example, as a robotically controlled instrument mounted to a robotic arm of a robotic surgical system. In this illustrated embodiment, electrode 2420 is connected to endoscope 2410. For example, electrode 2420 may be routed through a lumen in the endoscope 2410. In one embodiment, the endoscope is mounted to the robotic arm of a robotic surgical system and the electrode 2420 is routed through a lumen in the endoscope.

Electrode 2420 includes insulative portion 2426 and positive and negative electrically conductive terminals 2422. In some embodiments, electrode 2420 also includes needle 2428 to help electrode 2420 penetrate through tissue.

Any of the electrodes discussed herein may include a thermocouple thermally connected to either of its terminals.

Figures 25A, 25B:
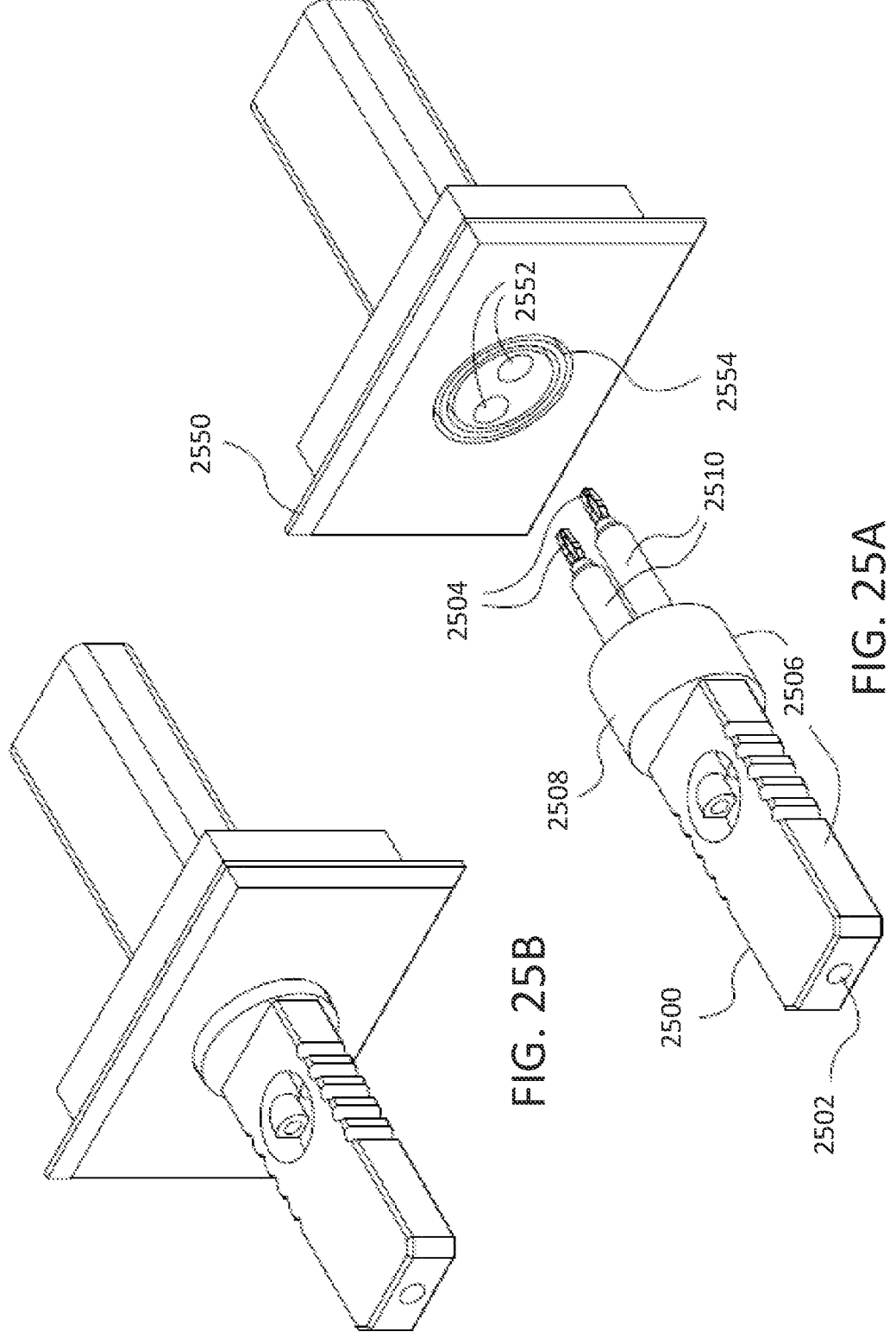
FIG. 25A is an illustration of a connector configured to be mated with a housing cutaway portion.
FIG. 25B is an illustration of a connector configured to be mated with a housing cutaway portion.

FIGS. 25A and 25B are illustrations of a connector 2500 configured to be mated with a housing cutaway portion 2550. Connector 2500 may, for example, be used in a robotic surgical system to connect an electrode to a robotic arm of the robotic system. When mated, connector 2500 electrically connects an electrode with the electronic components internal to the robotic system, such as an nsPEF pulse generator. FIG. 25A illustrates connector 2500 and cutaway portion 2550 in an unmated position. FIG. 25B illustrates connector 2500 and cutaway portion 2550 in a mated position.

Connector 2500 may include a hole 2502 configured to receive a cable electrically contacting an electrode. Connector 2500 also includes a shaft 2506 which includes internal conductors which electrically connect terminals 2504 with the cable. Shaft 2506 can also include an insulating safety structure, such as a standoff skirt 2508, which is configured to provide at least a minimum clearance distance $d_{min\_robot}$ along a surface of connector 2500 and terminals 2504 without increasing the total length of the connector 2700 or the actual physical distance between the terminals 2504 and conductive structures on the robotic surgical system.

A "minimum clearance distance from conductive structures on the robotic surgical system" ($d_{min\_robot}$) as used in the present disclosure includes a shortest distance that avoids an arc both in the air or along an insulative material surface path to conductive structures on the robotic surgical system. In other words, $d_{min\_robot}$ includes a distance that is a greater of the following two distances: 1) a shortest distance or path that prevents an arc between two conductive parts measured along any surface or combination of surfaces of an insulating material, and 2) a shortest path in air between two conductive parts that prevents an arc. Addition of a standoff skirt, like the skirt 2508, also allows one to reduce the total length of the connector while providing a desired $d_{min\_robot}$.

In some embodiments, the minimum clearance distance is equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

As shown, terminals 2504 are spaced apart from shaft 2506 by spacers 2510, for example, by a distance greater than 1 inch.

As shown, housing cutaway portion 2550 includes terminal receptacle holes 2552, which are configured to receive terminals 2504 of connector 2500 when connector 2500 is mated with housing cutaway portion 2550. In this embodiment, housing cutaway portion 2550 also includes one or more skirt receptacle holes 2554, which is configured to receive standoff skirt 2508 of connector 2500 when connector 2500 is mated with housing cutaway portion 2550.

To increase the distance of a shortest path along the surface of connector 2500 between electrically conductive terminals 2504 and conductive structures on the robotic surgical system, in this embodiment, standoff skirt 2508 includes two concentric ring portions. The concentric ring portions surround both spacers 2510 and may be centered between the two spacers 2510. In addition, housing cutaway portion 2550 includes two skirt receptacle holes 2554. In alternative embodiments, a connector has just one or more than two concentric ring portions and a corresponding housing cutaway portion has just one or more than two skirt receptacle holes.

Figure 26A:
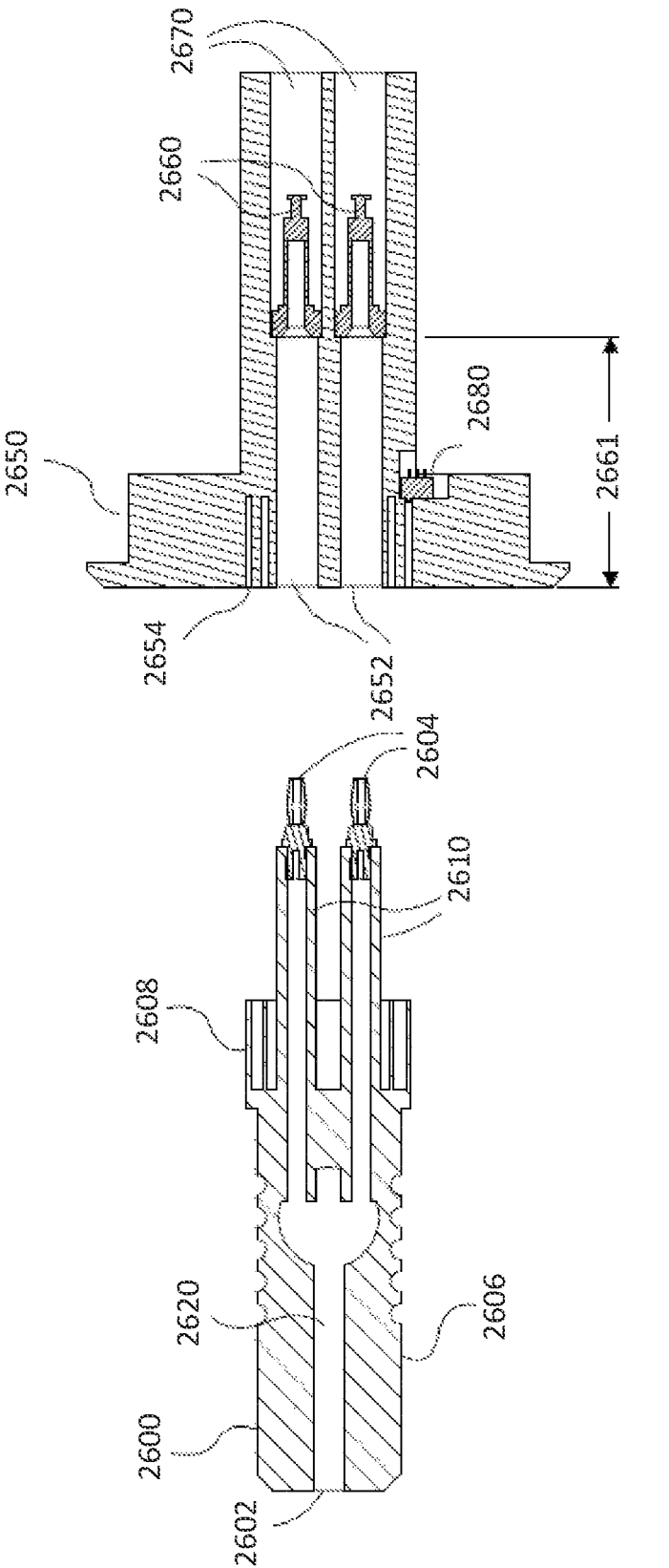
FIG. 26A is an illustration of a cross-sectional view of a connector and a housing cutaway portion.
Figure 26B:
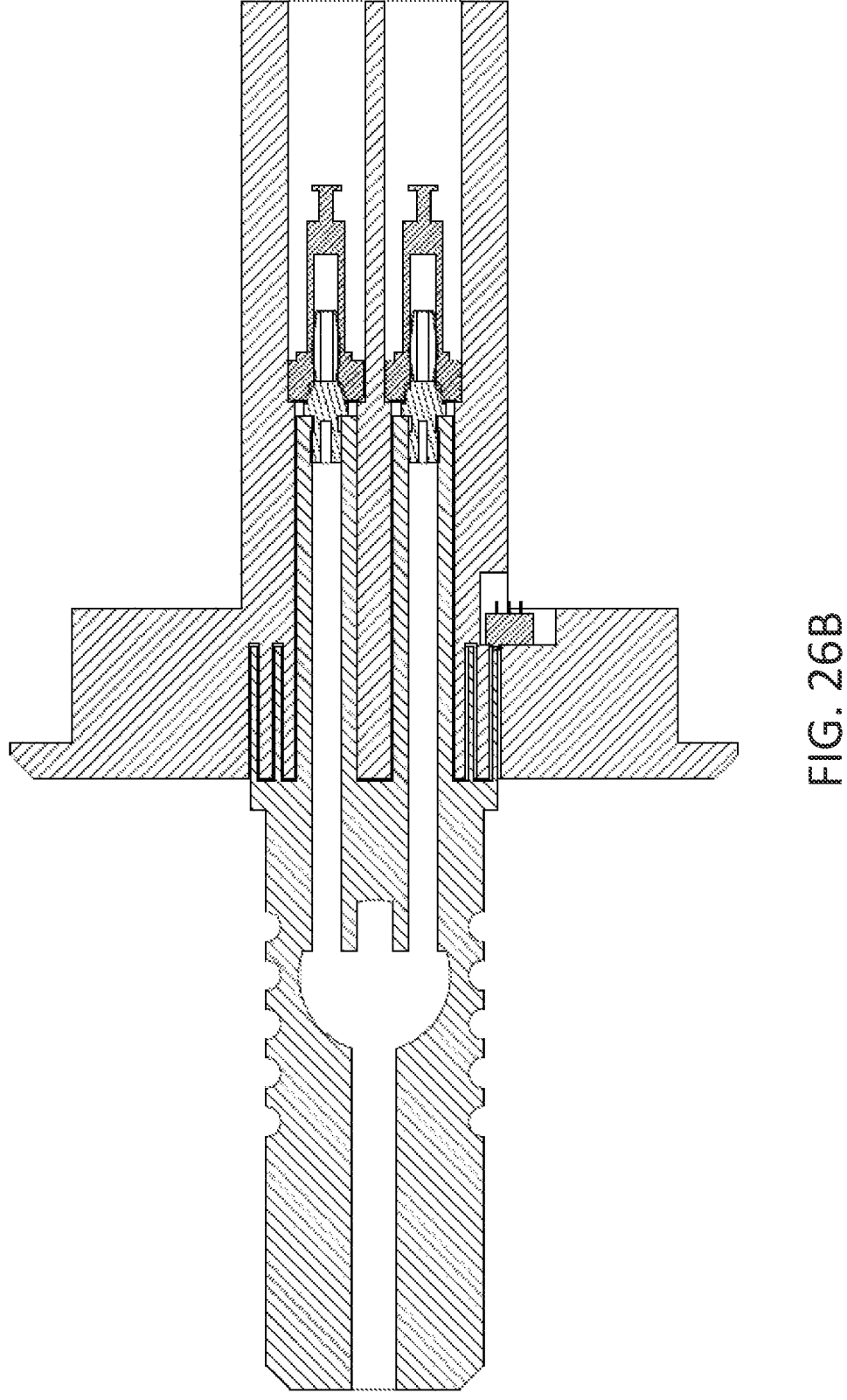
FIG. 26B is an illustration of a cross-sectional view of a connector and a housing cutaway portion.
Figure 26C:
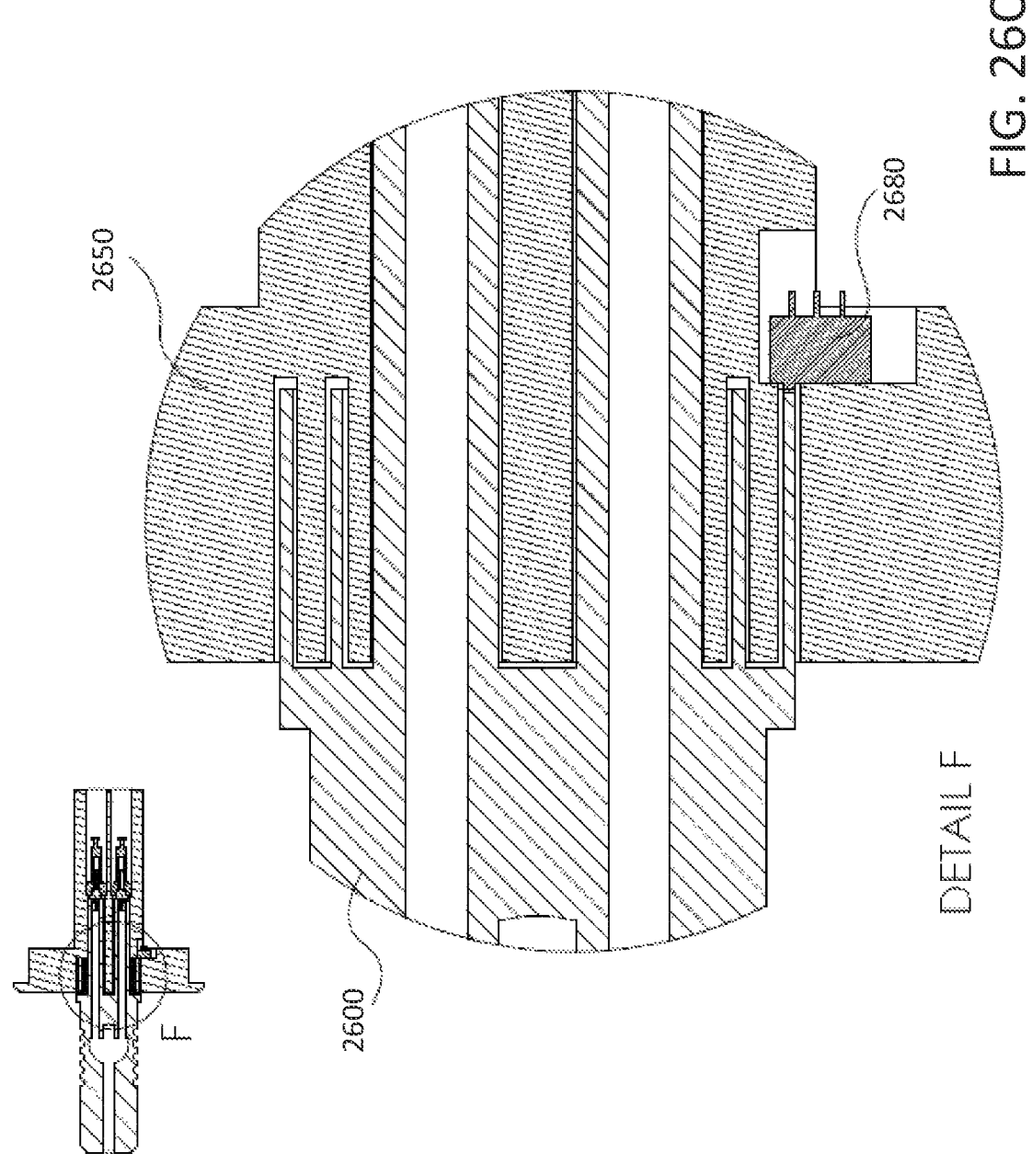
FIG. 26C is an illustration of a cross-sectional view of a connector and a housing cutaway portion.

FIGS. 26A, 26B, 26C, and 26D are illustrations of a cross-sectional view of connector 2600 and housing cutaway portion 2650. The plane of the cross-sectional view is defined by the axis of the terminal receptacle holes 2552 illustrated in FIG. 25A. FIG. 26A illustrates connector 2600 and cutaway portion 2650 in an unmated position. FIGS. 26B and 26C illustrate connector 2600 and cutaway portion 2650 in a mated position, where FIG. 26C illustrates in detail F an enlarged view of portions of connector 2600 and cutaway portion 2650.

As shown in FIG. 26A, connector 2600 includes cavity 2620 configured to include wiring (not shown) which electrically connects the cable with terminals 2604. Cavity 2620 may also include wiring to connect to one or more thermocouples connected to one or more of the terminals of the electrode.

Housing cutaway portion 2650 includes female terminals 2660 (FIG. 26A) which are configured to receive male terminals 2604 when connector 2600 and housing cutaway portion 2650 are in the mated position. Setback distance 2661 is from a face of housing 2650 to terminals 2660.

Cutaway portion 2650 also includes cavities 2670 which are configured to include wiring (not shown) which electrically connects terminals 2660 with the electronic components internal to the housing. As a result, when in the mated position, the electronic components internal to the housing are electrically connected with a therapeutic electrode via terminals 2660, terminals 2604, wiring between terminals 2604 and a cable, and the cable, which is electrically connected to the therapeutic electrode.

Housing cutaway portion 2650 also illustrates electromechanical switch 2680. As a result of connector 2600 and housing cutaway portion 2650 being in the mated position, electromechanical switch 2680 assumes a conductive state indicating that the connector 2600 and the housing cutaway portion 2650 are mated. In addition, as a result of connector 2600 and housing cutaway portion 2750 being in an unmaintained position, electromechanical switch 2680 assumes a conductive state indicating that the connector 2600 and the housing cutaway portion 2650 are unmated. Electromechanical switch 2680 may be connected to a controller (not shown) which may be configured to prevent electronic components internal to the housing from applying electrical signals to terminals 2660 as a result of connector 2600 and housing cutaway portion 2650 being unmated, or may be configured to allow electronic components internal to the housing to apply electrical signals to terminals 2660 as a result of connector 2600 and housing cutaway portion 2650 being mated.

In some embodiments, electromechanical switch 2680 includes circuitry configured to interface with the controller. For example, the controller may identify the connector 2600 or an electrode connected to the connector 2600 as a result of the controller receiving identifying information from the circuitry. In some embodiments, the circuitry may be configured to count and store the number of nsPEF pulses delivered through the connector 2600.

Figure 26D:
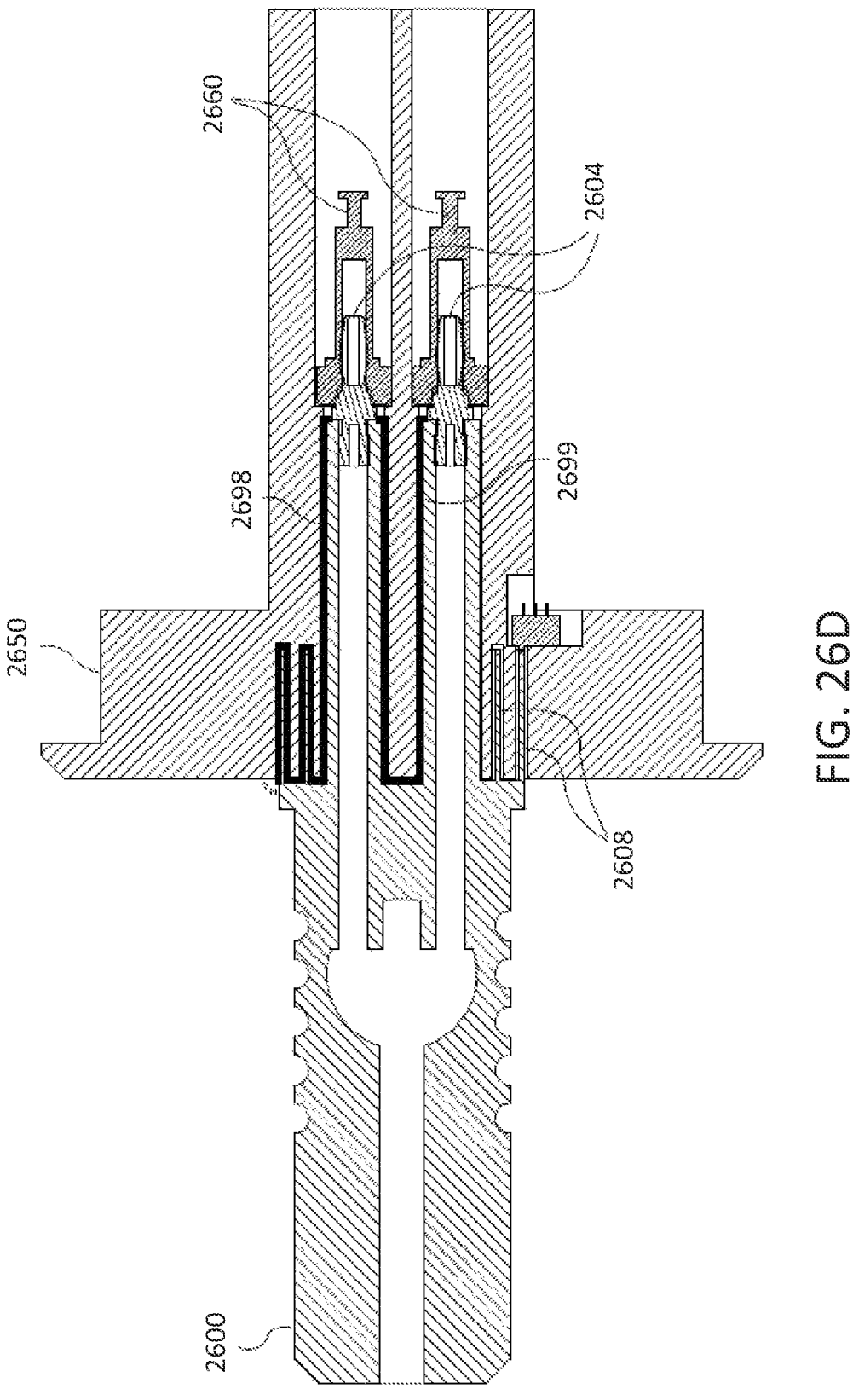
FIG. 26D is an illustration of a cross-sectional view of a connector and a housing cutaway portion with a minimum clearance distance shown.

FIG. 26D illustrate examples of minimum clearance distances. Female terminals 2660 provide electrical power to male plug terminals 2604. Terminals 2660 are shielded from or are spaced a minimum clearance distance $d_{min\_robot}$ 2698 apart from external portions of the housing which may be near conductive structures on the robotic surgical system. The minimum clearance distance may be determined based at least in part on an expected voltage applied to terminals 2660 to ensure that the voltage is insufficient to cause a shock to a conductive structure on the robotic surgical system if placed the minimum clearance distance from the terminals 2660.

Minimum clearance distance 2698 to conductive structures on the robotic surgical system are measured by following surfaces out of the receptacle's holes, around dual skirts 2608, and to conductive structures on the robotic surgical system, next to a visible seam between the connector 2600 when mated with the housing cutaway portion 2650 as shown. In some embodiments, the minimum clearance distance is at least 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

FIG. 26D also shows an example of another minimum clearance distance 2699, which representes minimum clearance distance between terminals ($d_{min\_terminals}$). This distance $d_{min\_terminals}$ is described in more detail in references to FIG. 27.

Either minimum clearance distance can be equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

Figure 27:
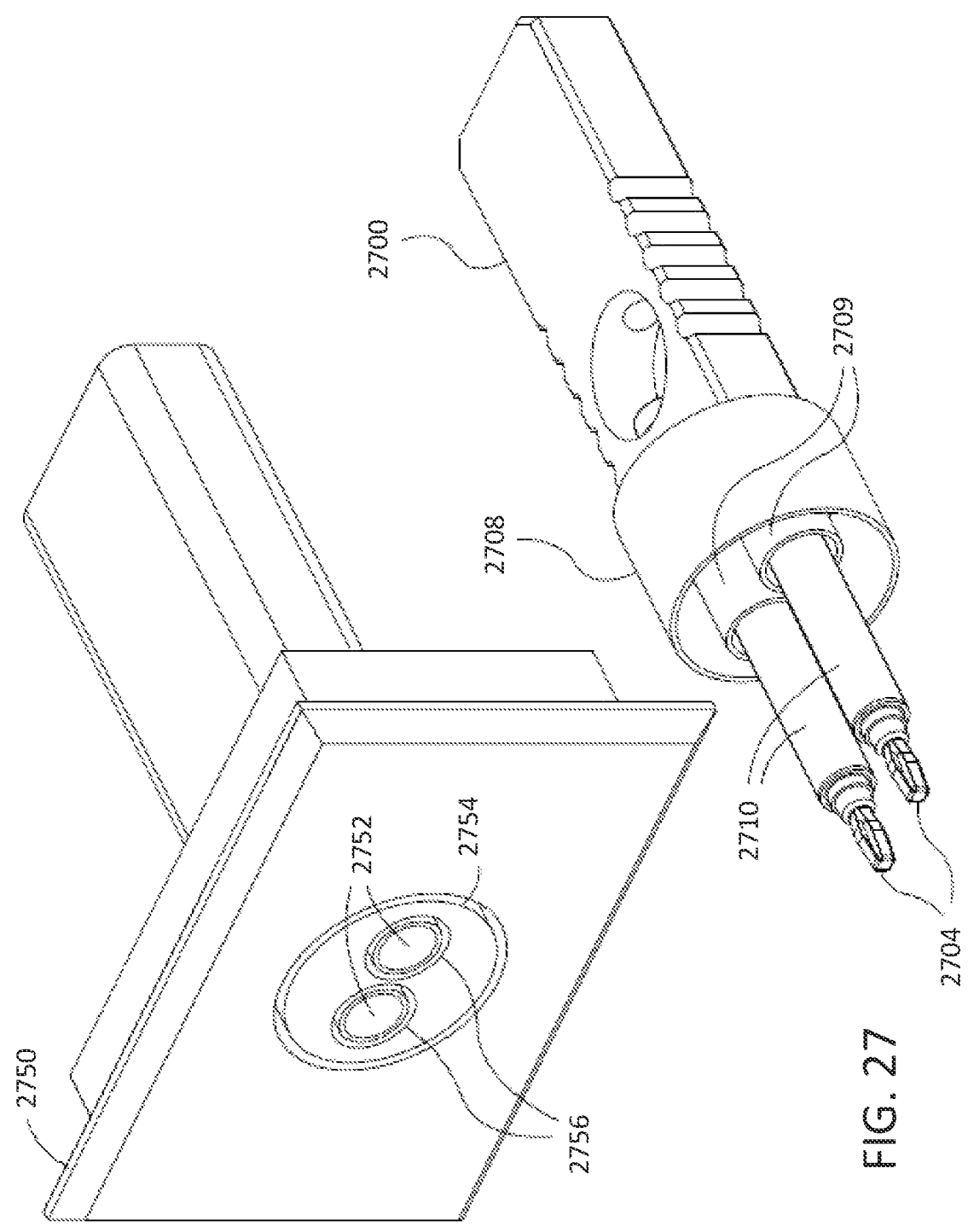
FIG. 27 is an illustration of a connector configured to be mated with a housing cutaway portion.

FIG. 27 is an illustration of connector 2700 configured to be mated with housing cutaway portion 2750. Connector 2700 may, for example, be used in a robotic surgical system to connect an electrode to a robotic arm. When mated, connector 2700 electrically connects the electrode with the electronic components internal to the robotic arm, such as an nsPEF pulse generator. FIG. 27 illustrates connector 2700 and cutaway portion 2750 in an unmated position.

As a comparison of exemplary embodiments, FIG. 25 illustrates the features and insulative structures of the present disclosure, such as the skirt 2508, configured to provide a minimum clearance distance between conductive structures on the robotic surgical system and the conductive terminals. FIG. 27 illustrates additional novel features configured to provide a minimum clearance distance 2799 between the conductive terminals themselves, such as a minimum clearance distance $d_{min\_terminals}$, shown in FIG. 26D. The minimum clearance distance $d_{min\_terminals}$ provides protection against an arc between the conductive terminals and protects, for example, a patient.

The "minimum clearance distance between the terminals" ($d_{min\_terminals}$) as used in the present disclosure includes a shortest distance that avoids an arc both in the air or along an insulating material surface path. In other words, $d_{min\_terminals}$ can include a distance that is the greater of the following two distances: 1) a shortest distance or path that prevents an arc between two conductive parts measured along any surface or combination of surfaces of an insulating material, and 2) a shortest path in air between two conductive parts that prevents an arc.

A "creepage distance" include a shortest distance that prevents arcs along the surface of the insulating material between two conductive parts, as defined by the International Electrotechnical Commission (IEC), or as otherwise known in the art. It can include the surface distance from one conductive part to another conductive part or an area accessible by a user.

"Air clearance" includes the shortest path that prevents arc in air between two conductive parts as defined by the IEC, or as otherwise known in the art. It can include the uninterrupted distance through the air or free space from one conductive part to another conductive part or an area accessible by a user.

Connector 2700 includes standoff skirt 2708, which is similar to standoff skirt 2508 of connector 2500. In addition, connector 2700 includes additional standoff skirts 2709. As shown, standoff skirts 2709 each surround a portion of one of the spacers 2710. Standoff skirts 2709 maintain a desired separation between terminals 2704.

In this embodiment, in addition to terminal receptacle holes 2752 and skirt receptacle hole 2754, housing cutaway portion 2750 also includes skirt receptacle holes 2756, which are configured to receive skirts 2709 of connector 2700 when connector 2700 is mated with housing cutaway portion 2750.

Figure 28A:
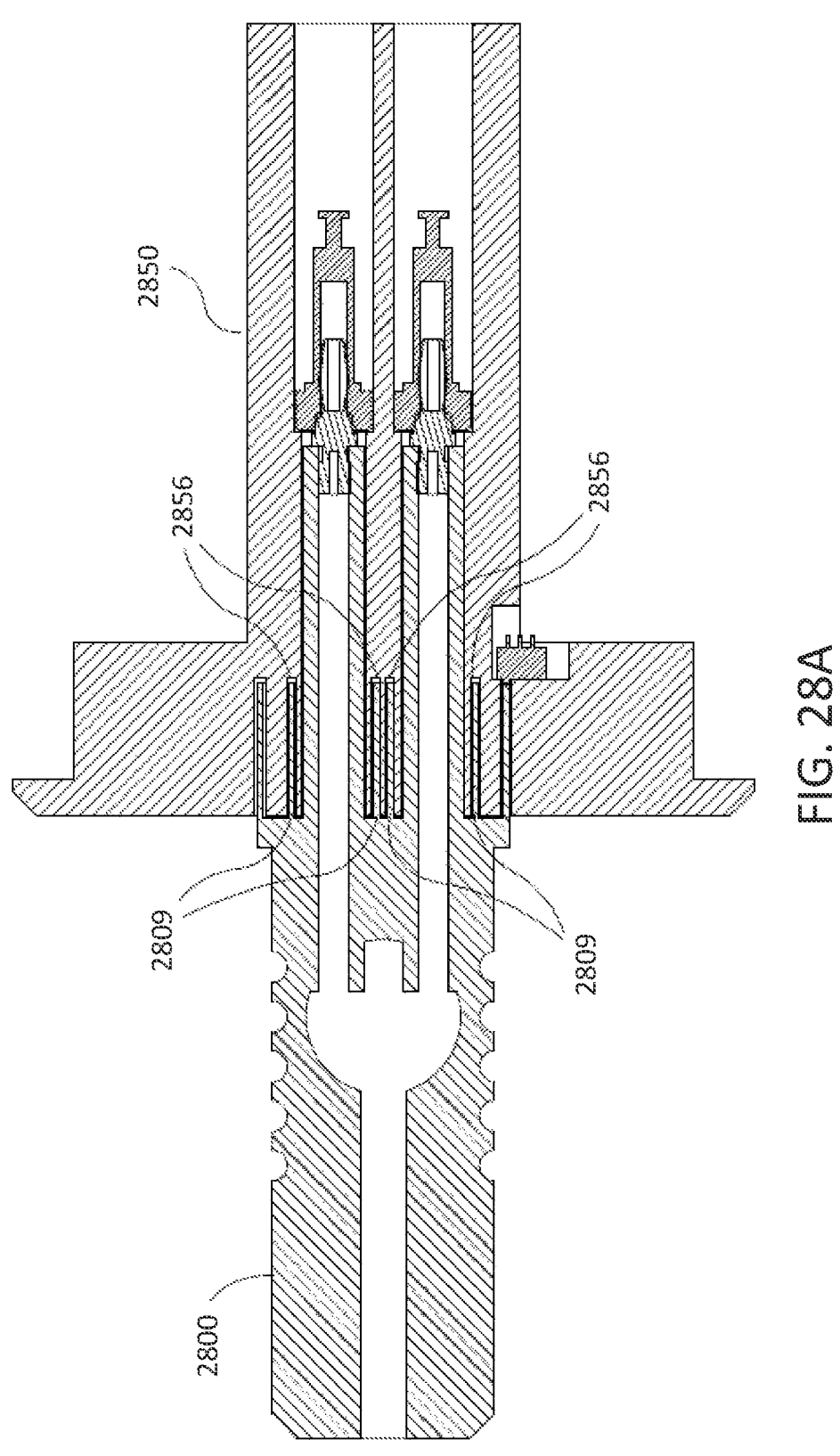
FIG. 28A is an illustration of a cross-sectional view of a connector and a housing cutaway portion.
Figure 28B:
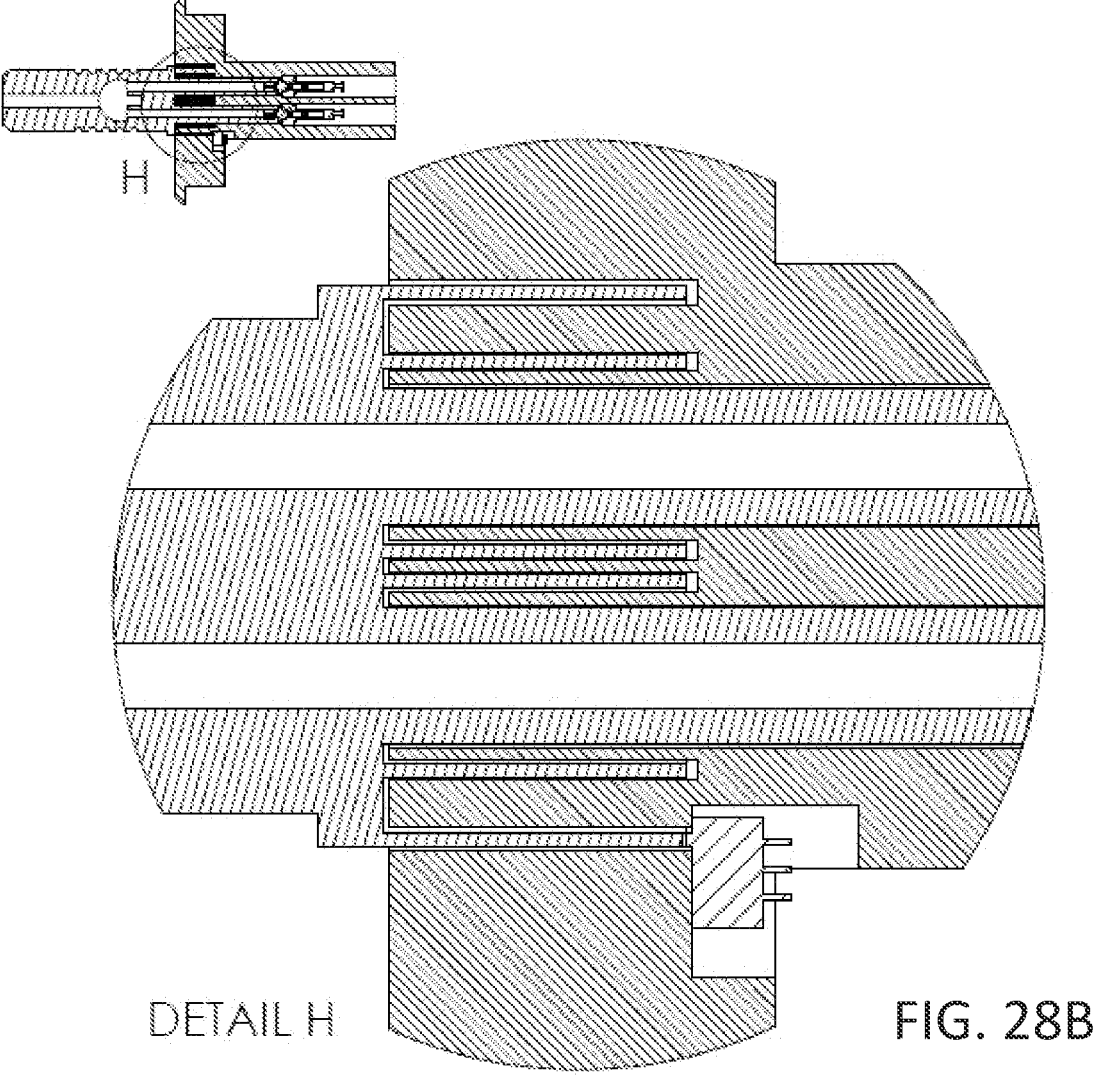
FIG. 28B is an illustration of a cross-sectional view of a connector and a housing cutaway portion.

FIGS. 28A and 28B are illustrations of a cross-sectional view of connector 2800 and housing cutaway portion 2850. FIGS. 28A and 28B illustrate connector 2800 and cutaway portion 2850 in a mated position, where FIG. 28B illustrates in detail H an enlarged view of portions of connector 2800 and cutaway portion 2850.

In some embodiments, a generator, such as an nsPEF pulse generator, may be connected with a cable to a therapeutic electrode, where the therapeutic electrode has terminals which are electrically connected to the cable by a connector/receptacle mating having characteristics similar or identical to the connectors described herein.

Figure 29A:
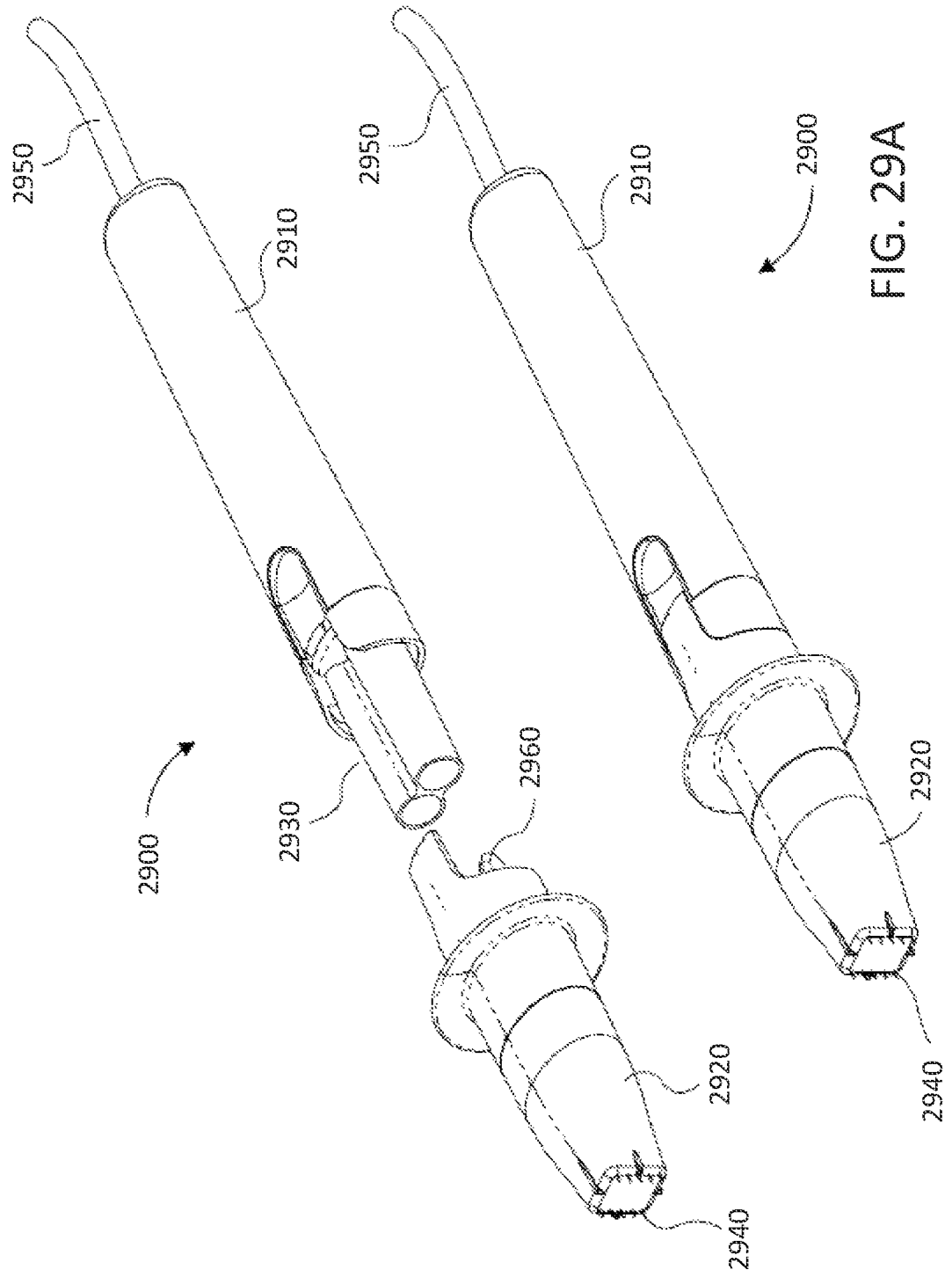
FIG. 29A illustrate an embodiment of an electrode.
Figure 29B:
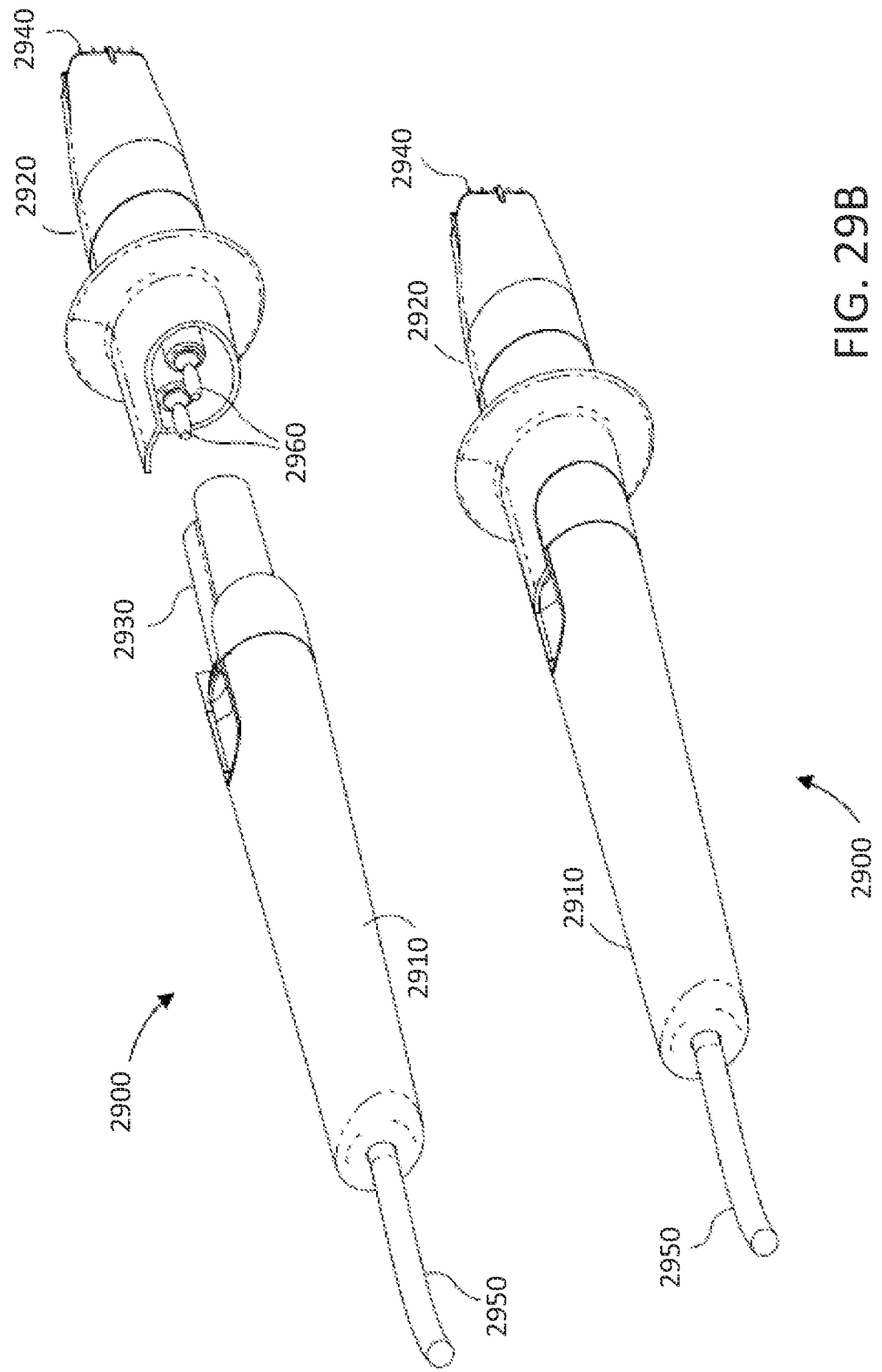
FIG. 29B illustrate an embodiment of an electrode.

For example, FIGS. 29A and 29B illustrate an electrode 2900 which has therapeutic terminals 2940 which are connected to cable 2950 through conductors which run through electrode shaft 2910 and electrode tip (or tip) 2920. Electrode 2900 may be mounted as an instrument to a robotic arm of the robotic surgical systems discussed herein. For example, cable 2950 may be connected to an nsPEF pulse generator by a connector (not shown) having features similar or identical to those of the connectors discussed elsewhere herein.

As shown, tip 2920 is removably connectable to shaft 2910. To connect tip 2920 to shaft 2910, connection terminals 2960 are inserted into skirt 2930. In some embodiments, tip 2920 is disposable, or may be discarded or disposed of after a single use.

Figure 30A:
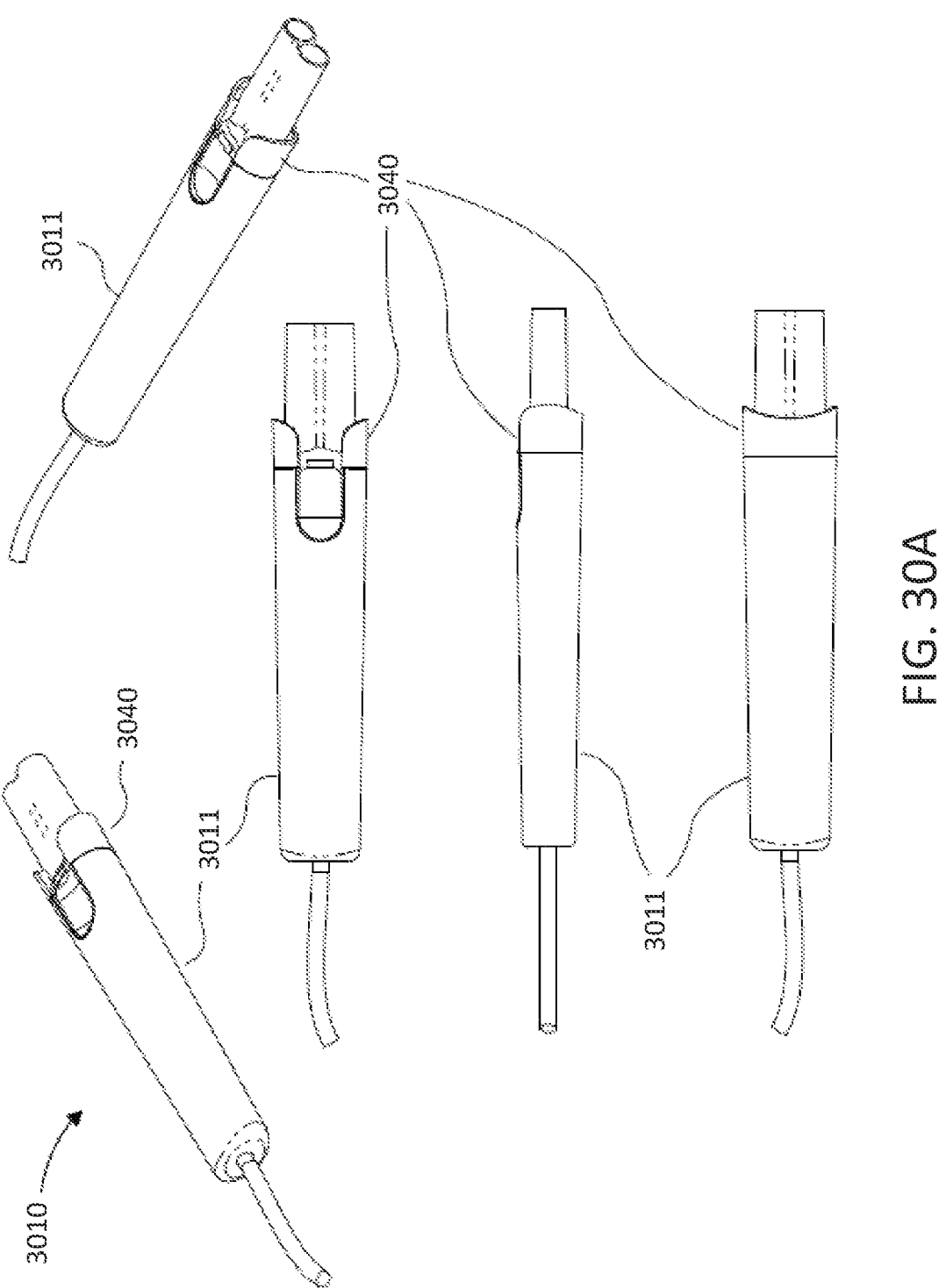
FIG. 30A illustrates an embodiment of a shaft.
Figure 30B:
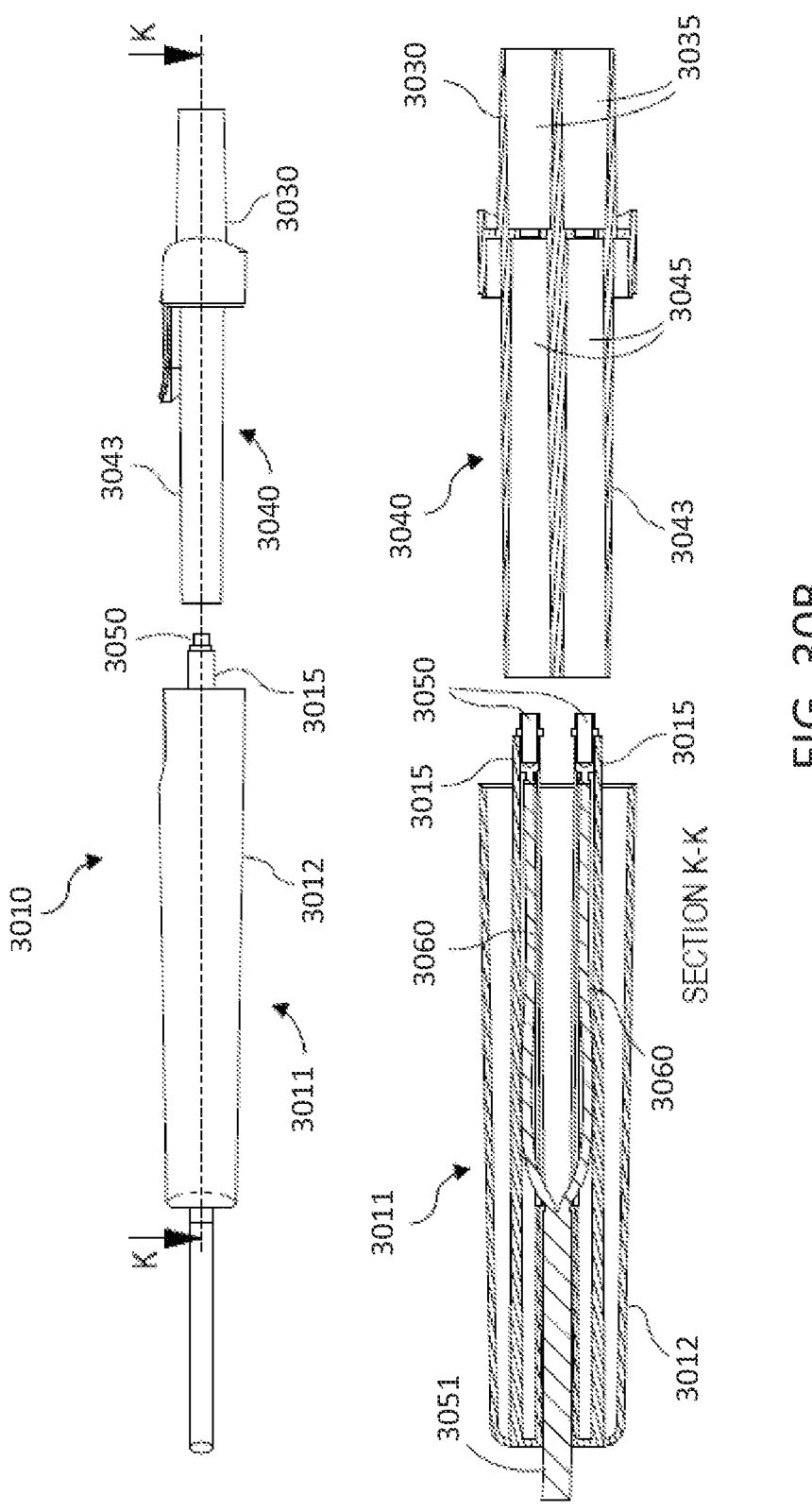
FIG. 30B illustrates an embodiment of a shaft.
Figure 30C:
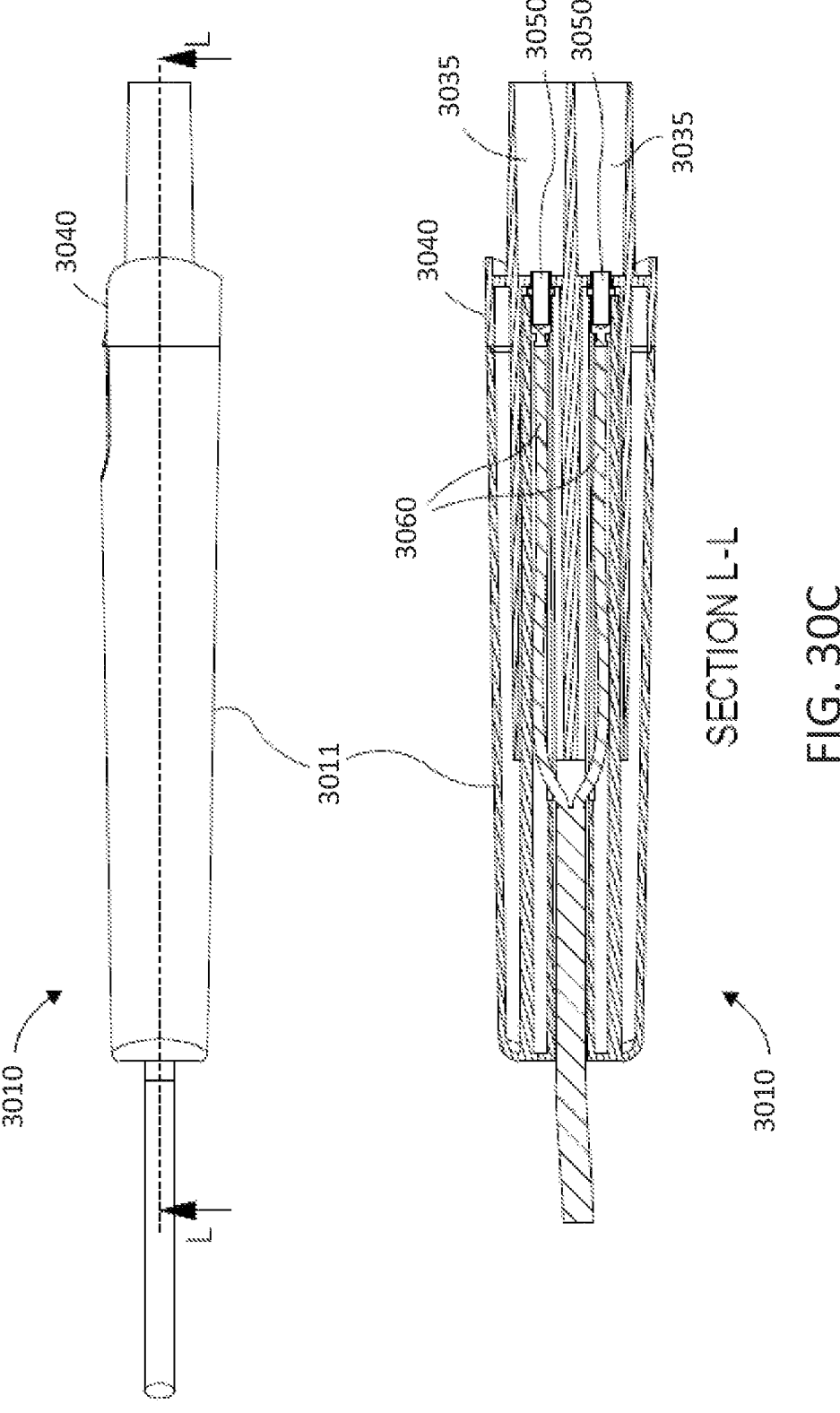
FIG. 30C illustrates an embodiment of a shaft.

FIGS. 30A, 30B, and 30C illustrate shaft 3010, which includes shaft base 3011 and its housing 3012 and shaft cap 3040. As shown in FIG. 30B, cable 3051 extends into shaft base 3011. First and second wires 3060 split from cable 3051, and respectively extend through shaft base 3011 within the first and second wire bosses 3015 (see FIG. 30A). Each of the first and second wires 3060 is connected, for example using a solder connection, with one of first and second connectors 3050 which extend from the first and second wire bosses 3015.

First and second connectors 3050 are configured to receive connection terminals 3060 from tip 3020. When tip 3020 is connected with shaft 3010, connection terminals 3360 extend into first and second connectors 3050, causing a mechanical and an electrical connection to be made between connection terminals 3360 and cable 3051.

Because the voltage between connectors 3050 can be very large, leakage may occur between connectors 3050 along a path on a surface or combination of connected surfaces between connectors 3050, causing an arc. In some embodiments, first and second wires 3060 are surrounded by insulation.

In some embodiments the electrode can be mounted or coupled to a robotic arm of a robotic surgical system. Shaft 3010 can also include an insulating safety structure, such as a standoff skirt, skirt hole, recess, or boss. The safety structure can be configured to provide at least a minimum clearance distance $d_{min\_robot}$ from electrical connectors 3050 through internal mating surfaces, which may or may not be glued together, to an outer surface where conductive structures on the robotic surgical system might be. These safety structures may eliminate the need to increase the total length of the shaft 3010 or the actual physical distance between the connectors 3050 and conductive structures on the robotic surgical system.

Shaft 3010 can also include an insulating safety structure to provide $d_{min\_terminals}$. This can take the form of skirts, skirt holes, notches, connector or wire channels, bosses, or other features. For example, connector channels 3045 provide additional clearance distance between connectors 3050 than if there were no such channels.

In some embodiments, the minimum clearance distance $d_{min\_terminals}$ is equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

In some embodiments, one of the first and second wires 3060 is covered by insulation, and the other of the first and second wires 3060 is not covered by insulation. In such embodiments, to prevent or at least minimize the leakage, the distance between the connector 3050 of the wire surrounded by insulation and the nearest portion of the wire without insulation along any path on any surface or combination of surfaces is equal to or greater than a minimum clearance distance. In some embodiments, the minimum clearance distance is equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

As shown in FIG. 30B, shaft cap 3040 can include skirt 3043, which has connector channels 3045. In addition, shaft cap 3040 can include skirt 3030 which includes terminal channels 3035.

When the shaft 3010 is assembled, as shown in FIG. 30C, first and second wires 3060 within the first and second wire bosses 3015 and first and second connectors 3050 extend through connector channels 3045 (see FIG. 30B) of shaft cap 3040. In addition, as shown in FIG. 30C, when the shaft 3010 is assembled, connectors 3050 are exposed through terminal channels 3035, such that when the shaft 3010 is connected with tip 3020, the connection terminals of 3060 of the tip 3020 mechanically and electrically connect to connectors 3050.

In this embodiment, female connectors 3050 receive male connection terminals 3060. In alternative embodiments, female connection terminals 3360 receive male connectors 3050.

Figure 31A:
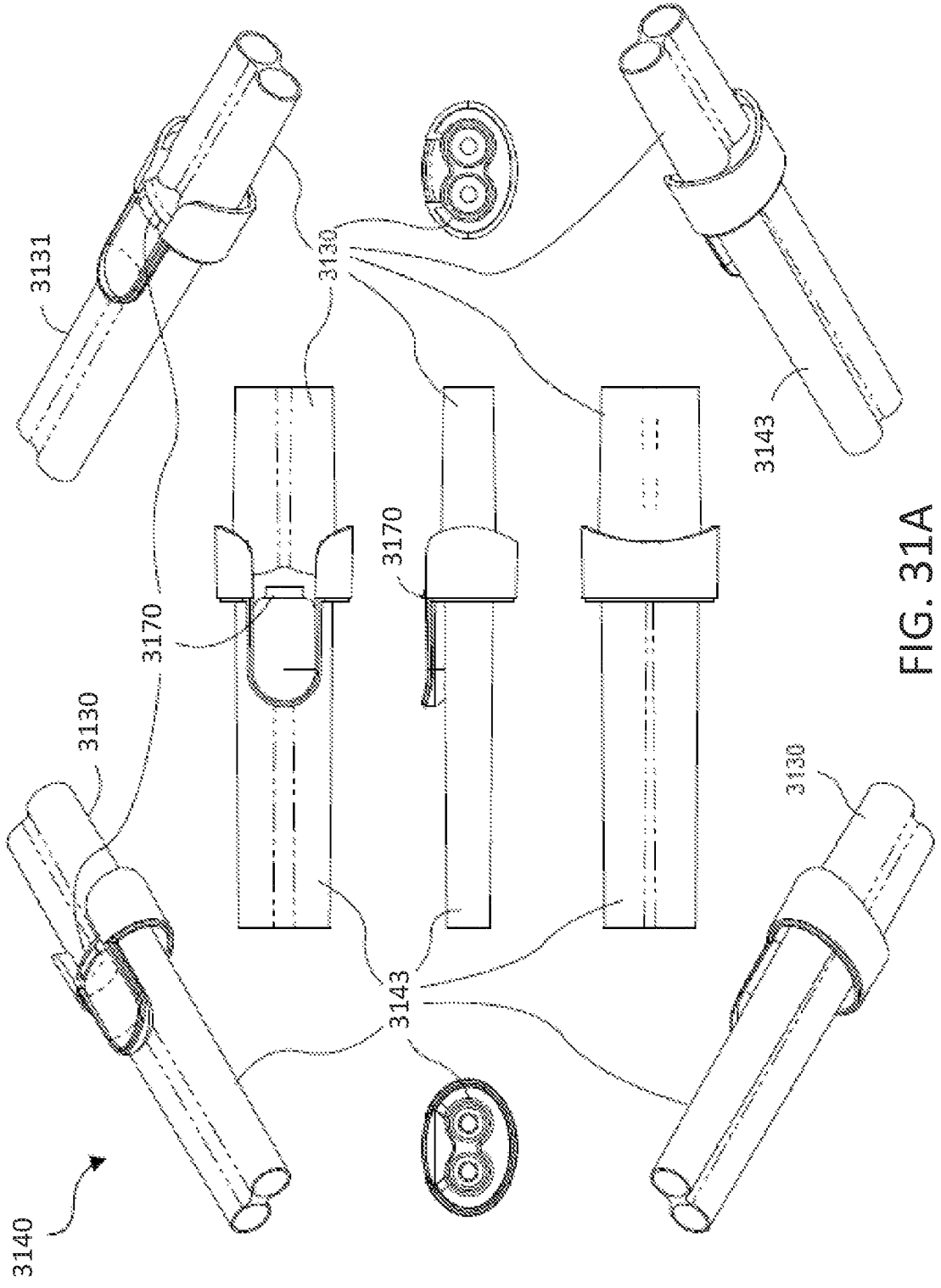
FIG. 31A illustrates an embodiment of a shaft cap.
Figure 31B:
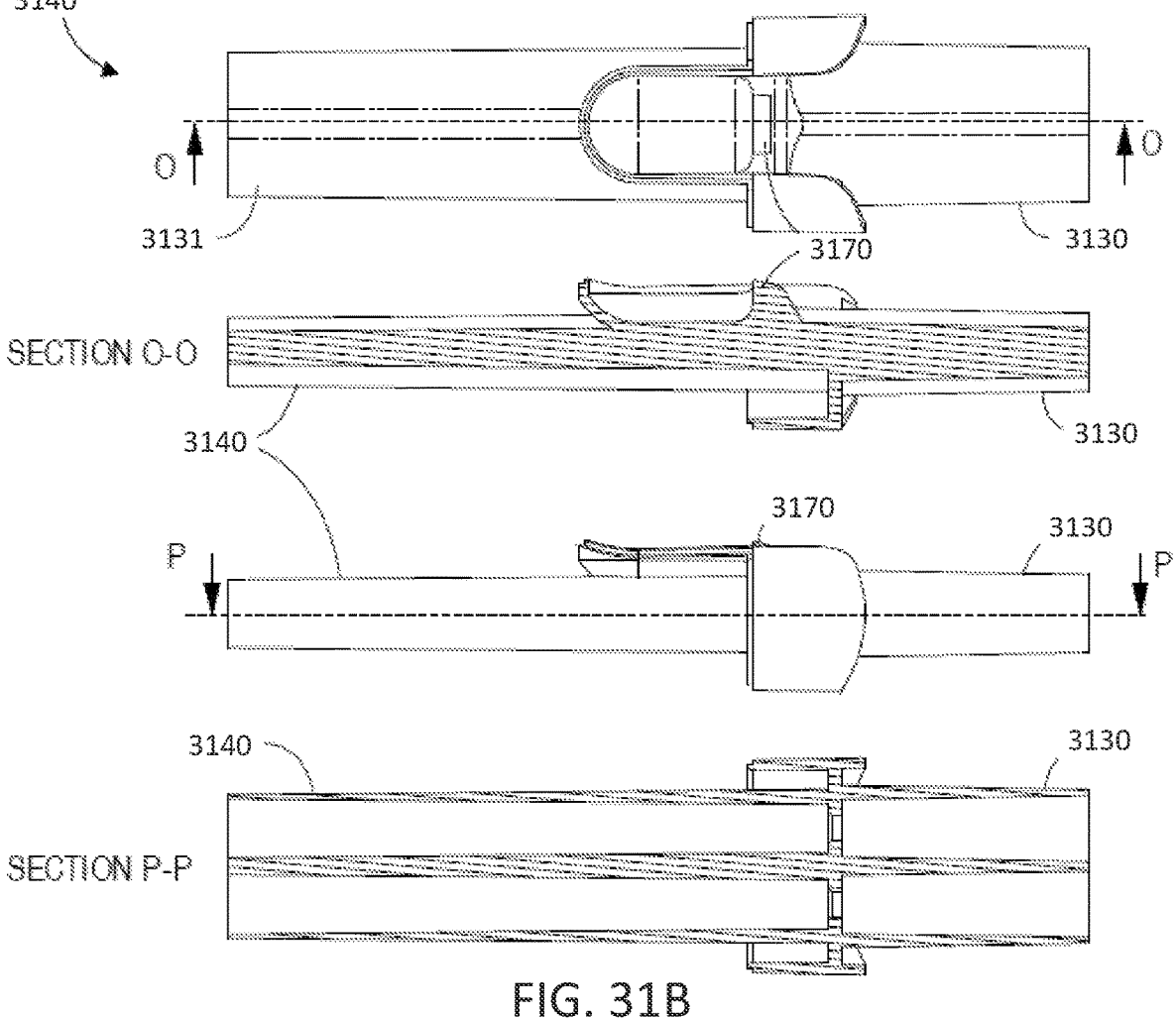
FIG. 31B illustrates an embodiment of a shaft cap.

FIGS. 31A and 31B illustrate shaft cap 3140. Shaft cap 3140 includes exposed portion 3130 and insert portion 3131. As shown, shaft cap 3140 includes latch hook 3170. Latch hook 3170 is used to secure tip 3120 to shaft 3110.

Figure 32A:
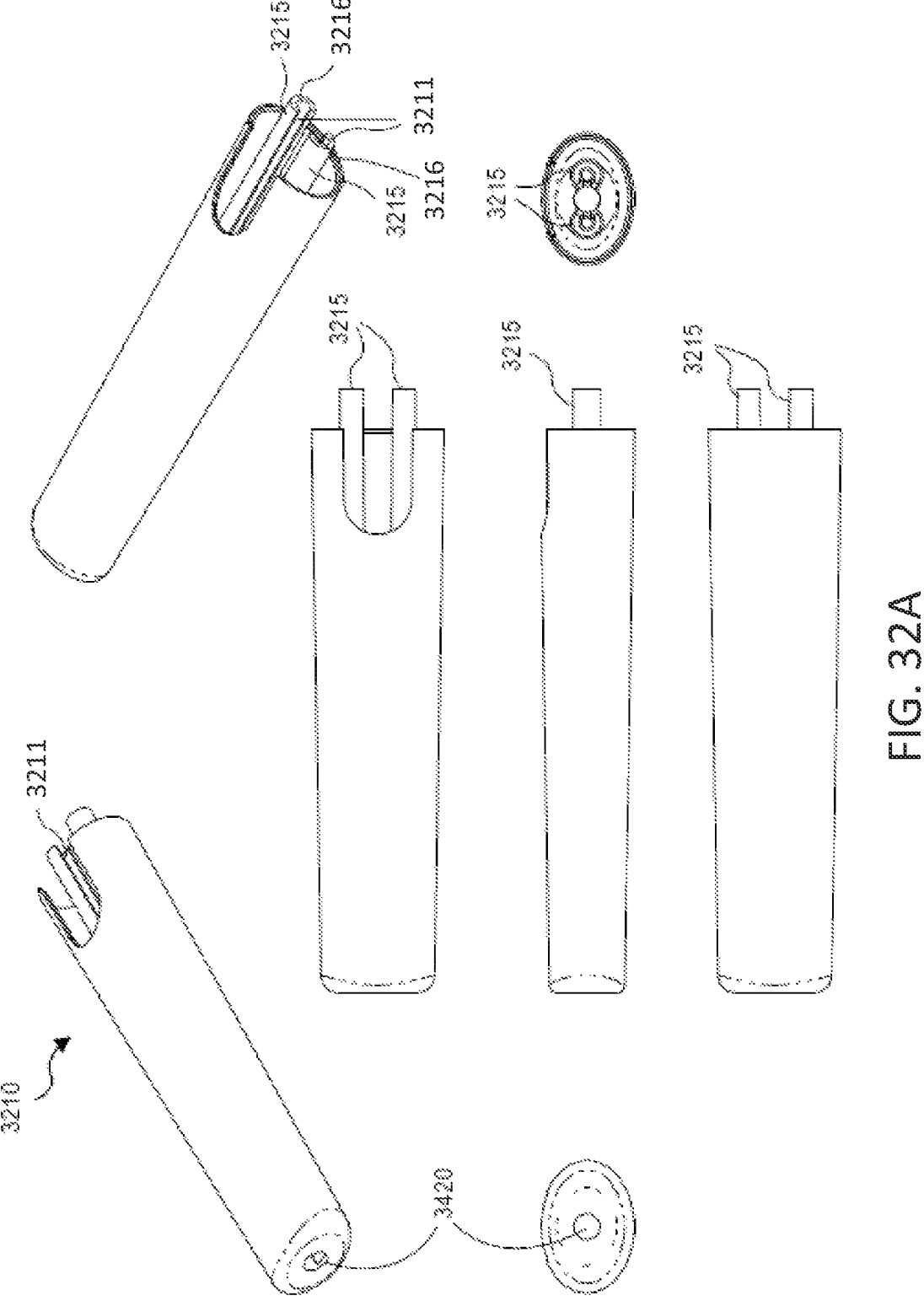
FIG. 32A illustrates an embodiment of a shaft base.
Figure 32B:
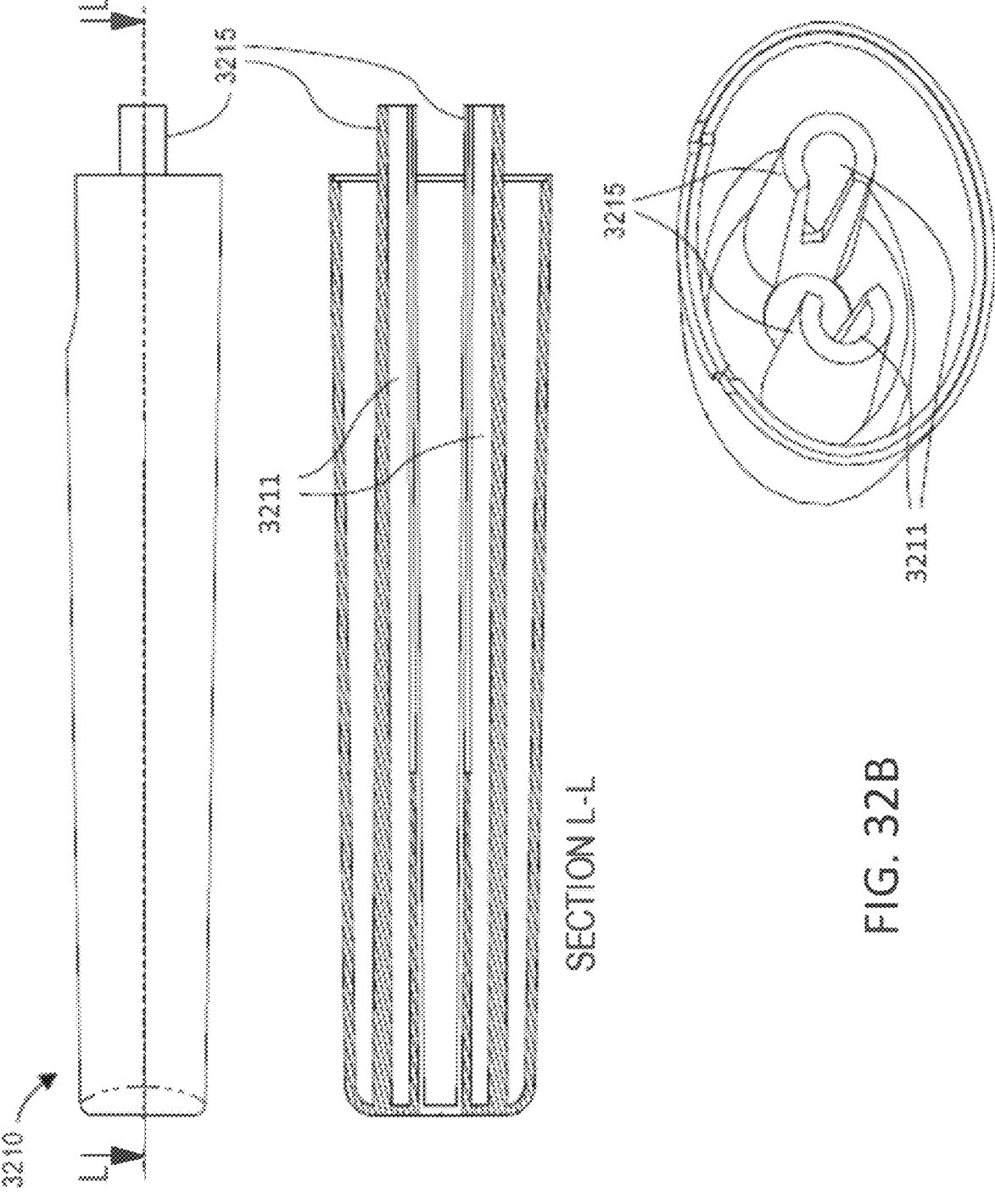
FIG. 32B illustrates an embodiment of a shaft base.

FIGS. 32A and 32B illustrate shaft base 3210. As shown, shaft base 3210 includes wire bosses 3215. Wire bosses 3215 are generally tubular with the inner portion of the tubes each forming a wire channel 3211. The wire channels 3211 have openings 3216 at their ends which extend from shaft base 3210 and are also open at slots extending along central portions or sides of the wire bosses 3215.

Figure 33A:
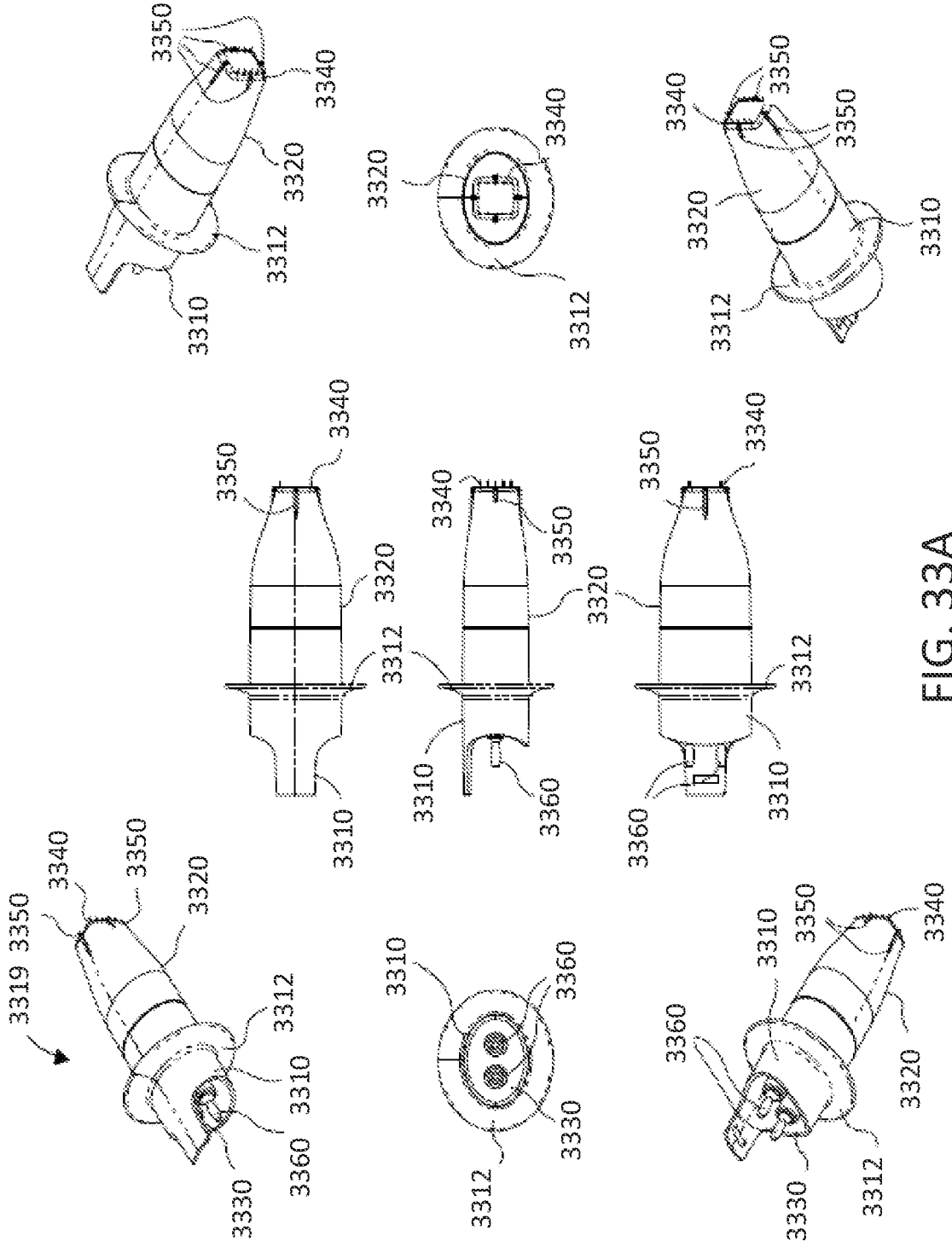
FIG. 33A illustrates an embodiment of a tip.
Figure 33B:
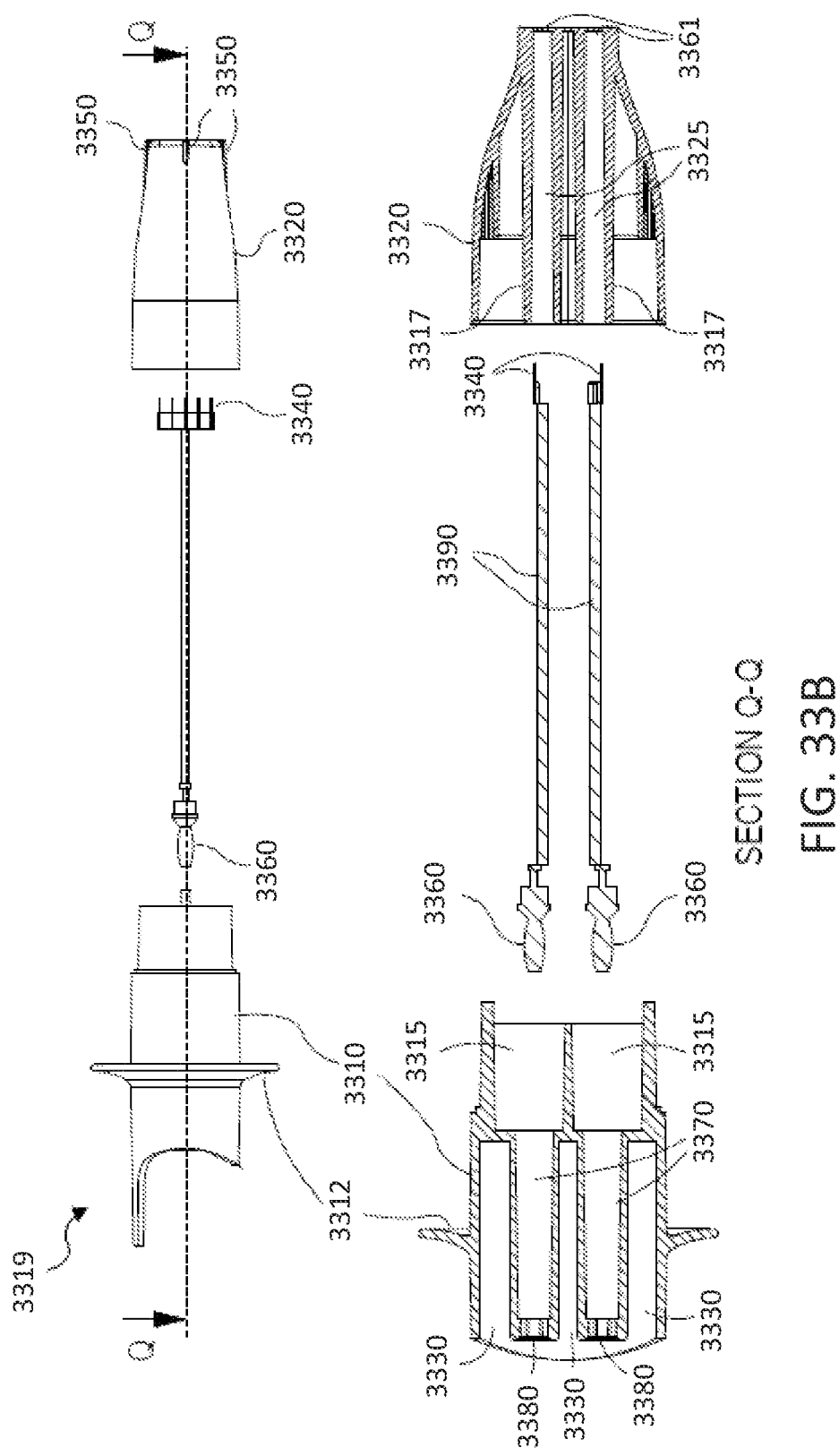
FIG. 33B illustrates an embodiment of a tip.

FIGS. 33A and 33B illustrate tip 3319. As shown, tip 3319 includes tip base 3310 and tip cap 3320. As shown, tip base 3310 and tip cap 3320 house wires 3390 which electrically connect connection terminals 3360 with therapeutic terminals 3340. When assembled, connection terminals 3160 protrude from tip base 3310 through holes 3380, wires 3390 extend through tip base wiring channels 3370 and tip cap wiring channels 3325, and therapeutic terminals 3340 extend through tip cap holes 3361. In some embodiments, one or more of the connection terminals 3360, wires 3390, and therapeutic terminals 3340 may be cemented in place, for example, with epoxy. In some embodiments, as part of the assembly process for tip 3319, tip base 3310 is cemented to tip cap 3320, for example, with epoxy.

As shown in FIG. 33B, tip base 3310 includes skirt holes 3315, which are configured to receive skirts 3317 of tip cap 3320 when tip base 3310 is connected with tip cap 3320. In alternative embodiments, tip cap 3320 has skirt holes configured to receive skirts of tip base 3310. In some embodiments each of tip cap 3320 and tip base 3310 have one skirt and one skirt hole, where the one skirt hole is configured to receive the skirt of the other of tip cap 3320 and tip base 3310. In some embodiments, a single skirt hole in either of tip cap 3320 and tip base 3310 is configured to receive both skirts of the other of tip cap 3320 and tip base 3310.

Because the voltage between therapeutic terminals 3340 can be very large, in some instances when proper insulation is missing and before the therapeutic terminals are inserted into a tissue, leakage may occur between therapeutic terminals 3340 along a path on an internal surface or combination of connected internal surfaces between therapeutic terminals 3340. To prevent or at least minimize the leakage, an insulative structure may be incorporated into the design such as the skirts and skirt holes. Such structures are configured to provide or cause the minimum clearance distance $d_{min\_terminals}$ between therapeutic terminals 3340 along any internal path on any surface or combination of surfaces. Such $d_{min\_terminals}$ can be equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

As shown in FIGS. 33A and 33B, tip base 3310 includes guard 3312. Guard 3312 serves at least to help ensure that conductive structures on the robotic surgical system remains a minimum clearance distance away from therapeutic terminals 3340. In some embodiments, the guard 3312 may be away from the therapeutic terminals 3340, for example, by 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

As shown in FIGS. 33A and 33B, tip base 3310 includes skirt hole 3331. In some embodiments tip 3311 has one skirt and one skirt hole, where the one skirt hole is configured to receive the skirt of tip base 3310. In some embodiments, a single skirt hole in tip base 3310 is configured to receive both skirts of the tip base 3310.

Tip 3319 can also include an insulating safety structure, such as a standoff skirt, recess, or boss. The safety structure can be configured to provide at least a minimum clearance distance $d_{min\_robot}$ from connection terminals 3360 through internal mating surfaces, which may or may not be glued together, to an outer surface where conductive structures on the robotic surgical system might be. These safety structures may eliminate the need to increase the total length of the tip 3319 or the actual physical distance between the terminals 3360 and conductive structures on the robotic surgical system.

Tip 3319 can also include an insulating safety structure to provide $d_{min\_terminals}$. This can take the form of skirts, notches, connector or wire channels, bosses, or other features. For example, wiring channels 3325 provide additional clearance distance between connectors 3360 than if there were no such channels.

Because the voltage between connection terminals 3360 can be very large, leakage may occur between connection terminals 3360 along a path in the air or on a surface or combination of connected surfaces between connection terminals 3360 causing an arc. To prevent or at least to minimize such potential arcs, insulative structures, such as skirts, skirt holes, bosses, and notches, lengthen the minimum clearance distance $d_{min\_terminals}$ between connection terminals 3360 along any path on any surface or combination of surfaces. In some embodiments, the minimum clearance distance is equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

As shown in FIGS. 33A and 33B, tip cap 3320 includes fiducials 3350. Fiducials 3350 are radially aligned with a central point and may, for example, indicate a geometric center of the therapeutic terminals 3340 are particularly useful during therapeutic use of electrode 3300. For example, prior to use the desired location of treatment is determined and marked with perpendicular lines which intersect at the desired center point of treatment and which are long enough to extend beyond the electrode fiducials 3350 when the electrode 3300 is positioned for treatment. To properly place electrode 3300 for use on the desired location, the user of electrode 3300 places electrode 3300 such that fiducials 3350 align with the portion of the perpendicular lines which extend beyond the fiducials 3350 of electrode 3300.

Figure 34:
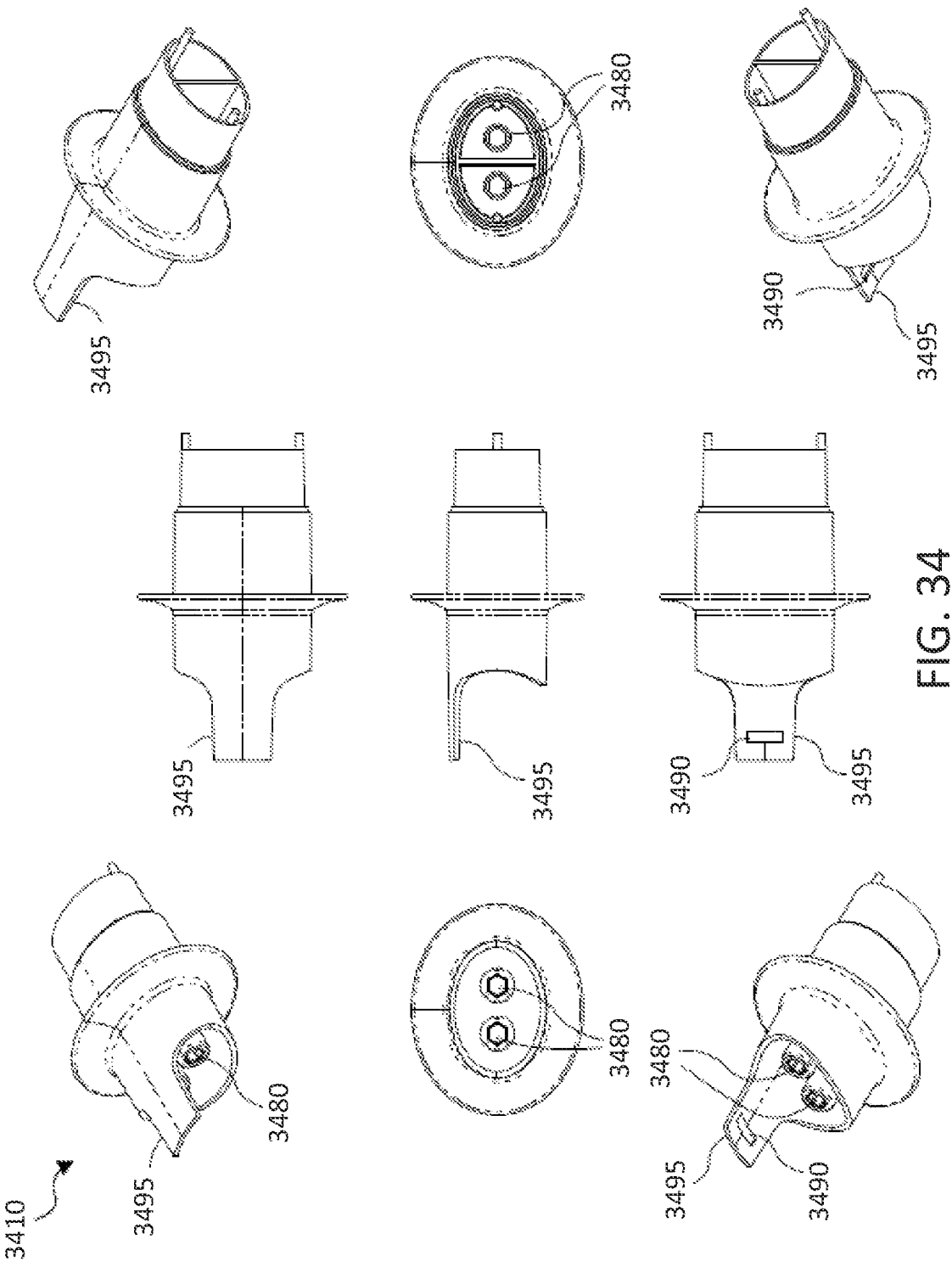
FIG. 34 illustrates an embodiment of a tip base.

FIG. 34 illustrates tip base 3410. As shown, tip base 3410 includes tab 3495 which has latch notch 3490. Tab 3495 and latch notch 3490 are used to secure and to release the connection of the tip and shaft described above. Through holes 3480 are shown for where connectors will be inserted.

Figure 35:
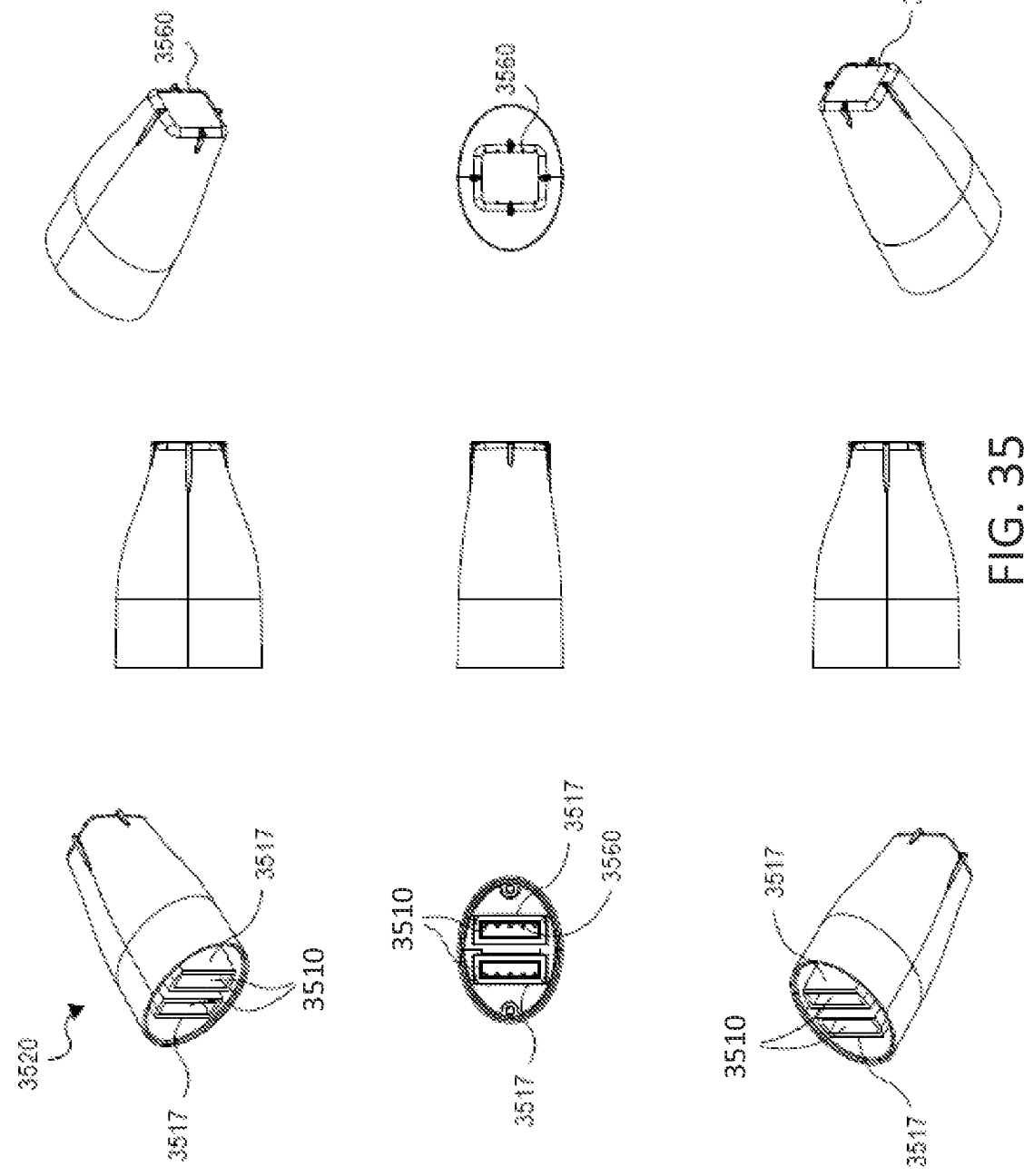
FIG. 35 illustrates an embodiment of a tip cap.
Figure 36:
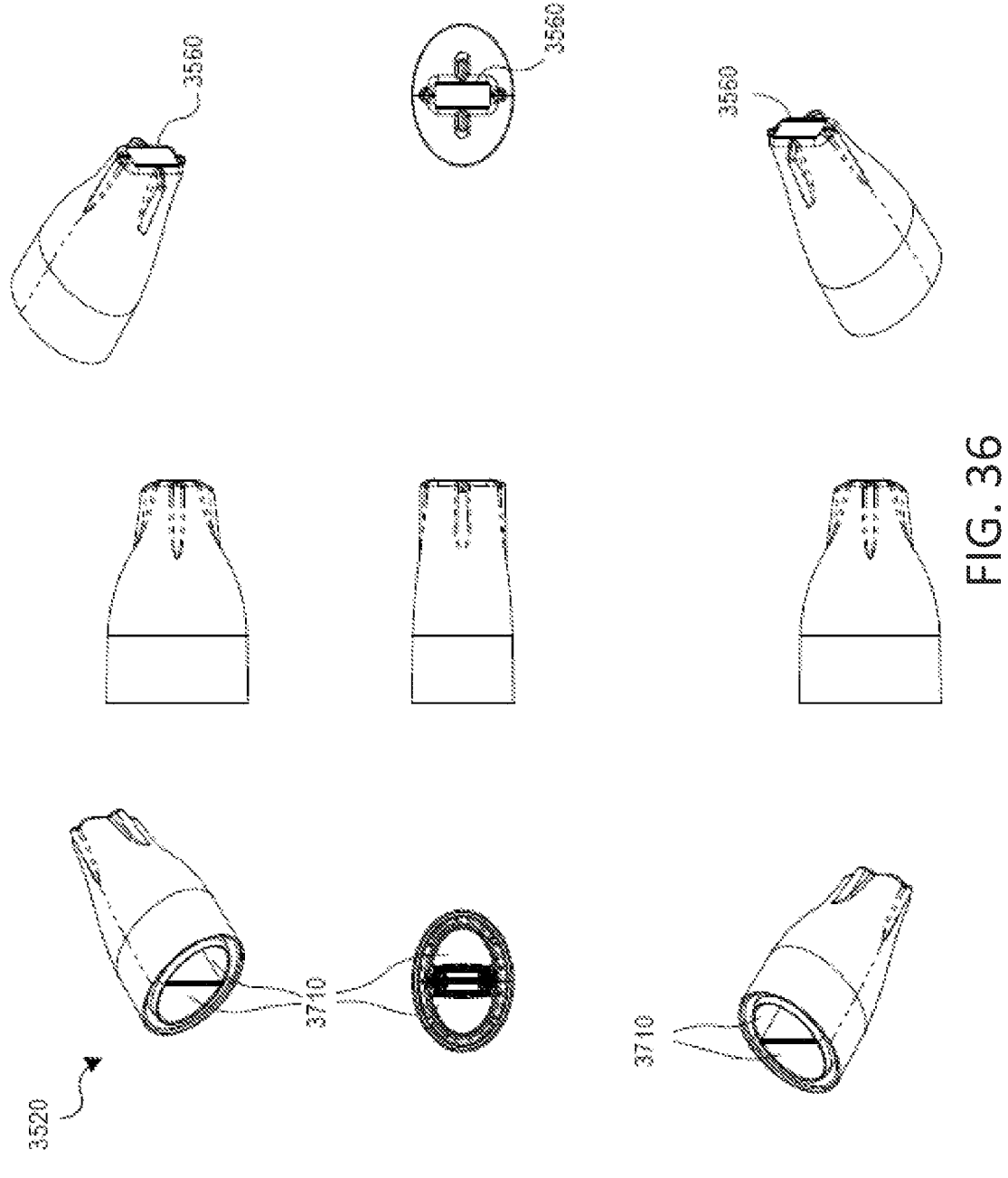
FIG. 36 illustrates an embodiment of a tip cap.
Figure 37:
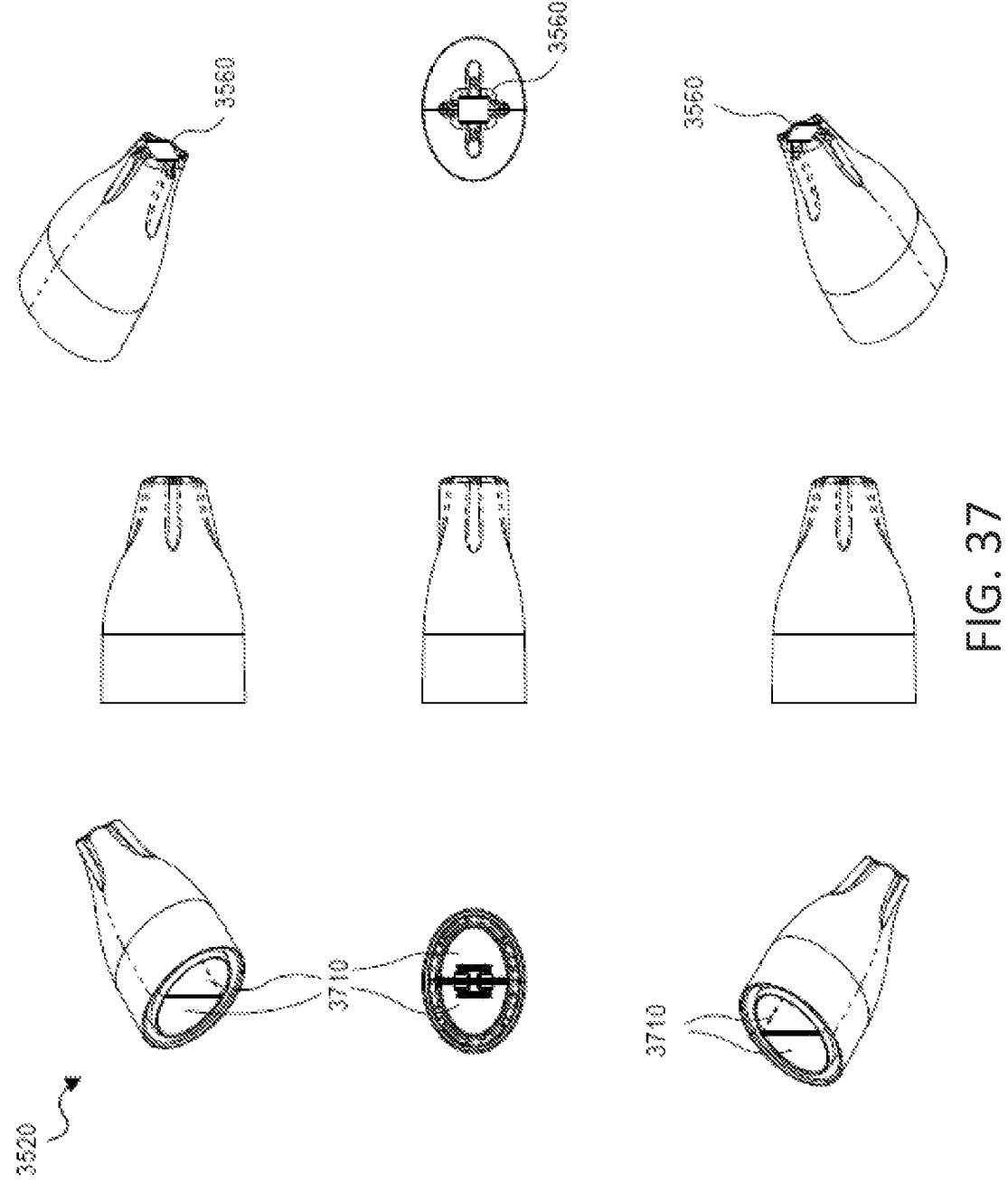
FIG. 37 illustrates an embodiment of a tip cap.
Figure 38:
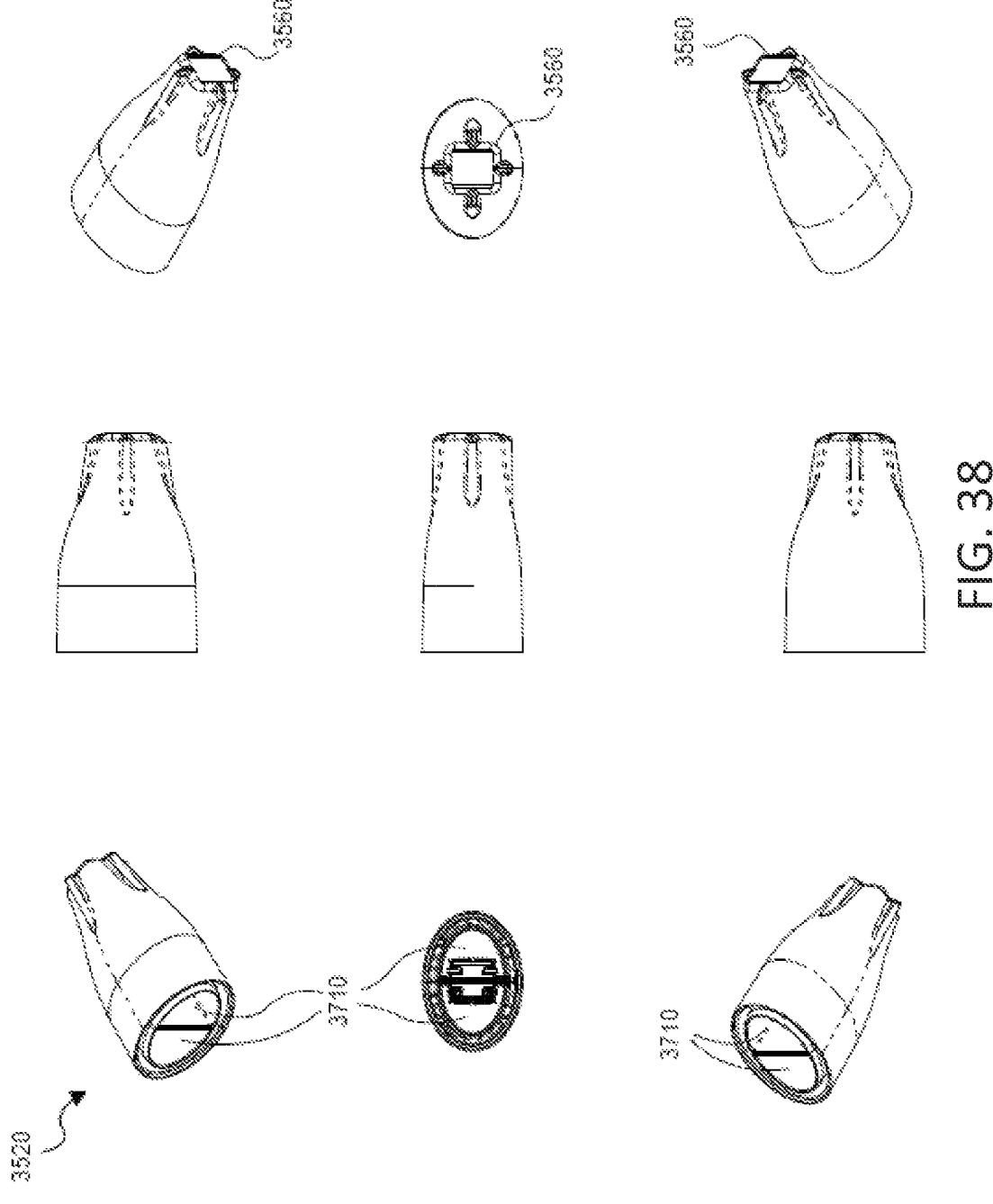
FIG. 38 illustrates an embodiment of a tip cap.
Figure 39:
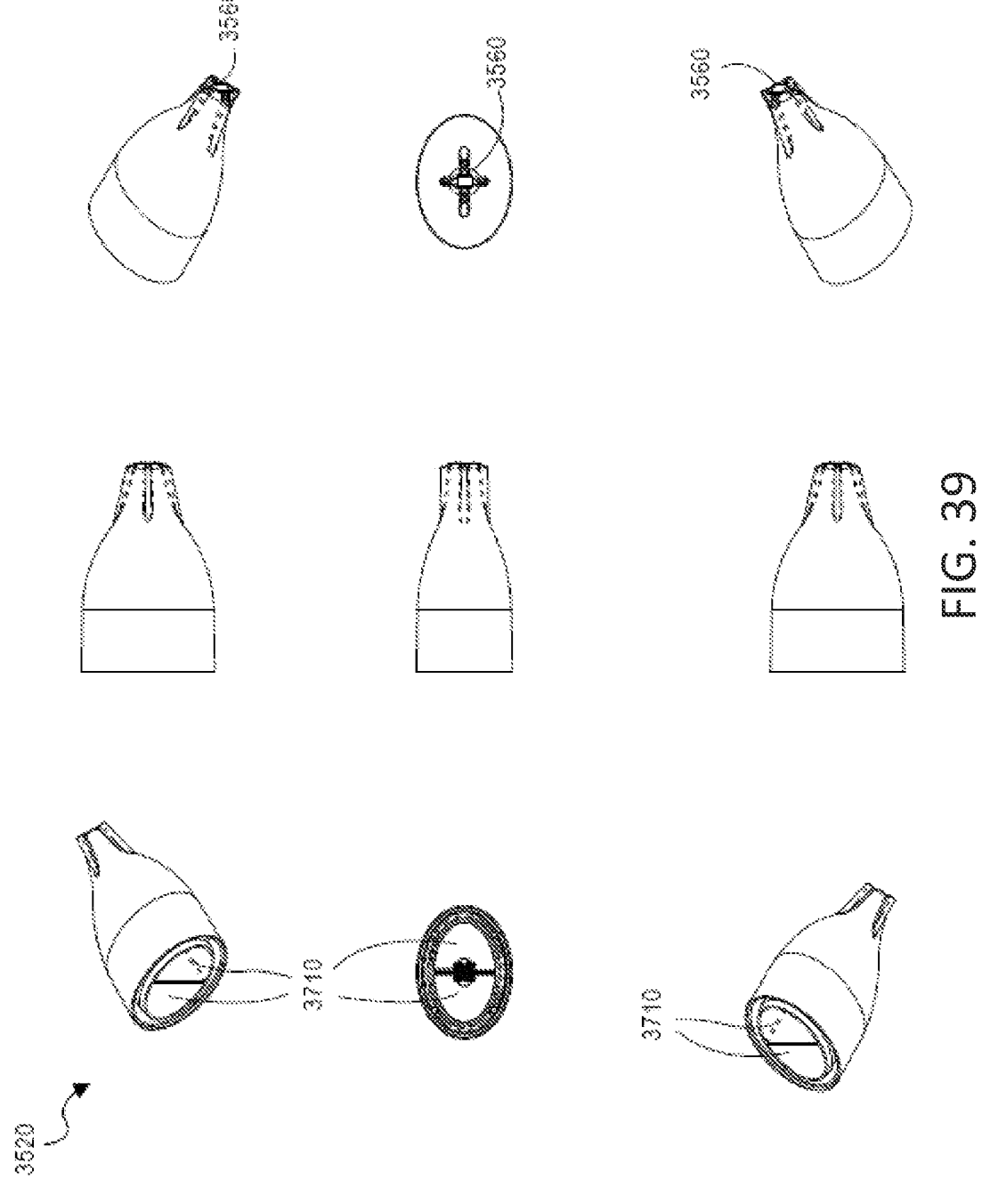
FIG. 39 illustrates an embodiment of a tip cap.

FIG. 35 illustrates tip cap 3520. As shown, tip cap 3520 includes holes 3510, which are openings in skirts 3517. In addition, tip cap 3520 includes therapeutic terminal holes 3560, through which therapeutic terminals described above extend, when the tip is assembled. In this embodiment, tip cap wiring channels 3525 have cross-sectional geometries which correspond with the arrays of the therapeutic terminals. As a result, during assembly, when the therapeutic terminals are fed through tip cap 3520, the therapeutic terminals align with therapeutic terminal holes 3560 in tip cap 3520 because of the geometry of the therapeutic terminal arrays and the geometry of the tip cap wiring channels 3525. In addition, in this embodiment, therapeutic terminal holes 3560 collectively have geometric characteristics which correspond with corresponding embodiments of the therapeutic terminals.

FIGS. 36-39 illustrate various embodiments of tip cap 3520. As shown, the tip caps 3520 of these embodiments include holes 3710, which are openings to tip cap wiring channels 3525 (see FIG. 35B). In addition, tip caps 3520 of these embodiments include therapeutic terminal holes 3560, through which the therapeutic terminals described above extend, when the tip is assembled. In these embodiments, tip cap wiring channels 3525 have cross-sectional geometries which correspond with the arrays of the therapeutic terminals. As a result, during assembly, when the therapeutic terminals are fed through tip cap 3520, the therapeutic terminals align with therapeutic terminal holes 3560 in tip cap 3520 because of the geometry of the therapeutic terminal arrays and the geometry of the tip cap wiring channels 3525. In addition, in these embodiments, therapeutic terminal holes 3560 collectively have geometric characteristics which correspond with corresponding embodiments of the therapeutic terminals.

In some embodiments, the therapeutic terminal holes 3560 collectively have geometric characteristics which define a rectangle which is about 10 mm×10 mm. Alternatively, the therapeutic terminal holes 3560 may collectively have geometric characteristics which define a rectangle which is one of about 10 mm×5 mm, about 7.5 mm×5 mm, about 2.5 mm×5 mm, about 7.5 mm×7.5 mm, about 5 mm×10 mm, about 5 mm×5 mm, and about 2.5 mm×2.5 mm. Other geometric arrangements may alternatively be used.

Figure 40A:
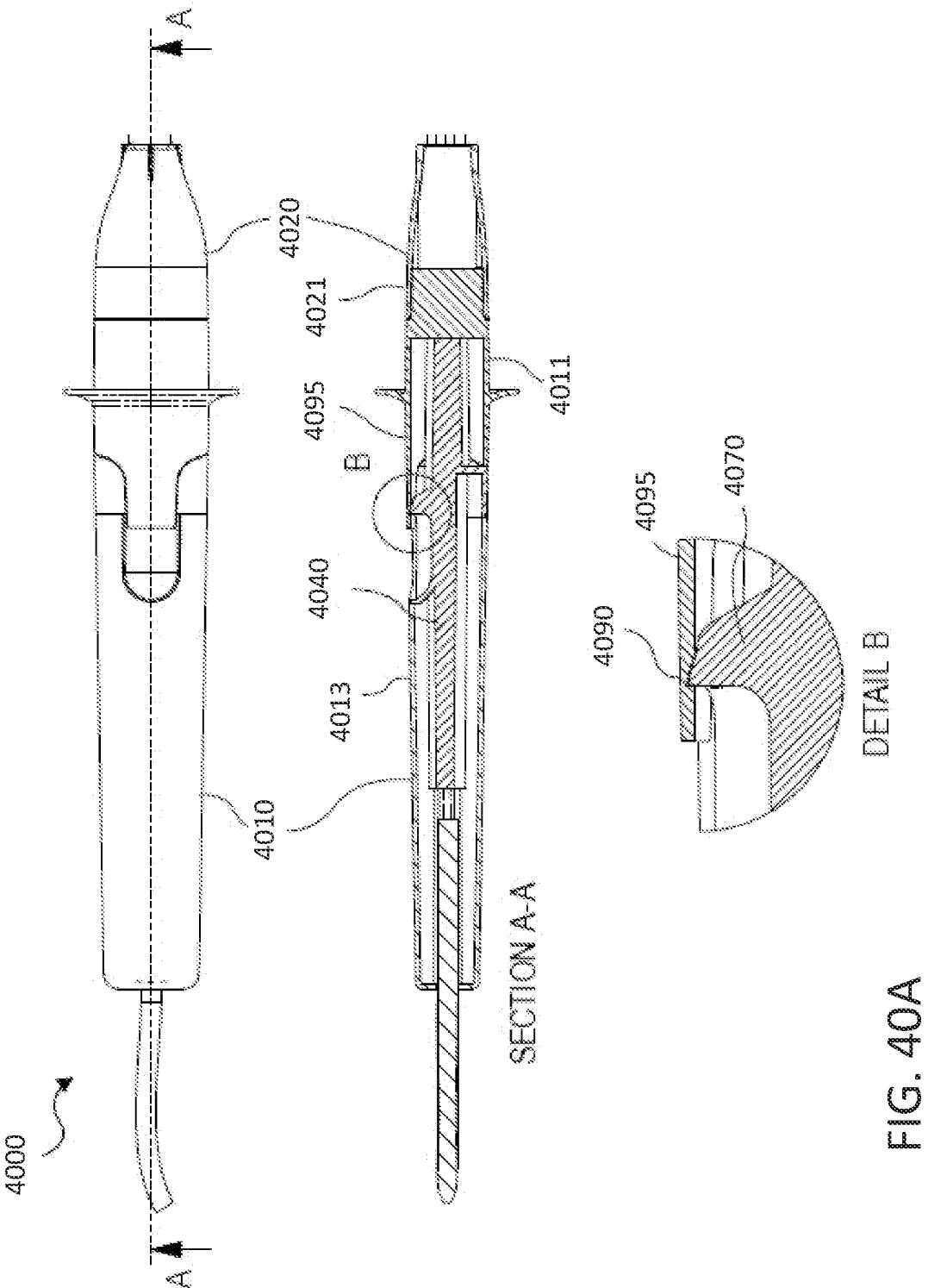
FIG. 40A illustrates an embodiment of an electrode.
Figure 40B:
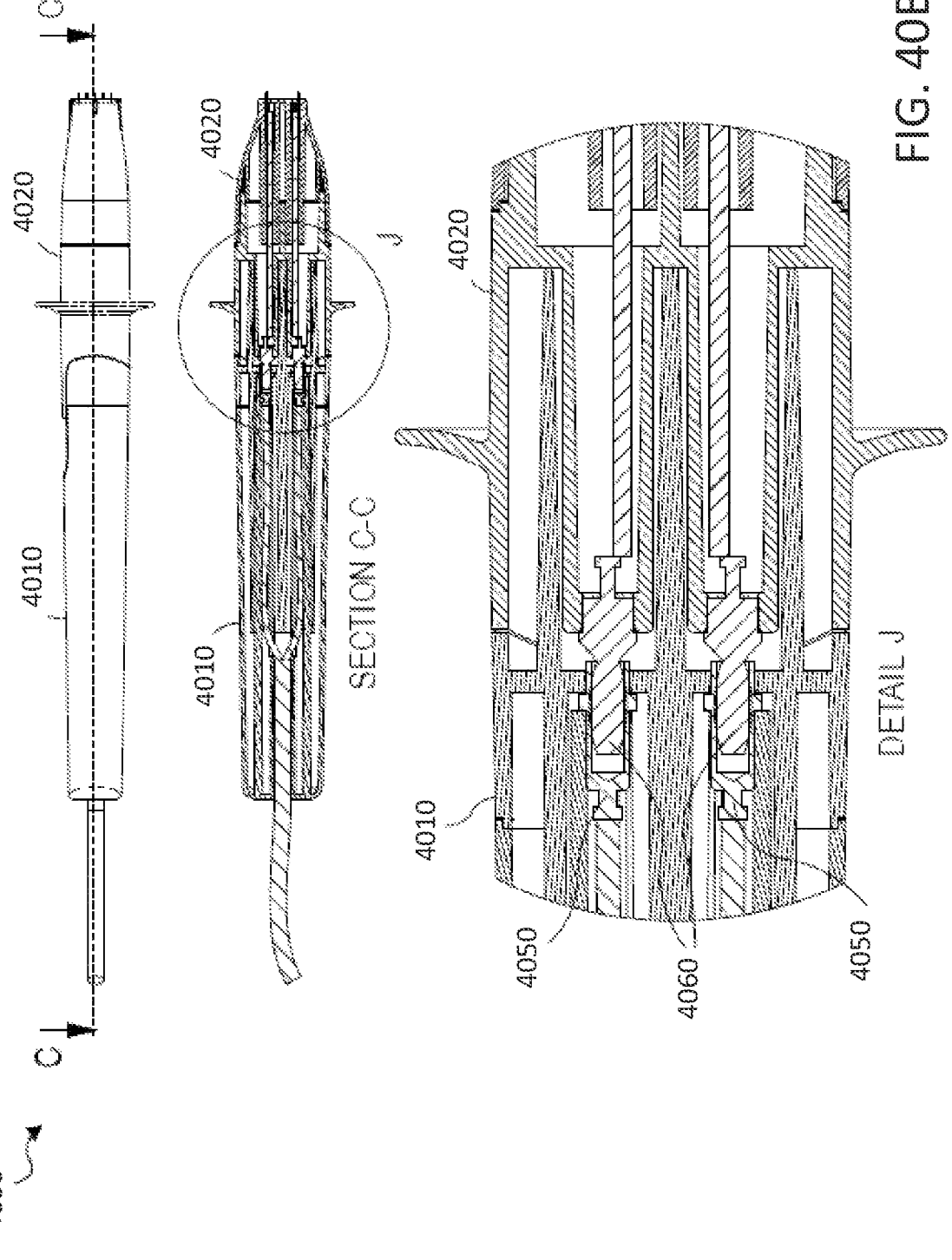
FIG. 40B illustrates an embodiment of an electrode.
Figure 40C:
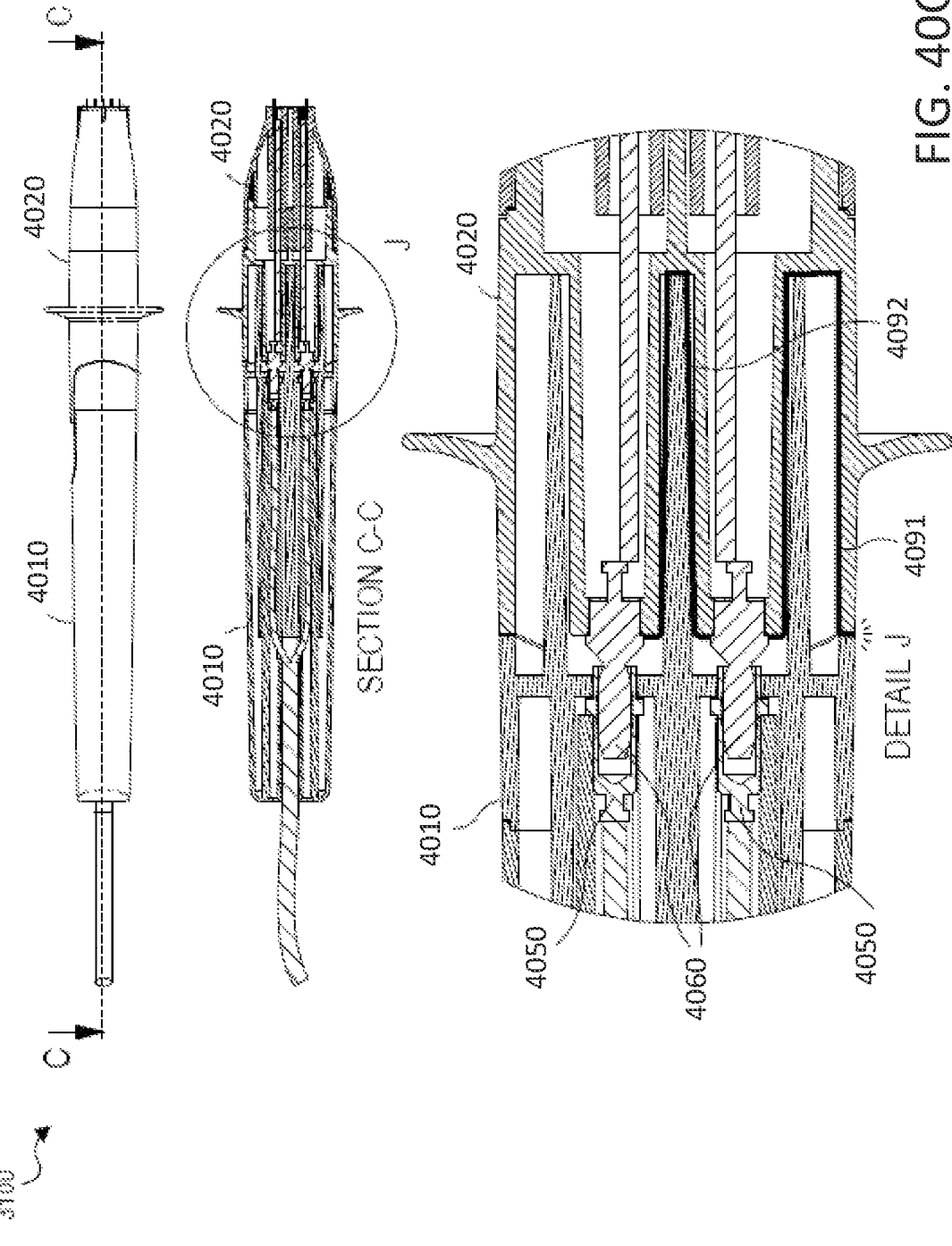
FIG. 40C illustrates an embodiment of an electrode with a minimum clearance distance shown.

FIGS. 40A, 40B, and 40C illustrate electrode 4000 in an assembled state with tip 4020 connected with shaft 4010. In some embodiments, electrode 4000 can be mounted as an instrument to a robotic arm of a robotic surgical system, as described above. As shown, tip 4020, which includes tip base 4511 and tip cap 4021, is connected with shaft 4010, which includes shaft base 4013 and shaft cap 4040. Tip 4020 is secured to shaft 4010 by a latch which has latch hook 4070 of shaft cap 4040 and latch notch 4090 in tab 4095 of tip base 4011. As shown in DETAIL B, latch hook 4070 is inserted in latch notch 4090 and prevents tip 4020 from detaching from shaft 4010.

To release tip 4020 from shaft 4010, a force is exerted on tab 4095 causing latch notch 4090 to move away from latch hook 4070, for example, by causing tab 4095 to flex. Once latch notch 4090 has moved enough that latch hook 4070 is no longer within latch notch 4090, a force exerted on tip 4020 may cause tip 4022 separate from shaft 4010.

To connect tip 4120 to shaft 4110, tip 4120 is pressed onto shaft 4110. The pressing action causes latch hook 4372 engage latch notch 4690, for example, by causing tab 4695 to flex.

As shown in FIG. 40B, when shaft 4110 is connected with tip 4120, connection terminals 4160 are mechanically and electrically connected with connectors 4251.

FIG. 40C illustrates some minimum clearance distances that may be provided where the tip 4120 meets the shaft 4110 of the electrode 4100. Female connectors 4251 provide electrical power to plug connection terminals 4160.

For example, minimum clearance distance 4091 to the user is measured by following surfaces and/or air gaps from a connection terminal 4060, between mating surfaces, to a conductive structure on the robotic surgical system that may be placed next to a visible seam between the shaft 4010 and tip 4020) as shown. An alternative minimum clearance distance takes a diagonal path from the upper right to the lower left of the air space in Detail J within the connector, essentially cutting a corner in the currently shown path 4091.

In another example, minimum clearance distance 4092 between terminals is measured by following mating surfaces and/or air gaps from a connection terminal 4060 to the other connection terminal 4060 as shown.

Either minimum clearance distance can be equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

Figure 41A:
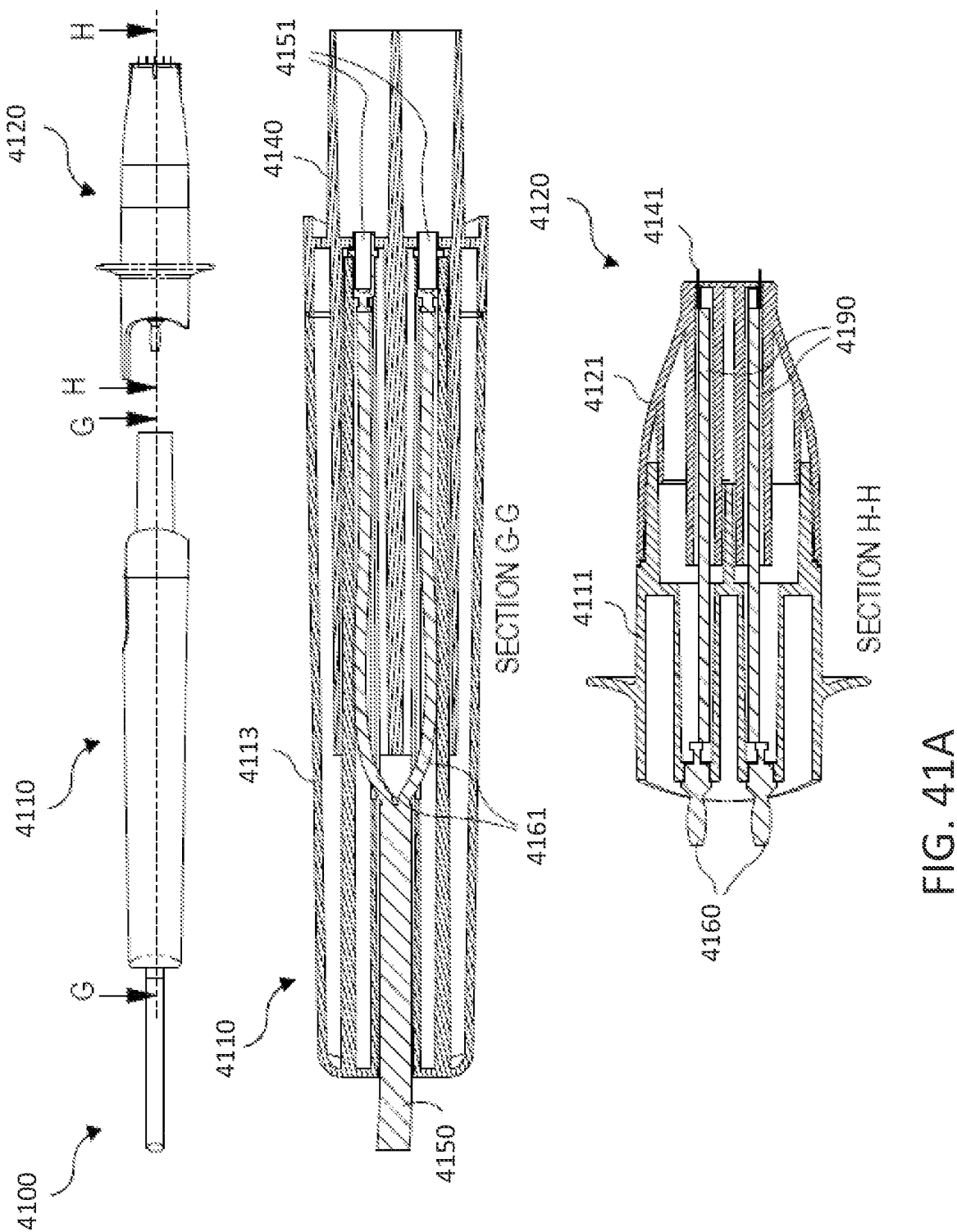
FIG. 41A illustrates an embodiment of an electrode.
Figure 41B:
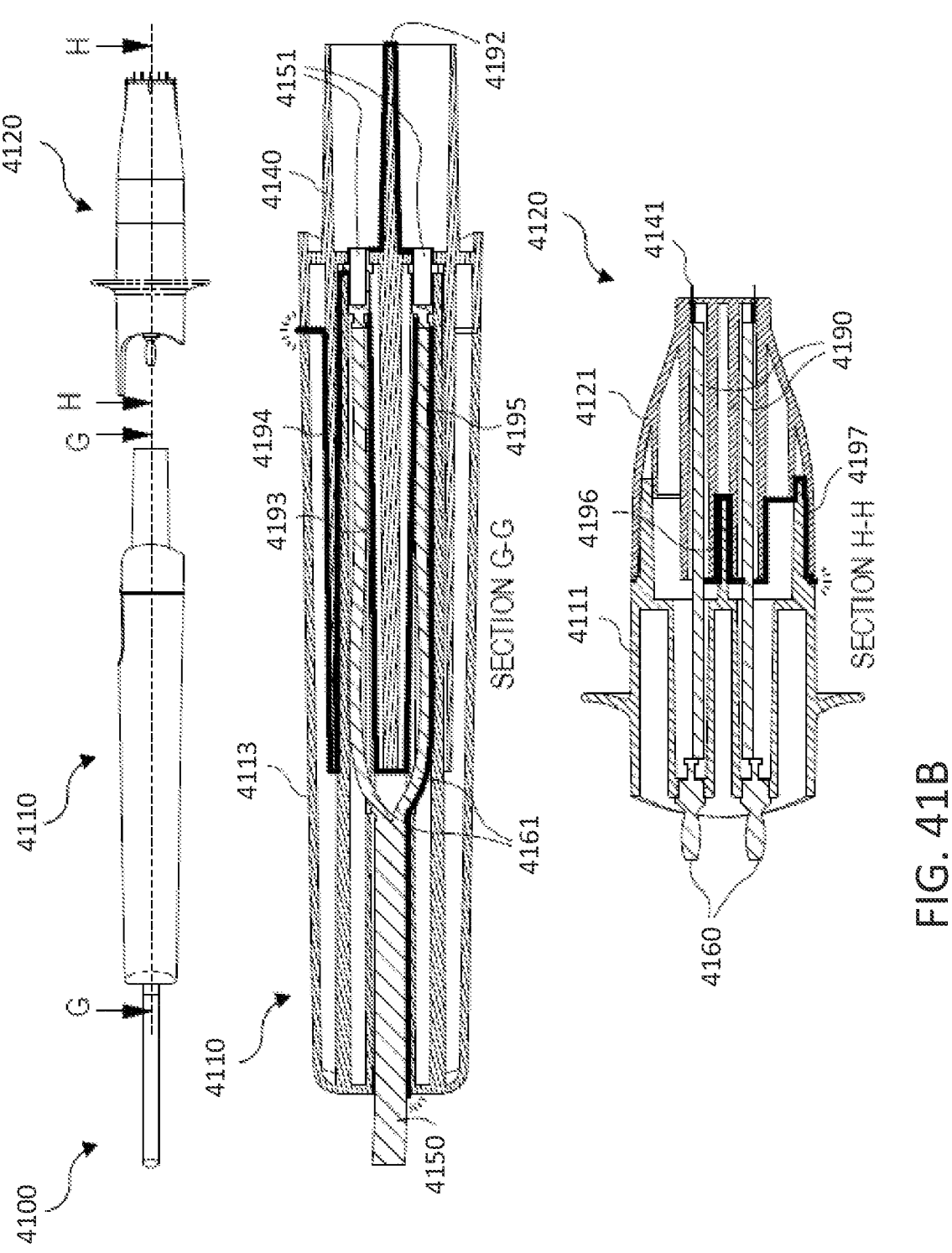
FIG. 41B illustrates an embodiment of an electrode with a minimum clearance distance shown.

FIGS. 41A and 41B illustrate electrode 4100 in an assembled state with tip 4120 disconnected from shaft 4110. In some embodiments, electrode 4100 can be mounted as an instrument to a robotic arm of a robotic surgical system, as described above. As shown, shaft 4110 includes shaft base 4113 and shaft cap 4140, which house connectors 4151, wires 4161, and a portion of cable 4150, such that connectors 4151 are accessible to connection terminals 4160 through shaft cap 4140 when tip 4120 is connected with shaft 4110. Also as shown, tip 4120 includes tip base 4111 and tip cap 4121, which house therapeutic terminals 4141, wires 4190, and connection terminals 4160, such that connection terminals 4160 connect with connectors 4151 when tip 4120 is connected with shaft 4110.

As shown in FIG. 41A and in other figures, each component (e.g. tip base 4111, tip cap 4121, shaft base 4113, and shaft cap 4140) is mated to one or more adjacent components such that the uninsulated electrical terminals and connectors are housed within a structure, such as a skirt of one component which extends into a skirt hole of the adjacent component. As a result, current leakage between the uninsulated electrical terminals and/or connectors is minimized or prevented or substantially prevented because the skirts and skirt holes cause the distance between the uninsulated electrical terminals and/or connectors along any path on any surface or combination of surfaces to be equal to or greater than a minimum clearance distance. In some embodiments, the minimum clearance distance is equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

FIG. 41B illustrates examples of the minimum clearance distances in electrode 4100 and in the tip 4120.

For example, minimum clearance distance 4195 to the user is measured by following wiring channel surfaces from a connector 4151, along wire 4161 to conductive structures on the robotic surgical system that may be placed next to a visible seam between shaft base 4113 and coaxial cable portion 4150 as shown. An alternative minimum distance follows a diagonal within an air gap within the connector, such as a lower left to upper right diagonal near 4194 in Section G-G or upper left to lower right through the air gap in Section H-H.

Another minimum clearance distance 4194 to the user is measured by following surfaces from a connector 4151, between mating surfaces and/or air gaps, to conductive structures on the robotic surgical system that may be placed next to a visible seam between the shaft base 4113 and shaft cap 4140 as shown.

Minimum clearance distance 4193 between connectors (conductive terminals) within shaft base 4113 is measured by following mating surfaces and/or air gaps from a connector 4151 to the other connector 4151 as shown.

Yet another minimum clearance distance 4192 between connectors around shaft cap 4140 is measured by following the surfaces from a connector 4151 out of one recessed connector hole to the other recessed connector hole to the connector 4151 as shown. Another minimum clearance distance is an air clearance from conductive structures on the robotic surgical system (when tip 4120 is not attached to shaft 4110) at the entrance to the recess down to connector 4151.

Minimum clearance distances may be provided also within the tip 4120 of the electrode 4100. For example, minimum clearance distance 4197 in tip 4120 to the user can be measured from wire 4190 out mating surfaces and/or air gaps between tip base 4111 and tip cap 4121 to a user where conductive structures on the robotic surgical system may be placed next to a visible seam between tip base 4111 and tip cap 4121 as shown.

Minimum clearance distance 4196 between wires 4190 in tip 4120 is measured by following mating surfaces and/or air gaps between tip base 4111 and within the tip cap 4121 from wire 4190 to another wire 4190 as shown.

Any of these minimum clearance distances, depending on a particular electrode or relevant procedure/treatment, can be equal to or greater than, for example, 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

Figure 42A:
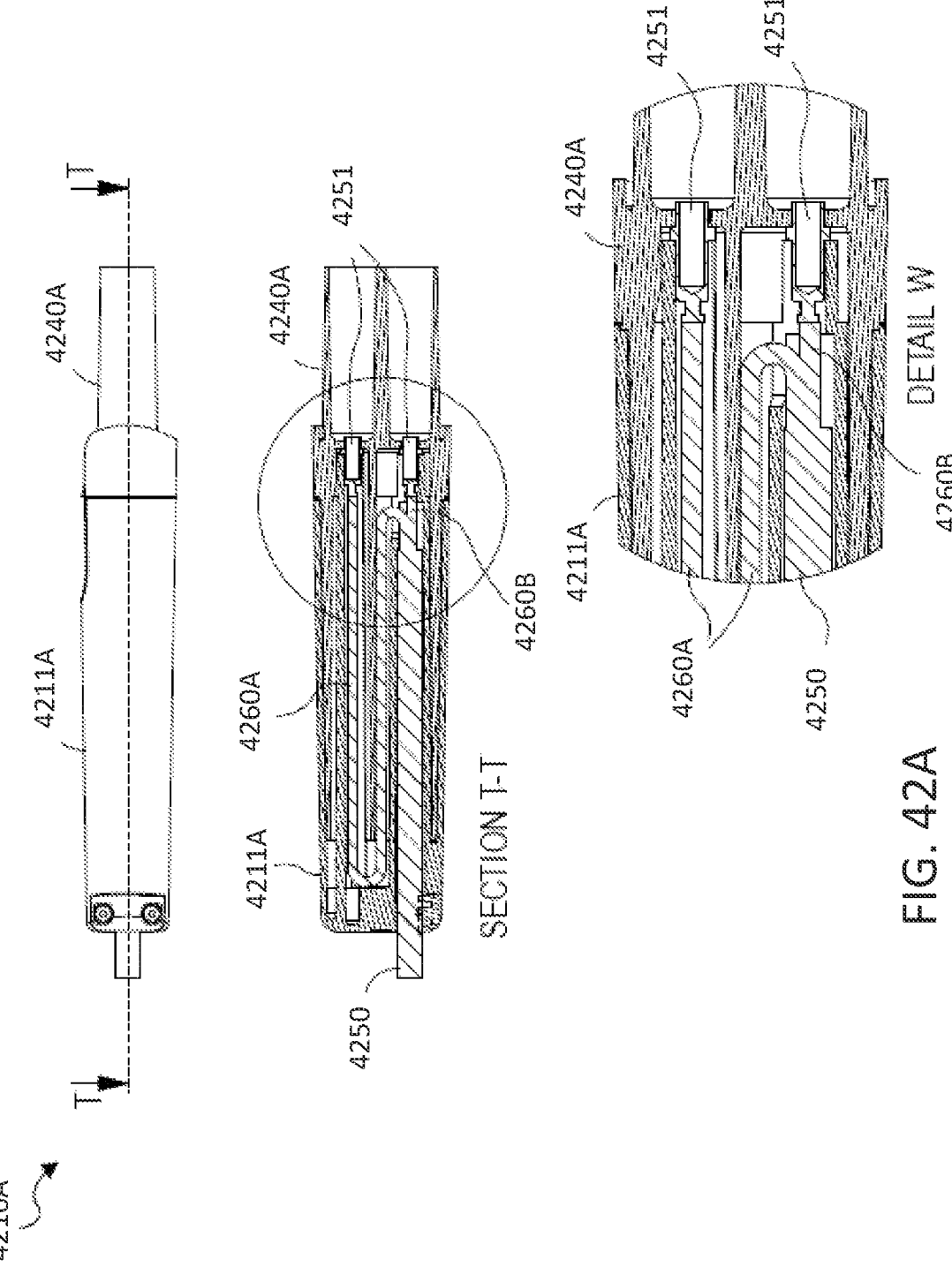
FIG. 42A illustrates an embodiment of a shaft.

FIGS. 42A and 42B illustrate an embodiment of an alternative shaft 4210A. In some embodiments, alternative shaft 4210A has features similar or identical to those of the shafts and electrodes, discussed above. Alternative shaft 4210A includes alternative shaft base 4211A and alternative shaft cap 4240A. Alternative shaft base 4211A has features similar or identical to those of the shaft base described above. Alternative shaft cap 4240A has features similar or identical to those of the shaft cap described above.

In some embodiments, cable 4250 is a co-axial cable, having a central wire surrounded by an insulator and a shielding conductor surrounding the insulator. An outer insulated sheath also surrounds the shielding conductor. In such embodiments, splitting wires 4260 from co-axial cable 4250 may include removing the outer insulated sheath from an end portion of co-axial cable 4250, thereby exposing the shielding conductor along the end portion. In addition, some of the shielding conductor is also removed such that a short portion of the shielding conductor remains exposed and the insulator surrounding the central wire is exposed along the remainder of the end portion. As a result, the modified end portion includes a relatively long section of insulated central wire extending from a short portion of the exposed shielding conductor. Accordingly, a stand-off surface path between the connector 4251 of the insulated central wire and the exposed shielding conductor is provided along the insulation of the insulated central wire. Accordingly, the relatively long section of insulated central wire is sized and configured to provide at least a minimum clearance distance. In some embodiments, the minimum clearance distance is equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches).

In the illustrated embodiment, the insulated central wire 4260A is circuitously routed from the exposed shielding conductor 4260B to the connector 4251 of the insulated central wire. This feature allows for the desired minimum clearance distance along the surface leakage path between connectors 4251 to be achieved with alternative shaft base 4210A being shorter than the desired minimum surface leakage path length.

In some embodiments, the distance between the shielding conductor 3260B and the hole in shaft 4210A by which cable 4250 enters shaft 4210A is greater than a minimum clearance distance. In some embodiments, the minimum clearance distance is equal to or greater than 0.85, 1.0, 1.27, 2.5, 3.2, 3.8, 4.4, 5.1, 6.4, 7.6, 10.2, 12.7, or more centimeters (i.e., 0.33, 0.39, 0.5, 1, 1.25, 1.5, 1.75, 2, 2.5, 3, 4, 5, or more inches). In some embodiments, a shaft may be shorter than the minimum clearance distance, which is accomplished by a circuitous routing of the cable between the hole and shielding conductor 4260B, similar, for example, to the routing of insulated central wire 4260A illustrated in FIG. 42A.

FIGS. 43A-43D illustrate an instrument 4300 adapted to be mounted or coupled to a robotic arm of a robotic system, such as robotic medical treatment system or robotic surgical system. The instrument 4300 can include a treatment tip 4302 that can comprise any of the treatment tips, retractable treatment tips, electrodes, or electrode tips described above, particularly those described with reference to FIGS. 8-21. Instrument 4300 can further include an instrument driver 4303 that can include any of the connectors described herein particularly those described with reference to FIGS. 23-42B.

Specifically, the instrument driver 4304 can include high-voltage connector 4306 configured to couple the treatment tip 4302 to a high-voltage source, and mechanical connections 4308 configured to control mechanical articulation of the instrument (e.g., actuation of the treatment tip).

Figure 43A:
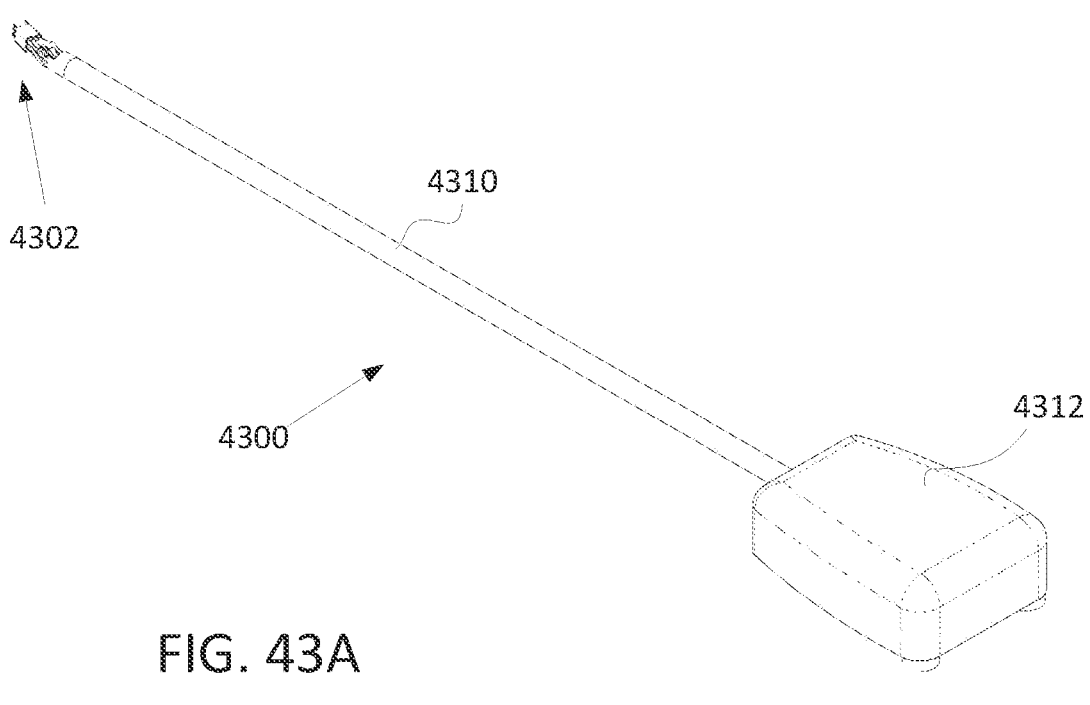
FIGS. 43A-43D illustrate one embodiment of an instrument for use with a robotic surgical system.
Figure 43B:
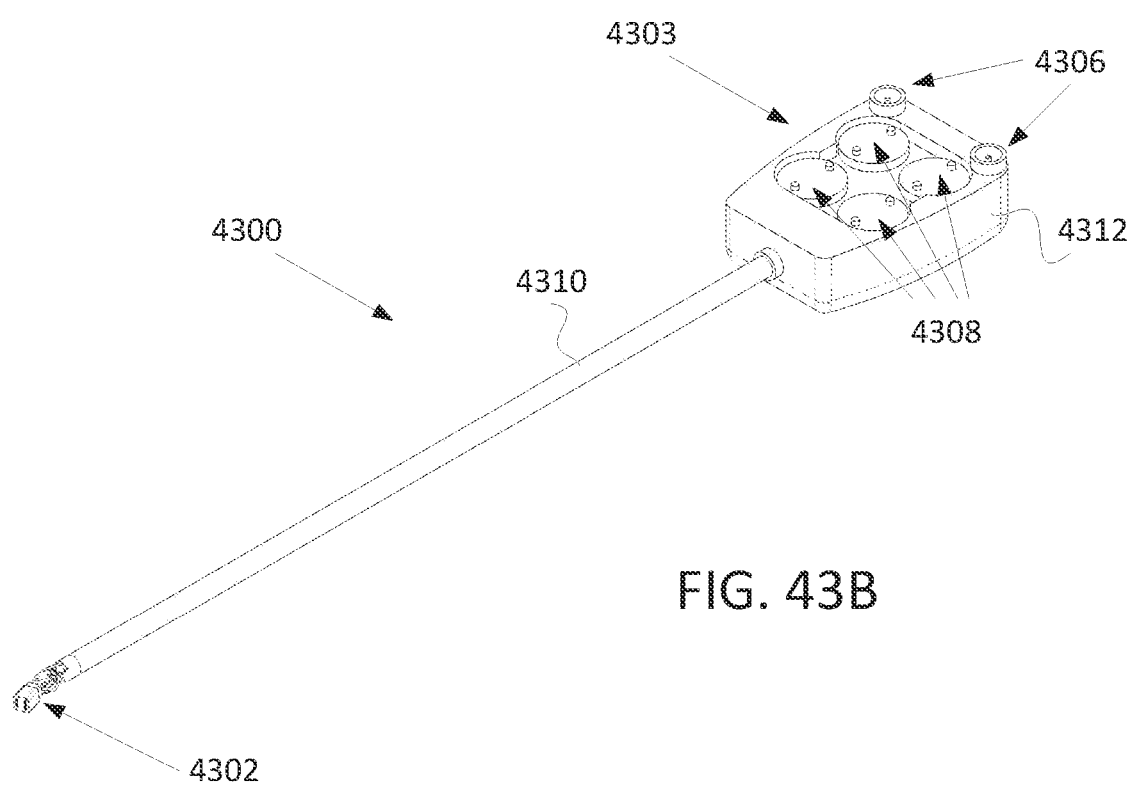

Referring to FIG. 43A, instrument 4300 further comprises an elongate shaft 4310 and a connector housing 4312. The elongate shaft can include a lumen or lumens to house mechanical cables and/or electrical wires or conductors connecting the instrument driver 4303 to the treatment tip 4302. The high-voltage connector 4306 can be configured to provide a high voltage source to the instrument 4300, such as high-voltage nsPEF pulses from a nsPEF pulse generator. Additionally, the mechanical connections 4308 can be, for example, spools with cables wrapped around them, such as for controlling or articulating the instrument or the treatment tip.

Figures 43C, 43D:
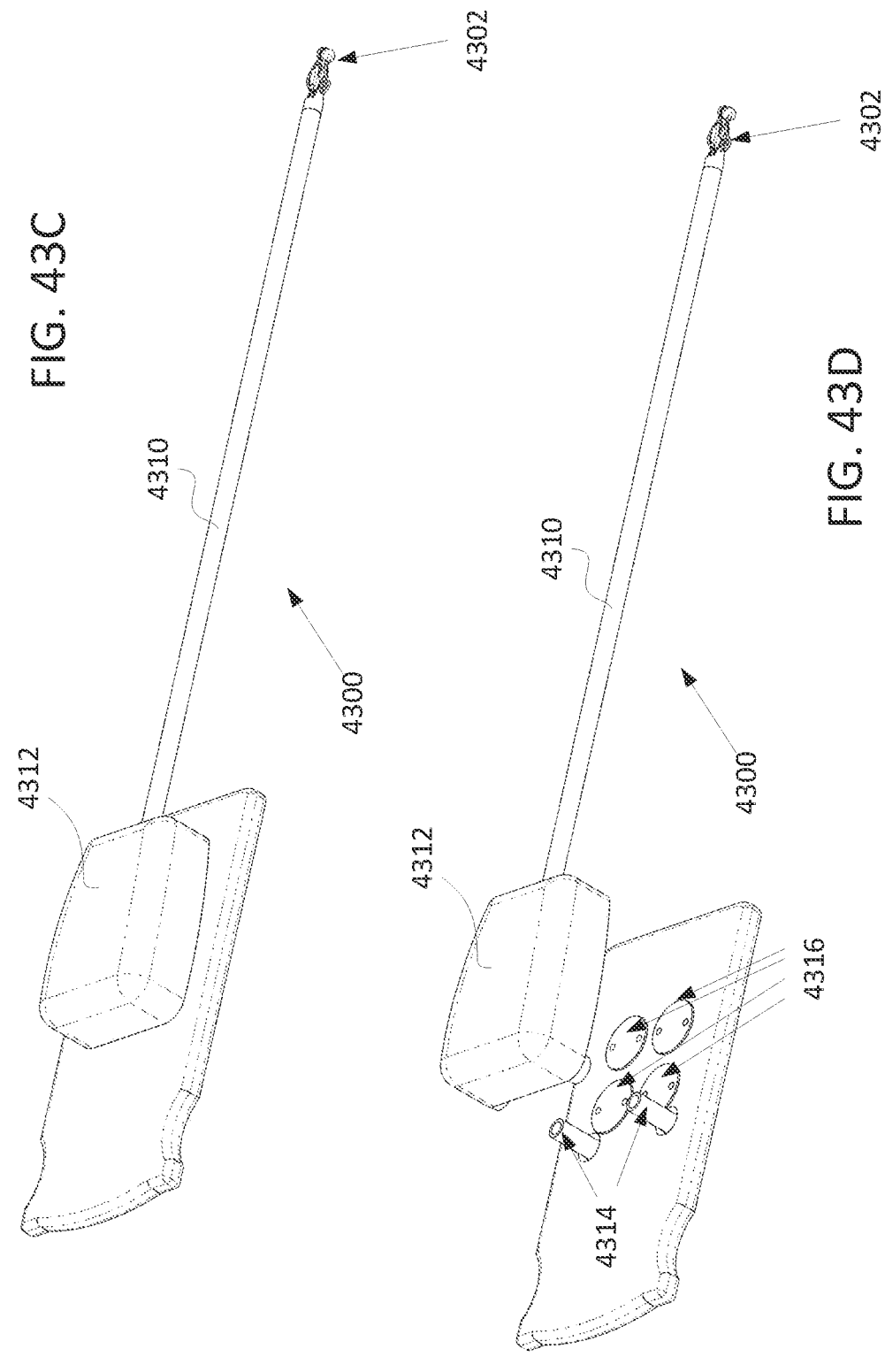

Referring to FIGS. 43C-43D, the high-voltage connector 4306 of instrument driver 4303 is configured to electrically mate with corresponding high-voltage receptacles 4314, as shown in FIGS. 43C-43D. The mechanical connections 4308 can similarly be configured to mechanically mate with corresponding mechanical receptacles 4316, as shown in FIGS. 43C-43D, to enable manipulation or articulation of the instrument including the treatment tip. The high-voltage receptacles 4314 and mechanical receptacles 4316 can be, for example, disposed on a robotic arm of a robotic surgical system, as described above.

The instrument driver 4303 and high-voltage connectors 4306 can include the features described above in reference to FIGS. 24 and 27, including providing a minimum clearance distance between the conductive terminals and conductive structures on the robotic surgical system, (e.g., conductors on the robotic arm of the robotic surgical system), and can further provide a minimum clearance distance between the conductive terminals themselves.

Figures 44A, 44B:
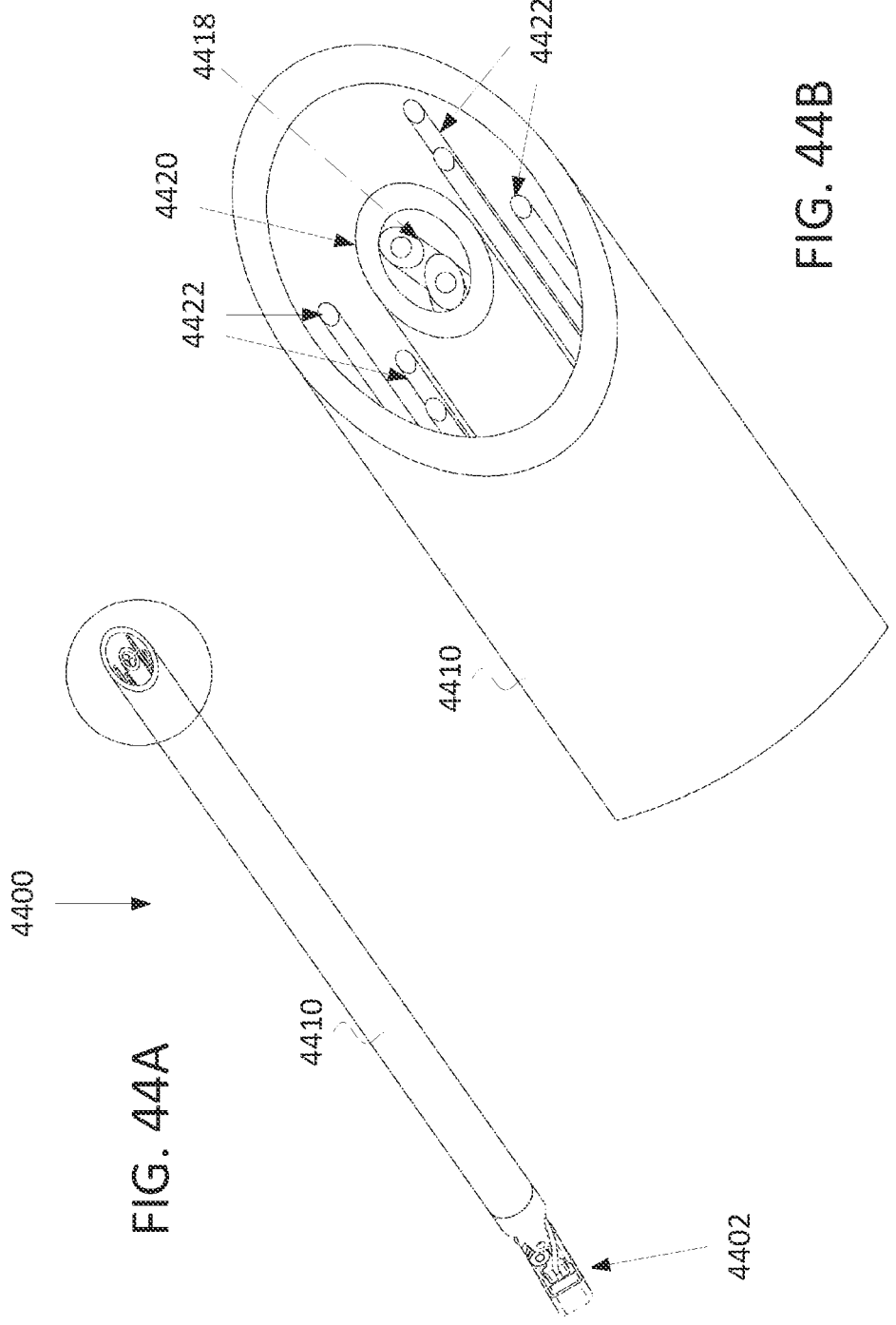
FIGS. 44A-44B illustrate cross-sectional views of a shaft of an instrument for use with a robotic surgical system.

FIGS. 44A-44B illustrate cross-sectional views of a shaft 4410 of instrument 4400, providing a view of the electrical conductors/wires and mechanical cables coupling the instrument driver described above to treatment tip 4402. Referring to FIG. 44B, the elongate shaft can carry high-voltage conductors 4418 in a twisted pair configuration, that can be optionally surrounded by a ground or shield wire 4420. The high-voltage conductors 4418 can electrically couple the high-voltage connector described above to the treatment tip 4402 of the instrument. Both the twisted pair configuration and the ground or shield wire are configured to reduce or eliminate electromagnetic interference (EMI) that can interfere with the operation of a robotic surgical system. The shaft can further carry mechanical cables 4422 to control mechanical features of the treatment tip, such as articulation or actuation of the treatment tip 4402 (e.g., manipulating the tip, extending/retracting needles, actuating a jaw, etc.).

Figures 45A, 45B:
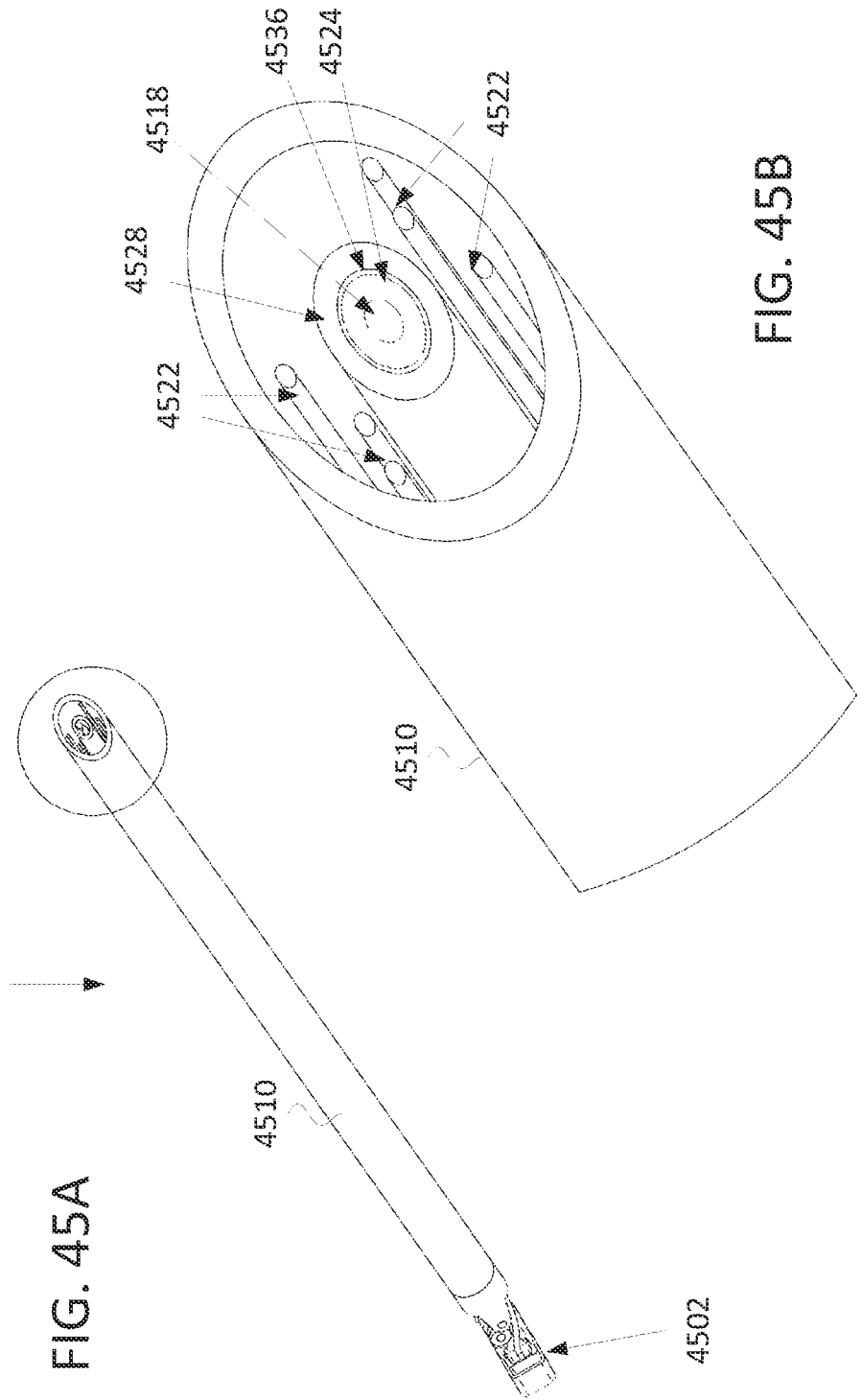
FIGS. 45A-45B illustrate cross-sectional views of a shaft of an instrument for use with a robotic surgical system.

FIGS. 45A-45B show a similar embodiment to that of FIGS. 44A-44B, except a high-voltage coaxial conductor 4218 is used for electrical connection between the high-voltage connector and the treatment tip 4502 in place of the twisted pair above. The coaxial conductor 4518 can include an inner insulation 4524, a coaxial ground or shield 4526, and an outer insulator 4528 to reduce or eliminate EMI from the coaxial conductor. Similar to above, the embodiment of FIGS. 45A-45B further includes mechanical cables 4522 to control mechanical features of the instrument, such as articulation of the treatment tip 4502.

Figures 46A, 46B, 46C:
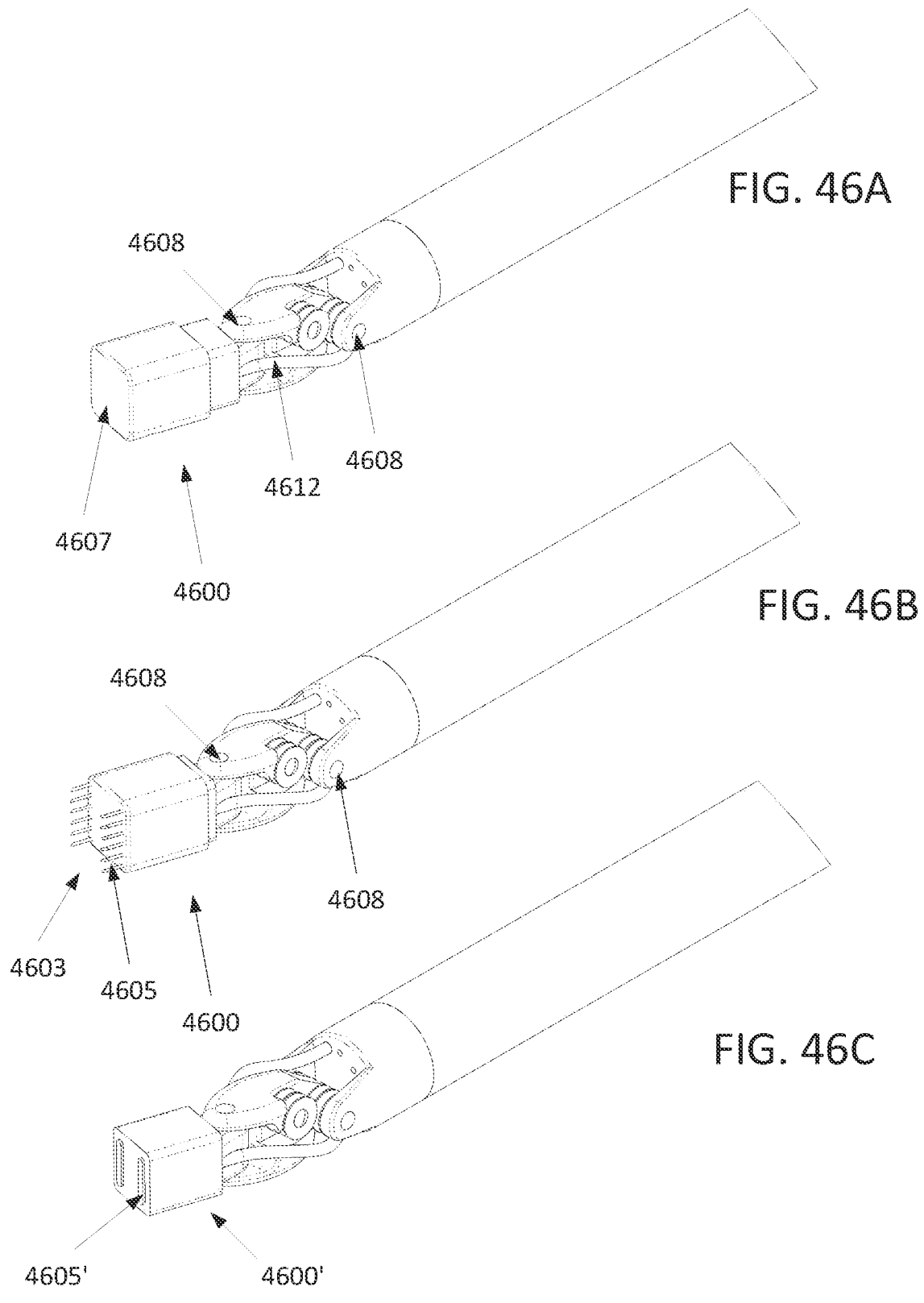
FIGS. 46A-46C illustrate a retractable treatment tip of an instrument for use with a robotic surgical system.

FIGS. 46A-46B illustrate a retractable treatment tip 4600 integrated into an instrument to be mounted or coupled to a robotic arm of a robotic surgical system. This retractable treatment tip can include any of the features described above with respect to FIGS. 10-18. FIG. 46B shows a close-up of the needle housing 4603, which is shown having a rectangular cross-section (any shape cross-section may be used). A plurality of treatment needle electrodes 4605 are shown projecting from the needle housing. In FIG. 46B, the needles are needle electrodes that may have a sharp and beveled distal end, but are cylindrical needles. Any shape needle electrode may be used. The needle electrodes may be insulated or un-insulated; in some variations the treatment needle electrodes are insulated along a portion of their length, but the distal end (e.g., the distal 0.5 mm, 1 mm, 1.2 mm, 1.5 mm, 1.7 mm, 2 mm, etc.) are un-insulated. Referring to FIG. 46A, the needle housing and needle electrodes may be covered and protected by insulating cover 4607.

The retractable treatment tip 4600 of FIGS. 46A-46B can further include articulating joints 4608 and high-voltage conductors 4612 configured to provide high-voltage energy from the connector described above to the retractable treatment tip 4600. The articulating joints 4608 can be mechanically articulated or manipulated with the mechanical cables as described above.

FIG. 46C provides another embodiment of a retractable treatment tip 4600' similar to the tip of FIGS. 46A-46B but including flat or surface electrodes 4605' instead of needle electrodes 4605. The treatment tip 4600' can include the insulating cover, articulating joints, and high-voltage conductors as described above.

FIGS. 47A-47B further provide another treatment tip 4700. The treatment tip 4700 includes grasping electrode tip 4705, which comprises a first high-voltage electrode 4707 and a second high-voltage electrode 4709. The high-voltage electrodes can be housed in a pair of insulating jaws 4711. FIG. 47A shows the grasping electrode tip 4705 in the open configuration, and FIG. 47B shows the grasping electrode tip 4705 in the closed configuration. The grasping electrode tip is designed and configured to maintain the high-voltage electrodes in parallel with each other when the grasping electrode is opened and closed.

FIG. 47C is an exploded view of the treatment tip 4700 of FIGS. 47A-47B, to further illustrate the components that facilitate parallel opening and closing of the grasping electrode tip 4705. As seen in FIG. 47C, the grasping electrode tip 4705 can include a pair of insulating jaws 4711 and top and bottom discs 4713. The discs and insulating jaws can be attached to the treatment tip with pins 4723. Each insulating jaw includes a recess 4717 and a slot 4719 on the top of the jaw (as shown) and an identical recess and slot on the bottom of the jaw (not shown). Both the top and bottom discs 4713 include a pair of pins 4715. A first pin of the top disc is configured to mate with a top recess of a first insulating jaw, and a second pin of the top disc is configured to mate with a top slot of a second insulating jaw (the jaw adjacent to the first jaw). The bottom disc and pins are similarly arranged on the bottom slots and recesses of the jaws. Mechanical cables, as described above, can be connected to each of the discs 4713, and are configured to rotate each disc in either direction. In one example, a pair of mechanical cables is attached to each disc (four mechanical cables in total). By pulling the appropriate combination of mechanical cables, the grasping electrode tip can be steered from side to side, opened, and closed. The pins of the top and bottom discs are configured to rotate in their respective recess while sliding along their respective slot so as to maintain a parallel configuration when the jaws are opened.

FIGS. 48A-48B illustrate another embodiment of an instrument 4800 configured to be mounted to a robotic system. Instrument 4800 of FIGS. 48A-48B comprises an external high-voltage connector 4804 that connects to a high-voltage pulse generator (not shown). In this embodiment, instrument 4800 can be attached to an existing robotic surgical system to enable high-voltage pulse treatment without having to retrofit or replace the robotic arms of the robotic surgical system to include high-voltage connectors. The instrument itself can include the mechanical connections as described above for manipulation/articulation of the instrument treatment tip. It should be understood that the external connector 4804 can also provide a connection to any type of generator, including a nanosecond generator, a microsecond generator, a millisecond generator, etc. The external high-voltage connector 4804 can include all the features described above, including high-voltage terminals, standoffs, insulators, and shields.

Figure 49:
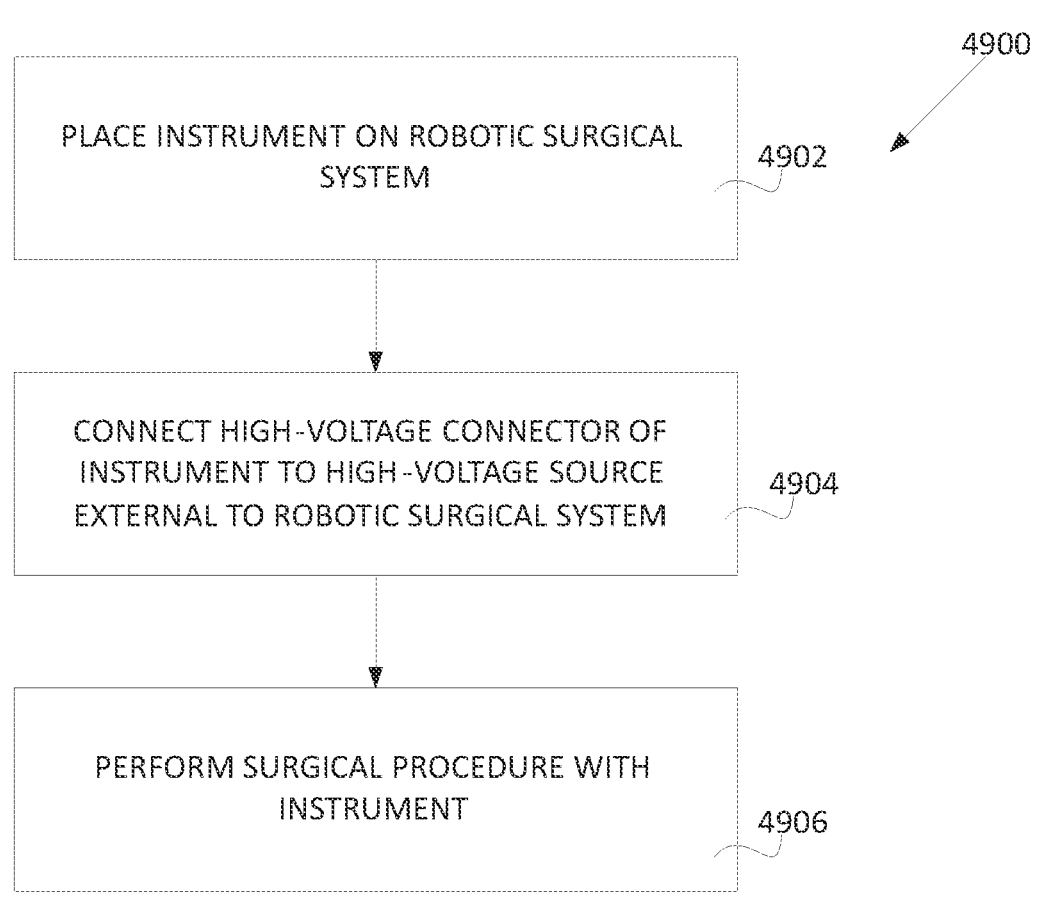
FIG. 49 is a flowchart 4900 describing an example of a method of using the instrument of FIGS. 48A-48B

FIG. 49 is a flowchart 4900 describing a method of using an instrument, such as the instrument of FIGS. 48A-48B. At a preliminary step 4902 of flowchart 4900, the method includes placing an instrument such as the instrument of FIGS. 48A-48B on a robotic surgical system. The placing step can include making the appropriate mechanical connections between the instrument and the robotic surgical system, such as connecting mechanical connections of the instrument to mechanical receptacles of the robotic surgical system. The mechanical connections/receptacles can, for example, control articulation or movement of a treatment tip of the instrument, as described above. Alternatively, the method may start with the instrument already present on the robotic system. Next, at step 4904 of flowchart 4900, the method can include connecting a high-voltage connector of the instrument to an external high-voltage source (e.g., a high-voltage source separate from the robotic surgical system). Finally, at step 4906 of flowchart 4900, the method can include performing a surgical procedure with the instrument. The method of FIG. 49 advantageously allows for the use of novel high-voltage surgical instruments with existing robotic surgical systems, without having to retrofit the robotic surgical systems with the high-voltage connectors described herein. Instead, existing robots can be used with external high-voltage sources according to the novel steps described above.

Figures 50, 51:
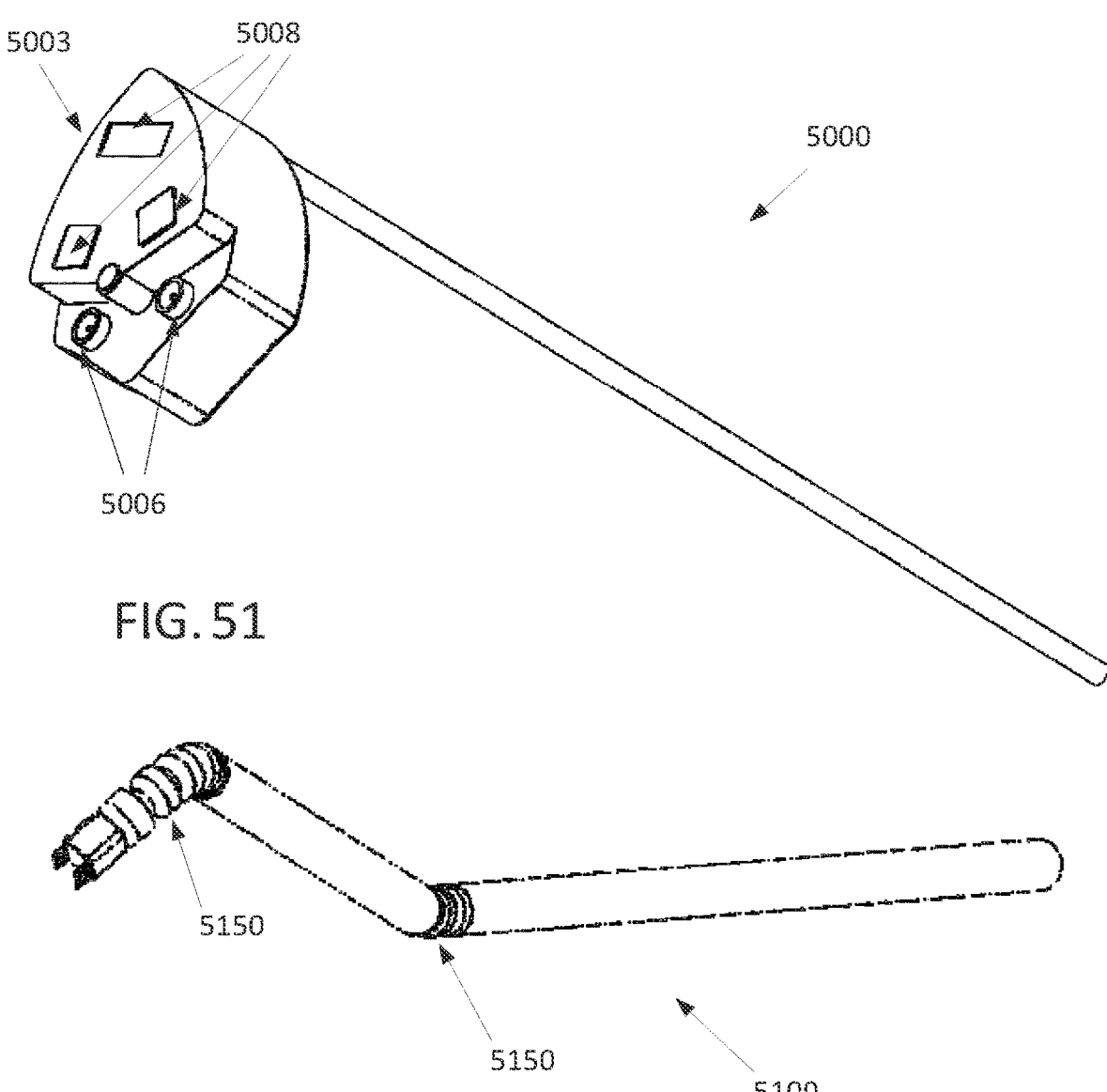
FIG. 50 illustrates an instrument adapted to be mounted or coupled to a robotic arm of a robotic surgical system, for example, a single port surgery or natural orifice trans-esophageal surgery (NOTES) robotic system.
FIG. 51 illustrates an instrument adapted to be mounted or coupled to a robotic arm of a robotic system.

FIG. 50 illustrates an instrument 5000 adapted to be mounted or coupled to a robotic arm of a robotic surgical system, for example, a single port surgery or natural orifice trans-esophageal surgery (NOTES) robotic system. The instrument 5000 can include a treatment tip that can comprise any of the treatment tips, retractable treatment tips, electrodes, or electrode tips described above, particularly those described with reference to FIGS. 8-21. Instrument 5000 can further include an instrument driver 5003 that can comprise any of the instrument drivers or connectors described herein particularly those described with reference to FIGS. 23-42B.

Referring to FIG. 50, instrument 5000 further comprises an elongate shaft and an instrument driver 5003, which includes high-voltage connectors 5006 and mechanical connectors 5008. The elongate shaft can include a lumen or lumens to house/conductors and mechanical cables connecting the instrument driver 5003 to the treatment tip. The high-voltage connectors 5006 can be configured to provide a high voltage source to the instrument 5000, such as high-voltage nsPEF pulses from a nsPEF pulse generator. Additionally, the mechanical connectors 5008 can provide a mechanical connection the instrument tip (e.g., mechanical cables), such as for controlling or articulating the instrument or the treatment tip.

FIG. 51 illustrates an instrument 5100 which can be used with various robotic systems. The instrument 5100 can include a treatment tip that can comprise any of the treatment tips, retractable treatment tips, electrodes, or electrode tips described above, particularly those described with reference to FIGS. 8-21 and 46-48. Instrument 5100 can further include a connector that can comprise any of the connectors described herein particularly those described with reference to FIGS. 23-42B. As shown in FIG. 50, the instrument 5100 can include a plurality of articulating joints 5150 to allow the instrument to navigate the tortuous pathways, for example, as required by single port or NOTES surgical treatments.

Figures 52A, 52B:
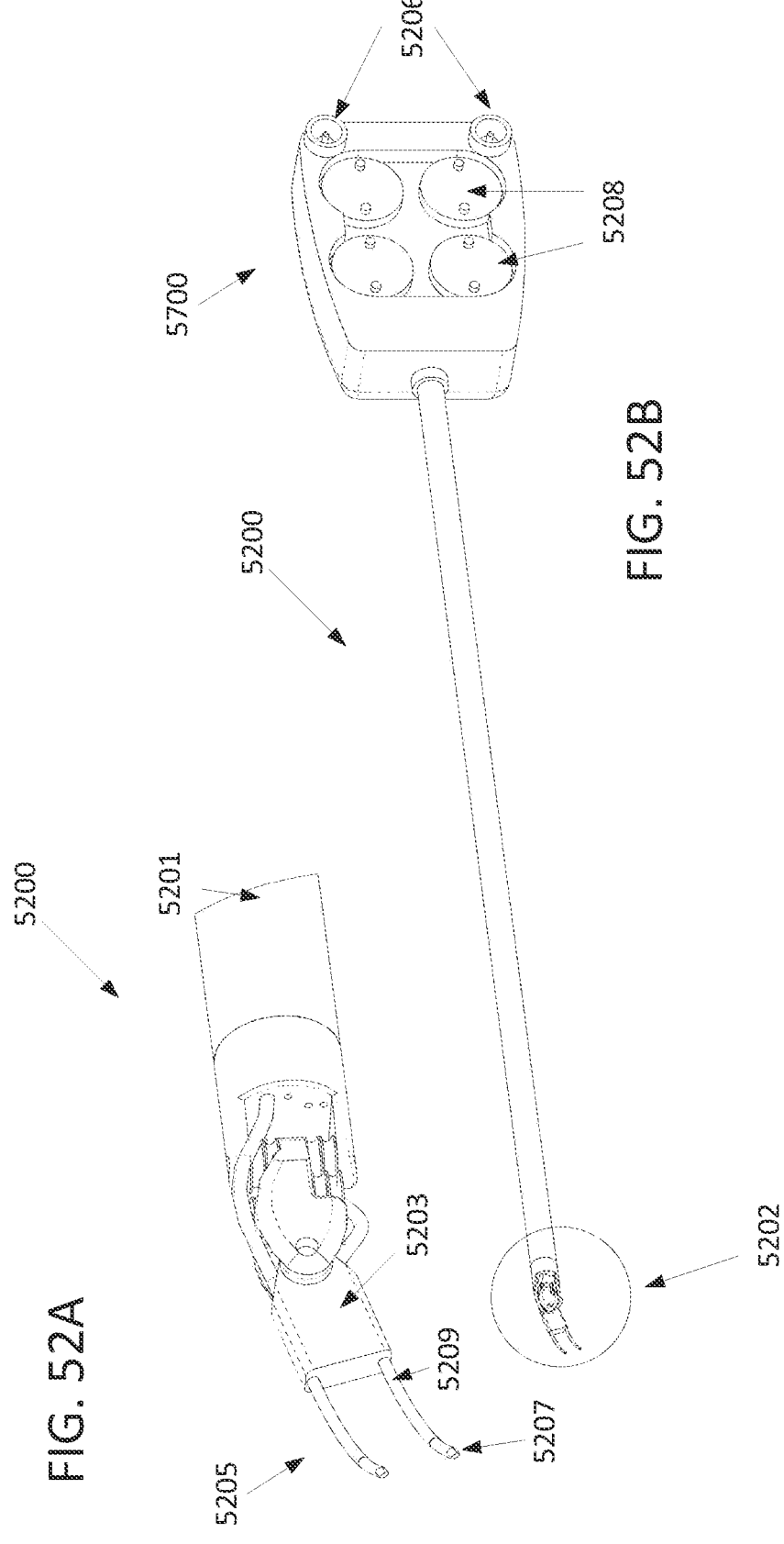
FIGS. 52A-52B disclose an instrument adapted to be mounted or coupled to a robotic arm of a robotic system.

FIGS. 52A-52B disclose another instrument 5200 adapted to be mounted or coupled to a robotic arm of a robotic surgical system. The instrument 5200 further includes a treatment tip 5202 that comprises a pair of curved electrodes 5205. A high-voltage energy can be delivered to the curved electrodes 5205 via an instrument driver 5700 that includes high-voltage connectors 5206 and mechanical connectors 5208, similar or identical to the connectors described in detail above, particularly the instrument driver 4303 of FIG. 43B. The curved electrodes 5205 can include an exposed portion 5207 and an insulated portion 5209. The insulated portion allows for some portion of the curved needle to be outside of a treatment tissue (e.g., tumor) during treatment without high-voltage arcing across the exposed needle outside of the tissue. The insulated portion also provides a distance between the shaft 5201 and body 5203 of the instrument to allow for treatment of tissue at depth without the body or shaft of the instrument impacting the tissue surface.

One example of a method of using the instrument 5200 of FIGS. 52A-52B will now be described, referring to flowchart 5300 of FIG. 53. At step 5302 of flowchart 5300, a size and/or shape of a target tissue, such as a tumor, can be identified. Next, at step 5304, a needle curvature of electrode needles can be chosen (for example, from a set of needles of various shapes and curvatures) based on the size and shape that were identified in step 5302. The needle curvature can be chosen automatically by a robotic system or can be chosen manually by a user. In one example, a robotic system can evaluate imaging of a target tissue site, such as a tumor, and can choose or recommend a needle shape and curvature to the user (e.g., via a display of the system). At step 5306, an instrument, such as any of the instruments described herein, can be placed with the chosen needle curvature onto a robotic surgical system, such as onto a robotic arm of a robotic surgical system. Any one or a combination of the steps of 5302, 5304 and 5306 may be performed separately, for example, in advance of the actual treatment using a robotic system according to the steps of the method described below.

At step 5308, the robotic surgical system can position the instrument and the curved needle electrodes at the target tissue. The positioning can be, for example, automatic robotic positioning, or master/slave positioning in which a user controls the positioning of the robot.

Finally, at step 5310 of flowchart 5300, one or more needle electrodes can be automatically inserted into the target tissue and the robotic surgical system can automatically adjust the orientation and position of the instrument and curved needle electrode(s) to follow the curvature of the needle electrode as it is inserted into the tissue.

Another example of a method of using the instrument 5200 of FIGS. 52A-52B will now be described, referring to flowchart 5400 of FIG. 54. At step 5402, a robotic surgical system can position an instrument selected based on a size/shape of a target tissue relative to the target tissue. The positioning can be, for example, automatic robotic positioning, or master/slave positioning in which a user controls the positioning of the robot. The instrument can include, for example, curved needle electrodes. A needle curvature of electrode needles can be chosen (for example, from a set of needles of various shapes and curvatures) based on the size and shape of the target tissue. The needle curvature can be chosen automatically by a robotic system, or can be chosen manually by a user. In one example, a robotic system can evaluate imaging of a target tissue site, such as a tumor, and can choose or recommend a needle shape and curvature to the user (e.g., via a display of the system).

Next, at step 5404 of flowchart 5400, the instrument (e.g., curved needle electrodes of an instrument) can be automatically inserted into the target tissue under control of a processor of the robotic surgical system, and the processor of the robotic surgical system can automatically change or adjust the orientation and position of the instrument (e.g., the curved needle electrodes) to follow the curvature of the target tissue.

Finally, at step 5406 of flowchart 5400, the method can include delivering or applying electrical energy, such as NPS pulses, to the target tissue with the instrument. In one specific example, as the instrument is being inserted into the target tissue the robotic surgical system can deliver pulsed energy, such as NPS pulses, to the target tissue with the instrument. In another example, the robotic surgical system can advance the needle further into the target tissue in between pulses so as to form a larger treatment volume in the target tissue. In another example, the robotic surgical system can advance the instrument during a pulse, with the same end result of increasing the size of the treatment volume.

Figure 55:
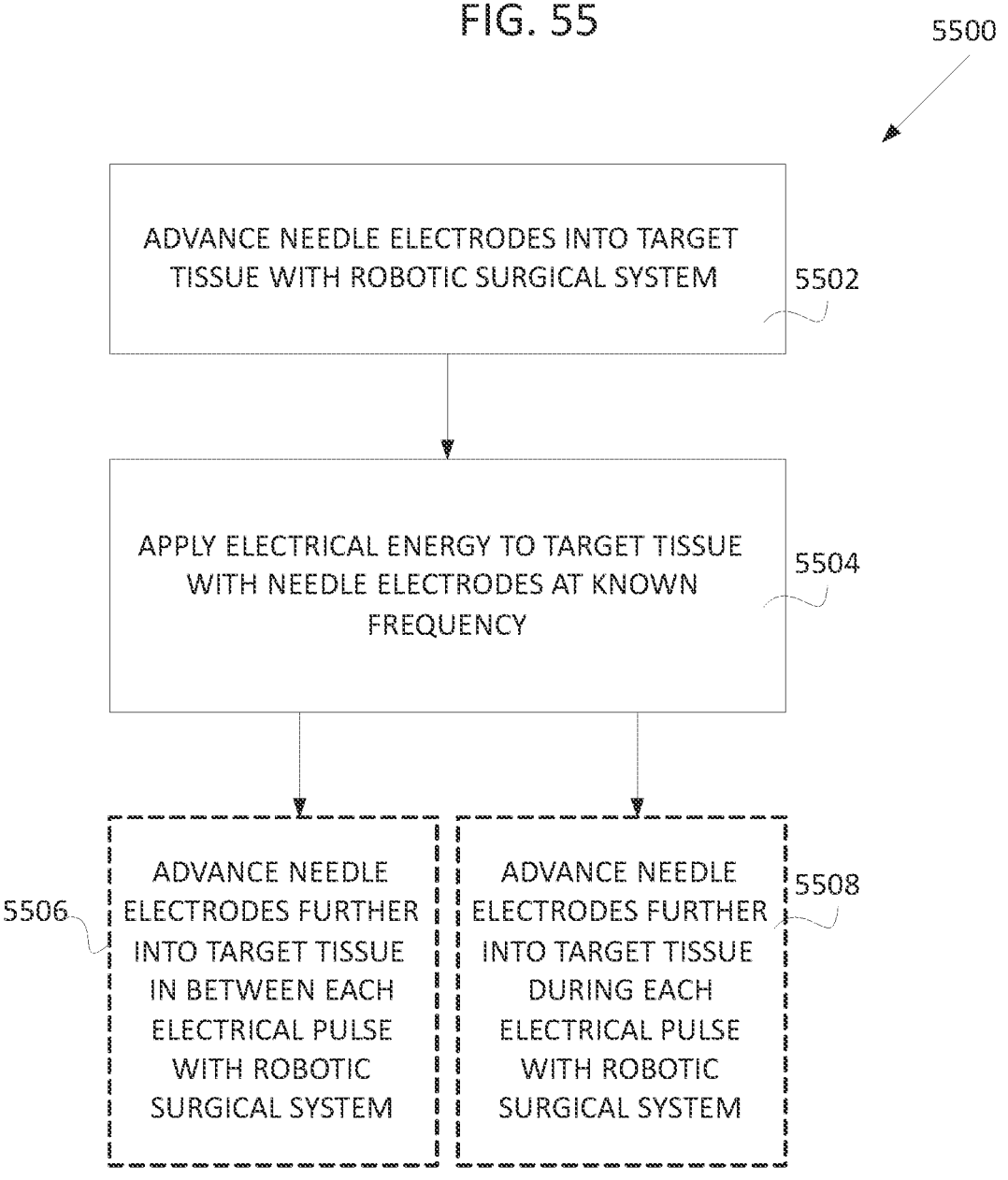
FIG. 55 illustrates a flowchart for performing a surgical procedure with a robotic surgical system.

FIG. 55 illustrates a flowchart 5500 for performing a surgical procedure with a robotic surgical system. At step 5502 of flowchart 5500, the method can include advancing needle electrodes into a target tissue with a robotic surgical system. The needle electrodes can be disposed on a surgical instrument and attached to a robotic arm of the robotic surgical system, as described above.

At step 5504 of flowchart 5500, electrical energy can be applied to the target tissue at a known frequency. For example, the electrical energy can comprise high-voltage pulsed energy, such as NPS pulses. However, it should be understood that any type of pulsed electrical energy can be applied to the target tissue.

Next, in optional steps 5506 and 5508 of flowchart 5500, the robotic surgical system can advance the needle further into the target tissue as the electrical energy is delivered to the target tissue. In optional step 5506, the robotic surgical system advances the electrodes further into the target tissue in between each electrical pulse. However, in optional step 5508, the robotic surgical system advances the electrodes further into the target tissue during each electrical pulse. In both instances (advancing in between pulses or advancing during each pulse), the technique results in formation of a larger treatment volume in the target tissue. The technique of pulsing the electrodes and advancing the needles either during the pulse or in between pulses can be applied to any type of needle electrode instrument described herein, including the treatment tips that include straight or curved needle electrodes, for example.

FIG. 56 illustrates a flowchart 5600 for performing a surgical procedure with a robotic surgical system. At step 5602 of flowchart 5600, the method can include advancing needle electrodes into a target tissue, for example under control of a robotic surgical system. The needle electrodes can be disposed on a surgical instrument and attached to a robotic arm of the robotic surgical system, as described above.

At step 5604 of flowchart 5600, the method can include measuring an impedance of the tissue with the needle electrodes. In some examples, the electrodes can be used to measure the impedance of the target tissue to be treated as well as the surrounding tissue.

At step 5606 of flowchart 5600, electrical energy can be applied to the target tissue at a known frequency. In a first example, the electrical energy can initially be a low-voltage pulsed energy until the needles are positioned within the target tissue. This proper positioning can be confirmed with the impedance measurement. Once the needles are positioned within the target tissue, the electrical energy can comprise high-voltage pulsed energy, such as NPS pulses. However, it should be understood that any type of pulsed electrical energy can be applied to the target tissue.

In step 5508 of flowchart 5600, the robotic surgical system can move the needle within the target tissue (in any appropriate direction, e.g., up, down, left, right, etc.) if certain condition is met: for example, when a change in the impedance of the target tissue (as a result of the therapy) exceeds an impedance threshold. For example, applying electrical energy to the tissue can change the impedance of the target tissue by breaking down the tissue itself. This change can be measured, and when the change in impedance exceeds an impedance threshold that indicates the tissue breakdown, the needle electrodes can be moved within the tissue. As described above, the movement of electrodes can occur either during each pulse or in between pulses, or during entire application of the electric energy.

At step 5510 of flowchart 5600, the robotic surgical system can stop applying electrical energy, for example, when the measured impedance indicates that the needle electrodes are positioned in surrounding tissue and not the target tissue. Step 5610 may be performed instead or in addition to step 5608.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "mounted", "attached" or "coupled" to another feature or element, it can be directly connected, mounted, attached or coupled to the other feature or element or intervening features or elements may be present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for case of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating a target tissue with a robotic system, comprising:
    positioning a treatment instrument coupled to a movable arm of the robotic system relative to the target tissue, the treatment instrument comprising an electrode housing extending from a distal end of a treatment tip housing and configured to retract proximally into the treatment tip housing;
    retracting the electrode housing proximally into the treatment tip housing to expose a plurality of treatment electrodes;
    applying sub-microsecond electric pulses to the target tissue from the plurality of treatment electrodes.

2. The method of claim 1, wherein the treatment tip housing is configured to be coupled to a high-voltage connector disposed on the movable arm of the robotic system.

3. The method of claim 2, the method comprising connecting the high-voltage connector of the instrument to a high-voltage source external to the robotic system.

4. The method of claim 1, the method comprising:
    advancing or directing advancement of the treatment instrument to position at least one of the plurality of treatment electrodes within the target tissue;
    measuring an impedance of the target tissue and/or a surrounding tissue;
    causing the at least one of the plurality of treatment electrodes to apply electrical energy to the target tissue; and
    initiating one of the following based on the measured impedance: 1) directing the treatment instrument to move to a new location within the target tissue, or 2) causing the at least one of the plurality of treatment electrodes to stop applying the electrical energy.

5. The method of claim 4, the method comprising directing the treatment instrument to move to the new location within the target tissue when either: 1) an application of the electrical energy at a current location is completed, or 2) a change in impedance at the current location exceeds an impedance threshold.

6. The method of claim 4, the method comprising causing the at least one of the plurality of treatment electrodes to stop applying the electrical energy when the measured impedance indicates that the at least one of the plurality of treatment electrodes is positioned in the surrounding tissue.

7. The method of claim 1, the method comprising causing the robotic system to advance the plurality of treatment electrodes into the target tissue in between applying the sub-microsecond electric pulses or during the application of the sub-microsecond electric pulses.

8. The method of claim 1, the method comprising selecting or adjusting a length of the plurality of treatment electrodes and/or a length of an insulated portion on the plurality of treatment electrodes, the insulated portion configured to reduce or prevent arcing.

9. The method of claim 1, the method comprising processing by a processor of the robotic system real time imaging data.

10. The method of claim 1, wherein the method is for treating one or more of the following: organ tissue, respiratory tissue, lung tissue, breast tissue, liver tissue, cancer, benign tumors, precancerous tumors, cherry angioma, warts, keloids/scars, molluscum angioma, necrobiosis lipoidica (NBL), melisma, lipoma epidermal/sebaceous cyst, basal cell carcinoma, aging skin.

11. The method of claim 1, wherein the treatment instrument comprises a grasping electrode tip having a first electrode and a second electrode, the method comprising maintaining a parallel orientation of the first and the second electrodes as the grasping electrode tip is opened and closed.

12. The method of claim 1, the method comprising controlling, by a controller based on images or data acquired by an image acquisition device, movements of the movable arm, the treatment instrument, or the plurality of treatment electrodes.

13. The method of claim 1, the method comprising using a sensor to provide a feedback for placement of the plurality of treatment electrodes.

14. The method of claim 1, the method comprising generating a feedback for adjusting a voltage level, polarity, and/or achieving a desired angle, speed or force.

15. The method of claim 1, the method comprising exerting a bias force to oppose conversion of the plurality of treatment electrodes between an un-deployed configuration in which distal ends of the plurality of treatment electrodes do not extend beyond a distal end face of the electrode housing and a deployed configuration in which the distal ends of the plurality of treatment electrodes extend beyond the distal end face of the electrode housing.

16. The method of claim 1, wherein the plurality of treatment electrodes are needle electrodes and at least a distal end face of the electrode housing comprises an electrical insulator having a soft body, the method comprising penetrating through the electrical insulator at the distal end face of the electrode housing with the needle electrodes.

17. The method of claim 1, wherein the plurality of treatment electrodes comprises at least one curved electrode, the method comprising automatically adjusting an orientation of the treatment instrument such that the at least one curved electrode follows a curvature of the target tissue.

18. The method of claim 1, the method comprising selecting the treatment instrument from a plurality of treatment instruments based at least on one or more of a size, shape or curvature of the target tissue.

19. The method of claim 1, the method comprising inputting, through a user interface, or automatically identifying various parameters of pulses of electric energy to be applied to the target tissue, wherein the parameters comprise one or more of an amplitude, a polarity, a width, a rise time, and a fall time of the pulses to be applied to the target tissue.

20. The method of claim 1, wherein the treatment tip housing is configured to be coupled to a high-voltage connector that comprises high-voltage terminals, insulators, standoffs and/or shields.

21. The method of claim 1, the method comprising connecting mechanical connections of the treatment instrument to mechanical receptacles of the robotic system.

22. The method of claim 1, wherein applying sub-microsecond electric pulses to the target tissue comprises applying electric pulses with a field strength between 10 kV/cm and 100 kV/cm.

* * * * *